(12) United States Patent
Curry et al.

(10) Patent No.: US 8,404,718 B2
(45) Date of Patent: Mar. 26, 2013

(54) COMBINATIONS OF PYRAZOLE KINASE INHIBITORS

(75) Inventors: Jayne Elizabeth Curry, Cambridge (GB); John Francis Lyons, London (GB); Matthew Simon Squires, Cambridge (GB); Neil Thomas Thompson, Cambridge (GB); Kyla Merriom Thompson, Cambridge (GB); Paul Graham Wyatt, Perth (GB)

(73) Assignee: Astex Therapeutics Limited, Cambridge (GB)

( * ) Notice: Subject to any disclaimer, the term of this patent is extended or adjusted under 35 U.S.C. 154(b) by 263 days.

(21) Appl. No.: 12/752,772

(22) Filed: Apr. 1, 2010

(65) Prior Publication Data

US 2011/0002879 A1    Jan. 6, 2011

Related U.S. Application Data

(63) Continuation-in-part of application No. 11/814,456, filed as application No. PCT/GB2006/000204 on Jan. 20, 2006, now abandoned, application No. 12/752,772, which is a continuation-in-part of application No. 11/814,461, filed as application No.

(Continued)

(51) Int. Cl.
*A61K 31/4465* (2006.01)
*A61K 31/4468* (2006.01)
*A61K 31/454* (2006.01)
*C07D 401/12* (2006.01)

(52) U.S. Cl. ........................ 514/326; 546/211
(58) Field of Classification Search .................. None
See application file for complete search history.

(56) References Cited

U.S. PATENT DOCUMENTS

| | | | |
|---|---|---|---|
| 2,917,432 A | 12/1959 | Timmis et al. | |
| 3,046,301 A | 7/1962 | Phillips et al. | |
| 4,005,063 A | 1/1977 | Gendrich et al. | |
| 4,100,274 A | 7/1978 | Dutta et al. | |
| 4,282,361 A | 8/1981 | Hecht et al. | |
| 4,377,687 A | 3/1983 | Eisenbrand | |
| 4,950,668 A | 8/1990 | Okada et al. | |
| 4,978,672 A | 12/1990 | Bowman et al. | |
| 5,002,755 A | 3/1991 | Mitchell et al. | |
| 5,164,196 A | 11/1992 | Plata et al. | |
| 5,502,068 A | 3/1996 | Lown et al. | |
| 5,514,664 A | 5/1996 | Ulrich | |
| 5,744,491 A | 4/1998 | Boigegrain et al. | |
| 5,877,296 A | 3/1999 | Hamann et al. | |
| 6,020,357 A | 2/2000 | Pinto et al. | |
| 6,066,738 A | 5/2000 | Dinsmore et al. | |
| 6,306,393 B1 | 10/2001 | Goldenberg | |
| 6,455,559 B1 | 9/2002 | Pevarello et al. | |
| 6,878,714 B2 | 4/2005 | Askew et al. | |
| 7,385,059 B2 * | 6/2008 | Berdini et al. | 546/188 |
| 7,745,638 B2 | 6/2010 | Berdini et al. | |
| 7,825,140 B2 | 11/2010 | Berdini et al. | |
| 8,013,163 B2 * | 9/2011 | Wyatt et al. | 546/211 |
| 8,080,666 B2 | 12/2011 | Berdini et al. | |
| 2002/0091116 A1 | 7/2002 | Zhu et al. | |
| 2003/0092095 A1 | 5/2003 | Huang | |
| 2003/0149001 A1 | 8/2003 | Barvian et al. | |
| 2004/0087798 A1 | 5/2004 | Yamada | |
| 2004/0097517 A1 | 5/2004 | Dwyer et al. | |

(Continued)

FOREIGN PATENT DOCUMENTS

| EP | 0100172 B1 | 12/1987 |
|---|---|---|
| EP | 0289879 A1 | 11/1988 |

(Continued)

OTHER PUBLICATIONS

U.S. Appl. No. 13/289,373, filed Nov. 2011, Berdini et al.*

(Continued)

*Primary Examiner* — Eric S Olson
(74) *Attorney, Agent, or Firm* — Geslin Rothenberg Farley & Mesiti P.C.

(57) ABSTRACT

The invention provides a combination comprising a cytotoxic compound, a signalling inhibitor, an ancillary agent, or two or more further anti-cancer agents, and a compound having the formula (Ib):

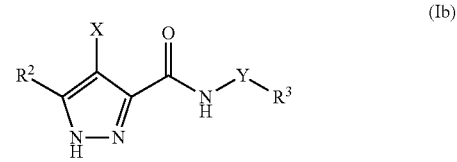

(Ib)

or salts or tautomers or N-oxides or solvates thereof;
wherein
X is a group $R^1$-A-$NR^4$—;
A is a bond, C=O, $NR^g$(C=O) or O(C=O) wherein $R^g$ is hydrogen or $C_{1-4}$ hydrocarbyl optionally substituted by hydroxy or $C_{1-4}$ alkoxy;
Y is a bond or an alkylene chain of 1, 2 or 3 carbon atoms in length;
$R^1$ is a carbocyclic or heterocyclic group having from 3 to 12 ring members; or a $C_{1-8}$ hydrocarbyl group optionally substituted by one or more substituents selected from fluorine, hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$;
$R^2$ is hydrogen; halogen; $C_{1-4}$ alkoxy (e.g. methoxy); or a $C_{1-4}$ hydrocarbyl group optionally substituted by halogen (e.g. fluorine), hydroxyl or $C_{1-4}$ alkoxy (e.g. methoxy);
$R^3$ is selected from carbocyclic and heterocyclic groups having from 3 to 12 ring members; and
$R^4$ is hydrogen or a $C_{1-4}$ hydrocarbyl group optionally substituted by halogen (e.g. fluorine), hydroxyl or $C_{1-4}$ alkoxy (e.g. methoxy).

22 Claims, 11 Drawing Sheets

Related U.S. Application Data

PCT/GB2006/000210 on Jan. 20, 2006, now abandoned, application No. 12/752,772, which is a continuation-in-part of application No. 11/814,455, filed as application No. PCT/GB2006/000206 on Jan. 20, 2006, now abandoned, application No. 12/752,772, which is a continuation-in-part of application No. 12/373,713, filed as application No. PCT/GB2007/002640 on Jul. 13, 2007, now abandoned.

(60) Provisional application No. 60/645,987, filed on Jan. 21, 2005, provisional application No. 60/645,986, filed on Jan. 21, 2005, provisional application No. 60/646,113, filed on Jan. 21, 2005, provisional application No. 60/645,976, filed on Jan. 21, 2005, provisional application No. 60/645,975, filed on Jan. 21, 2005, provisional application No. 60/645,988, filed on Jan. 21, 2005, provisional application No. 60/645,974, filed on Jan. 21, 2005, provisional application No. 60/646,216, filed on Jan. 21, 2005, provisional application No. 60/646,001, filed on Jan. 21, 2005, provisional application No. 60/646,003, filed on Jan. 21, 2005, provisional application No. 60/645,963, filed on Jan. 21, 2005, provisional application No. 60/831,043, filed on Jul. 14, 2006.

(56) References Cited

U.S. PATENT DOCUMENTS

| | | | |
|---|---|---|---|
| 2004/0116399 A1 | 6/2004 | Zhu et al. | |
| 2004/0127523 A1 | 7/2004 | Bacopoulos et al. | |
| 2004/0204339 A1 | 10/2004 | DiMartino | |
| 2004/0214870 A1 | 10/2004 | Xin et al. | |
| 2005/0054850 A1 | 3/2005 | Wu et al. | |
| 2005/0119305 A1 | 6/2005 | Naka et al. | |
| 2005/0260277 A1 | 11/2005 | Giles | |
| 2006/0084691 A1* | 4/2006 | Piperdi | 514/394 |
| 2006/0194843 A1 | 8/2006 | Berdini et al. | |
| 2008/0139620 A1 | 6/2008 | Wyatt et al. | |
| 2008/0161251 A1 | 7/2008 | Curry et al. | |
| 2008/0161355 A1 | 7/2008 | Curry et al. | |
| 2008/0194562 A1 | 8/2008 | Wyatt et al. | |
| 2008/0200509 A1 | 8/2008 | Berdini et al. | |
| 2008/0269207 A1 | 10/2008 | Berdini et al. | |
| 2008/0306069 A1 | 12/2008 | Wyatt et al. | |
| 2009/0012124 A1 | 1/2009 | Wyatt et al. | |
| 2009/0036435 A1 | 2/2009 | Curry et al. | |
| 2010/0179145 A1 | 7/2010 | Gallagher et al. | |
| 2011/0002879 A1 | 1/2011 | Curry et al. | |
| 2011/0003799 A1 | 1/2011 | Berdini et al. | |
| 2011/0159111 A1 | 6/2011 | Curry et al. | |
| 2011/0274616 A1 | 11/2011 | Wyatt et al. | |

FOREIGN PATENT DOCUMENTS

| | | |
|---|---|---|
| EP | 0492125 A1 | 7/1992 |
| EP | 0538231 A1 | 4/1993 |
| EP | 0947500 A1 | 10/1999 |
| EP | 1020471 A1 | 7/2000 |
| EP | 1348707 A1 | 10/2003 |
| EP | 1642594 A1 | 4/2006 |
| EP | 1847531 A1 | 10/2007 |
| GB | 1354939 | 5/1974 |
| WO | 94/11026 A2 | 5/1994 |
| WO | 94/13643 A1 | 6/1994 |
| WO | 96/14843 | 5/1996 |
| WO | 97/19052 A1 | 5/1997 |
| WO | 97/19062 A1 | 5/1997 |
| WO | 97/36881 A1 | 10/1997 |
| WO | 97/36897 A1 | 10/1997 |
| WO | 9736585 A1 | 10/1997 |
| WO | 97/41824 A2 | 11/1997 |
| WO | 97/48672 A2 | 12/1997 |
| WO | 98/28269 A1 | 7/1998 |
| WO | 98/49166 A1 | 11/1998 |
| WO | 98/52941 A1 | 11/1998 |
| WO | 98/57937 A2 | 12/1998 |
| WO | 99/32454 A1 | 7/1999 |
| WO | 99/32477 A1 | 7/1999 |
| WO | 99/67235 A1 | 12/1999 |
| WO | 00/39108 A1 | 7/2000 |
| WO | 00/59902 A2 | 10/2000 |
| WO | 00/62778 A1 | 10/2000 |
| WO | 00/68191 A1 | 11/2000 |
| WO | 00/71516 A2 | 11/2000 |
| WO | 01/02369 A2 | 1/2001 |
| WO | 01/02385 A1 | 1/2001 |
| WO | 01/14331 A2 | 3/2001 |
| WO | 01/19788 A2 | 3/2001 |
| WO | 01/19798 A2 | 3/2001 |
| WO | 01/53274 A1 | 7/2001 |
| WO | 01/57022 A2 | 8/2001 |
| WO | 01/58869 A2 | 8/2001 |
| WO | 01/64642 A2 | 9/2001 |
| WO | 01/64643 A2 | 9/2001 |
| WO | 01/81316 A2 | 11/2001 |
| WO | 01/81345 A1 | 11/2001 |
| WO | 01/98290 A2 | 12/2001 |
| WO | 02/00651 A2 | 1/2002 |
| WO | 02/10146 A1 | 2/2002 |
| WO | 02/18346 A1 | 3/2002 |
| WO | 02/22601 A1 | 3/2002 |
| WO | 02/22603 A1 | 3/2002 |
| WO | 02/22605 A1 | 3/2002 |
| WO | 02/22608 A1 | 3/2002 |
| WO | 02/34721 A1 | 5/2002 |
| WO | 02/50065 A2 | 6/2002 |
| WO | 02/051810 A2 | 7/2002 |
| WO | 02/059111 A2 | 8/2002 |
| WO | 02/062804 A1 | 8/2002 |
| WO | 02/064586 A2 | 8/2002 |
| WO | 02/066470 A1 | 8/2002 |
| WO | 02/068406 A2 | 9/2002 |
| WO | 02/070483 A1 | 9/2002 |
| WO | 02/074312 A1 | 9/2002 |
| WO | 02/074774 A1 | 9/2002 |
| WO | 02/083624 A1 | 10/2002 |
| WO | 02/094183 A2 | 11/2002 |
| WO | 02/094791 A1 | 11/2002 |
| WO | 02/101007 A2 | 12/2002 |
| WO | 03/011287 A1 | 2/2003 |
| WO | 03/011854 A1 | 2/2003 |
| WO | 03/018536 A1 | 3/2003 |
| WO | 03/020217 A2 | 3/2003 |
| WO | 03/024448 A2 | 3/2003 |
| WO | 03/037899 A1 | 5/2003 |
| WO | 03/040147 A1 | 5/2003 |
| WO | 03/048081 A2 | 6/2003 |
| WO | 03/048158 A1 | 6/2003 |
| WO | 03/068767 A1 | 8/2003 |
| WO | 03/077918 A1 | 9/2003 |
| WO | 03/082872 A1 | 10/2003 |
| WO | 03/101953 A2 | 12/2003 |
| WO | 2004/000318 A2 | 12/2003 |
| WO | 2004/014864 A1 | 2/2004 |
| WO | 2004/039795 A2 | 5/2004 |
| WO | 2004/060306 A1 | 7/2004 |
| WO | 2004/062601 A2 | 7/2004 |
| WO | 2004/085385 A2 | 10/2004 |
| WO | 2004/099127 A1 | 11/2004 |
| WO | 2004/099148 A1 | 11/2004 |
| WO | 2004/099156 A1 | 11/2004 |
| WO | 2004/110381 A2 | 12/2004 |
| WO | 2005/000309 A2 | 1/2005 |
| WO | 2005/002552 A2 | 1/2005 |
| WO | 2005/012256 A1 | 2/2005 |
| WO | 2005/058881 A1 | 6/2005 |
| WO | 2005/082340 A2 | 9/2005 |
| WO | 2005/087724 A2 | 9/2005 |
| WO | 2006/014290 A2 | 2/2006 |
| WO | 2007/003962 A2 | 1/2007 |
| WO | 2007/129062 A1 | 11/2007 |
| WO | 2007/129066 A1 | 11/2007 |

| WO | 2008/001101 A2 | 1/2008 |
| WO | 2008/007113 A2 | 1/2008 |
| WO | 2008/007122 A2 | 1/2008 |
| WO | 2008/007123 A2 | 1/2008 |
| WO | 2008/009954 A1 | 1/2008 |
| WO | 2008/044041 A1 | 4/2008 |

OTHER PUBLICATIONS

The Merck Manual of Diagnosis and Therapy, Seventeenth Edition, published 1999 by Merck Research Laboratories, pp. 397, 398, 948, 949, 973-977, 989-995, 1916, and 1979-1981.*
Jain et al., "Polymorphism in Pharnacy" Indian Drugs (1986) vol. 23 No. 6, pp. 315-329.*
Braga et al., "Making Crystals from Crystals: a green route to crystal engineering and polymorphism" Chemical Communications (2005) pp. 3635-3645.*
Lieberman et al., Pharmaceutical Dosage Forms, vol. 2, Published 1980 by Marcel Dekker, Inc, pp. 462-472.*
Vippagunta et al., "Crystalline SOlids" Advanced Drug Delivery Reviews (2001) vol. 48 pp. 3-26.*
Silverman, "The Organic Chemistry of Drug Design and Drug Action" published 1992 by Academic Press, pp. 4-47.*
The Oxford Textbook of Oncology, published 1995 by Oxford University Press, edited by Peckham et al., pp. 447-453.*
STN Database Descriptions, 2006 chemical abstracts catalog, published 2006 by Chemical Abstracts Service, p. 52.*
Squires et al., "Biological characterization of AT7519, a small-molecule inhibitor of cyclin-dependent kinases, in human tumor cell lines" Mol Cancer Ther (2009) vol. 8 No. 2 pp. 324-332.*
Voskoglou-Nomikos, Theodora, et al., "Clinical Predictive value of the in Vitro Cell Line, Human Xenograft and Mouse Allograft Preclininical Cancer Models", Clinical Cancer Research, 2003, pp. 4227-4239.
Wyatt, Paul G., et al., "Identification of N-(4-Piperidinyl)-4-(2,6-dichlorobenzoylamino)-1H-pyrazole-3- carboxamide (AT7519), a Novel Cyclin Dependent Kinase Inhibitor Using Fragment-Based X-Ray Crystallography and Structure Based Drug Design", J. Med. Chem., 2008, vol. 51, pp. 4986-4999.
Squires, Matthew S., et al., "Biological characterization of AT7519, a small-molecule inhibitor of cyclin-dependent kinases, in human tumor cell lines", Mol. Cancer Ther., 2009, vol. 8(2), pp. 324-332.
Vippagunta, Sudha R., et al., "Crystalline solids", Advanced Drug Delivery Reviews, 2001, vol. 48, pp. 3-26.
Patani, George A., et al., "Bioisosterism: A Rational Approach in Drug Design", Chem. Rev. 1996, vol. 96, pp. 3147-3176.
Zips, Daniel, et al., "New Anticancer Agents: In Vitro and In Vivo Evaluation", In vivo, 2005, vol. 19, p. 1-7.
Kislyi, V. P., et al. "Hydrogenation on Granular Palladium-containing Catalysts: II. Hydrogenation of Nitroheterocyclic Compounds", Russian Journal of Organic Chemistry 2002, vol. 38, No. 2, pp. 269-271 (Translation of Zhurnal Organicheskoi Khimii (2002), 38(2), 290-293).
Jordan, V. Craig, "Tamoxifen: A Most Unlikely Pioneering Medicine", Nature Reviews: Drug Discovery, 2003, vol. 2, p. 205-213.
Dorwald, F. Zaragoza, "Side Reactions in Organic Synthesis: A Guide to Successful Synthesis Design", 2005, Wiley, Preface.
Wolff, Manfred E., Editor, "Burger's Medicinal Chemistry and Drug Discovery", Wiley, 1996, Fifth Edition, vol. 1, pp. 975-977.
Beers, Mark H., et al., Editors, "The Merck Manual of Diagnosis and Therapy", Seventeenth Edition, published 1999 by Merck Research Laboratories, pp. 397, 398, 948, 949, 973-979, 989-995, 1916, and 1979-1981.
Jain, N. K., et al., "Polymorphism in Pharmacy", Indian Drugs, 1986, vol. 23, No. 6, pp. 315-329.
Braga, Dario, et al., "Making crystals from crystals: a green route to crystal engineering and polymorphism", Chemical Communications, 2005, pp. 3635-3645.
Lieberman Herbert A., et al., Editors, "Pharmaceutical Dosage Forms", published 1980 by Marcel Dekker, Inc., vol. 2, pp. 462-472.
Silverman, Richard B. "The Organic Chemistry of Drug Design and Drug Action" published by Academic Press, 1992, pp. 4-47.

Peckham, Michael, et al., Editors, "The Oxford Textbook of Oncology", published by Oxford University Press, 1995, pp. 447-453.
"STN Database Descriptions", 2006 chemical abstracts catalog, published 2006 by Chemical Abstracts Service, p. 52.
"Miriam Websters Collegiate Dictionary", Tenth Edition (1998).
Ciddi, V., et al, "Elicitation of Taxus sp. cell cultures for production of taxol", Biotechnol. Lett. 1995, 17(12), 1343-6.
STN CAPLUS, Feb. 19, 1996, XP002125277.
Qu G., et al., "Gemcitabine and Targeted Therapy in Metastatic Breast Cancer" Seminars in Oncology, vol. 29, No. 3, Suppl 11, Jun. 2002, pp. 44-52.
Rakhit, A., et al., "Lack of Pharmacokinetic Interaction Between Erlotinib, Docetaxel and Capecitabine in Breast Cancer Patients" European Journal of Cancer. Supplement, Pergamon, Oxford, GB, vol. 1, No. 5, Sep. 2003, p. S115.
Widemann. B. C., et al., "Pediatric phase I trial and pharmacokinetic study of 'Tomudex' (Ralitrexed)" European Journal of Cancer, vol. 35, Sep. 1999, p. S287.
Lindauer, M., et al., "Interferon-Alpha Combined With Cytarabine in Chronic Myelogenous Leukemia—Clinical Benefits" Leukemia and Lymphoma, vol. 41, No. 5/6, 2001, pp. 523-533.
Verweij, J., et al., "Phase II studies of docetaxel in the treatment of various solid tumours" European Journal of Cancer, vol. 31, No. 1004, Oct. 1995, pp. S21-S24.
Xiong, Henry Q., et al., "Cetuximab, A Monoclonal Antibody targeting the epidermal growth factor receptor, in combination with Gemcitabine for advanced pancreatic cancer: A multicenter phase II Trial" Journal of Clinical Oncology, vol. 22, No. 13, Jul. 1, 2004, pp. 2610-2616.
Laissue, Jean A., et al., "Survival of Tumor-Bearing Mice Exposed to Heavy Water or Heavy Water Plus Methotrexate" Cancer Research, vol. 42, Mar. 1982, pp. 1125-1129.
Delord, J.P., et al., "A Phase IB Dose-Escalation Trial of Erlotinib, Capecitabine and Oxaliplatin in Metastatic Colorectal Cancer (MCRC) Patients" Program/Proceedings—American Society of Clinical Oncology, The Society, US, vol. 23, 2004, p. 266, ABSTRNO3585.
Mayor, S., "Pemetrexed improves survival in mesothelioma" The Lancet Oncology, vol. 3, No. 7, Jul. 2002, p. 386.
Lynch, Thomas J., et al., "Activating mutations in the epidermal growth factor receptor underlying responsiveness of non-small-cell lung cancer to gefitinib" New England Journal of Medicine, vol. 350, No. 21, May 20, 2004, pp. 2129-2139.
Stone, R., et al., "Skin Reactions to Imatinib Mesylate (STI-571) in Patients With Chronic Myeloid Leukemia (CML): Clinical Features and Histopathology" Blood, vol. 98, No. 11, Part 1, Nov. 16, 2001, p. 141A.
Takahashi, M., et al., "Metastatic Breast Cancer of HER2 Scored 2+ by IHC and HER2 Gene Amplification Assayed by Fish Has a Good Response to Single Agent Therapy With Trastuzumab: A Case Report" Breast Cancer, vol. 10, No. 2, Apr. 2003, pp. 170-174.
Yang, J. C., et al., "A Randomized Trial of Bevacizumab, an Anti-Vascular Endothelial Growth Factor Antibody, for Metastatic Renal Cancer" New England Journal of Medicine, vol. 349, No. 5, Jul. 31, 2003, pp. 427-434.
Cortesi, R., et al. "Formulation study for the antitumor drug camptothecin: liposomes, micellar solutions and a microemulsion" International Journal of Pharmaceutics, vol. 159, 1997, pp. 95-103.
Hardman, W. E., et al., "Efficacy of Treatment of Colon, Lung and Breast Human Carcinoma Xenograft With: Doxorubicin, Cisplatin, Irinotecan or Topotecan" Anticancer Research, vol. 19, 1999, pp. 2269-2274.
Kriegmair, et al., "Interferon-alpha and vinblastine versus medroxyprogesteronacetat in the treatment of metastatic renal cell carcinoma" European Journal of Cancer, Pergamon Press, Oxford, GB, vol. 31, No. 1003, Oct. 1995, p. S35.
Kantarjian, H. M., et al., "Experience With Vincristine, Doxorubicin, and Dexamethasone (VAD) Chemotherapy in Adults with Refractory Acute Lymphocytic Leukemia" Cancer, vol. 64, No. 1, Jul. 1, 1989, pp. 16-22.
Bayes, M., et al. "Gateways to Clinical Trials" Methods and Findings in Experimental and Clinical Pharmacology, vol. 26, No. 2, Mar. 2004, pp. 129-161.

Jekunen, A. P., et al., "Modulation of Cisplatin Cytotoxicity by Permeabilization of the Plasma Membrane by Digitonin in Vitro" Biochemical Pharmacology, vol. 45, No. 10, 1993, pp. 2079-2085.

Blesing, C. H., et al., "Fractionated TBI with idarubicin and cyclophosphamide prior to paediatric allogeneic bone marrow transplant, Early outcome and toxicity" Radiotherapy and Oncology, vol. 40, 1996, p. S36.

Giannios, J., et al., "Antisense chemoradioimmunotherapy consisting of anti-HER-2 scFv linked to high-energy radioisotopes, vinorelbine and 21-nucleotide double-stranded siRNA targeted to DNMT1 induce apoptosis in metastatic breast Ca characterised by hypermethylated oncosuppressor BRCA1 promoter CpG islands an" Radiotherapy and Oncology, vol. 73, Oct. 2004, p. S370, 869 poster.

Yalowich, J.C., et al., "Teniposide (VM-26)- and Etoposide (VP-16-213)-Induced Augmentation of Methotrexate Transport and Polyglutamylation in Ehrlich Ascites Tumor Cells in Vitro" Cancer Research, vol. 42, 1982, pp. 3648-3653.

Edan, C., et al., "Demonstration of the efficacy of mitoxantrone (MTX) using MRI in MS patients with a very active disease" Journal of Neuroimmunology, Elsevier Science Publishers BV, XX, vol. 56-63, 1995, p. 16.

Soldan, M., et al., "Metabolic Inactivation and Efflux of Daunorubicin as Complementary Mechanisms in Tumor Cell Resistance" Advances in Experimental Medicine and Biology, vol. 414, 1997, pp. 537-544.

Konecny, G., et al., "Adjuvant high dose epirubicin and cyclophosphamide with G-CSF support in patients with locally advanced breast cancer" European Journal of Cancer, vol. 31, No. 1003, Oct. 1995, p. S36.

Retzloff, et al., "GnRH antagonist compares favorably, but is not superior, to GnRH agonist microflare for poor responders in IVF." Fertility and Sterility, vol. 80, No. S3, Sep. 2003, pp. S189-S189.

Emanuel, et al., "Inhibition of human tumor xenograft growth by a novel, potent and selective CDK inhibitor" Proceedings of the American Association for Cancer Research Annual Meeting, vol. 44, Jul. 2003, pp. 135-136.

Mazucco R., et al., "American Association for Cancer Research—93rd Annual Meeting. Immunotherapy, chemoprevention and angiogenesis. Apr. 6-10, 2002, San Francisco, CA, USA." IDRUGS: The Investigational Drugs Journal, vol. 5, No. 5, pp. 408-411.

Saito R., et al., "Convection-Enhanced Delivery of Tumor Necrosis Factor-Related Apoptosis-Inducing Ligand With Systemic Administration of Temozolomide Prolongs Survival in an Intracranial Glioblastoma Xenograft Model" Cancer Research, vol. 64, No. 19, Oct. 1, 2004, pp. 6858-6862.

Wong, et al., "Phase II study of two-weekly temozolomide in patients with high-grade gliomas" Journal of Clinical Neuroscience, vol. 13, No. 1, Jan. 2006, pp. 18-22.

Misra, et al., "N-(cycloalkylamino)acyl-2-aminothiazole inhibitors of cyclin-dependent kinase 2. N-[5-[[[5-(1,1-dimethylethyl)-2-oxazolyl]m ethyl]thio]-2-thi azolyl]-4-piperidinecarboxamide (BMS-387032), a highly efficacious and selective antitumor agent" Journal of Medicinal Chemistry, vol. 47, No. 7, Mar. 25, 2004, pp. 1719-1728.

Handrick, R., et al., "Effects of celecoxib and irradiation treatment on prostate cancer cell lines" European Journal of Cancer. Supplement, vol. 2, No. 8, Sep. 2004, p. 196, poster 651.

Takigawa, N., et al. "Modulation of DNA damage induced apoptosis by the proteasome inhibitor bortezomib (PS) in human colorectal and non-small cell lung cancer cells is p53-dependent and NK-kB-independent" European Journal of Cancer. Supplement, vol. 2, No. 8, Sep. 2004, p. 63, poster 203.

Bischoff, et al., "Tamoxifen resistance: the RXR-selective ligand LGD1069 causes complete regression of tamoxifen-resistant mammary carcinoma" Proceedings of the Annual Meeting of the American Association for Cancer Research, New York, NY, US, vol. 40, Mar. 1999, p. 309.

Teixeira, M., et al., "Temozolamide (TMZ) in second-line treatment after pcv in glioblastoma multiforme (GBM). Experience from a single Portuguese institution" European Journal of Cancer, vol. 37, Apr. 2001, p. S344.

Campbell, D. A., et al., "Molecular Pathology in Oncology—The Astrazeneca Perspective" Pharmacogenomics, vol. 5, No. 8, 2004, pp. 1167-1173.

Grant, S., "Targeted Therapies in Cancer" Idrugs, Current Drugs Ltd, vol. 6, No. 10, 2003, pp. 946-948.

Kristeleit, R., et al., "Histone Modification Enzymes: Novel Targets for Cancer Drugs" Expert Opinion on Emerging Drugs, vol. 9, No. 1, 2004, pp. 135-154.

Byrn, et al., Solid State chemistry of drugs, 2d, Chapters 10 & 11. (1999).

Mashkovskii, M., Lekarstvennye sredstva (Medicinal Drugs) Moscow, Novaya Volna, (2001) p. 11 (in Russian).

Pokrovskij, Kratkaja medicinskaja enciklopedija, M oscow, Nauchno-prakiceskoe obedinenie "Medicinskaja enciklopedija", "Kron-press", 1994, vol. II, pp. 49-50, incompatibility of medicaments (in Russian).

* cited by examiner

SEQUENCE LISTING

```
<160> NUMBER OF SEQ ID NOS: 5

<210> SEQ ID NO 1
<211> LENGTH: 5
<212> TYPE: PRT
<213> ORGANISM: artificial
<220> FEATURE:
<223> OTHER INFORMATION: consensus peptide substrate sequence recognised
      by GSK3
<220> FEATURE:
<221> NAME/KEY: MISC_FEATURE
<222> LOCATION: (2)..(4)
<223> OTHER INFORMATION: X is any amino acid
<220> FEATURE:
<221> NAME/KEY: MOD_RES
<222> LOCATION: (5)..(5)
<223> OTHER INFORMATION: PHOSPHORYLATION

<400> SEQUENCE: 1

Ser Xaa Xaa Xaa Ser
1               5

<210> SEQ ID NO 2
<211> LENGTH: 5
<212> TYPE: PRT
<213> ORGANISM: artificial
<220> FEATURE:
<223> OTHER INFORMATION: consensus peptide substrate sequence recognised
      by GSK3
<220> FEATURE:
<221> NAME/KEY: MISC_FEATURE
<222> LOCATION: (2)..(4)
<223> OTHER INFORMATION: X is any amino acid
<220> FEATURE:
<221> NAME/KEY: MOD_RES
<222> LOCATION: (5)..(5)
<223> OTHER INFORMATION: PHOSPHORYLATION
```

```
<400> SEQUENCE: 2

Ser Xaa Xaa Xaa Thr
1               5

<210> SEQ ID NO 3
<211> LENGTH: 5
<212> TYPE: PRT
<213> ORGANISM: artificial
<220> FEATURE:
<223> OTHER INFORMATION: consensus peptide substrate sequence recognised
      by GSK3
<220> FEATURE:
<221> NAME/KEY: MISC_FEATURE
<222> LOCATION: (2)..(4)
<223> OTHER INFORMATION: X is any amino acid
<220> FEATURE:
<221> NAME/KEY: MOD_RES
<222> LOCATION: (5)..(5)
<223> OTHER INFORMATION: PHOSPHORYLATION

<400> SEQUENCE: 3

Thr Xaa Xaa Xaa Ser
1               5

<210> SEQ ID NO 4
<211> LENGTH: 5
<212> TYPE: PRT
<213> ORGANISM: artificial
<220> FEATURE:
<223> OTHER INFORMATION: consensus peptide substrate sequence recognised
      by GSK3
<220> FEATURE:
<221> NAME/KEY: MISC_FEATURE
<222> LOCATION: (2)..(4)
<223> OTHER INFORMATION: X is any amino acid
<220> FEATURE:
<221> NAME/KEY: MOD_RES
<222> LOCATION: (5)..(5)
<223> OTHER INFORMATION: PHOSPHORYLATION

<400> SEQUENCE: 4

Thr Xaa Xaa Xaa Thr
1               5

<210> SEQ ID NO 5
<211> LENGTH: 26
<212> TYPE: PRT
<213> ORGANISM: artificial
<220> FEATURE:
<223> OTHER INFORMATION: phospho GS2 peptide
<220> FEATURE:
<221> NAME/KEY: MOD_RES
<222> LOCATION: (21)..(21)
<223> OTHER INFORMATION: PHOSPHORYLATION

<400> SEQUENCE: 5

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25
```

COMBINATIONS OF PYRAZOLE KINASE INHIBITORS

CROSS REFERENCE TO RELATED APPLICATIONS

This application is a continuation-in-part of U.S. application Ser. Nos. 11/814,456, 11/814,461, 11/814,455, and 12/373,713, the entire contents of which are incorporated herein by reference.

U.S. application Ser. No. 11/814,456 (which published on Jul. 3, 2008 as US 2008-0161251 A1), was filed Jul. 20, 2007 as a national phase filing under 35 USC §371 of PCT International Application PCT/GB2006/000204, filed Jan. 20, 2006 and published under PCT Article 21(2) in English as WO 2006/077424 on Jul. 27, 2006. PCT/GB2006/000204 claimed priority from U.S. provisional applications 60/645,987; 60/645,986; 60/646,113; 60/645,976; and 60/645,975; all filed Jan. 21, 2005. The entire contents of each of the prior applications are incorporated herein by reference.

U.S. application Ser. No. 11/814,461 (which published on Feb. 5, 2009 as US 2009-0036435 A1) was filed Jul. 20, 2007 as a national phase filing under 35 USC §371 of PCT International Application PCT/GB2006/000210, filed Jan. 20, 2006, and published under PCT Article 21(2) in English as WO 2006/077428 on Jul. 27, 2006. PCT/GB2006/000210 claimed priority from U.S. provisional applications 60/645,988; 60/645,974; 60/646,216; 60/646,001; and 60/646,003; all filed Jan. 21, 2005. The entire contents of each of the prior applications are incorporated herein by reference.

U.S. application Ser. No. 11/814,455 (which published on Jul. 3, 2008 as US 2008-0161355 A1) was filed Jul. 20, 2007 as a national phase filing under 35 USC §371 of PCT International Application PCT/GB2006/000206, filed Jan. 20, 2006, and published under PCT Article 21(2) in English as WO 2006/077425 on Jul. 27, 2006. PCT/GB2006/000206 claimed priority from U.S. provisional application 60/645,963, filed Jan. 21, 2005. The entire contents of each of the prior applications are incorporated herein by reference.

U.S. application Ser. No. 12/373,713 (which published on Oct. 22, 2009 as US 2009-0263398 A1) was filed Jan. 13, 2009 as a national phase filing under 35 U.S.C. §371 of PCT International Application PCT/GB2007/002640, filed Jul. 13, 2007, and published under PCT Article 21(2) in English as WO 2008/007113 on Jan. 17, 2008. PCT/GB2007/002640 claimed priority from U.S. provisional patent application No. 60/831,043 filed on Jul. 14, 2006. The entire contents of each of the prior applications are incorporated herein by reference.

BACKGROUND OF THE INVENTION

The compounds of Formula (I) and subgroups thereof and the compound 4-(2,6-dichloro-benzoylamino)-1H-pyrazole-3-carboxylic acid piperidin-4-ylamide and the hydrochloric acid addition salt thereof are disclosed in our earlier International patent application number PCT/GB2004/003179 (Publication No. WO 2005/012256) as being inhibitors of Cyclin Dependent Kinases (CDK kinases) and Glycogen Synthase Kinase-3 (GSK3).

The methanesulphonic acid and acetic acid addition salts of compound 4-(2,6-dichloro-benzoylamino)-1H-pyrazole-3-carboxylic acid piperidin-4-ylamide and crystals thereof and method of making them are disclosed in our earlier applications U.S. Ser. No. 60/645,973 and GB 0501475.8.

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

Cyclin Dependent Kinases

The process of eukaryotic cell division may be broadly divided into a series of sequential phases termed G1, S, G2 and M. Correct progression through the various phases of the cell cycle has been shown to be critically dependent upon the spatial and temporal regulation of a family of proteins known as cyclin dependent kinases (cdks) and a diverse set of their cognate protein partners termed cyclins. Cdks are cdc2 (also known as cdk1) homologous serine-threonine kinase proteins that are able to utilise ATP as a substrate in the phosphorylation of diverse polypeptides in a sequence dependent context. Cyclins are a family of proteins characterised by a homology region, containing approximately 100 amino acids, termed the "cyclin box" which is used in binding to, and defining selectivity for, specific cdk partner proteins.

Modulation of the expression levels, degradation rates, and activation levels of various cdks and cyclins throughout the cell cycle leads to the cyclical formation of a series of cdk/cyclin complexes, in which the cdks are enzymatically active. The formation of these complexes controls passage through discrete cell cycle checkpoints and thereby enables the process of cell division to continue. Failure to satisfy the prerequisite biochemical criteria at a given cell cycle checkpoint, i.e. failure to form a required cdk/cyclin complex, can lead to cell cycle arrest and/or cellular apoptosis. Aberrant cellular proliferation, as manifested in cancer, can often be attributed to loss of correct cell cycle control. Inhibition of cdk enzymatic activity therefore provides a means by which abnormally dividing cells can have their division arrested and/or be killed. The diversity of cdks, and cdk complexes, and their critical roles in mediating the cell cycle, provides a broad spectrum of potential therapeutic targets selected on the basis of a defined biochemical rationale.

Progression from the G1 phase to the S phase of the cell cycle is primarily regulated by cdk2, cdk3, cdk4 and cdk6 via association with members of the D and E type cyclins. The D-type cyclins appear instrumental in enabling passage beyond the G1 restriction point, where as the cdk2/cyclin E complex is key to the transition from the G1 to S phase. Subsequent progression through S phase and entry into G2 is thought to require the cdk2/cyclin A complex. Both mitosis, and the G2 to M phase transition which triggers it, are regulated by complexes of cdk1 and the A and B type cyclins.

During G1 phase Retinoblastoma protein (Rb), and related pocket proteins such as p130, are substrates for cdk(2, 4, & 6)/cyclin complexes. Progression through G1 is in part facilitated by hyperphosphorylation, and thus inactivation, of Rb and p130 by the cdk(4/6)/cyclin-D complexes. Hyperphosphorylation of Rb and p130 causes the release of transcription factors, such as E2F, and thus the expression of genes necessary for progression through G1 and for entry into S-phase, such as the gene for cyclin E. Expression of cyclin E facilitates formation of the cdk2/cyclin E complex which amplifies, or maintains, E2F levels via further phosphorylation of Rb. The cdk2/cyclin E complex also phosphorylates other proteins necessary for DNA replication, such as NPAT, which has been implicated in histone biosynthesis. G1 progression and the G1/S transition are also regulated via the mitogen stimulated Myc pathway, which feeds into the cdk2/cyclin E pathway. Cdk2 is also connected to the p53 mediated DNA damage response pathway via p53 regulation of p21 levels. p21 is a protein inhibitor of cdk2/cyclin E and is thus capable of blocking, or delaying, the G1/S transition. The cdk2/cyclin E complex may thus represent a point at which biochemical stimuli from the Rb, Myc and p53 pathways are to some degree integrated. Cdk2 and/or the cdk2/cyclin E complex therefore represent good targets for therapeutics designed at arresting, or recovering control of, the cell cycle in aberrantly dividing cells.

The exact role of cdk3 in the cell cycle is not clear. As yet no cognate cyclin partner has been identified, but a dominant negative form of cdk3 delayed cells in G1, thereby suggesting that cdk3 has a role in regulating the G1/S transition.

Although most cdks have been implicated in regulation of the cell cycle there is evidence that certain members of the cdk family are involved in other biochemical processes. This is exemplified by cdk5 which is necessary for correct neuronal development and which has also been implicated in the phosphorylation of several neuronal proteins such as Tau, NUDE-1, synapsin1, DARPP32 and the Munc18/Syntaxin1A complex. Neuronal cdk5 is conventionally activated by binding to the p35/p39 proteins. Cdk5 activity can, however, be deregulated by the binding of p25, a truncated version of p35. Conversion of p35 to p25, and subsequent deregulation of cdk5 activity, can be induced by ischemia, excitotoxicity, and β-amyloid peptide. Consequently p25 has been implicated in the pathogenesis of neurodegenerative diseases, such as Alzheimer's, and is therefore of interest as a target for therapeutics directed against these diseases.

Cdk7 is a nuclear protein that has cdc2 CAK activity and binds to cyclin H. Cdk7 has been identified as component of the TFIIH transcriptional complex which has RNA polymerase II C-terminal domain (CTD) activity. This has been associated with the regulation of HIV-1 transcription via a Tat-mediated biochemical pathway. Cdk8 binds cyclin C and has been implicated in the phosphorylation of the CTD of RNA polymerase II. Similarly the cdk9/cyclin-T1 complex (P-TEFb complex) has been implicated in elongation control of RNA polymerase II. PTEF-b is also required for activation of transcription of the HIV-1 genome by the viral transactivator Tat through its interaction with cyclin T1. Cdk7, cdk8, cdk9 and the P-TEFb complex are therefore potential targets for anti-viral therapeutics.

At a molecular level mediation of cdk/cyclin complex activity requires a series of stimulatory and inhibitory phosphorylation, or dephosphorylation, events. Cdk phosphorylation is performed by a group of cdk activating kinases (CAKs) and/or kinases such as wee1, Myt1 and Mik1. Dephosphorylation is performed by phosphatases such as cdc25(a & c), pp2a, or KAP.

Cdk/cyclin complex activity may be further regulated by two families of endogenous cellular proteinaceous inhibitors: the Kip/Cip family, or the INK family. The INK proteins specifically bind cdk4 and cdk6. $p16^{ink4}$ (also known as MTS1) is a potential tumour suppressor gene that is mutated, or deleted, in a large number of primary cancers. The Kip/Cip family contains proteins such as $p21^{Cip1,\ Waf1}$, $p27^{Kip1}$ and $p57^{kip2}$. As discussed previously p21 is induced by p53 and is able to inactivate the cdk2/cyclin(E/A) and cdk4/cyclin(D1/D2/D3) complexes. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of cdks, and their associated proteins, in co-ordinating and driving the cell cycle in proliferating cells have been outlined above. Some of the biochemical pathways in which cdks play a key role have also been described. The development of monotherapies for the treatment of proliferative disorders, such as cancers, using therapeutics targeted generically at cdks, or at specific cdks, is therefore potentially highly desirable. Cdk inhibitors could conceivably also be used to treat other conditions such as viral infections, autoimmune diseases and neuro-degenerative diseases, amongst others. Cdk targeted therapeutics may also provide clinical benefits in the treatment of the previously described diseases when used in combination therapy with either existing, or new, therapeutic agents. Cdk targeted anticancer therapies could potentially have advantages over many current antitumour agents as they would not directly interact with DNA and should therefore reduce the risk of secondary tumour development.

Glycogen Synthase Kinase

Glycogen Synthase Kinase-3 (GSK3) is a serine-threonine kinase that occurs as two ubiquitously expressed isoforms in humans (GSK3α & beta GSK3β). GSK3 has been implicated as having roles in embryonic development, protein synthesis, cell proliferation, cell differentiation, microtubule dynamics, cell motility and cellular apoptosis. As such GSK3 has been implicated in the progression of disease states such as diabetes, cancer, Alzheimer's disease, stroke, epilepsy, motor neuron disease and/or head trauma. Phylogenetically GSK3 is most closely related to the cyclin dependent kinases (CDKs).

The consensus peptide substrate sequence recognised by GSK3 is (Ser/Thr)-X-X-X-(pSer/pThr), where X is any amino acid (at positions (n+1), (n+2), (n+3)) and pSer and pThr are phospho-serine and phospho-threonine respectively (n+4). GSK3 phosphorylates the first serine, or threonine, at position (n). Phospho-serine, or phospho-threonine, at the (n+4) position appears necessary for priming GSK3 to give maximal substrate turnover. Phosphorylation of GSK3α at Ser21, or GSK3β at Ser9, leads to inhibition of GSK3. Mutagenesis and peptide competition studies have led to the model that the phosphorylated N-terminus of GSK3 is able to compete with phospho-peptide substrate (S/TXXXpS/pT) via an autoinhibitory mechanism. There are also data suggesting that GSK3α and GSKβ may be subtly regulated by phosphorylation of tyrosines 279 and 216 respectively. Mutation of these residues to a Phe caused a reduction in in vivo kinase activity. The X-ray crystallographic structure of GSK3β has helped to shed light on all aspects of GSK3 activation and regulation.

GSK3 forms part of the mammalian insulin response pathway and is able to phosphorylate, and thereby inactivate, glycogen synthase. Upregulation of glycogen synthase activity, and thereby glycogen synthesis, through inhibition of GSK3, has thus been considered a potential means of combating type II, or non-insulin-dependent diabetes mellitus (NIDDM): a condition in which body tissues become resistant to insulin stimulation. The cellular insulin response in liver, adipose, or muscle tissues is triggered by insulin binding to an extracellular insulin receptor. This causes the phosphorylation, and subsequent recruitment to the plasma membrane, of the insulin receptor substrate (IRS) proteins. Further phosphorylation of the IRS proteins initiates recruitment of phosphoinositide-3 kinase (PI3K) to the plasma membrane where it is able to liberate the second messenger phosphatidylinosityl 3,4,5-trisphosphate (PIP3). This facilitates co-localisation of 3-phosphoinositide-dependent protein kinase 1 (PDK1) and protein kinase B (PKB or Akt) to the membrane, where PDK1 activates PKB. PKB is able to phosphorylate, and thereby inhibit, GSK3α and/or GSKβ through phosphorylation of Ser9, or ser21, respectively. The inhibition of GSK3 then triggers upregulation of glycogen synthase activity. Therapeutic agents able to inhibit GSK3 may thus be able to induce cellular responses akin to those seen on insulin stimulation. A further in vivo substrate of GSK3 is the eukaryotic protein synthesis initiation factor 2B (eIF2B). eIF2B is inactivated via phosphorylation and is thus able to suppress protein biosynthesis. Inhibition of GSK3, e.g. by inactivation of the "mammalian target of rapamycin" protein (mTOR), can thus upregulate protein biosynthesis. Finally there is some evidence for regulation of GSK3 activity via the mitogen activated protein kinase (MAPK) pathway through phosphorylation of GSK3 by kinases such as mitogen activated protein kinase activated protein kinase 1 (MAPKAP-K1 or RSK). These data suggest that GSK3 activity may be modulated by mitogenic, insulin and/or amino acid stimulii.

It has also been shown that GSK3β is a key component in the vertebrate Wnt signalling pathway. This biochemical pathway has been shown to be critical for normal embryonic development and regulates cell proliferation in normal tissues. GSK3 becomes inhibited in response to Wnt stimulii. This can lead to the de-phosphorylation of GSK3 substrates such as Axin, the adenomatous polyposis coli (APC) gene product and β-catenin. Aberrant regulation of the Wnt pathway has been associated with many cancers. Mutations in APC, and/or β-catenin, are common in colorectal cancer and other tumours. β-catenin has also been shown to be of importance in cell adhesion. Thus GSK3 may also modulate cellular adhesion processes to some degree. Apart from the biochemical pathways already described there are also data implicating GSK3 in the regulation of cell division via phosphorylation of cyclin-D1, in the phosphorylation of transcription factors such as c-Jun, CCAAT/enhancer binding protein α (C/EBPα), c-Myc and/or other substrates such as Nuclear Factor of Activated T-cells (NFATc), Heat Shock Factor-1 (HSF-1) and the c-AMP response element binding protein (CREB). GSK3 also appears to play a role, albeit tissue specific, in regulating cellular apoptosis. The role of GSK3 in modulating cellular apoptosis, via a pro-apoptotic mechanism, may be of particular relevance to medical conditions in which neuronal apoptosis can occur. Examples of these are head trauma, stroke, epilepsy, Alzheimer's and motor neuron diseases, progressive supranuclear palsy, corticobasal degeneration, and Pick's disease. In vitro it has been shown that GSK3 is able to hyper-phosphorylate the microtubule associated protein Tau. Hyperphosphorylation of Tau disrupts its normal binding to microtubules and may also lead to the formation of intra-cellular Tau filaments. It is believed that the progressive accumulation of these filaments leads to eventual neuronal dysfunction and degeneration. Inhibition of Tau phosphorylation, through inhibition of GSK3, may thus provide a means of limiting and/or preventing neurodegenerative effects.

Diffuse Large B-Cell Lymphomas (DLBCL)

Cell cycle progression is regulated by the combined action of cyclins, cyclin-dependent kinases (CDKs), and CDK-inhibitors (CDKi), which are negative cell cycle regulators. p27KIP1 is a CDKi key in cell cycle regulation, whose degradation is required for G1/S transition. In spite of the absence of p27KIP1 expression in proliferating lymphocytes, some aggressive B-cell lymphomas have been reported to show an anomalous p27KIP1 staining. An abnormally high expression of p27KIP1 was found in lymphomas of this type. Analysis of the clinical relevance of these findings showed that a high level of p27KIP1 expression in this type of tumour is an adverse prognostic marker, in both univariate and multivariate analysis. These results show that there is abnormal p27KIP1 expression in Diffuse Large B-cell Lymphomas (DLBCL), with adverse clinical significance, suggesting that this anomalous p27KIP1 protein may be rendered non-functional through interaction with other cell cycle regulator proteins. (Br. J. Cancer. 1999 July; 80(9):1427-34. p27KIP1 is abnormally expressed in Diffuse Large B-cell Lymphomas and is associated with an adverse clinical outcome. Saez A, Sanchez E, Sanchez-Beato M, Cruz M A, Chacon I, Munoz E, Camacho F I, Martinez-Montero J C, Mollejo M, Garcia J F, Piris M A. Department of Pathology, Virgen de la Salud Hospital, Toledo, Spain.)

Chronic Lymphocytic Leukemia

B-Cell chronic lymphocytic leukaemia (CLL) is the most common leukaemia in the Western hemisphere, with approximately 10,000 new cases diagnosed each year (Parker S L, Tong T, Bolden S, Wingo P A: Cancer statistics, 1997. Ca. Cancer. J. Clin. 47:5, (1997)). Relative to other forms of leukaemia, the overall prognosis of CLL is good, with even the most advanced stage patients having a median survival of 3 years.

The addition of fludarabine as initial therapy for symptomatic CLL patients has led to a higher rate of complete responses (27% v 3%) and duration of progression-free survival (33 v 17 months) as compared with previously used alkylator-based therapies. Although attaining a complete clinical response after therapy is the initial step toward improving survival in CLL, the majority of patients either do not attain complete remission or fail to respond to fludarabine. Furthermore, all patients with CLL treated with fludarabine eventually relapse, making its role as a single agent purely palliative (Rai K R, Peterson B, Elias L, Shepherd L, Hines J, Nelson D, Cheson B, Kolitz J, Schiffer C A: A randomized comparison of fludarabine and chlorambucil for patients with previously untreated chronic lymphocytic leukemia. A CALGB SWOG, CTG/NCI-C and ECOG Inter-Group Study. Blood 88:141a, 1996 (abstr 552, suppl 1). Therefore, identifying new agents with novel mechanisms of action that complement fludarabine's cytotoxicity and abrogate the resistance induced by intrinsic CLL drug-resistance factors will be necessary if further advances in the therapy of this disease are to be realized.

The most extensively studied, uniformly predictive factor for poor response to therapy and inferior survival in CLL patients is aberrant p53 function, as characterized by point mutations or chromosome 17p13 deletions. Indeed, virtually no responses to either alkylator or purine analog therapy have been documented in multiple single institution case series for those CLL patients with abnormal p53 function. Introduction of a therapeutic agent that has the ability to overcome the drug resistance associated with p53 mutation in CLL would potentially be a major advance for the treatment of the disease.

Flavopiridol and CYC 202, inhibitors of cyclin-dependent kinases induce in vitro apoptosis of malignant cells from B-cell chronic lymphocytic leukemia (B-CLL).

Flavopiridol exposure results in the stimulation of caspase 3 activity and in caspase-dependent cleavage of p27(kip1), a negative regulator of the cell cycle, which is overexpressed in B-CLL (Blood. 1998 Nov. 15; 92(10):3804-16 Flavopiridol induces apoptosis in chronic lymphocytic leukemia cells via activation of caspase-3 without evidence of bcl-2 modulation or dependence on functional p53. Byrd J C, Shinn C, Waselenko J K, Fuchs E J, Lehman T A, Nguyen P L, Flinn I W, Diehl L F, Sausville E, Greyer M R).

Cytotoxic Compounds and Signalling Inhibitors

A wide variety of cytotoxic compounds and signalling inhibitors find application in the combinations of the invention, as described in detail below.

It is an object of the invention to provide therapeutic combinations of pyrazole compounds that inhibit or modulate (in particular inhibit) the activity of cyclin dependent kinases (CDK) and/or glycogen synthase kinase (e.g. GSK-3) with a cytotoxic compound or signalling inhibitor. Such combinations may have an advantageous efficacious effect against tumour cell growth, in comparison with the respective effects shown by the individual components of the combination.

Prior Art

WO 02/34721 from Du Pont discloses a class of indeno[1,2-c]pyrazol-4-ones as inhibitors of cyclin dependent kinases.

WO 01/81348 from Bristol Myers Squibb describes the use of 5-thio-, sulphinyl- and sulphonylpyrazolo[3,4-b]-pyridines as cyclin dependent kinase inhibitors.

WO 00/62778 also from Bristol Myers Squibb discloses a class of protein tyrosine kinase inhibitors.

WO 01/72745A1 from Cyclacel describes 2-substituted 4-heteroaryl-pyrimidines and their preparation, pharmaceutical compositions containing them and their use as inhibitors of cyclin-dependant kinases (CDKs) and hence their use in the treatment of proliferative disorders such as cancer, leukaemia, psoriasis and the like.

WO 99/21845 from Agouron describes 4-aminothiazole derivatives for inhibiting cyclin-dependent kinases (CDKs), such as CDK1, CDK2, CDK4, and CDK6. The invention is also directed to the therapeutic or prophylactic use of pharmaceutical compositions containing such compounds and to methods of treating malignancies and other disorders by administering effective amounts of such compounds.

WO 01/53274 from Agouron discloses as CDK kinase inhibitors a class of compounds which can comprise an amide-substituted benzene ring linked to an N-containing heterocyclic group.

WO 01/98290 (Pharmacia & Upjohn) discloses a class of 3-aminocarbonyl-2-carboxamido thiophene derivatives as protein kinase inhibitors.

WO 01/53268 and WO 01/02369 from Agouron disclose compounds that mediate or inhibit cell proliferation through the inhibition of protein kinases such as cyclin dependent kinase or tyrosine kinase. The Agouron compounds have an aryl or heteroaryl ring attached directly or though a CH=CH or CH=N group to the 3-position of an indazole ring.

WO 00/39108 and WO 02/00651 (both to Du Pont Pharmaceuticals) describe heterocyclic compounds that are inhibitors of trypsin-like serine protease enzymes, especially factor Xa and thrombin. The compounds are stated to be useful as anticoagulants or for the prevention of thromboembolic disorders.

US 2002/0091116 (Zhu et al.), WO 01/19798 and WO 01/64642 each disclose diverse groups of heterocyclic compounds as inhibitors of Factor Xa. Some 1-substituted pyrazole carboxamides are disclosed and exemplified.

U.S. Pat. No. 6,127,382, WO 01/70668, WO 00/68191, WO 97/48672, WO 97/19052 and WO 97/19062 (all to Allergan) each describe compounds having retinoid-like activity for use in the treatment of various hyperproliferative diseases including cancers.

WO 02/070510 (Bayer) describes a class of amino-dicarboxylic acid compounds for use in the treatment of cardiovascular diseases. Although pyrazoles are mentioned generically, there are no specific examples of pyrazoles in this document.

WO 97/03071 (Knoll A G) discloses a class of heterocyclyl-carboxamide derivatives for use in the treatment of central nervous system disorders. Pyrazoles are mentioned generally as examples of heterocyclic groups but no specific pyrazole compounds are disclosed or exemplified.

WO 97/40017 (Novo Nordisk) describes compounds that are modulators of protein tyrosine phosphatases.

WO 03/020217 (Univ. Connecticut) discloses a class of pyrazole 3-carboxamides as cannabinoid receptor modulators for treating neurological conditions. It is stated (page 15) that the compounds can be used in cancer chemotherapy but it is not made clear whether the compounds are active as anti-cancer agents or whether they are administered for other purposes.

WO 01/58869 (Bristol Myers Squibb) discloses cannabinoid receptor modulators that can be used inter alia to treat a variety of diseases. The main use envisaged is the treatment of respiratory diseases, although reference is made to the treatment of cancer.

WO 01/02385 (Aventis Crop Science) discloses 1-(quinoline-4-yl)-1H-pyrazole derivatives as fungicides. 1-Unsubstituted pyrazoles are disclosed as synthetic intermediates.

WO 2004/039795 (Fujisawa) discloses amides containing a 1-substituted pyrazole group as inhibitors of apolipoprotein B secretion. The compounds are stated to be useful in treating such conditions as hyperlipidemia.

WO 2004/000318 (Cellular Genomics) discloses various amino-substituted monocycles as kinase modulators. None of the exemplified compounds are pyrazoles.

SUMMARY OF THE INVENTION

The invention provides combinations of (i) a cytotoxic compound or signalling inhibitor; or (ii) an ancillary agent; or (iii) two or more further anti-cancer agents; with pyrazole compounds that have cyclin dependent kinase inhibiting or modulating activity, wherein the combinations have efficacy against abnormal cell growth. The invention further provides combinations as described above which are further combined with other classes of therapeutic agents or treatments that may be administered together (whether concurrently or at different time intervals) as described in more detail hereinafter.

Thus, for example, it is envisaged that the combinations of the invention will be useful in alleviating or reducing the incidence of cancer.

Accordingly, in one aspect, the invention provides a combination comprising or consisting essentially of (i) a cytotoxic compound or signalling inhibitor; or (ii) an ancillary agent; or (iii) two or more further anti-cancer agents; and a compound having the formula (0):

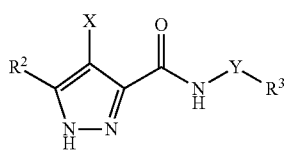

or salts or tautomers or N-oxides or solvates thereof; wherein

X is a group $R^1$-A-$NR^4$- or a 5- or 6-membered carbocyclic or heterocyclic ring;

A is a bond, $SO_2$, C=O, $NR^g$(C=O) or O(C=O) wherein $R^g$ is hydrogen or $C_{1-4}$ hydrocarbyl optionally substituted by hydroxy or $C_{1-4}$ alkoxy;

Y is a bond or an alkylene chain of 1, 2 or 3 carbon atoms in length;

$R^1$ is hydrogen; a carbocyclic or heterocyclic group having from 3 to 12 ring members; or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$;

$R^2$ is hydrogen; halogen; $C_{1-4}$ alkoxy (e.g. methoxy); or a $C_{1-4}$ hydrocarbyl group optionally substituted by halogen (e.g. fluorine), hydroxyl or $C_{1-4}$ alkoxy (e.g. methoxy);

$R^3$ is selected from hydrogen and carbocyclic and heterocyclic groups having from 3 to 12 ring members; and $R^4$ is hydrogen or a $C_{1-4}$ hydrocarbyl group optionally substituted by halogen (e.g. fluorine), hydroxyl or $C_{1-4}$ alkoxy (e.g. methoxy).

In one embodiment, the invention provides a combination of (i) a cytotoxic compound or signalling inhibitor; or (ii) an ancillary agent; or (iii) two or more further anti-cancer agents; and a compound having the formula ($I^0$):

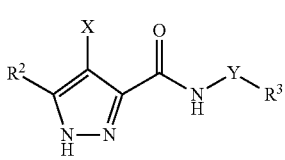

or salts or tautomers or N-oxides or solvates thereof; wherein

X is a group $R^1$-A-$NR^4$- or a 5- or 6-membered carbocyclic or heterocyclic ring;

A is a bond, C=O, $NR^g$(C=O) or O(C=O) wherein $R^g$ is hydrogen or $C_{1-4}$ hydrocarbyl optionally substituted by hydroxy or $C_{1-4}$ alkoxy;

Y is a bond or an alkylene chain of 1, 2 or 3 carbon atoms in length;

$R^1$ is hydrogen; a carbocyclic or heterocyclic group having from 3 to 12 ring members; or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$;

$R^2$ is hydrogen; halogen; $C_{1-4}$ alkoxy (e.g. methoxy); or a $C_{1-4}$ hydrocarbyl group optionally substituted by halogen (e.g. fluorine), hydroxyl or $C_{1-4}$ alkoxy (e.g. methoxy);

$R^3$ is selected from hydrogen and carbocyclic and heterocyclic groups having from 3 to 12 ring members; and $R^4$ is hydrogen or a $C_{1-4}$ hydrocarbyl group optionally substituted by halogen (e.g. fluorine), hydroxyl or $C_{1-4}$ alkoxy (e.g. methoxy).

In a further embodiment, the invention provides a combination of (i) a cytotoxic compound or signalling inhibitor; or (ii) an ancillary agent; or (iii) two or more further anti-cancer agents; and a compound having the formula (I):

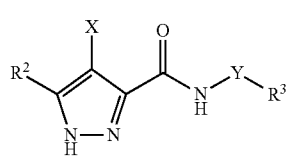

or salts or tautomers or N-oxides or solvates thereof; wherein

X is a group $R^1$-A-$NR^4$—;

A is a bond, C=O, $NR^g$(C=O) or O(C=O) wherein $R^g$ is hydrogen or $C_{1-4}$ hydrocarbyl optionally substituted by hydroxy or $C_{1-4}$ alkoxy;

Y is a bond or an alkylene chain of 1, 2 or 3 carbon atoms in length;

$R^1$ is hydrogen; a carbocyclic or heterocyclic group having from 3 to 12 ring members; or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$;

$R^2$ is hydrogen; halogen; $C_{1-4}$ alkoxy (e.g. methoxy); or a $C_{1-4}$ hydrocarbyl group optionally substituted by halogen (e.g. fluorine), hydroxyl or $C_{1-4}$ alkoxy (e.g. methoxy);

$R^3$ is selected from hydrogen and carbocyclic and heterocyclic groups having from 3 to 12 ring members; and $R^4$ is hydrogen or a $C_{1-4}$ hydrocarbyl group optionally substituted by halogen (e.g. fluorine), hydroxyl or $C_{1-4}$ alkoxy (e.g. methoxy).

Any one or more of the following optional provisos, in any combination, may apply to the compounds of formulae (0), ($I^0$), (I) and sub-groups thereof:

(a-i) When A is a bond and Y—$R^3$ is an alkyl, cycloalkyl, optionally substituted phenyl or optionally substituted phenylalkyl, then R¹ is other than a substituted or unsubstituted dihydronaphthalene, dihydrochroman, dihydrothiochroman, tetrahydroquinoline or tetrahydrobenzfuranyl group.

(a-ii) X and R³ are each other than a moiety containing a maleimide group wherein the maleimide group has nitrogen atoms attached to the 3- and 4-positions thereof.

(a-iii) R¹ is other than a moiety containing a purine nucleoside group.

(a-iv) X and R³ are each other than a moiety containing a cyclobutene-1,2-dione group wherein the cyclobutene-1,2-dione group has nitrogen atoms attached to the 3- and 4-positions thereof.

(a-v) R³ is other than a moiety containing a 4-monosubstituted or 4,5-disubstituted 2-pyridyl or 2-pyrimidinyl group or a 5-monosubstituted or 5,6-disubstituted 1,2,4-triazin-3-yl or 3-pyridazinyl group.

(a-vi) X and R³ are each other than a moiety containing a substituted or unsubstituted pyrazol-3-ylamine group linked to a substituted or unsubstituted pyridine, diazine or triazine group.

(a-vii) When A is C=O and Y—R³ is an alkyl, cycloalkyl, optionally substituted phenyl or optionally substituted phenylalkyl group, then R¹ is other than a substituted or unsubstituted tetrahydronaphthalene, tetrahydroquinolinyl, tetrahydrochromanyl or tetrahydrothiochromanyl group.

(a-viii) When R³ is H and A is a bond, R¹ is other than a moiety containing a bis-aryl, bis-heteroaryl or aryl heteroaryl group.

(a-ix) R³ is other than a moiety containing a 1,2,8,8a-tetrahydro-7-methyl-cyclopropa[c]pyrrolo[3,2,e]indole-4-(5H)-one group.

(a-x) When Y is a bond, R³ is hydrogen, A is CO and R¹ is a substituted phenyl group, each substituent on the phenyl group is other than a group CH₂—P(O)R$^x$R$^y$ where R$^x$ and R$^y$ are each selected from alkoxy and phenyl groups.

(a-xi) X is other than 4-(tert-butyloxycarbonylamino)-3-methylimidazol-2-ylcarbonylamino.

In another embodiment, the invention provides a combination of (i) a cytotoxic compound or signalling inhibitor; or (ii) an ancillary agent; or (iii) two or more further anti-cancer agents; and a compound having the formula (Ia):

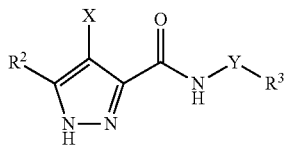
(Ia)

or salts or tautomers or N-oxides or solvates thereof;
wherein
X is a group R¹-A-NR⁴—;
A is a bond, C=O, NR$^g$(C=O) or O(C=O) wherein R$^g$ is hydrogen or C$_{1-4}$ hydrocarbyl optionally substituted by hydroxy or C$_{1-4}$ alkoxy;
Y is a bond or an alkylene chain of 1, 2 or 3 carbon atoms in length;
R¹ is a carbocyclic or heterocyclic group having from 3 to 12 ring members; or a C$_{1-8}$ hydrocarbyl group optionally substituted by one or more substituents selected from fluorine, hydroxy, C$_{1-4}$ hydrocarbyloxy, amino, mono- or di-C$_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, SO₂;
R² is hydrogen; halogen; C$_{1-4}$ alkoxy (e.g. methoxy); or a C$_{1-4}$ hydrocarbyl group optionally substituted by halogen (e.g. fluorine), hydroxyl or C$_{1-4}$ alkoxy (e.g. methoxy);
R³ is selected from hydrogen and carbocyclic and heterocyclic groups having from 3 to 12 ring members; and
R⁴ is hydrogen or a C$_{1-4}$ hydrocarbyl group optionally substituted by halogen (e.g. fluorine), hydroxyl or C$_{1-4}$ alkoxy (e.g. methoxy).

Any one or more of the following optional provisos, in any combination, may apply to the compounds of formula (Ia) and sub-groups thereof:

Provisos (a-i) to (a-xi) above.

(b-i) R³ is other than a bridged azabicyclo group.

(b-ii) When A is a bond, then R³ is other than a moiety containing an unsubstituted or substituted phenyl group having attached to an ortho position thereof, a substituted or unsubstituted carbamoyl or thiocarbamoyl group.

(b-iii) When A is a bond, then R³ is other than a moiety containing an isoquinoline or quinoxaline group each having attached thereto a substituted or unsubstituted piperidine or piperazine ring.

(b-iv) When A is a bond and R¹ is an alkyl group, then R³ is other than a moiety containing a thiatriazine group.

(b-v) When R¹ or R³ contain a moiety in which a heterocyclic ring having an S(=O)₂ ring member is fused to a carbocyclic ring, the said carbocyclic ring is other than a substituted or unsubstituted benzene ring (b-vi) When A is a bond, R¹ is other than an arylalkyl, heteroarylalkyl or piperidinylalkyl group each having attached thereto a substituent selected from cyano, and substituted or unsubstituted amino, aminoalkyl, amidine, guanidine, and carbamoyl groups.

(b-vii) When X is a group R¹-A-NR⁴—, A is a bond and R¹ is a non-aromatic group, then R³ is other than a six membered monocyclic aryl or heteroaryl group linked directly to a 5,6-fused bicyclic heteroaryl group.

In another embodiment, the invention provides a combination of (i) a cytotoxic compound or signalling inhibitor; or (ii) an ancillary agent; or (iii) two or more further anti-cancer agents; and a compound of the formula (Ib):

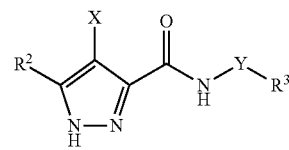
(Ib)

or salts or tautomers or N-oxides or solvates thereof;
wherein
X is a group R¹-A-NR⁴—;
A is a bond, C=O, NR$^g$(C=O) or O(C=O) wherein R$^g$ is hydrogen or C$_{1-4}$ hydrocarbyl optionally substituted by hydroxy or C$_{1-4}$ alkoxy;
Y is a bond or an alkylene chain of 1, 2 or 3 carbon atoms in length;
R¹ is a carbocyclic or heterocyclic group having from 3 to 12 ring members; or a C$_{1-8}$ hydrocarbyl group optionally substituted by one or more substituents selected from fluorine, hydroxy, C$_{1-4}$ hydrocarbyloxy, amino, mono- or di-C$_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$;

$R^2$ is hydrogen; halogen; $C_{1-4}$ alkoxy (e.g. methoxy); or a $C_{1-4}$ hydrocarbyl group optionally substituted by halogen (e.g. fluorine), hydroxyl or $C_{1-4}$ alkoxy (e.g. methoxy);

$R^3$ is selected from carbocyclic and heterocyclic groups having from 3 to 12 ring members; and $R^4$ is hydrogen or a $C_{1-4}$ hydrocarbyl group optionally substituted by halogen (e.g. fluorine), hydroxyl or $C_{1-4}$ alkoxy (e.g. methoxy).

Any one or more of the following optional provisos, in any combination, may apply to the compounds of formula (Ib) and sub-groups thereof:

Provisos (a-i) to (a-vii), (a-ix) and (a-xi).

Provisos (b-i) to (b-vii).

(c-i) When A is a bond, $R^1$ is other than a substituted arylalkyl, heteroarylalkyl or piperidinylalkyl group.

(c-ii) When X is an amino or alkylamino group and Y is a bond, $R^3$ is other than a disubstituted thiazolyl group wherein one of the substituents is selected from cyano and fluoroalkyl.

The reference in proviso (a-iii) to a purine nucleoside group refers to substituted and unsubstituted purine groups having attached thereto a monosaccharide group (e.g. a pentose or hexose) or a derivative of a monosaccharide group, for example a deoxy monosaccharide group or a substituted monosaccharide group.

The reference in proviso (b-i) to a bridged azabicyclo group refers to bicycloalkane bridged ring systems in which one of the carbon atoms of the bicycloalkane has been replaced by a nitrogen atom. In bridged ring systems, two rings share more than two atoms, see for example *Advanced Organic Chemistry*, by Jerry March, 4$^{th}$ Edition, Wiley Interscience, pages 131-133, 1992.

The provisos (a-i) to (a-x), (b-i) to (b-vii), (c-i) and (c-ii) in formulae (I), (Ia) and (Ib) above refer to the disclosures in the following prior art documents.

(a-i) US 2003/0166932, U.S. Pat. No. 6,127,382, U.S. Pat. No. 6,093,838

(a-ii) WO 03/031440

(a-iii) WO 03/014137

(a-iv) WO 02/083624

(a-v) WO 02/064586

(a-vi) WO 02/22608, WO 02/22605, WO 02/22603 & WO 02/22601

(a-vii) WO 97/48672, WO 97/19052

(a-viii) WO 00/06169

(a-ix) U.S. Pat. No. 5,502,068

(a-x) JP 07188269

(b-i) WO 03/040147

(b-ii) WO 01/70671

(b-iii) WO 01/32626

(b-iv) WO 98/08845

(b-v) WO 00/59902

(b-vi) U.S. Pat. No. 6,020,357, WO 99/32454 & WO 98/28269

(b-vii) WO 2004/012736

(c-i) U.S. Pat. No. 6,020,357, WO 99/32454 & WO 98/28269

(c-ii) US 2004/0082629

Any one or more of the foregoing optional provisos, (a-i) to (a-xi), (b-i) to (b-vii), (c-i) and (c-ii) in any combination, may also apply to the compounds of formulae (Ib), (II), (III), (IV), (IVa), (Va), (Vb), (VIa), (VIb), (VII) or (VIII) and sub-groups thereof or salts or tautomers or N-oxides or solvates thereof as defined herein.

In the following aspects and embodiments of the invention, references to "a combination according to the invention" refer to the combination of (i) a cytotoxic compound or signalling inhibitor; or (ii) an ancillary agent; or (iii) two or more further anti-cancer agents; and a compound of formula (0), (I$^o$), (I), (Ia), (Ib), (II), (III), (IV), (IVa), (Va), (Vb), (VIa), (VIb), (VII) or (VIII). In this section, as in all other sections of this application, unless the context indicates otherwise, references to a compound of formula (0), (I$^o$), (I), (Ia), (Ib), (II), (III), (IV), (IVa), (Va), (Vb), (VIa), (VIb), (VII) or (VIII) includes all other subgroups as defined herein. The term 'subgroups' includes all preferences, examples and particular compounds defined herein.

Moreover, a reference to a compound of formula (0), (I$^o$), (I), (Ia), (Ib), (II), (III), (IV), (IVa), (Va), (Vb), (VIa), (VIb), (VII) or (VIII) and sub-groups thereof includes ionic, salt, solvate, isomers, tautomers, N-oxides, ester, prodrugs, isotopes and protected forms thereof, as discussed below. Preferably, the salts or tautomers or isomers or N-oxides or solvates thereof. More preferably, the salts or tautomers or N-oxides or solvates thereof.

The invention also provides:

A combination according to the invention for use in alleviating or reducing the incidence of a disease or condition comprising or arising from abnormal cell growth in a mammal.

A combination of the invention for use in the prophylaxis or treatment of a disease state or condition mediated by a cyclin dependent kinase or glycogen synthase kinase-3.

A method for the prophylaxis or treatment of a disease state or condition mediated by a cyclin dependent kinase or glycogen synthase kinase-3, which method comprises administering to a subject in need thereof a combination of the invention.

A method for alleviating or reducing the incidence of a disease state or condition mediated by a cyclin dependent kinase or glycogen synthase kinase-3, which method comprises administering to a subject in need thereof a combination of the invention.

A method for alleviating or reducing the incidence of a disease or condition comprising or arising from abnormal cell growth in a mammal, which method comprises administering to the mammal a combination according to the invention in an amount effective in inhibiting abnormal cell growth.

A method for treating a disease or condition comprising or arising from abnormal cell growth in a mammal, which method comprises administering to the mammal a combination according to the invention in an amount effective in inhibiting abnormal cell growth.

A combination according to the invention for use in inhibiting tumour growth in a mammal.

A method of inhibiting tumour growth in a mammal, which method comprises administering to the mammal an effective tumour growth-inhibiting amount of a combination according to the invention.

A combination according to the invention for use in inhibiting the growth of tumour cells.

A method of inhibiting the growth of tumour cells, which method comprises contacting the tumour cells with administering to the mammal an effective tumour cell growth-inhibiting amount of a combination according to the invention.

A pharmaceutical composition comprising a combination according to the invention and a pharmaceutically acceptable carrier.

A combination according to the invention for use in medicine.

The use of a combination according to the invention, for the manufacture of a medicament for the prophylaxis or treatment of any one of the disease states or conditions disclosed herein.

A method for the treatment or prophylaxis of any one of the disease states or conditions disclosed herein, which method comprises administering to a patient (e.g. a patient in need thereof) a combination according to the invention.

A method for alleviating or reducing the incidence of a disease state or condition disclosed herein, which method comprises administering to a patient (e,g, a patient in need thereof) a combination according to the invention.

A method for the diagnosis and treatment of a cancer in a mammalian patient, which method comprises (a) screening a patient to determine whether a cancer from which the patient is or may be suffering is one which would be susceptible to treatment with a compound having activity against cyclin dependent kinases and (i) a cytotoxic compound or signalling inhibitor; or (ii) an ancillary agent; or (iii) two or more further anti-cancer agents; and (b) where it is indicated that the disease or condition from which the patient is thus susceptible, thereafter administering to the patient a combination according to the invention.

The use of a combination according to the invention for the manufacture of a medicament for the treatment or prophylaxis of a cancer in a patient who has been screened and has been determined as suffering from, or being at risk of suffering from, a cancer which would be susceptible to treatment with a combination of (i) a cytotoxic compound or signalling inhibitor; or (ii) an ancillary agent; or (iii) two or more further anti-cancer agents; and a compound having activity against cyclin dependent kinase.

A method for treating a cancer in a patient comprising administration of a combination according to the invention to said patient in an amount and in a schedule of administration that is therapeutically efficaceous in the treatment of said cancer.

A method for preventing, treating or managing cancer in a patient in need thereof, said method comprising administering to said patient a prophylactically or therapeutically effective amount of a combination according to the invention.

The use of a combination according to the invention for the manufacture of a medicament for use in the production of an anti-cancer effect in a warm-blooded animal such as a human.

A kit comprising a combination according to the invention.

A method for the treatment of a cancer in a warm-blooded animal such as a human, which comprises administering to said animal an effective amount of (i) a cytotoxic compound or signalling inhibitor; or (ii) an ancillary agent; or (iii) two or more further anti-cancer agents; sequentially e.g. before or after, or simultaneously with an effective amount of a compound of the formula (0), ($I^0$), (I), (Ia), (Ib), (II), (III), (IV), (IVa), (Va), (Vb), (VIa), (VIb), (VII) or (VIII) and sub-groups thereof as defined herein.

A pharmaceutical kit for anticancer therapy comprising (i) a cytotoxic compound or signalling inhibitor; or (ii) an ancillary agent; or (iii) two or more further anti-cancer agents; in dosage form and a compound of the formula (0), ($I^0$), (I), (Ia), (Ib), (II), (III), (IV), (IVa), (Va), (Vb), (VIa), (VIb), (VII) or (VIII) and sub-groups thereof as defined herein, also in dosage form (e.g. wherein the dosage forms are packaged together in common outer packaging).

A method of combination cancer therapy in a mammal comprising administering a therapeutically effective amount of (i) a cytotoxic compound or signalling inhibitor; or (ii) an ancillary agent; or (iii) two or more further anti-cancer agents; and a therapeutically effective amount of a compound of the formula (0), ($I^0$), (I), (Ia), (Ib), (II), (III), (IV), (IVa), (Va), (Vb), (VIa), (VIb), (VII) or (VIII) and sub-groups thereof as defined herein.

A compound of the formula (0), ($I^0$), (I), (Ia), (Ib), (II), (III), (IV), (IVa), (Va), (Vb), (VIa), (VIb), (VII) or (VIII) and sub-groups thereof as defined herein for use in combination therapy with (i) a cytotoxic compound or signalling inhibitor; or (ii) an ancillary agent; or (iii) two or more further anti-cancer agents; to alleviate or reduce the incidence of a disease or condition comprising or arising from abnormal cell growth in a mammal.

A compound of the formula (0), ($I^0$), (I), (Ia), (Ib), (II), (III), (IV), (IVa), (Va), (Vb), (VIa), (VIb), (VII) or (VIII) and sub-groups thereof as defined herein for use in combination therapy with (i) a cytotoxic compound or signalling inhibitor; or (ii) an ancillary agent; or (iii) two or more further anti-cancer agents; to inhibit tumour growth in a mammal.

A compound of the formula (0), ($I^0$), (I), (Ia), (Ib), (II), (III), (IV), (IVa), (Va), (Vb), (VIa), (VIb), (VII) or (VIII) and sub-groups thereof as defined herein for use in combination therapy with (i) a cytotoxic compound or signalling inhibitor; or (ii) an ancillary agent; or (iii) two or more further anti-cancer agents; to prevent, treat or manage cancer in a patient in need thereof.

A compound of the formula (0), ($I^0$), (I), (Ia), (Ib), (II), (III), (IV), (IVa), (Va), (Vb), (VIa), (VIb), (VII) or (VIII) and sub-groups thereof as defined herein for use in enhancing or potentiating the response rate in a patient suffering from a cancer where the patient is being treated with (i) a cytotoxic compound or signalling inhibitor; or (ii) an ancillary agent; or (iii) two or more further anti-cancer agents.

A method of enhancing or potentiating the response rate in a patient suffering from a cancer where the patient is being treated with (i) a cytotoxic compound or signalling inhibitor; or (ii) an ancillary agent; or (iii) two or more further anti-cancer agents; which method comprises administering to the patient, in combination with the (i) cytotoxic compound or signalling inhibitor; or (ii) an ancillary agent; or (iii) two or more further anti-cancer agents; a compound of the formula (0), ($I^0$), (I), (Ia), (Ib), (II), (III), (IV), (IVa), (Va), (Vb), (VIa), (VIb), (VII) or (VIII) and sub-groups thereof as defined herein.

The use of a combination according to the invention for the manufacture of a medicament for any of the therapeutic uses as defined herein.

In each of the foregoing uses, methods and other aspects of the invention, as well as any aspects and embodiments of the invention as set out below, references to compounds of the formulae (0), ($I^0$), (I), (Ia), (Ib), (II), (III), (IV), (IVa), (Va), (Vb), (VIa), (VIb), (VII) or (VIII) and sub-groups thereof as defined herein include within their scope the salts or solvates or tautomers or N-oxides of the compounds.

The invention also provides the further combinations, uses, methods, compounds and processes as set out in the claims below.

DETAILED DESCRIPTION OF THE INVENTION

General Preferences and Definitions

Figure 1:
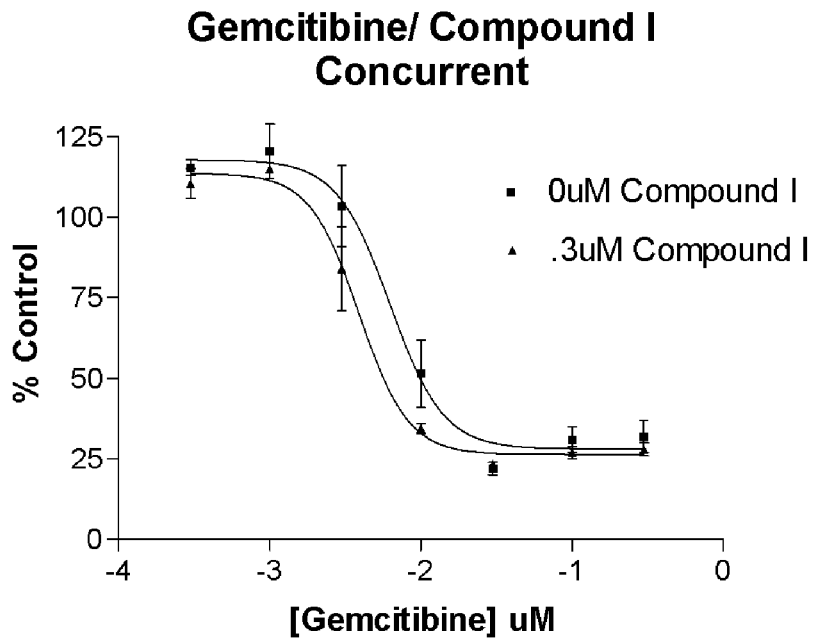
FIG. 1 depicts the percent control proliferation in A2780 cells for Gemcitibine in the presence and absence of 0.3 μM Compound I added concurrently, using the example of the $IC_{50}$ response curves to Gemcitibine.

As used herein, the term "modulation", as applied to the activity of cyclin dependent kinase (CDK) and glycogen synthase kinase (GSK, e.g. GSK-3), is intended to define a change in the level of biological activity of the kinase(s). Thus, modulation encompasses physiological changes which effect an increase or decrease in the relevant kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of cyclin dependent kinase (CDK) and/or glycogen synthase kinase-3 (GSK-3) activity, or at the level of enzyme (e.g. cyclin dependent kinase (CDK) and/or glycogen synthase kinase-3 (GSK-3)) activity (for example by allosteric mechanisms, competitive inhibition, active-site inactivation, perturbation of feedback inhibitory pathways etc.). Thus, modulation may imply elevated/suppressed expression or over- or under-expression of the cyclin dependent kinase (CDK) and/or glycogen synthase kinase-3 (GSK-3), including gene amplification (i.e. multiple gene copies) and/or increased or decreased expression by a transcriptional effect, as well as hyper- (or hypo-)activity and (de)activation of the cyclin dependent kinase (CDK) and/or glycogen synthase kinase-3 (GSK-3) (including (de)activation) by mutation(s). The terms "modulated" and "modulate" are to be interpreted accordingly.

As used herein, the term "mediated", as used e.g. in conjunction with the cyclin dependent kinases (CDK) and/or glycogen synthase kinase-3 (GSK-3) as described herein (and applied for example to various physiological processes, diseases, states, conditions, therapies, treatments or interventions) is intended to operate limitatively so that the various processes, diseases, states, conditions, treatments and interventions to which the term is applied are those in which cyclin dependent kinase (CDK) and/or glycogen synthase kinase-3 (GSK-3) plays a biological role. In cases where the term is applied to a disease, state or condition, the biological role played by cyclin dependent kinase (CDK) and/or glycogen synthase kinase-3 (GSK-3) may be direct or indirect and may be necessary and/or sufficient for the manifestation of the symptoms of the disease, state or condition (or its aetiology or progression). Thus, cyclin dependent kinase (CDK) and/or glycogen synthase kinase-3 (GSK-3) activity (and in particular aberrant levels of cyclin dependent kinase (CDK) and/or glycogen synthase kinase-3 (GSK-3) activity, e.g. cyclin dependent kinases (CDK) and/or glycogen synthase kinase-3 (GSK-3) over-expression) need not necessarily be the proximal cause of the disease, state or condition: rather, it is contemplated that the CDK- and/or GSK- (e.g. GSK-3-) mediated diseases, states or conditions include those having multifactorial aetiologies and complex progressions in which CDK and/or GSK-3 is only partially involved. In cases where the term is applied to treatment, prophylaxis or intervention (e.g. in the "CDK-mediated treatments" and "GSK-3-mediated prophylaxis" of the invention), the role played by CDK and/or GSK-3 may be direct or indirect and may be necessary and/or sufficient for the operation of the treatment, prophylaxis or outcome of the intervention.

The term "intervention" is a term of art used herein to define any agency which effects a physiological change at any level. Thus, the intervention may comprises the induction or repression of any physiological process, event, biochemical pathway or cellular/biochemical event. The interventions of the invention typically effect (or contribute to) the therapy, treatment or prophylaxis of a disease or condition.

The combinations of the invention are combinations of a cytotoxic compound or signalling inhibitor and a compound of the formulae (0), (I⁰), (I), (Ia), (Ib), (II), (III), (IV), (IVa), (Va), (Vb), (VIa), (VIb), (VII) or (VIII) and sub-groups thereof that produce a therapeutically efficacious effect.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect.

A "synergistic" effect in the present context refers to a therapeutic effect produced by the combination which is larger than the sum of the therapeutic effects of the components of the combination when presented individually.

An "additive" effect in the present context refers to a therapeutic effect produced by the combination which is larger than the therapeutic effect of any of the components of the combination when presented individually.

The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50%.

As used herein, the term "combination", as applied to two or more compounds, may define material in which the two or more compounds are associated. The terms "combined" and "combining" in this context are to be interpreted accordingly.

The association of the two or more compounds in a combination may be physical or non-physical. Examples of physically associated combined compounds include:

compositions (e.g. unitary formulations) comprising the two or more compounds in admixture (for example within the same unit dose);

compositions comprising material in which the two or more compounds are chemically/physicochemically linked (for example by crosslinking, molecular agglomeration or binding to a common vehicle moiety);

compositions comprising material in which the two or more compounds are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds are co-packaged or co-presented (e.g. as part of an array of unit doses);

Examples of non-physically associated combined compounds include:

material (e.g. a non-unitary formulation) comprising at least one of the two or more compounds together with instructions for the extemporaneous association of the at least one compound to form a physical association of the two or more compounds;

material (e.g. a non-unitary formulation) comprising at least one of the two or more compounds together with instructions for combination therapy with the two or more compounds;

material comprising at least one of the two or more compounds together with instructions for administration to a patient population in which the other(s) of the two or more compounds have been (or are being) administered;

material comprising at least one of the two or more compounds in an amount or in a form which is specifically adapted for use in combination with the other(s) of the two or more compounds.

As used herein, the term "combination therapy" is intended to define therapies which comprise the use of a combination of two or more compounds (as defined above). Thus, references to "combination therapy", "combinations" and the use of compounds "in combination" in this application may refer to compounds that are administered as part of the same overall treatment regimen. As such, the posology of each of the two or more compounds may differ: each may be administered at the same time or at different times. It will therefore be appreciated that the compounds of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds, the individual compounds may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds, the individual compounds may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The combinations of the invention may produce a therapeutically efficacious effect relative to the therapeutic effect of the individual compounds when administered separately.

The following general preferences and definitions shall apply to each of the moieties X, Y, $R^g$, $R^1$ to $R^4$ and any sub-definition, sub-group or embodiment thereof, unless the context indicates otherwise.

In this specification, references to formula (I) include formulae (0), ($I^0$), (Ia), (Ib), (II), (III), (IV), (IVa), (Va), (Vb), (VIa), (VIb), (VII) or (VIII) and sub-groups, examples or embodiments of formulae (0), ($I^0$), (Ia), (Ib), (II), (III), (IV), (IVa), (Va), (Vb), (VIa), (VIb), (VII) or (VIII) unless the context indicates otherwise.

Thus for example, references to inter alia therapeutic uses, pharmaceutical formulations and processes for making compounds, where they refer to formula (I), are also to be taken as referring to formulae (0), ($I^0$), (Ia), (Ib), (II), (III), (IV), (IVa), (Va), (Vb), (VIa), (VIb), (VII) or (VIII) and sub-groups, examples or embodiments of formulae (0), ($I^0$), (Ia), (Ib), (II), (III), (IV), (IVa), (Va), (Vb), (VIa), (VIb), (VII) or (VIII).

Similarly, where preferences, embodiments and examples are given for compounds of the formula (I), they are also applicable to formulae (0), ($I^0$), (Ia), (Ib), (II), (III), (IV), (IVa), (Va), (Vb), (VIa), (VIb), (VII) or (VIII) and sub-groups, examples or embodiments of formulae (0), ($I^0$), (Ia), (Ib), (II), (III), (IV), (IVa), (Va), (Vb), (VIa), (VIb), (VII) or (VIII) unless the context requires otherwise.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups $R^{10}$ as defined herein.

The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, CC or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl. A further example of a cycloalkenyl group is cyclohexenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
  a) a benzene ring fused to a 5- or 6-membered ring containing 1, 2 or 3 ring heteroatoms;
  b) a pyridine ring fused to a 5- or 6-membered ring containing 1, 2 or 3 ring heteroatoms;
  c) a pyrimidine ring fused to a 5- or 6-membered ring containing 1 or 2 ring heteroatoms;
  d) a pyrrole ring fused to a a 5- or 6-membered ring containing 1, 2 or 3 ring heteroatoms;
  e) a pyrazole ring fused to a 5- or 6-membered ring containing 1 or 2 ring heteroatoms;
  f) an imidazole ring fused to a 5- or 6-membered ring containing 1 or 2 ring heteroatoms;
  g) an oxazole ring fused to a 5- or 6-membered ring containing 1 or 2 ring heteroatoms;
  h) an isoxazole ring fused to a 5- or 6-membered ring containing 1 or 2 ring heteroatoms;
  i) a thiazole ring fused to a 5- or 6-membered ring containing 1 or 2 ring heteroatoms;
  j) an isothiazole ring fused to a 5- or 6-membered ring containing 1 or 2 ring heteroatoms;
  k) a thiophene ring fused to a 5- or 6-membered ring containing 1, 2 or 3 ring heteroatoms;

l) a furan ring fused to a 5- or 6-membered ring containing 1, 2 or 3 ring heteroatoms;
m) an oxazole ring fused to a 5- or 6-membered ring containing 1 or 2 ring heteroatoms;
n) an isoxazole ring fused to a 5- or 6-membered ring containing 1 or 2 ring heteroatoms;
o) a cyclohexyl ring fused to a 5- or 6-membered ring containing 1, 2 or 3 ring heteroatoms; and
p) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

One sub-group of heteroaryl groups comprises pyridyl, pyrrolyl, furanyl, thienyl, imidazolyl, oxazolyl, oxadiazolyl, oxatriazolyl, isoxazolyl, thiazolyl, isothiazolyl, pyrazolyl, pyrazinyl, pyridazinyl, pyrimidinyl, triazinyl, triazolyl, tetrazolyl, quinolinyl, isoquinolinyl, benzfuranyl, benzthienyl, chromanyl, thiochromanyl, benzimidazolyl, benzoxazolyl, benzisoxazole, benzthiazolyl and benzisothiazole, isobenzofuranyl, indolyl, isoindolyl, indolizinyl, indolinyl, isoindolinyl, purinyl (e.g., adenine, guanine), indazolyl, benzodioxolyl, chromenyl, isochromenyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups include unsubstituted or substituted (by one or more groups $R^{10}$) heterocyclic groups having from 3 to 12 ring members, typically 4 to 12 ring members, and more usually from 5 to 10 ring members. Such groups can be monocyclic or bicyclic, for example, and typically have from 1 to 5 heteroatom ring members (more usually 1,2,3 or 4 heteroatom ring members) typically selected from nitrogen, oxygen and sulphur.

When sulphur is present, it may, where the nature of the adjacent atoms and groups permits, exist as —S—, —S(O)— or —S(O)$_2$—.

The heterocyclic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ester moieties (e.g. as in butyrolactone), cyclic sulphones (e.g. as in sulpholane and sulpholene), cyclic sulphoxides, cyclic sulphonamides and combinations thereof (e.g. morpholine and thiomorpholine and its S-oxide and S,S-dioxide). Further examples of heterocyclic groups are those containing a cyclic urea moiety (e.g. as in imidazolidin-2-one), In one sub-set of heterocyclic groups, the heterocyclic groups contain cyclic ether moieties (e.g as in tetrahydrofuran and dioxane), cyclic thioether moieties (e.g. as in tetrahydrothiophene and dithiane), cyclic amine moieties (e.g. as in pyrrolidine), cyclic sulphones (e.g. as in sulpholane and sulpholene), cyclic sulphoxides, cyclic sulphonamides and combinations thereof (e.g. thiomorpholine).

Examples of monocyclic non-aromatic heterocyclic groups include 5-, 6- and 7-membered monocyclic heterocyclic groups. Particular examples include morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine.

One preferred sub-set of non-aromatic heterocyclic groups consists of saturated groups such as azetidine, pyrrolidine, piperidine, morpholine, thiomorpholine, thiomorpholine S,S-dioxide, piperazine, N-alkyl piperazines, and N-alkyl piperidines.

Another sub-set of non-aromatic heterocyclic groups consists of pyrrolidine, piperidine, morpholine, thiomorpholine, thiomorpholine S,S-dioxide, piperazine and N-alkyl piperazines such as N-methyl piperazine.

One particular sub-set of heterocyclic groups consists of pyrrolidine, piperidine, morpholine and N-alkyl piperazines (e.g. N-methyl piperazine), and optionally thiomorpholine.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Preferred non-aromatic carbocyclic groups are monocyclic rings and most preferably saturated monocyclic rings.

Typical examples are three, four, five and six membered saturated carbocyclic rings, e.g. optionally substituted cyclopentyl and cyclohexyl rings.

One sub-set of non-aromatic carboyclic groups includes unsubstituted or substituted (by one or more groups $R^{10}$) monocyclic groups and particularly saturated monocyclic groups, e.g. cycloalkyl groups. Examples of such cycloalkyl groups include cyclopropyl, cyclobutyl, cyclopentyl, cyclohexyl and cycloheptyl; more typically cyclopropyl, cyclobutyl, cyclopentyl and cyclohexyl, particularly cyclohexyl.

Further examples of non-aromatic cyclic groups include bridged ring systems such as bicycloalkanes and azabicycloalkanes although such bridged ring systems are generally less preferred. By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged ring systems include bicyclo[2.2.1]heptane, azabicyclo[2.2.1]heptane, bicyclo[2.2.2]octane, aza-bicyclo [2.2.2]octane, bicyclo[3.2.1]octane and aza-bicyclo[3.2.1] octane. A particular example of a bridged ring system is the 1-aza-bicyclo[2.2.2]octan-3-yl group.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I), such further substituent groups $R^{10}$ may include carbocyclic or heterocyclic groups, which are typically not themselves further substituted. In another sub-group of compounds of the formula (I), the said further substituents do not include carbocyclic or heterocyclic groups but are otherwise selected from the groups listed above in the definition of $R^{10}$.

The substituents $R^{10}$ may be selected such that they contain no more than 20 non-hydrogen atoms, for example, no more than 15 non-hydrogen atoms, e.g. no more than 12, or 11, or 10, or 9, or 8, or 7, or 6, or 5 non-hydrogen atoms.

Where the carbocyclic and heterocyclic groups have a pair of substituents on adjacent ring atoms, the two substituents may be linked so as to form a cyclic group. Thus, two adjacent groups $R^{10}$, together with the carbon atoms or heteroatoms to which they are attached may form a 5-membered heteroaryl ring or a 5- or 6-membered non-aromatic carbocyclic or heterocyclic ring, wherein the said heteroaryl and heterocyclic groups contain up to 3 heteroatom ring members selected from N, O and S. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group.

Examples of such linked substituent groups include:

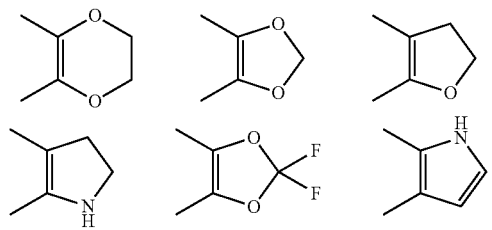

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone and consisting of carbon and hydrogen atoms, except where otherwise stated.

In certain cases, as defined herein, one or more of the carbon atoms making up the carbon backbone may be replaced by a specified atom or group of atoms.

Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, substituted by one or more substituents as defined herein. The examples and preferences expressed below apply to each of the hydrocarbyl substituent groups or hydrocarbyl-containing substituent groups referred to in the various definitions of substituents for compounds of the formula (I) unless the context indicates otherwise.

Preferred non-aromatic hydrocarbyl groups are saturated groups such as alkyl and cycloalkyl groups.

Generally by way of example, the hydrocarbyl groups can have up to eight carbon atoms, unless the context requires otherwise. Within the sub-set of hydrocarbyl groups having 1 to 8 carbon atoms, particular examples are $C_{1-6}$ hydrocarbyl groups, such as $C_{1-4}$ hydrocarbyl groups (e.g. $C_{1-3}$ hydrocarbyl groups or $C_{1-2}$ hydrocarbyl groups), specific examples being any individual value or combination of values selected from $C_1$, $C_2$, $C_3$, $C_4$, $C_5$, $C_6$, $C_7$ and $C_8$ hydrocarbyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 8 carbon atoms, particular examples being $C_{3-6}$ cycloalkyl groups.

Examples of alkenyl groups include, but are not limited to, ethenyl(vinyl), 1-propenyl, 2-propenyl(allyl), isopropenyl, butenyl, buta-1,4-dienyl, pentenyl, and hexenyl. Within the sub-set of alkenyl groups the alkenyl group will have 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-6}$ cycloalkenyl groups.

Examples of alkynyl groups include, but are not limited to, ethynyl and 2-propynyl(propargyl) groups. Within the sub-set of alkynyl groups having 2 to 8 carbon atoms, particular examples are $C_{2-6}$ alkynyl groups, such as $C_{2-4}$ alkynyl groups.

Examples of carbocyclic aryl groups include substituted and unsubstituted phenyl groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members, more usually 3, 4, 5 or 6 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members, more usually 5 to 6 ring members.

The term "aza-cycloalkyl" as used herein refers to a cycloalkyl group in which one of the carbon ring members has been replaced by a nitrogen atom. Thus examples of aza-cycloalkyl groups include piperidine and pyrrolidine. The term "oxa-cycloalkyl" as used herein refers to a cycloalkyl group in which one of the carbon ring members has been replaced by an oxygen atom. Thus examples of oxa-cycloalkyl groups include tetrahydrofuran and tetrahydropyran. In an analogous manner, the terms "diaza-cycloalkyl", "dioxa-cycloalkyl" and "aza-oxa-cycloalkyl" refer respectively to cycloalkyl groups in which two carbon ring members have been replaced by two nitrogen atoms, or by two oxygen atoms, or by one nitrogen atom and one oxygen atom.

The definition "$R^a$-$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), $NR^cC(O)$, OC(S), SC(S), $NR^cC(S)$, OC($NR^c$), SC($NR^c$), $NR^cC(NR^c)$, C(O)O, C(O)S, C(O)$NR^c$, C(S)O, C(S)S, C(S)$NR^c$, C($NR^c$)O, C($NR^c$)S, C($NR^c$)$NR^c$, OC(O) O, SC(O)O, $NR^cC(O)O$, OC(S)O, SC(S)O, $NR^cC(S)O$, OC($NR^c$)O, SC($NR^c$)O, $NR^cC(NR^c)O$, OC(O)S, SC(O)S, $NR^cC(O)S$, OC(S)S, SC(S)S, $NR^cC(S)S$, OC($NR^c$)S, SC(N-$R^c$)S, $NR^cC(NR^c)S$, OC(O)$NR^c$, SC(O)$NR^c$, $NR^cC(O) NR^c$, OC(S)$NR^c$, SC(S) $NR^c$, $NR^cC(S)NR^c$, OC($NR^c$)$NR^c$, SC(N-$R^c$)$NR^c$, $NR^cC(NR^cNR^c$, S, SO, $SO_2NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-8}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups substituted by a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-8}$ hydrocarbyl group, examples of hydrocarbyl groups $R^a$-$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl and trifluoromethyl), or hydroxy (e.g. hydroxymethyl and hydroxyethyl), $C_{1-8}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl and pyridylmethyl groups.

When $R^a$ is $SO_2NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $SO_2NR^c$ include aminosulphonyl, $C_{1-4}$ alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$-$R^b$ where $R^a$ is $SO_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $NR^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Specific Embodiments of and Preferences for Moieties X, Y, A, $R^g$, $R^1$ to $R^4$ and $R^{10}$

X

In formula (I), X is a group $R^1$-A-$NR^4$— or a 5- or 6-membered carbocyclic or heterocyclic ring.

In one embodiment, X is a group $R^1$-A-$NR^4$—.

In another embodiment, X is a 5- or 6-membered carbocyclic or heterocyclic ring.

A

In formula (I), A is a bond, C=O, $NR^g$(C=O) or O(C=O). It will be appreciated that the moiety $R^1$-A-$NR^4$ linked to the 4-position of the pyrazole ring can therefore take the form of an amine $R^1$—$NR^4$, an amide $R^1$—C(=O)$NR^4$, a urea $R^1$—$NR^g$C(=O)$NR^4$ or a carbamate $R^1$—OC(=O)$NR^4$.

In one preferred group of compounds of the invention, A is C=O and hence the group $R^1$-A-$NR^4$ takes the form of an amide $R^1$—C(=O)$NR^4$. In another group of compounds of the invention, A is a bond and hence the group $R^1$-A-$NR^4$ takes the form of an amine $R^1$—$NR^4$.

$R^4$ $R^4$ is hydrogen or a $C_{1-4}$ hydrocarbyl group optionally substituted by halogen (e.g. fluorine), hydroxyl or $C_{1-4}$ alkoxy (e.g. methoxy).

The number of optional substitutents on the hydrocarbyl group typically will vary according to the nature of the substituent. For example, where the substituent is halogen, there may be from one to three halogen atoms present, preferably two or three. Where the substituent is hydroxyl or an alkoxy group, typically there will be only a single such substituent present $R^4$ is preferably hydrogen or $C_{1-3}$ alkyl, more preferably hydrogen or methyl and most preferably is hydrogen.

$R^g$ $R^g$ is hydrogen or a $C_{1-4}$ hydrocarbyl group optionally substituted by hydroxyl or $C_{1-4}$ alkoxy (e.g. methoxy).

When $R^g$ is $C_{1-4}$ hydrocarbyl substituted by hydroxyl or $C_{1-4}$ alkoxy, typically there is only one such substituent present.

Preferably $R^g$ is hydrogen or $C_{1-3}$ alkyl, more preferably hydrogen or methyl and most preferably $R^g$ is hydrogen.

$R^2$ $R^2$ is hydrogen, halogen, $C_{1-4}$ alkoxy, or a $C_{1-4}$ hydrocarbyl group optionally substituted by halogen, hydroxyl or $C_{1-4}$ alkoxy.

When $R^2$ is halogen, preferably it is selected from chlorine and fluorine and more preferably it is fluorine.

When $R^2$ is $C_{1-4}$ alkoxy, it can be, for example, $C_{1-3}$ alkoxy, more preferably $C_{1-2}$ alkoxy and most preferably methoxy.

When $R^2$ is an optionally substituted $C_{1-4}$ hydrocarbyl group, the hydrocarbyl group is preferably a $C_{1-3}$ hydrocarbyl group, more preferably a $C_{1-2}$ hydrocarbyl group, for example an optionally substituted methyl group. The optional substituents for the optionally substituted hydrocarbyl group are preferably selected from fluorine, hydroxyl and methoxy.

The number of optional substituents on the hydrocarbyl group typically will vary according to the nature of the substituent. For example, where the substituent is halogen, there may be from one to three halogen atoms present, preferably two or three. Where the substituent is hydroxyl or methoxy, typically there will be only a single such substituent present.

The hydrocarbyl groups constituting $R^2$ are preferably saturated hydrocarbyl groups. Examples of saturated hydrocarbyl groups include methyl, ethyl, n-propyl, i-propyl and cyclopropyl.

In one embodiment, $R^2$ is hydrogen, halogen, $C_{1-4}$ alkoxy, or a $C_{1-4}$ hydrocarbyl group optionally substituted by halogen, hydroxyl or $C_{1-4}$ alkoxy.

In another embodiment, $R^2$ is hydrogen, fluorine, chlorine, methoxy, or a $C_{1-3}$ hydrocarbyl group optionally substituted by fluorine, hydroxyl or methoxy.

In a preferred embodiment, $R^2$ is hydrogen or methyl, most preferably hydrogen.

$R^1$ $R^1$ is hydrogen, a carbocyclic or heterocyclic group having from 3 to 12 ring members, or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$. Examples of carbocyclic or heterocyclic groups and hydrocarbyl groups and general preferences for such groups are as set out above in the General Preferences and Definitions section, and as set out below.

In one embodiment, $R^1$ is an aryl or heteroaryl group.

When $R^1$ is a heteroaryl group, particular heteroaryl groups include monocyclic heteroaryl groups containing up to three heteroatom ring members selected from O, S and N, and bicyclic heteroaryl groups containing up to 2 heteroatom ring members selected from O, S and N and wherein both rings are aromatic.

Examples of such groups include furanyl (e.g. 2-furanyl or 3-furanyl), indolyl (e.g. 3-indolyl, 6-indolyl), 2,3-dihydrobenzo[1,4]dioxinyl (e.g. 2,3-dihydro-benzo[1,4]dioxin-5-yl), pyrazolyl (e.g. pyrazole-5-yl), pyrazolo[1,5-a]pyridinyl (e.g. pyrazolo[1,5-a]pyridine-3-yl), oxazolyl (e.g.), isoxazolyl (e.g. isoxazol-4-yl), pyridyl (e.g. 2-pyridyl, 3-pyridyl, 4-pyridyl), quinolinyl (e.g. 2-quinolinyl), pyrrolyl (e.g. 3-pyrrolyl), imidazolyl and thienyl (e.g. 2-thienyl, 3-thienyl).

One sub-group of heteroaryl groups $R^1$ consists of furanyl (e.g. 2-furanyl or 3-furanyl), indolyl, oxazolyl, isoxazolyl, pyridyl, quinolinyl, pyrrolyl, imidazolyl and thienyl.

A preferred sub-set of $R^1$ heteroaryl groups includes 2-furanyl, 3-furanyl, pyrrolyl, imidazolyl and thienyl.

Preferred aryl groups $R^1$ are phenyl groups.

The group $R^1$ can be an unsubstituted or substituted carbocyclic or heterocyclic group in which one or more substituents can be selected from the group $R^{10}$ as hereinbefore defined. In one embodiment, the substituents on $R^1$ may be selected from the group $R^{10a}$ consisting of halogen, hydroxy, trifluoromethyl, cyano, nitro, carboxy, a group $R^a$-$R^b$ wherein $R^a$ is a bond, O, CO, $X^3C(X^4)$, $C(X^4)X^3$, $X^3C(X^4)X^3$, S, SO, $SO_2$, and $R^b$ is selected from hydrogen and a $C_{1-8}$ hydrocarbyl group optionally substituted by one or more substituents selected from hydroxy, oxo, halogen, cyano, nitro, carboxy and monocyclic non-aromatic carbocyclic or heterocyclic groups having from 3 to 6 ring members; wherein one or more carbon atoms of the $C_{1-8}$ hydrocarbyl group may optionally be replaced by O, S, SO, $SO_2$, $X^3C(X^4)$, $C(X^4)X^3$ or $X^3C(X^4)X^3$; $X^3$ is O or S; and $X^4$ is =O or =S.

Where the carbocyclic and heterocyclic groups have a pair of substituents on adjacent ring atoms, the two substituents may be linked so as to form a cyclic group. Thus, two adjacent groups $R^{10}$, together with the carbon atoms or heteroatoms to which they are attached may form a 5-membered heteroaryl ring or a 5- or 6-membered non-aromatic carbocyclic or heterocyclic ring, wherein the said heteroaryl and heterocyclic groups contain up to 3 heteroatom ring members selected from N, O and S. In particular the two adjacent groups $R^{10}$, together with the carbon atoms or heteroatoms to which they are attached, may form a 6-membered non-aromatic heterocyclic ring, containing up to 3, in particular 2, heteroatom ring members selected from N, O and S. More particularly the two adjacent groups $R^{10}$ may form a 6-membered non-aromatic heterocyclic ring, containing 2 heteroatom ring members selected from N, or O, such as dioxan e.g. [1,4 dioxan]. In one embodiment $R^1$ is a carbocyclic group e.g. phenyl having a pair of substituents on adjacent ring atoms linked so as to form a cyclic group e.g. to form 2,3-dihydro-benzo[1,4]dioxine.

More particularly, the substituents on $R^1$ may be selected from halogen, hydroxy, trifluoromethyl, a group $R^a$-$R^b$ wherein $R^a$ is a bond or O, and $R^b$ is selected from hydrogen and a $C_{1-4}$ hydrocarbyl group optionally substituted by one or more substituents selected from hydroxyl, halogen (preferably fluorine) and 5 and 6 membered saturated carbocyclic and heterocyclic groups (for example groups containing up to two heteroatoms selected from O, S and N, such as unsubstituted piperidine, pyrrolidino, morpholino, piperazino and N-methyl piperazino).

The group $R^1$ may be substituted by more than one substituent. Thus, for example, there may be 1 or 2 or 3 or 4 substituents. In one embodiment, where $R^1$ is a six membered ring (e.g. a carbocyclic ring such as a phenyl ring), there may be one, two or three substituents and these may be located at the 2-, 3-, 4- or 6-positions around the ring. By way of example, a phenyl group $R^1$ may be 2-monosubstituted, 3-monosubstituted, 2,6-disubstituted, 2,3-disubstituted, 2,4-disubstituted 2,5-disubstituted, 2,3,6-trisubstituted or 2,4,6-trisubstituted. More particularly, a phenyl group $R^1$ may be monosubstituted at the 2-position or disubstituted at positions 2- and 6- with substituents selected from fluorine, chlorine and $R^a$-$R^b$, where $R^a$ is O and $R^b$ is $C_{1-4}$ alkyl (e.g. methyl or ethyl). In one embodiment, fluorine is a preferred substituent. In another embodiment, preferred substituents are selected from fluorine, chlorine and methoxy.

Particular examples of non-aromatic groups $R^1$ include unsubstituted or substituted (by one or more groups $R^{10}$) monocyclic cycloalkyl groups. Examples of such cycloalkyl groups include cyclopropyl, cyclobutyl, cyclopentyl, cyclohexyl and cycloheptyl; more typically cyclopropyl, cyclobutyl, cyclopentyl and cyclohexyl, particularly cyclohexyl.

Further examples of non-aromatic groups $R^1$ include unsubstituted or substituted (by one or more groups $R^{10}$) heterocyclic groups having from 3 to 12 ring members, typically 4 to 12 ring members, and more usually from 5 to 10 ring members. Such groups can be monocyclic or bicyclic, for example, and typically have from 1 to 5 heteroatom ring members (more usually 1, 2, 3 or 4 heteroatom ring members) typically selected from nitrogen, oxygen and sulphur.

When sulphur is present, it may, where the nature of the adjacent atoms and groups permits, exist as —S—, —S(O)— or —S(O)$_2$—.

The heterocylic groups can contain, for example, cyclic ether moieties (e.g as in tetrahydrofuran and dioxane), cyclic thioether moieties (e.g. as in tetrahydrothiophene and dithiane), cyclic amine moieties (e.g. as in pyrrolidine), cyclic amides (e.g. as in pyrrolidone), cyclic esters (e.g. as in butyrolactone), cyclic thioamides and thioesters, cyclic sulphones (e.g. as in sulpholane and sulpholene), cyclic sulphoxides, cyclic sulphonamides and combinations thereof (e.g. morpholine and thiomorpholine and its S-oxide and S,S-dioxide).

In one sub-set of heterocyclic groups $R^1$, the heterocyclic groups contain cyclic ether moieties (e.g as in tetrahydrofuran and dioxane), cyclic thioether moieties (e.g. as in tetrahydrothiophene and dithiane), cyclic amine moieties (e.g. as in pyrrolidine), cyclic sulphones (e.g. as in sulpholane and sulpholene), cyclic sulphoxides, cyclic sulphonamides and combinations thereof (e.g. thiomorpholine).

Examples of monocyclic non-aromatic heterocyclic groups $R^1$ include 5-, 6- and 7-membered monocyclic heterocyclic groups such as morpholine, piperidine (e.g. 1-piperidinyl, 2-piperidinyl 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include N-alkyl piperidines such as N-methyl piperidine.

One sub-group of non-aromatic heterocyclic groups $R^1$ includes unsubstituted or substituted (by one or more groups $R^{10}$) 5-, 6- and 7-membered monocyclic heterocyclic groups such as morpholine, piperidine (e.g. 1-piperidinyl, 2-piperidinyl 3-piperidinyl and 4-piperidinyl), pyrrolidine (e.g. 1-pyrrolidinyl, 2-pyrrolidinyl and 3-pyrrolidinyl), pyrrolidone, piperazine, and N-alkyl piperazines such as N-methyl piperazine, wherein a particular sub-set consists of pyrrolidine, piperidine, morpholine, thiomorpholine and N-methyl piperazine.

In general, preferred non-aromatic heterocyclic groups include pyrrolidine, piperidine, morpholine, thiomorpholine, thiomorpholine S,S-dioxide, piperazine, N-alkyl piperazines, and N-alkyl piperidines.

Another particular sub-set of heterocyclic groups consists of pyrrolidine, piperidine, morpholine and N-alkyl piperazines, and optionally, N-methyl piperazine and thiomorpholine.

When $R^1$ is a $C_{1-8}$ hydrocarbyl group substituted by a carbocyclic or heterocyclic group, the carbocyclic and heterocyclic groups can be aromatic or non-aromatic and can be selected from the examples of such groups set out hereinabove. The substituted hydrocarbyl group is typically a saturated C$_{1-4}$ hydrocarbyl group such as an alkyl group, preferably a CH$_2$ or CH$_2$CH$_2$ group. Where the substituted hydrocarbyl group is a C$_{2-4}$ hydrocarbyl group, one of the carbon atoms and its associated hydrogen atoms may be replaced by a sulphonyl group, for example as in the moiety SO$_2$CH$_2$.

When the carbocyclic or heterocylic group attached to the a C$_{1-8}$ hydrocarbyl group is aromatic, examples of such groups include monocyclic aryl groups and monocyclic heteroaryl groups containing up to four heteroatom ring members selected from O, S and N, and bicyclic heteroaryl groups containing up to 2 heteroatom ring members selected from O, S and N and wherein both rings are aromatic.

Examples of such groups are set out in the "General Preferences and Definitions" section above.

Particular examples of such groups include furanyl (e.g. 2-furanyl or 3-furanyl), indolyl, oxazolyl, isoxazolyl, pyridyl, quinolinyl, pyrrolyl, imidazolyl and thienyl. Particular examples of aryl and heteroaryl groups as substituents for a C$_{1-8}$ hydrocarbyl group include phenyl, imidazolyl, tetrazolyl, triazolyl, indolyl, 2-furanyl, 3-furanyl, pyrrolyl and thienyl. Such groups may be substituted by one or more substituents R$^{10}$ or R$^{10a}$ as defined herein.

When R$^1$ is a C$_{1-8}$ hydrocarbyl group substituted by a non-aromatic carbocyclic or heterocyclic group, the non-aromatic or heterocyclic group may be a group selected from the lists of such groups set out hereinabove. For example, the non-aromatic group can be a monocyclic group having from 4 to 7 ring members, e.g. 5 to 7 ring members, and typically containing from 0 to 3, more typically 0, 1 or 2, heteroatom ring members selected from O, S and N. When the cyclic group is a carbocyclic group, it may additionally be selected from monocyclic groups having 3 ring members. Particular examples include monocyclic cycloalkyl groups such as cyclopropyl, cyclobutyl, cyclopentyl, cyclohexyl and cycloheptyl, and 5-, 6- and 7-membered monocyclic heterocyclic groups such as morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, piperazine, and N-alkyl piperazines such as N-methyl piperazine. In general, preferred non-aromatic heterocyclic groups include pyrrolidine, piperidine, morpholine, thiomorpholine and N-methyl piperazine.

When R$^1$ is an optionally substituted C$_{1-8}$ hydrocarbyl group, the hydrocarbyl group may be as hereinbefore defined, and is preferably up to four carbon atoms in length, more usually up to three carbon atoms in length for example one or two carbon atoms in length.

In one embodiment, the hydrocarbyl group is saturated and may be acyclic or cyclic, for example acyclic. An acyclic saturated hydrocarbyl group (i.e. an alkyl group) may be a straight chain or branched alkyl group.

Examples of straight chain alkyl groups R$^1$ include methyl, ethyl, propyl and butyl.

Examples of branched chain alkyl groups R$^1$ include isopropyl, isobutyl, tent-butyl and 2,2-dimethylpropyl.

In one embodiment, the hydrocarbyl group is a linear saturated group having from 1-6 carbon atoms, more usually 1-4 carbon atoms, for example 1-3 carbon atoms, e.g. 1, 2 or 3 carbon atoms. When the hydrocarbyl group is substituted, particular examples of such groups are substituted (e.g. by a carbocyclic or heterocyclic group) methyl and ethyl groups.

A C$_{1-8}$ hydrocarbyl group R$^1$ can be optionally substituted by one or more substituents selected from halogen (e.g. fluorine), hydroxy, C$_{1-4}$ hydrocarbyloxy, amino, mono- or di-C$_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, SO$_2$. Particular substituents for the hydrocarbyl group include hydroxy, chlorine, fluorine (e.g. as in trifluoromethyl), methoxy, ethoxy, amino, methylamino and dimethylamino, preferred substituents being hydroxy and fluorine.

When A is C=O, particular groups R$^1$—CO are the groups set out in Table 1 below.

In Table 1, the point of attachment of the group to the nitrogen atom of the pyrazole-4-amino group is represented by the terminal single bond extending from the carbonyl group. Thus, by way of illustration, group B in the table is the trifluoroacetyl group, group D in the table is the phenylacetyl group and group I in the table is the 3-(4-chlorophenyl)propionyl group.

TABLE 1

Examples of the group R$^1$—CO

CH$_3$—C(=O)—
A

CF$_3$—C(=O)—
B

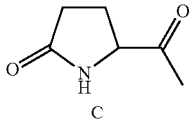
C

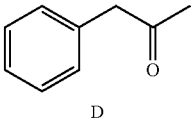
D

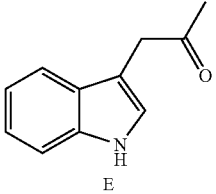
E

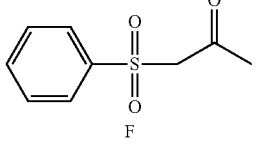
F

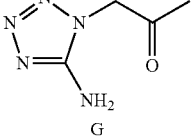
G

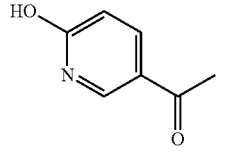
H

TABLE 1-continued
Examples of the group R[1]—CO
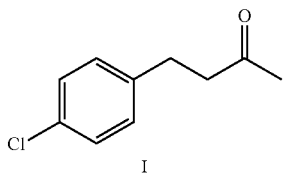
I
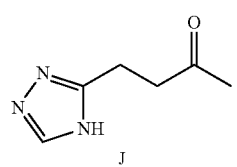
J
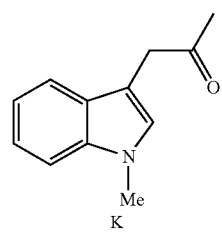
K
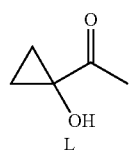
L
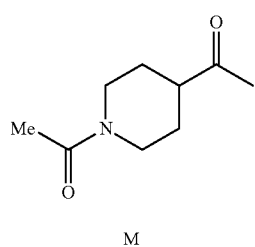
M
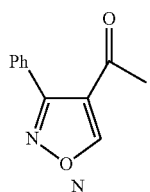
N
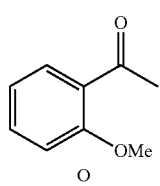
O
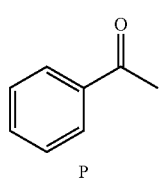
P
TABLE 1-continued
Examples of the group R[1]—CO
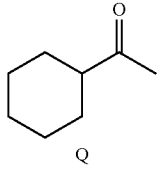
Q
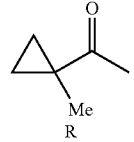
R
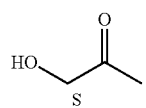
S
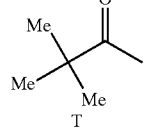
T
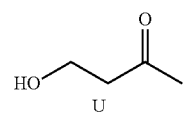
U
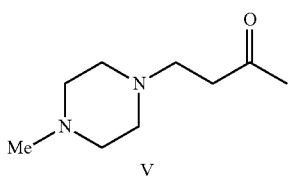
V
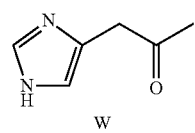
W
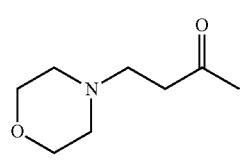
X
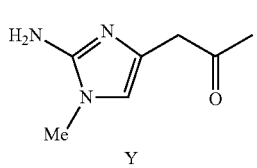
Y
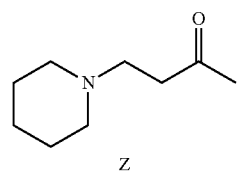
Z TABLE 1-continued
| Examples of the group R¹—CO |
|---|
| 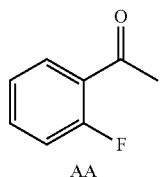 AA |
| 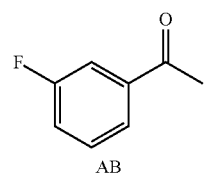 AB |
| 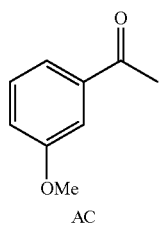 AC |
| 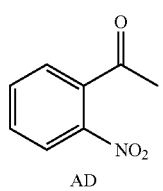 AD |
| 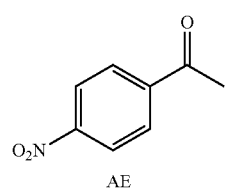 AE |
| 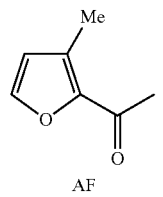 AF |
| 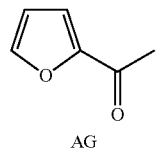 AG |
| 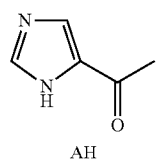 AH |
TABLE 1-continued
| Examples of the group R¹—CO |
|---|
| 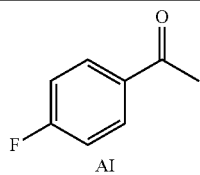 AI |
| 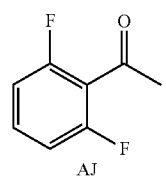 AJ |
| 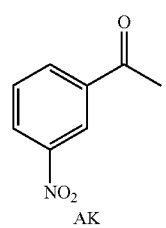 AK |
| 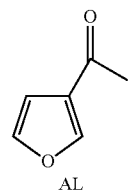 AL |
| 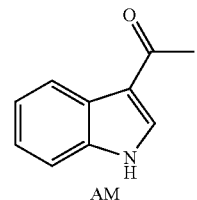 AM |
| 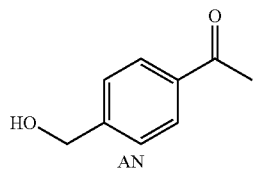 AN |
| 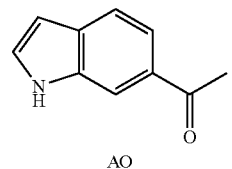 AO |
| 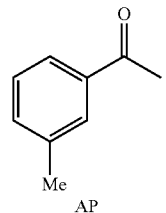 AP |

TABLE 1-continued
Examples of the group R¹—CO
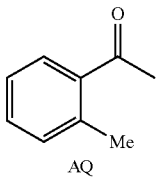
AQ
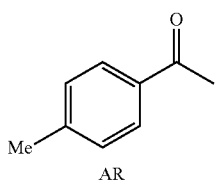
AR
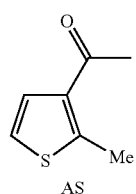
AS
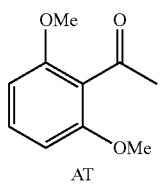
AT
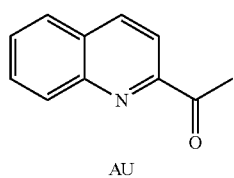
AU
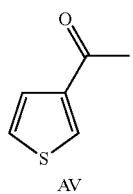
AV
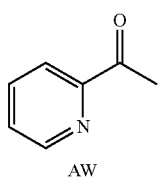
AW
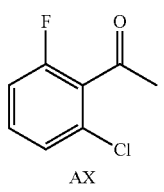
AX
TABLE 1-continued
Examples of the group R¹—CO
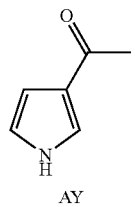
AY
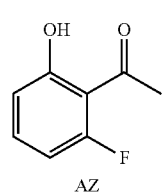
AZ
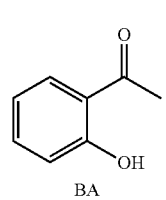
BA
BB
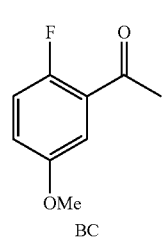
BC
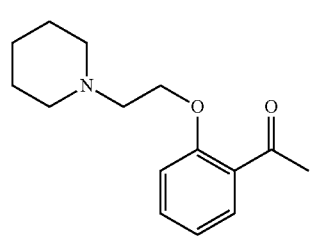 [SMILES: CC(=O)c1ccccc1OCCN1CCCCC1]
BD
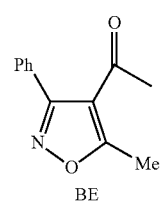
BE TABLE 1-continued
Examples of the group R¹—CO
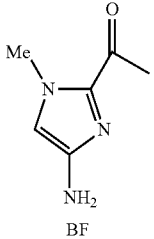
BF
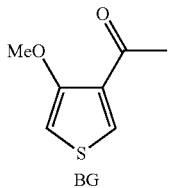
BG
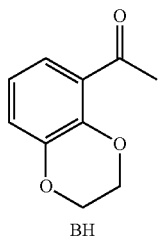
BH
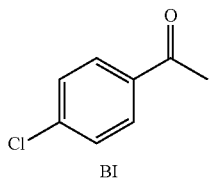
BI
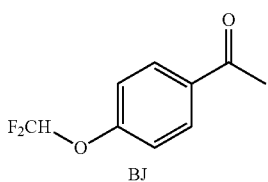
BJ
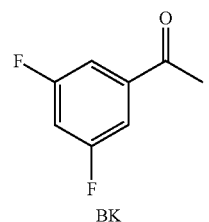
BK
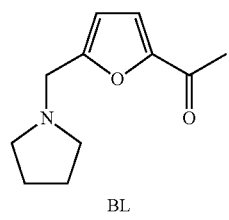
BL
TABLE 1-continued
Examples of the group R¹—CO
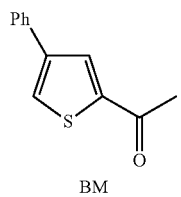
BM
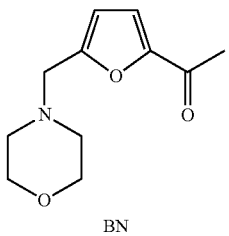
BN
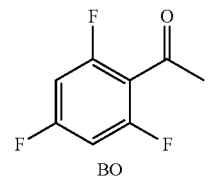
BO
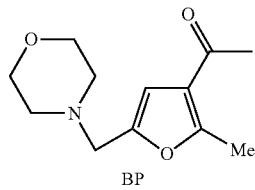
BP
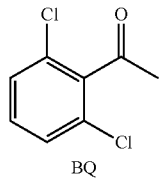
BQ
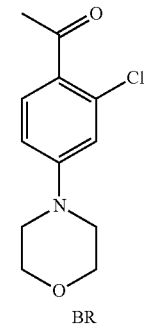
BR
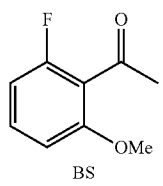
BS TABLE 1-continued
Examples of the group R¹—CO
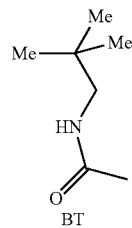
BT
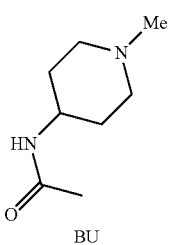
BU
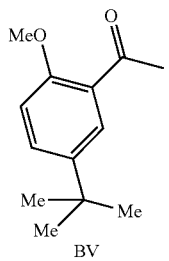
BV
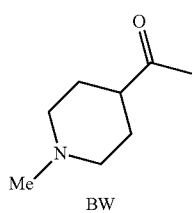
BW
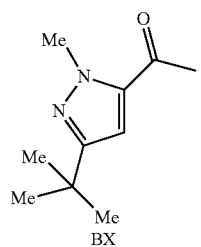
BX
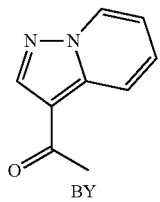
BY
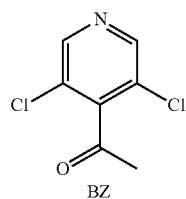
BZ
TABLE 1-continued
Examples of the group R¹—CO
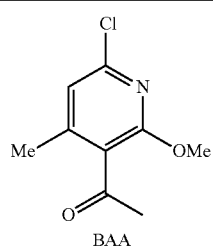
BAA
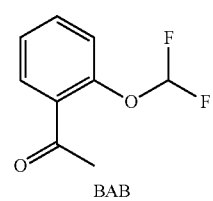
BAB
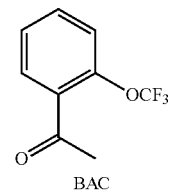
BAC
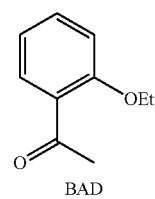
BAD
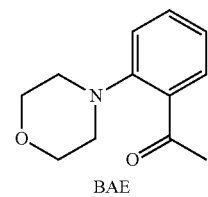
BAE
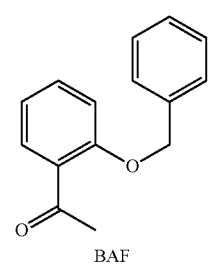
BAF
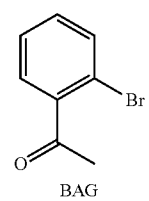
BAG

TABLE 1-continued

Examples of the group R¹—CO

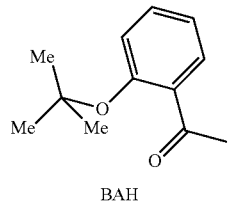
BAH

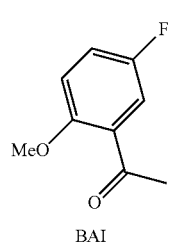
BAI

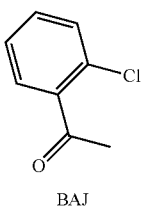
BAJ

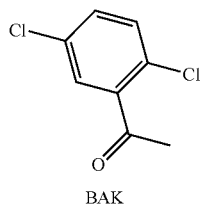
BAK

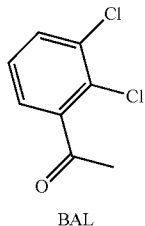
BAL

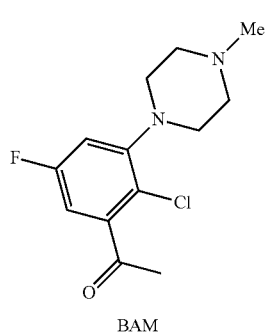
BAM

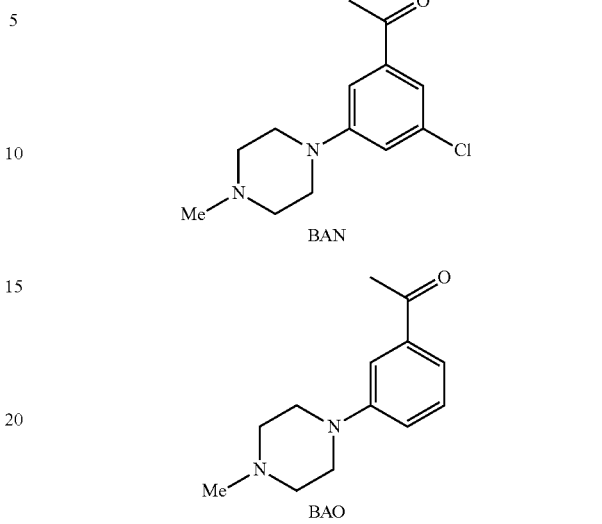
BAN

BAO

One sub-group of groups R¹—CO consists of groups A to BF in Table 1 above.

Another sub-group of groups R¹—CO consists of groups A to BS in Table 1 above.

One set of preferred groups R¹—CO consists of the groups J, AB, AH, AJ, AL, AS, AX, AY, AZ, BA, BB, BD, BH, BL, BQ, BS and BAI Another set of preferred groups R¹—CO consists of the groups J, AB, AH, AJ, AL, AS, AX, AY, AZ, BA, BB, BD, BH, BL, BQ and BS.

More preferred groups R¹—CO— are AJ, AX, BQ, BS and BAI.

One particularly preferred sub-set of groups R¹—CO— consists of AJ, BQ and BS.

Another particularly preferred sub-set of groups R¹—CO— consists of AJ and BQ.

When X is R¹-A-NR⁴ and A is C=O, and R¹ is a phenyl ring bearing a substituent at the 4-position, the substituent at the 4-position is preferably other than a phenyl group having a group $SO_2NH_2$ or $SO_2Me$ at the ortho-position.

In one general embodiment, R¹ may be other than a substituted or unsubstituted tetrahydroquinoline, chroman, chromene, thiochroman, thiochromene, dihydro-naphthalene or tetrahydronaphthalene group. More particularly, R¹ may be other than a substituted or unsubstituted tetrahydroquinoline, chroman, chromene, thiochroman, thiochromene, dihydro-naphthalene or tetrahydronaphthalene group linked by its aromatic ring to the moiety A-NR⁴—.

In another general embodiment, when R¹ is a substituted or unsubstituted phenyl group, the moiety Y—R³ may be other than hydrogen, unsubstituted $C_{1-10}$ alkyl, unsubstituted $C_{5-10}$ cycloalkyl, unsubstituted phenyl, unsubstituted $C_{1-10}$ alkylphenyl or unsubstituted phenyl-$C_{1-10}$ alkyl.

In the context of the group R¹-A-NR⁴—, when R¹ is an optionally substituted hydrocarbyl group and the hydrocarbyl group comprises or contains a substituted or unsubstituted alkene group, it is preferred that the carbon-carbon double bond of the alkene group is not directly bonded to the group A.

Also in the context of the group R¹-A-NR⁴—, when R¹ is an optionally substituted hydrocarbyl group, the hydrocarbyl group may be other than an alkene group.

In another general embodiment, when Y is a bond, $R^3$ is hydrogen, A is CO and $R^1$ is a substituted phenyl group, each substituent on the phenyl group may be other than a group $CH_2$—$P(O)R^xR^y$ where $R^x$ and $R^y$ are each selected from alkoxy and phenyl groups.

Y

In the compounds of the formula (I), Y is a bond or an alkylene chain of 1, 2 or 3 carbon atoms in length.

The term "alkylene" has its usual meaning and refers to a divalent saturated acyclic hydrocarbon chain. The hydrocarbon chain may be branched or unbranched. Where an alkylene chain is branched, it may have one or more methyl group side chains. Examples of alkylene groups include —$CH_2$—, —$CH_2$—$CH_2$—, —$CH_2$—$CH_2$—$CH_2$—, $CH(CH_3)$—, —$C(CH_3)_2$—, —$CH_2$—$CH(CH_3)$—, —$CH_2$—$C(CH_3)_2$— and —$CH(CH_3)$—$CH(CH_3)$—.

In one embodiment, Y is a bond.

In another embodiment, Y is an alkylene chain.

When Y is an alkylene chain, preferably it is unbranched and more particularly contains 1 or 2 carbon atoms, preferably 1 carbon atom. Thus preferred groups Y are —$CH_2$— and —$CH_2$—$CH_2$—, a most preferred group being $(CH_2)$—.

Where Y is a branched chain, preferably it has no more than two methyl side chains. For example, it may have a single methyl side chain. In one embodiment, Y is a group —CH(Me)-.

In one sub-group of compounds, Y is a bond, $CH_2$, $CH_2CH_2$ or $CH_2CH(CH_3)$.

$R^3$

The group $R^3$ is selected from hydrogen and carbocyclic and heterocyclic groups having from 3 to 12 ring members.

In one sub-group of compounds, Y is a bond and $R^3$ is hydrogen.

In another sub-group of compounds Y is an alkylene chain as hereinbefore defined and $R^3$ is hydrogen.

In a another sub-group of compounds, Y is a bond or an alkylene chain (e.g. a group —$(CH_2)$—) and $R^3$ is a carbocyclic or heterocyclic group.

In a further sub-group of compounds, Y is a bond and $R^3$ is a carbocyclic or heterocyclic group.

In a still further sub-group of compounds, Y is an alkylene chain (e.g. a group —$(CH_2)$—) and $R^3$ is a carbocyclic or heterocyclic group.

The carbocyclic and heterocyclic groups $R^3$ can be aryl, heteroaryl, non-aromatic carbocyclic or non-aromatic heterocyclic and examples of such groups are as set out in detail above in the General Preferences and Definitions section, and as set out below.

Preferred aryl groups $R^3$ are unsubstituted and substituted phenyl groups.

Examples of heteroaryl groups $R^3$ include monocyclic heteroaryl groups containing up to three (and more preferably up to two) heteroatom ring members selected from O, S and N. Preferred heteroaryl groups include five membered rings containing one or two heteroatom ring members and six membered rings containing a single heteroatom ring member, most preferably nitrogen. Particular examples of heteroaryl groups include unsubstituted or substituted pyridyl, imidazole, pyrazole, thiazole, isothiazole, isoxazole, oxazole, furyl and thiophene groups.

Particular heteroaryl groups are unsubstituted and substituted pyridyl groups, e.g. 2-pyridyl, 3-pyridyl and 4-pyridyl groups, especially 3- and 4-pyridyl groups. When the pyridyl groups are substituted, they can bear one or more substituents, typically no more than two, and more usually one substituent selected, for example, from $C_{1-4}$ alkyl (e.g. methyl), halogen (e.g. fluorine or chlorine, preferably chlorine), and $C_{1-4}$ alkoxy (e.g. methoxy). Substituents on the pyridyl group may further be selected from amino, mono-$C_{1-4}$ alkylamino and di-$C_{1-4}$ alkylamino, particularly amino.

In one embodiment, when $R^3$ is an aryl (e.g. phenyl) or heteroaryl group, the substituents on the carbocyclic or heterocyclic group may be selected from the group $R^{10a}$ consisting of halogen, hydroxy, trifluoromethyl, cyano, monocyclic carbocyclic and heterocyclic groups having from 3 to 7 (typically 5 or 6) ring members, and a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, a carbocyclic or heterocyclic group with 3-7 ring members and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, a carbocyclic or heterocyclic group with 3-7 ring members and wherein one or more carbon atoms of the $C_{1-8}$ hydrocarbyl group may optionally be replaced by O, S, SO, $SO_2NR^c$, $X^1C(X^2)$, $C(X^2)X^1$ or $X^1C(X^2)X^1$; and $R^c$, $X^1$ and $X^2$ are as hereinbefore defined.

Examples of non-aromatic groups $R^3$ include optionally substituted (by $R^{10}$ or $R^{10a}$)cycloalkyl, oxa-cycloalkyl, aza-cycloalkyl, diaza-cycloalkyl, dioxa-cycloalkyl and aza-oxa-cycloalkyl groups. Further examples include $C_{7-10}$ aza-bicycloalkyl groups such as 1-aza-bicyclo[2.2.2]octan-3-yl.

Particular examples of such groups include unsubstituted or substituted cyclopropyl, cyclobutyl, cyclopentyl, cyclohexyl, tetrahydropyran, morpholine, tetrahydrofuran, piperidine and pyrrolidine groups.

One sub-set of non-aromatic groups $R^3$ consists of cyclopropyl, cyclobutyl, cyclopentyl, cyclohexyl, tetrahydropyran, tetrahydrofuran, piperidine and pyrrolidine groups.

Preferred non-aromatic groups $R^3$ include unsubstituted or substituted cyclopentyl, cyclohexyl, tetrahydropyran, tetrahydrofuran, piperidine and pyrrolidine groups, The non-aromatic groups may be unsubstituted or substituted with one or more groups $R^{10}$ or $R^{10a}$ as hereinbefore defined.

Particular substituents for $R^3$ (e.g. (i) when $R^3$ is an aryl or heteroaryl group or (ii) when $R^3$ is a non-aromatic group) are selected from the group $R^{10a}$ consisting of halogen; hydroxy; monocyclic carbocyclic and heterocyclic groups having from 3 to 6 ring members and containing up to 2 heteroatom ring members selected from O, N and S; and a group $R^a$-$R^b$ wherein $R^a$ is a bond, O, CO, $CO_2$, $SO_2NH$, $SO_2NH$ or $NHSO_2$; and $R^b$ is selected from hydrogen, a carbocyclic or heterocyclic group with 3-6 ring members and containing up to 2 heteroatom ring members selected from O, N and S; and a $C_{1-6}$ hydrocarbyl group optionally substituted by one or more substituents selected from hydroxy, oxo, halogen, carboxy, amino, mono- or di-$C_{1-4}$ hydrocarbylamino, a carbocyclic or heterocyclic group with 3-6 ring members and containing up to 2 heteroatom ring members selected from O, N and S; and wherein one or two carbon atoms of the $C_{1-6}$ hydrocarbyl group may optionally be replaced by O, S, SO, $SO_2$ or NH.

In one embodiment, preferred $R^{10a}$ substituent groups on $R^3$ (e.g. (i) when $R^3$ is an aryl or heteroaryl group or (ii) when $R^3$ is a non-aromatic group) include halogen, a group $R^a$-$R^b$ wherein $R^a$ is a bond, O, CO, $C(X^2)X^1$, and $R^b$ is selected from hydrogen, heterocyclic groups having 3-7 ring members and a $C_{1-4}$ hydrocarbyl group optionally substituted by one or more substituents selected from hydroxy, carboxy, amino, mono- or di-$C_{1-4}$ hydrocarbylamino, and heterocyclic groups having 3-7 ring members.

Particularly preferred substituent groups $R^{10a}$ on $R^3$ (e.g. (i) when $R^3$ is an aryl or heteroaryl group or (ii) when $R^3$ is a non-aromatic group) include halogen, especially fluorine, $C_{1-3}$ alkoxy such as methoxy, and $C_{1-3}$ hydrocarbyl optionally substituted by fluorine, hydroxy (e.g. hydroxymethyl), $C_{1-2}$ alkoxy or a 5- or 6-membered saturated heterocyclic ring such as piperidino, morpholino, piperazino and N-methylpiperazino.

In another embodiment, the substituents for $R^3$ (whether aromatic or non-aromatic) are selected from:
halogen (e.g. fluorine and chlorine)
$C_{1-4}$ alkoxy (e.g. methoxy and ethoxy) optionally substituted by one or substituents selected from halogen, hydroxy, $C_{1-2}$ alkoxy and five and six membered saturated heterocyclic rings containing 1 or 2 heteroatoms selected from O, N and S, the heterocyclic rings being optionally further substituted by one or more $C_{1-4}$ groups (e.g. methyl) and wherein the S, when present, may be present as S, SO or $SO_2$;
$C_{1-4}$ alkyl optionally substituted by one or substituents selected from halogen, hydroxy, $C_{1-4}$ alkoxy, amino, $C_{1-4}$ alkylsulphonylamino, 3 to 6 membered cycloalkyl groups (e.g. cyclopropyl), phenyl (optionally substituted by one or more substituents selected from halogen, methyl, methoxy and amino) and five and six membered saturated heterocyclic rings containing 1 or 2 heteroatoms selected from O, N and S, the heterocyclic rings being optionally further substituted by one or more $C_{1-4}$ groups (e.g. methyl) and wherein the S, when present, may be present as S, SO or $SO_2$;
hydroxy;
amino, mono-$C_{1-4}$ alkylamino, di-$C_{1-4}$ alkylamino, benzyloxycarbonylamino and $C_{1-4}$ alkoxycarbonylamino;
carboxy and $C_{1-4}$ alkoxycarbonyl;
$C_{1-4}$ alkylaminosulphonyl and $C_{1-4}$ alkylsulphonylamino;
$C_{1-4}$ alkylsulphonyl;
a group O-$Het^s$ or NH-$Het^s$ where $Het^s$ is a five or six membered saturated heterocyclic ring containing 1 or 2 heteroatoms selected from O, N and S, the heterocyclic rings being optionally further substituted by one or more $C_{1-4}$ groups (e.g. methyl) and wherein the S, when present, may be present as S, SO or $SO_2$;
five and six membered saturated heterocyclic rings containing 1 or 2 heteroatoms selected from O, N and S, the heterocyclic rings being optionally further substituted by one or more $C_{1-4}$ groups (e.g. methyl) and wherein the S, when present, may be present as S, SO or $SO_2$;
oxo; and
six membered aryl and heteroaryl rings containing up to two nitrogen ring members and being optionally substituted by one or substituents selected from halogen, methyl and methoxy.

In one preferred sub-group of compounds, $R^3$ is a carbocyclic or heterocyclic group $R^{3a}$ selected from phenyl; $C_{3-6}$ cycloalkyl; five and six membered saturated non-aromatic heterocyclic rings containing up to two heteroatom ring members selected from N, O, S and $SO_2$; six membered heteroaryl rings containing one, two or three nitrogen ring members; and five membered heteroaryl rings having up to three heteroatom ring members selected from N, O and S;
wherein each carbocyclic or heterocyclic group $R^{3a}$ is optionally substituted by up to four, preferably up to three, and more preferably up to two (e.g. one) substituents selected from amino; hydroxy; oxo; fluorine; chlorine; $C_{1-4}$ alkyl-$(O)_q$— wherein q is 0 or 1 and the $C_{1-4}$ alkyl moiety is optionally substituted by fluorine, hydroxy or $C_{1-2}$ alkoxy; mono-$C_{1-4}$ alkylamino; di-$C_{1-4}$ alkylamino; $C_{1-4}$ alkoxycarbonyl; carboxy; a group $R^e$—$R^{16}$ where $R^e$ is a bond or a $C_{1-3}$ alkylene chain and $R^{16}$ is selected from $C_{1-4}$ alkylsulphonyl; $C_{1-4}$ alkylaminosulphonyl; $C_{1-4}$ alkylsulphonylamino-; amino; mono-$C_{1-4}$ alkylamino; di-$C_{1-4}$ alkylamino; $C_{1-7}$-hydrocarbyloxycarbonylamino; six membered aromatic groups containing up to three nitrogen ring members; $C_{3-6}$ cycloalkyl; five or six membered saturated non-aromatic heterocyclic groups containing one or two heteroatom ring members selected from N, O, S and $SO_2$, the group $R^{16}$ when a saturated non-aromatic group being optionally substituted by one or more methyl groups, and the group $R^{16}$ when aromatic being optionally substituted by one or more groups selected from fluorine, chlorine, hydroxy, $C_{1-2}$ alkoxy and $C_{1-2}$ alkyl.

In a further embodiment, $R^3$ is selected from:
monocyclic aryl groups optionally substituted by 1-4 (for example 1-2, e.g. 1) substituents $R^{10}$ or $R^{10a}$;
$C_3$-$C_7$ cycloalkyl groups optionally substituted by 1-4 (for example 1-2, e.g. 1) substituents $R^{10}$ or $R^{10a}$;
saturated five membered heterocyclic rings containing 1 ring heteroatom selected from O, N and S and being optionally substituted by an oxo group and/or by 1-4 (for example 1-2, e.g. 1) substituents $R^{10}$ or $R^{10a}$;
saturated six membered heterocyclic rings containing 1 or 2 ring heteroatoms selected from O, N and S and being optionally substituted by an oxo group and/or by 1-4 (for example 1-2, e.g. 1) substituents $R^{10}$ or $R^{10a}$;
five membered heteroaryl rings containing 1 or 2 ring heteroatoms selected from O, N and S and being optionally substituted by 1-4 (for example 1-2, e.g. 1) substituents $R^{10}$ or $R^{10a}$;
six membered heteroaryl rings containing 1 or 2 nitrogen ring members (preferably 1 nitrogen ring member) and being optionally substituted by 1-4 (for example 1-2, e.g. 1) substituents $R^{10}$ or $R^{10a}$;
mono-azabicycloalkyl and diazabicycloalkyl groups each having 7 to 9 ring members and being optionally substituted by 1-4 (for example 1-2, e.g. 1) substituents $R^{10}$ or $R^{10a}$.

Specific examples of the group Y—$R^3$ are set out in Table 2. In Table 2, the point of attachment of the group to the nitrogen atom of the pyrazole-3-carboxamide group is represented by the terminal single bond extending from the group. Thus, by way of illustration, group CA in the table is the 4-fluorophenyl, group CB in the table is the 4-methoxybenzyl group and group CC in the table is the 4-(4-methylpiperazino)-phenylmethyl group.

TABLE 2

Examples of the Group Y—$R^3$

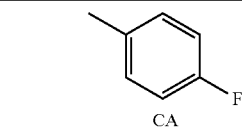

CA

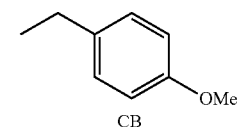

CB

CC

TABLE 2-continued
Examples of the Group Y—R³
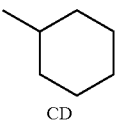
CD
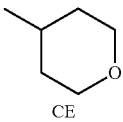
CE
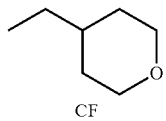
CF
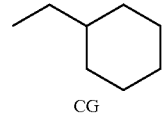
CG
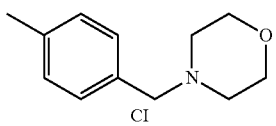
CH
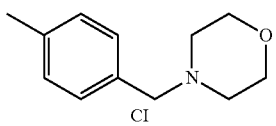
CI
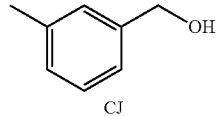
CJ
CK
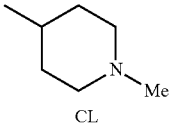
CL
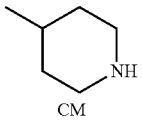
CM
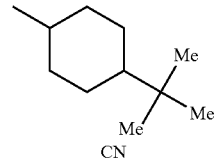
CN
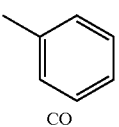
CO
TABLE 2-continued
Examples of the Group Y—R³
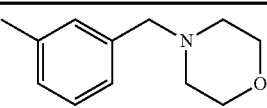
CP
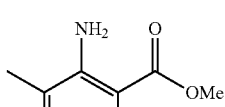
CQ
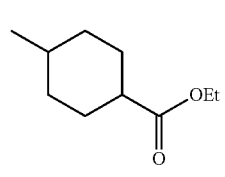
CR
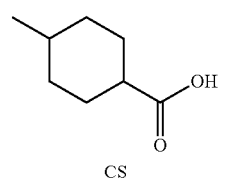
CS
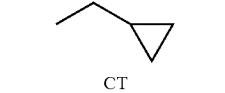
CT
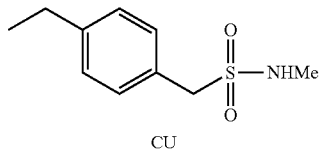
CU
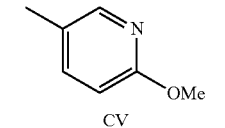
CV
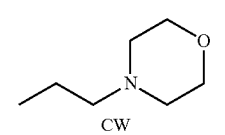
CW
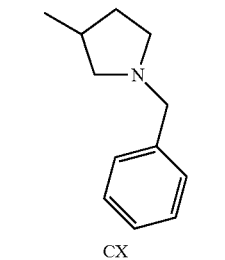
CX TABLE 2-continued
Examples of the Group Y—R³
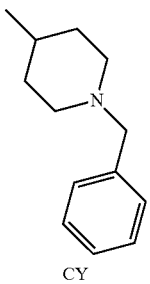
CY
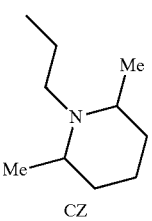
CZ
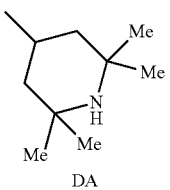
DA
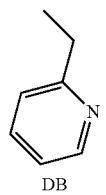
DB
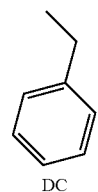
DC
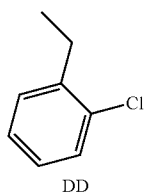
DD
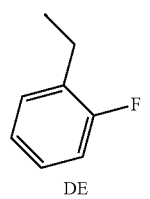
DE
TABLE 2-continued
Examples of the Group Y—R³
DF
DG
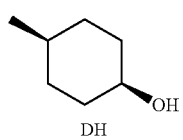
DH
DI
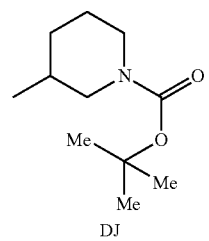
DJ
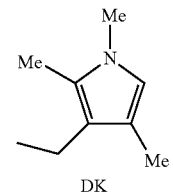
DK
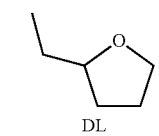
DL
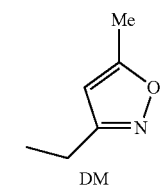
DM TABLE 2-continued
Examples of the Group Y—R³
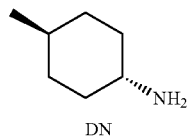
DN
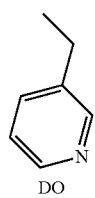
DO
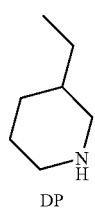
DP
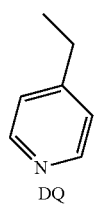
DQ
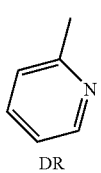
DR
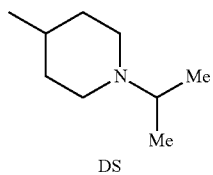
DS
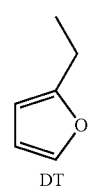
DT
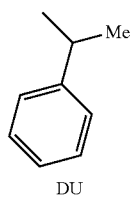
DU
TABLE 2-continued
Examples of the Group Y—R³
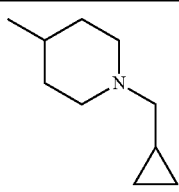
DV
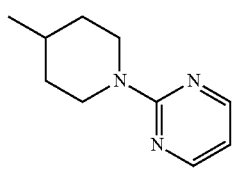
DW
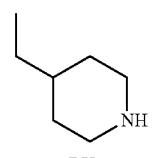
DX
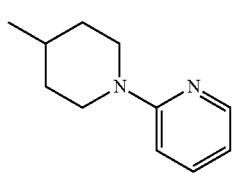
DY
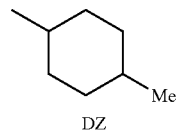
DZ
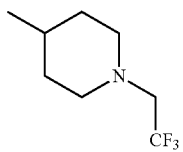
EA
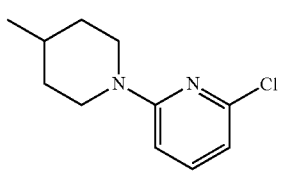
EB
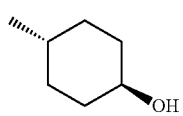
EC TABLE 2-continued
Examples of the Group Y—R³
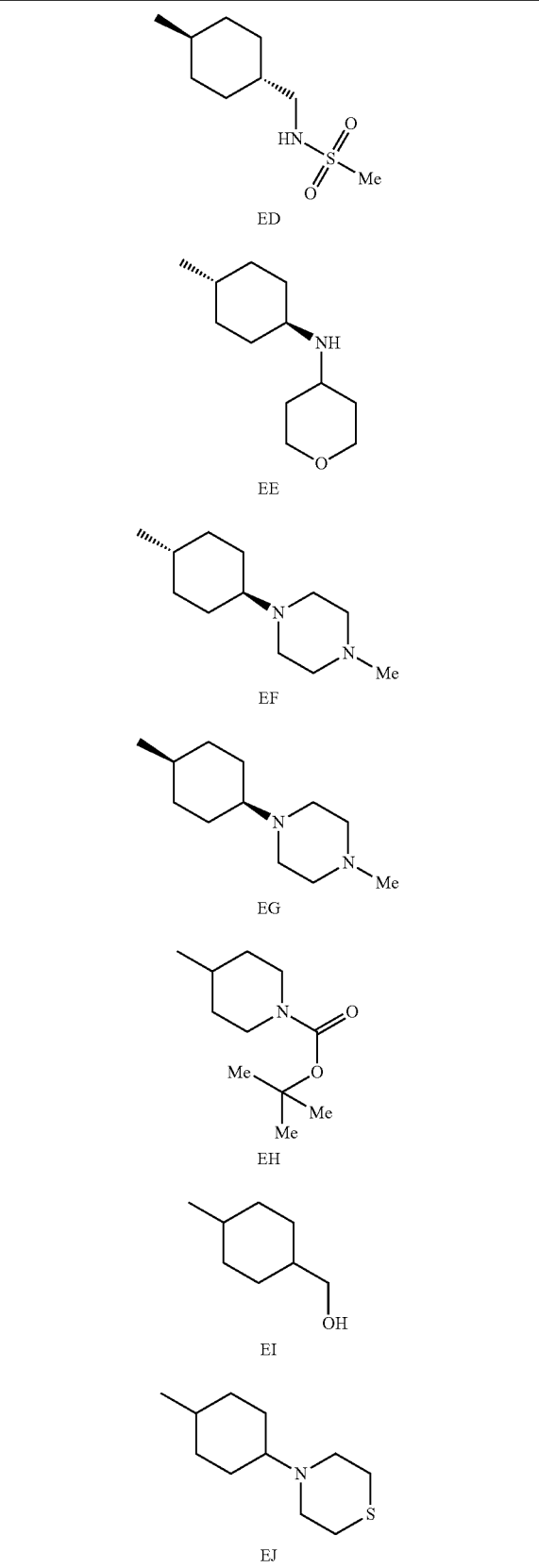
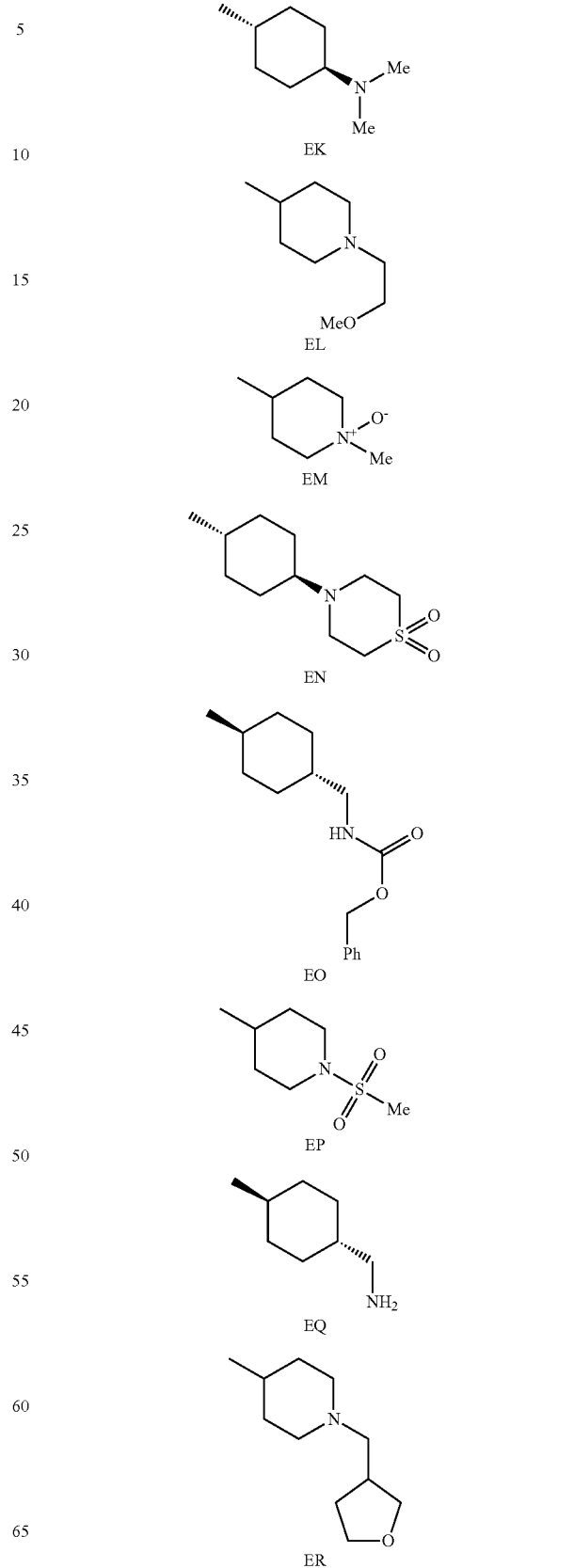

TABLE 2-continued
Examples of the Group Y—R³
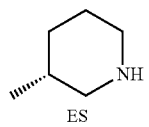
ES
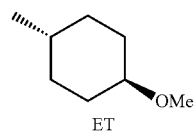
ET
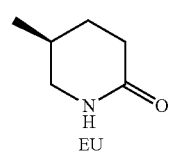
EU
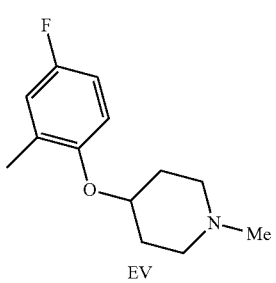
EV
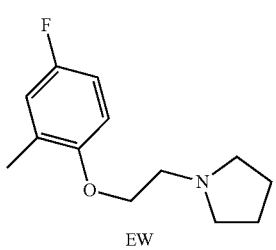
EW
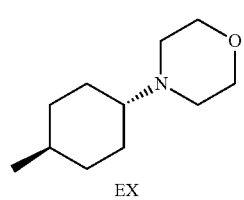
EX
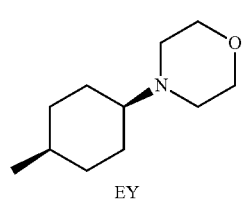
EY
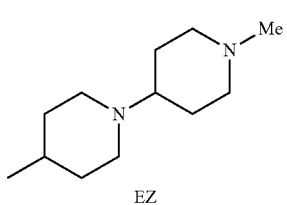
EZ
TABLE 2-continued
Examples of the Group Y—R³
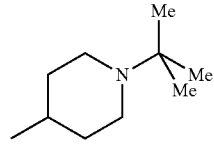
FA
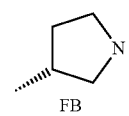
FB
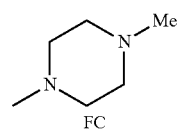
FC
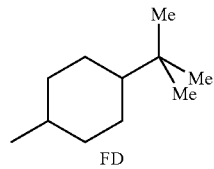
FD
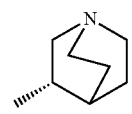
FE
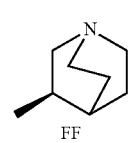
FF
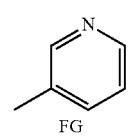
FG
FH
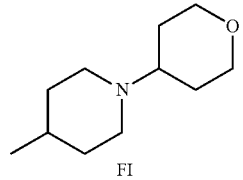
FI
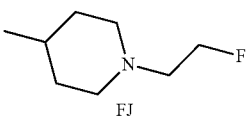
FJ
FK TABLE 2-continued Examples of the Group Y—R³

FL

FM

FN

One sub-set of groups selected from table 2 consists of groups CA to EU.

Another sub-set of groups selected from table 2 consists of groups CA to CV.

Preferred groups selected from Table 2 include groups CL, CM, ES, ET, FC, FG and FH.

Particularly preferred groups selected from Table 2 include groups CL, CM and ES, and most preferably CL and CM.

In another general embodiment, when $R^3$ is an aza-cycloalkyl group, the group X in the compound of the formula (I) is preferably $R^1$-A-$NR^4$ wherein A is CO, $NR^g$(C=O) or O(C=O). Additionally, or alternatively, when $R^3$ is an aza-cycloalkyl group, the nitrogen atom of the aza-cycloalkyl group is preferably not substituted with an alkylene chain linked to a 2,3-dihydro-benzo[1,4]dioxine or tetrahydronaphthalene group.

In another general embodiment, when Y is an alkylene chain of 1 carbon atom in length, $R^3$ is other than an optionally substituted phenyl group bearing a substituted or unsubstituted cyclohexyloxy or cyclohexylthio group.

In another general embodiment, $R^3$ is other than a moiety containing a five membered heteroaryl ring linked directly by a single bond to a monocyclic or bicyclic aryl group or $R^3$ is other than a moiety containing a bis heteroaryl group comprising two five membered heteroaryl rings linked together by a single bond.

In a further general embodiment, $R^1$ is other than a moiety containing a five membered heteroaryl ring linked directly by a single bond to a monocyclic or bicyclic aryl group or $R^1$ is other than a moiety containing a bis heteroaryl group comprising two five membered heteroaryl rings linked together by a single bond.

In another general embodiment, $R^1$-A-$NR^4$ is other than an optionally substituted nicotinoyl-amino or benzoyl-amino group when Y—$R^3$ is an alkyl, cycloalkyl, optionally substituted phenyl or optionally substituted phenylalkyl group.

When A is a bond (and optionally when A is CO, $NR^g$ (C=O) or O(C=O)), Y—$R^3$ may be other than a cycloalkyl group substituted at the 1-position with a hydrocarbon chain simultaneously bearing an oxy substituent such as hydroxy, an aryl substituent and a diazole or triazole substituent.

Preferably, $R^1$ or $R^3$ each are other than a moiety containing a substituted phenyl group having thio and/or oxy substituents such as hydroxy, alkoxy and alkylthio at both the 3- and 4-positions of the phenyl ring.

In a further general embodiment, when Y—$R^3$ is unsubstituted or substituted benzyl or phenethyl or naphthylmethyl, X may be other than $C_{1-5}$ alkylamino or $C_{1-7}$ acylamino.

The group Y—$R^3$ preferably does not include a benzo-fused lactam group having attached thereto an unsubstituted or substituted imidazole group.

The group Y—$R^3$ preferably does not include the moiety —CH=C(CO₂$R^q$)—S— where $R^q$ is hydrogen or alkyl.

In another general embodiment, neither $R^1$ nor $R^3$ contain a moiety in which a five membered nitrogen-containing heteroaryl group is linked directly or via an alkylene, oxa-alkylene, thia-alkylene or aza-alkylene group to an unsubstituted pyridyl group or to a substituted aryl, heteroaryl or piperidine ring, each said ring having attached thereto a substituent selected from cyano, and substituted or unsubstituted amino, aminoalkyl, amidine, guanidine, and carbamoyl groups.

In a further general embodiment, $R^1$ and $R^3$ are each other than an unsaturated nitrogen-containing heterocyclic group or a nitrogen-containing heteroaryl group, or a benzfuran or benzthiophene group wherein the said nitrogen-containing heterocyclic group, nitrogen-containing heteroaryl group, bicyclic benzfuran or benzthiophene group are linked directly by a single bond to a substituted pyridyl or phenyl group.

In another general embodiment, neither $R^1$ nor $R^3$ contain a moiety in which a five membered nitrogen-containing heteroaryl group is linked directly or via an alkylene, oxa-alkylene, thia-alkylene or aza-alkylene group to a substituted aryl, heteroaryl or piperidine group or to an unsubstituted pyridyl group.

In general, it is preferred that the compounds of the invention, where they contain a carboxylic acid group, contain no more than one such group.

Particular and Preferred Sub-Groups of the Formulae (I), (Ia) and (Ib)

One particular group of compounds of the invention is represented by the formula (II):

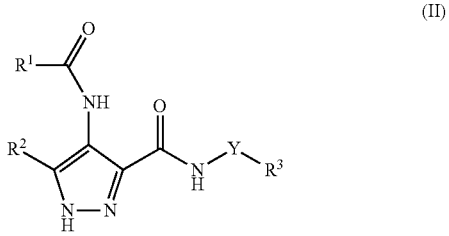

(II)

or salts or tautomers or N-oxides or solvates thereof;
wherein $R^1$, $R^2$, $R^3$ and Y are each independently selected from $R^1$, $R^2$, $R^3$ and Y as defined herein.

Within formula (II), it is preferred that $R^2$ is hydrogen or $C_{1-4}$ alkyl (e.g. $C_{1-3}$ alkyl), and more preferably $R^2$ is hydrogen.

In one sub-group of compounds of the formula (II), $R^1$ is:
phenyl optionally substituted by one or more substituents (e.g. 1, 2 or 3) selected from fluorine; chlorine; hydroxy; 5- and 6-membered saturated heterocyclic groups containing 1 or 2 heteroatoms selected from O, N and S, the heterocyclic groups being optionally substituted by one or more $C_{1-4}$ alkyl groups; $C_{1-4}$ hydrocarbyloxy; and $C_{1-4}$ hydrocarbyl; wherein the $C_{1-4}$ hydrocarbyl and $C_{1-4}$ hydrocarbyloxy groups are optionally substituted by one or more substituents chosen from hydroxy, fluorine, $C_{1-2}$ alkoxy, amino, mono and di-$C_{1-4}$ alkylamino, phenyl, halophenyl, saturated carbocyclic groups having 3 to 7 ring members (more preferably 4, 5 or 6 ring members, e.g. 5 or 6 ring members) or saturated heterocyclic groups of 5 or 6 ring members and containing up to 2 heteroatoms selected from O, S and N; or 2,3-dihydro-benzo[1,4]dioxine; or (ii) a monocyclic heteroaryl group containing one or two heteroatoms selected from O, S and N; or a bicyclic heteroaryl group containing a single heteroatom selected from O, S and N; the monocyclic and bicyclic heteroaryl groups each being optionally substituted by one or more substituents selected from fluorine; chlorine; $C_{1-3}$ hydrocarbyloxy; and $C_{1-3}$ hydrocarbyl optionally substituted by hydroxy, fluorine, methoxy or a five or six membered saturated carbocyclic or heterocyclic group containing up to two heteroatoms selected from O, S and N; or (iii) a substituted or unsubstituted cycloalkyl group having from 3 to 6 ring members; or (iv) a $C_{1-4}$ hydrocarbyl group optionally substituted by one or more substituents selected from fluorine; hydroxy; $C_{1-4}$ hydrocarbyloxy; amino; mono- or di-$C_{1-4}$ hydrocarbylamino; and carbocyclic or heterocyclic groups having from 3 to 12 ring members, and wherein one of the carbon atoms of the hydrocarbyl group may optionally be replaced by an atom or group selected from O, NH, SO and $SO_2$.

Within group (i), a sub-group of groups $R^1$ consists of phenyl optionally substituted by one or more substituents selected from fluorine; chlorine; hydroxy; $C_{1-3}$ hydrocarbyloxy; and $C_{1-3}$ hydrocarbyl wherein the $C_{1-3}$ hydrocarbyl group is optionally substituted by one or more substituents chosen from hydroxy, fluorine, $C_{1-2}$ alkoxy, amino, mono and di-$C_{1-4}$ alkylamino, saturated carbocyclic groups having 3 to 7 ring members (more preferably 4, 5 or 6 ring members, e.g. 5 or 6 ring members) or saturated heterocyclic groups of 5 or 6 ring members and containing up to 2 heteroatoms selected from O, S and N.

In another sub-group of compounds of the formula (II), $R^1$ is selected from (i) and (iii) above and additionally from a sub-set (aii) where sub-set (aii) consists of 2-furanyl, 3-furanyl, imidazolyl, 2-pyridyl, indolyl, 2-thienyl and 3-thienyl, each optionally substituted by one or more substituents selected from fluorine, chlorine, $C_{1-3}$ hydrocarbyloxy, and $C_{1-3}$ hydrocarbyl optionally substituted by hydroxy, fluorine or methoxy.

Within the group of compounds defined by the formula (II), where $R^1$ is (i) an optionally substituted phenyl group, it may be, for example, an unsubstituted phenyl group or a 2-mono-substituted, 3-monosubstituted, 2,3 disubstituted, 2,5 disubstituted or 2,6 disubstituted phenyl group or 2,3-dihydrobenzo[1,4]dioxine, where the substituents are selected from halogen; hydroxyl; $C_{1-3}$ alkoxy; and $C_{1-3}$ alkyl groups wherein the $C_{1-3}$ alkyl group is optionally substituted by hydroxy, fluorine, $C_{1-2}$ alkoxy, amino, mono and di-$C_{1-4}$ alkylamino, or saturated carbocyclic groups having 3 to 6 ring members and/or saturated heterocyclic groups of 5 or 6 ring members and containing 1 or 2 heteroatoms selected from N and O.

In one embodiment, $R^1$ is selected from unsubstituted phenyl, 2-fluorophenyl, 2-hydroxyphenyl, 2-methoxyphenyl, 2-methylphenyl, 2-(2-(pyrrolidin-1-yl)ethoxy)-phenyl, 3-fluorophenyl, 3-methoxyphenyl, 2,6-difluorophenyl, 2-fluoro-6-hydroxyphenyl, 2-fluoro-3-methoxyphenyl, 2-fluoro-5-methoxyphenyl, 2-chloro-6-methoxyphenyl, 2-fluoro-6-methoxyphenyl, 2,6-dichlorophenyl and 2-chloro-6-fluorophenyl, and is optionally further selected from 5-fluoro-2-methoxyphenyl.

In another embodiment, $R^1$ is selected from unsubstituted phenyl, 2-fluorophenyl, 2-hydroxyphenyl, 2-methoxyphenyl, 2-methylphenyl, 2-(2-(pyrrolidin-1-yl)ethoxy)-phenyl, 3-fluorophenyl, 3-methoxyphenyl, 2,6-difluorophenyl, 2-fluoro-6-hydroxyphenyl, 2-fluoro-3-methoxyphenyl and 2-fluoro-5-methoxyphenyl.

Particular groups $R^1$ are 2,6-difluorophenyl, 2-fluoro-6-methoxyphenyl and 2,6-dichlorophenyl.

One particularly preferred group $R^1$ is 2,6-difluorophenyl.

Another particularly preferred group $R^1$ is 2,6-dichlorophenyl.

When $R^1$ is (ii) a monocyclic heteroaryl group containing one or two heteroatoms selected from O, S and N or a bicyclic heteroaryl group containing a single heteroatom, examples of monocyclic and bicyclic heteroaryl groups include furanyl (e.g. 2-furanyl and 3-furanyl), imidazolyl, pyridyl (e.g. 2-pyridyl), indolyl, thienyl (e.g. 2-thienyl and 3-thienyl) groups. The optional substituents for such groups can include chlorine, fluorine, methyl, methoxy, hydroxymethyl, methoxymethyl, morpholinomethyl, piperazinomethyl, N-methylpiperazinomethyl and piperidinylmethyl groups. Particular examples of groups (ii) include unsubstituted 2-furanyl, 3-methyl-2-furanyl, unsubstituted 4-(1H)-imidazolyl, unsubstituted 5-(1H)-imidazolyl, unsubstituted 3-furanyl, unsubstituted 3-thienyl, 2-methyl-3-thienyl and unsubstituted 3-pyrrolyl, and further examples include 4-methoxy-3-thienyl, 5-(1-pyrrolidinyl)methyl-2-furyl and 5-(4-morpholino)methyl-2-furyl groups.

When $R^1$ is (iii) an optionally substituted cycloalkyl group, it can be for example a substituted or unsubstituted cyclopropyl, cyclobutyl, cyclopentyl or cyclohexyl group. When the cycloalkyl group is substituted, preferred substituents include methyl, fluorine and hydroxyl. Particular examples of cycloalkyl groups include 1-methylcyclopropyl, 1-hydroxycyclopropyl, and unsubstituted cyclohexyl, cyclopentyl and cyclobutyl.

In the context of formula (II) and the group $R^1$, examples of optionally substituted hydrocarbyl groups are optionally substituted methyl, ethyl and propyl groups wherein one of the carbon atoms of the hydrocarbyl group is optionally replaced by O, NH, SO or $SO_2$. Particular examples of such groups include methyl, ethyl, trifluoromethyl, methyl and ethyl substituted with a carbocyclic or heterocyclic group having from 3 to 12 ring members, sulphonylmethyl substituted with a carbocyclic or heterocyclic group having from 3 to 12 ring members, hydroxymethyl, hydroxyethyl, 3-hydroxy-2-propyl, propyl, isopropyl, butyl and tertiary butyl. Examples of hydrocarbyl groups and carbocylic and heteroacyclic groups are as set out above in the general definitions of such groups. Particular carbocyclic and heterocyclic groups include unsubstituted or substituted phenyl, indolyl, tetrazolyl, triazolyl, piperidinyl, morpholinyl, piperazinyl, N-methylpiperazinyl, imidazolyl wherein the optional substituents may be selected from the group $R^{10}$, and sub-groups thereof, as defined herein.

In another sub-group of compounds of the formula (II), $R^1$ is a $C_{1-4}$ hydrocarbyl group optionally substituted by one or more substituents selected from fluorine, hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 of the carbon atoms of the hydrocarbyl group may optionally be replaced by an atom or group selected from O, NH, SO and $SO_2$.

In one embodiment, $R^1$ is a group $R^{1a}$—$(V)_n$— where:
n is 0 or 1;
V is selected from $CH_2$, $CH_2CH_2$ and $SO_2CH_2$; and
$R^{1a}$ is a carbocyclic or heterocyclic group selected from phenyl;
five membered heteroaryl rings having up to 4 heteroatom ring members selected from N, O and S;

six membered heteroaryl rings containing one or two nitrogen ring members;

five or six membered saturated non-aromatic heterocyclic rings containing one or two heteroatom ring members selected from N, O, S and $SO_2$;

$C_{3-6}$ cycloalkyl groups; indole; and quinoline;

wherein each of the carbocyclic and heterocyclic groups $R^{1a}$ can be optionally substituted by one or more substituents selected from five or six membered saturated non-aromatic carbocyclic and heterocyclic groups containing up to two heteroatom ring members selected from N, O, S and $SO_2$; hydroxy; amino; oxo; mono-$C_{1-4}$ alkylamino; di-$C_{1-4}$ alkylamino; fluorine; chlorine; nitro; $C_{1-4}$ alkyl-$(O)_q$—wherein q is 0 or 1 and the $C_{1-4}$ alkyl moiety is optionally substituted by fluorine, hydroxy, $C_{1-2}$ alkoxy or a five or six membered saturated non-aromatic carbocyclic or heterocyclic group containing up to two heteroatom ring members selected from N, O, S and $SO_2$; phenyl and $C_{1-2}$-alkylene dioxy.

Specific examples of groups $R^1$—CO— in formula (II) are set out in Table 1 above.

One sub-group of preferred groups $R^1$—CO consists of the groups J, AB, AH, AJ, AL, AS, AX, AY, AZ, BA, BB, BD, BH, BL, BQ and BS.

Another sub-group of groups $R^1$—CO consists of the groups A to BF.

A further sub-group of groups $R^1$—CO consists of the groups A to BS.

Particularly preferred groups are the groups AJ, BQ and BS in Table 1, e.g. the sub-set consisting of AJ and BQ.

Another group of compounds of the invention is represented by the formula (III):

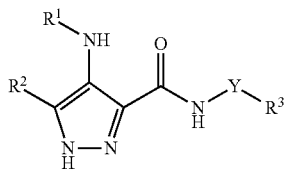

(III)

or salts or tautomers or N-oxides or solvates thereof;

wherein $R^1$, $R^2$, $R^3$ and Y are as defined herein.

Examples of, and preferences, for the groups $R^1$, $R^2$, $R^3$ and Y are as set out above for compounds of the formulae (0), ($I^0$), (I), (Ia), (Ib) and (II) unless the context indicates otherwise.

Particular sub-groups of compounds of the formula (III) include:

compounds wherein $R^1$ is a heteroaryl group containing 1, 2 or 3 heteroatom ring members selected from N, O and S;

(ii) compounds wherein $R^1$ is a $C_{1-6}$ hydrocarbyl group optionally substituted by one or more substituents selected from fluorine, hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 of the carbon atoms of the hydrocarbyl group may optionally be replaced by an atom or group selected from O, NH, SO and $SO_2$; and (iii) compounds wherein $R^1$ is a non-aromatic carbocyclic or heterocyclic group having from 3 to 12 ring members.

Examples of compounds of the formula (III) wherein $R^1$ is (i) a heteroaryl group include 5- and 6-membered monocyclic heteroaryl groups, e.g. containing for 2 heteroatom ring members selected from O, N and S. In one embodiment, the heteroaryl group is a monocyclic group containing 1 or 2 nitrogen ring members. In another embodiment, the heteroaryl groups are selected from 6-membered rings containing 1 or 2 nitrogen ring members, for example pyridine, pyrimidine, pyrazine and pridazine groups, one particular sub-group consisting of pyrazinyl and pyridyl.

The heteroaryl groups can be unsubstituted or substituted by one or more groups $R^{10}$ as defined herein.

Examples of compounds of the formula (III) wherein $R^1$ is (ii) an optionally substituted $C_{1-6}$ hydrocarbyl group include those in which the hydrocarbyl group is unsubstituted hydrocarbyl, for example unsubstituted alkyl such as methyl, ethyl, propyl, isopropyl, butyl, isobutyl, t-butyl, 1-pentyl, 2-pentyl and 3-pentyl.

Examples of compounds wherein $R^1$ is a non-aromatic carbocyclic or heterocyclic group include those wherein the carbocyclic or heterocyclic group is monocyclic and contains up to 2 heteroatoms selected from oxygen and nitrogen. Particular examples of such groups are cyclohexyl and piperidino.

Another sub-group of compounds of the formula (I) can be represented by the formula (IV):

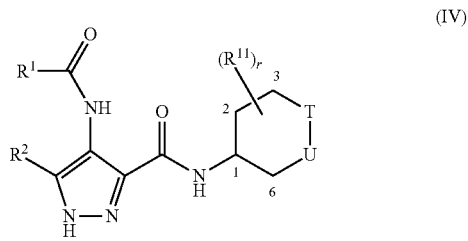

(IV)

or salts or tautomers or N-oxides or solvates thereof;

wherein $R^1$ and $R^2$ are as defined herein;

an optional second bond may be present between carbon atoms numbered 1 and 2;

one of U and T is selected from $CH_2$, $CHR^{13}$, $CR^{11}R^{13}$, $NR^{14}$, $N(O)R^{15}$, O and $S(O)_t$; and the other of U and T is selected from, $NR^{14}$, O, $CH_2$, $CHR^{11}$, $C(R^{11})_2$, and C=O; r is 0, 1, 2, 3 or 4; t is 0, 1 or 2;

$R^{11}$ is selected from hydrogen, halogen (particularly fluorine), $C_{1-3}$ alkyl (e.g. methyl) and $C_{1-3}$ alkoxy (e.g. methoxy);

$R^{13}$ is selected from hydrogen, $NHR^{14}$, NOH, $NOR^{14}$ and $R^a$-$R^b$;

$R^{14}$ is selected from hydrogen and $R^d$—$R^b$;

$R^d$ is selected from a bond, CO, $C(X^2)X^1$, $SO_2$ and $SO_2NR^c$;

$R^a$, $R^b$ and $R^c$ are as hereinbefore defined; and $R^{15}$ is selected from $C_{1-4}$ saturated hydrocarbyl optionally substituted by hydroxy, $C_{1-2}$ alkoxy, halogen or a monocyclic 5- or 6-membered carbocyclic or heterocyclic group, provided that U and T cannot be O simultaneously.

Examples of, and preferences, for the groups $R^1$ and $R^2$ are as set out above for compounds of the formulae (I), (Ia), (Ib) and (II) unless the context indicates otherwise.

Within formula (IV), r can be 0, 1, 2, 3 or 4. In one embodiment, r is 0. In another embodiment, r is 2, and in a further embodiment r is 4.

Within formula (IV), one sub-set of preferred compounds is the set of compounds where there is only a single bond between the carbon atoms numbered 1 and 2.

However, in another sub-set of compounds, there is a double bond between the carbon atoms numbered 1 and 2.

Another sub-set of compounds is characterised by gem disubstitution at the 2-carbon (when there is a single bond between carbon atoms numbers 1 and 2) and/or the 6-carbon. Preferred gem disubstituents include difluoro and dimethyl.

A further sub-set of compounds is characterised by the presence of an alkoxy group, for example a methoxy group at the carbon atom numbered 3, i.e. at a position α with respect to the group T.

Within formula (IV) are compounds wherein, for example, $R^3$ is selected from any of the following ring systems:

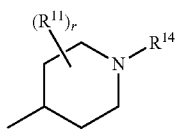
G1

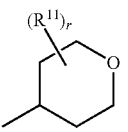
G2

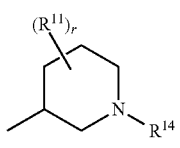
G3

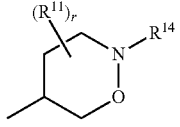
G4

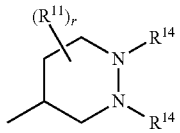
G5

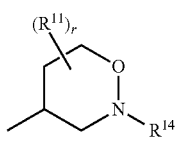
G6

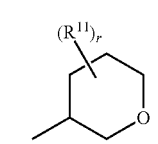
G7

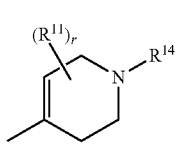
G8

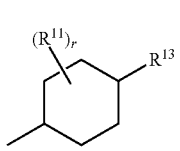
G9

Preferred ring systems include G1 and G3.

A preferred sub-group of compounds within formula (IV) can be represented by the formula (IVa):

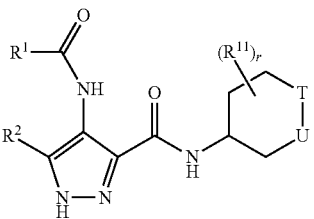
(IVa)

or salts or tautomers or N-oxides or solvates thereof;
wherein $R^1$ and $R^2$ are as hereinbefore defined;
one of U and T is selected from $CH_2$, $CHR^{13}$, $CR^{11}R^{13}$, $NR^{14}$, $N(O)R^{15}$, O and $S(O)_t$; and the other of U and T is selected from $CH_2$, $CHR^{11}$, $C(R^{11})_2$, and C=O; r is 0, 1 or 2; t is 0, 1 or 2;
$R^{11}$ is selected from hydrogen and $C_{1-3}$ alkyl;
$R^{13}$ is selected from hydrogen and $R^a$-$R^b$;
$R^{14}$ is selected from hydrogen and $R^d$—$R^b$;
$R^d$ is selected from a bond, CO, $C(X^2)X^1$, $SO_2$ and $SO_2NR^c$;
$R^a$, $R^b$ and $R^c$ are as hereinbefore defined; and
$R^{15}$ is selected from $C_{1-4}$ saturated hydrocarbyl optionally substituted by hydroxy, $C_{1-2}$ alkoxy, halogen or a monocyclic 5- or 6-membered carbocyclic or heterocyclic group.

Examples of, and preferences, for the groups $R^1$ and $R^2$ are as set out above for compounds of the formulae (0), (I°), (I), (Ia), (Ib) and (II) unless the context indicates otherwise.

In formula (IVa), T is preferably selected from $CH_2$, $CHR^{13}$, $CR^{11}R^{13}$, $NR^{14}$, $N(O)R^{15}$, O and $S(O)_t$; and U is preferably selected from $CH_2$, $CHR^{11}$, $C(R^{11})_2$, and C=O.

In the definitions for substituents $R^{11}$ and $R^{14}$, $R^b$ is preferably selected from hydrogen; monocyclic carbocyclic and heterocyclic groups having from 3 to 7 ring members; and $C_{1-4}$ hydrocarbyl (more preferably acyclic saturated $C_{1-4}$ groups) optionally substituted by one or more substituents selected from hydroxy, oxo, halogen, amino, mono- or di-$C_{1-4}$ hydrocarbylamino, and monocyclic carbocyclic and heterocyclic groups having from 3 to 7 ring members (more preferably 3 to 6 ring members) and wherein one or more carbon atoms of the $C_{1-4}$ hydrocarbyl group may optionally be replaced by O, S, SO, $SO_2$, $NR^c$, $X^1C(X^2)$, $C(X^2)X^1$;
$R^c$ is selected from hydrogen and $C_{1-4}$ hydrocarbyl; and
$X^1$ is O, S or $NR^c$ and $X^2$ is =O, =S or =$NR^c$.

$R^{11}$ is preferably selected from hydrogen and methyl and most preferably is hydrogen.

$R^{13}$ is preferably selected from hydrogen; hydroxy; halogen; cyano; amino; mono-$C_{1-4}$ saturated hydrocarbylamino; di-$C_{1-4}$ saturated hydrocarbylamino; monocyclic 5- or 6-membered carbocyclic and heterocyclic groups; $C_{1-4}$ saturated hydrocarbyl optionally substituted by hydroxy, $C_{1-2}$ alkoxy, halogen or a monocyclic 5- or 6-membered carbocyclic or heterocyclic group.

Particular examples of $R^{13}$ are hydrogen, hydroxy, amino, $C_{1-2}$ alkylamino (e.g. methylamino) $C_{1-4}$ alkyl (e.g. methyl, ethyl, propyl and butyl), $C_{1-2}$ alkoxy (e.g. methoxy), $C_{1-2}$ alkylsulphonamido (e.g. methanesulphonamido), hydroxy-$C_{1-2}$ alkyl (e.g. hydroxymethyl), $C_{1-2}$-alkoxy-$C_{1-2}$ alkyl (e.g. methoxymethyl and methoxyethyl), carboxy, $C_{1-4}$ alkoxycarbonyl (e.g. ethoxycarbonyl) and amino-$C_{1-2}$-alkyl (e.g. aminomethyl).

Particular examples of $R^{14}$ are hydrogen; $C_{1-4}$ alkyl optionally substituted by fluoro or a five or six membered saturated heterocyclic group (e.g. a group selected from (i) methyl, ethyl, n-propyl, i-propyl, butyl, 2,2,2-trifluoroethyl and tetrahydrofuranylmethyl; and/or (ii) 2-fluoroethyl and 2,2-difluoroethyl); cyclopropylmethyl; substituted or unsubstituted pyridyl-$C_{1-2}$ alkyl (e.g. 2-pyridylmethyl); substituted or unsubstituted phenyl-$C_{1-2}$ alkyl (e.g. benzyl); $C_{1-4}$ alkoxycarbonyl (e.g. ethoxycarbonyl and t-butyloxycarbonyl); substituted and unsubstituted phenyl-$C_{1-2}$ alkoxycarbonyl (e.g. benzyloxycarbonyl); substituted and unsubstituted 5- and 6-membered heteroaryl groups such as pyridyl (e.g. 2-pyridyl and 6-chloro-2-pyridyl) and pyrimidinyl (e.g. 2-pyrimidinyl); $C_{1-2}$-alkoxy-$C_{1-2}$ alkyl (e.g. methoxymethyl and methoxyethyl); $C_{1-4}$ alkylsulphonyl (e.g. methanesulphonyl).

Preferred compounds include those in which (i) U is $CHR^{13}$ (more preferably $CH_2$) and T is $NR^{14}$, and (ii) T is $CHR^{13}$ (more preferably $CH_2$) and U is $NR^{14}$.

One particular preferred sub-group of compounds of the formula (IV) can be represented by the formula (Va):

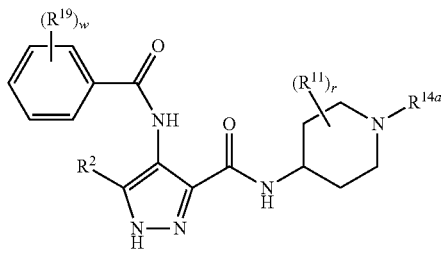

(Va)

or salts or tautomers or N-oxides or solvates thereof;

wherein $R^{14a}$ is selected from hydrogen, $C_{1-4}$ alkyl optionally substituted by fluoro (e.g. methyl, ethyl, n-propyl, i-propyl, butyl and 2,2,2-trifluoroethyl), cyclopropylmethyl, phenyl-$C_{1-2}$ alkyl (e.g. benzyl), $C_{1-4}$ alkoxycarbonyl (e.g. ethoxycarbonyl and t-butyloxycarbonyl), phenyl-$C_{1-2}$ alkoxycarbonyl (e.g. benzyloxycarbonyl), $C_{1-2}$-alkoxy-$C_{1-2}$ alkyl (e.g. methoxymethyl and methoxyethyl), and $C_{1-4}$ alkylsulphonyl (e.g. methanesulphonyl), wherein the phenyl moieties when present are optionally substituted by one to three substituents selected from fluorine, chlorine, $C_{1-4}$ alkoxy optionally substituted by fluoro or $C_{1-2}$-alkoxy, and $C_{1-4}$ alkyl optionally substituted by fluoro or $C_{1-2}$-alkoxy;

w is 0, 1, 2 or 3;
$R^2$ is hydrogen or methyl, most preferably hydrogen;
$R^{11}$ and r are as hereinbefore defined; and
$R^{19}$ is selected from fluorine; chlorine; $C_{1-4}$ alkoxy optionally substituted by fluoro or $C_{1-2}$-alkoxy; and $C_{1-4}$ alkyl optionally substituted by fluoro or $C_{1-2}$-alkoxy.

Another particular preferred sub-group of compounds of the formula (IV) can be represented by the formula (Vb):

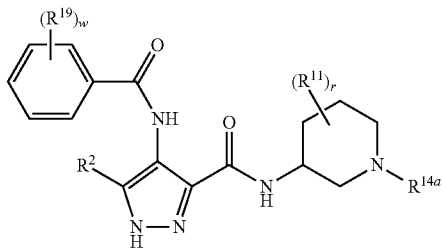

(Vb)

or salts or tautomers or N-oxides or solvates thereof;

wherein $R^{14a}$ is selected from hydrogen, $C_{1-4}$ alkyl optionally substituted by fluoro (e.g. methyl, ethyl, n-propyl, i-propyl, butyl and 2,2,2-trifluoroethyl), cyclopropylmethyl, phenyl-$C_{1-2}$ alkyl (e.g. benzyl), $C_{1-4}$ alkoxycarbonyl (e.g. ethoxycarbonyl and t-butyloxycarbonyl), phenyl-$C_{1-2}$ alkoxycarbonyl (e.g. benzyloxycarbonyl), $C_{1-2}$-alkoxy-$C_{1-2}$ alkyl (e.g. methoxymethyl and methoxyethyl), and $C_{1-4}$ alkylsulphonyl (e.g. methanesulphonyl), wherein the phenyl moieties when present are optionally substituted by one to three substituents selected from fluorine, chlorine, $C_{1-4}$ alkoxy optionally substituted by fluoro or $C_{1-2}$-alkoxy, and $C_{1-4}$ alkyl optionally substituted by fluoro or $C_{1-2}$-alkoxy;

w is 0, 1, 2 or 3;
$R^2$ is hydrogen or methyl, most preferably hydrogen;
$R^{11}$ and r are as hereinbefore defined; and
$R^{19}$ is selected from fluorine; chlorine; $C_{1-4}$ alkoxy optionally substituted by fluoro or $C_{1-2}$-alkoxy; and $C_{1-4}$ alkyl optionally substituted by fluoro or $C_{1-2}$-alkoxy.

In formulae (Va) and (Vb), when w is 1, 2 or 3, it is preferred that the phenyl ring is 2-monosubstituted, 3-monosubstituted, 2,6-disubstituted, 2,3-disubstituted, 2,4-disubstituted 2,5-disubstituted, 2,3,6-trisubstituted or 2,4,6-trisubstituted. Most preferably the phenyl ring is disubstituted at positions 2- and 6- with substituents selected from fluorine, chlorine and methoxy.

$R^{11}$ is preferably hydrogen (or r is 0).
$R^{14a}$ is most preferably hydrogen or methyl.

One preferred sub-group of compounds of the formula (Va) can be represented by the formula (VIa):

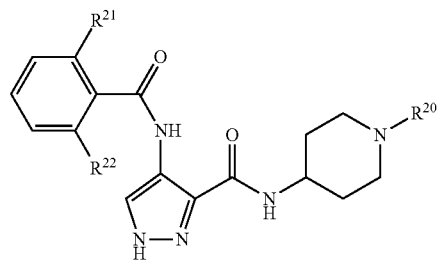

(VIa)

or salts or tautomers or N-oxides or solvates thereof;

wherein $R^{20}$ is selected from hydrogen and methyl;
$R^{21}$ is selected from fluorine and chlorine; and
$R^{22}$ is selected from fluorine, chlorine and methoxy; or
one of $R^{21}$ and $R^{22}$ is hydrogen and the other is selected from chlorine, methoxy, ethoxy, difluoromethoxy, trifluoromethoxy and benzyloxy.

Another preferred sub-group of compounds of the formula (Va) can be represented by the formula (VIb):

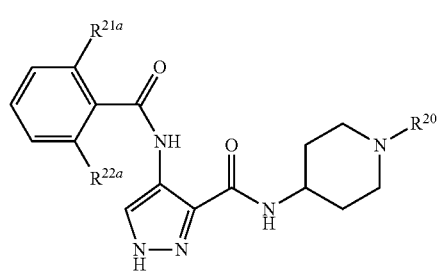

(VIb)

or salts or tautomers or N-oxides or solvates thereof;

wherein $R^{20}$ is selected from hydrogen and methyl;

$R^{21a}$ is selected from fluorine and chlorine; and
$R^{22a}$ is selected from fluorine, chlorine and methoxy.

Particular compounds within formula (VIb) include:
4-(2,6-difluoro-benzoylamino)-1H-pyrazole-3-carboxylic acid piperidin-4-ylamide;
4-(2,6-difluoro-benzoylamino)-1H-pyrazole-3-carboxylic acid (1-methyl-piperidin-4-yl)-amide;
4-(2,6-dichloro-benzoylamino)-1H-pyrazole-3-carboxylic acid piperidin-4-ylamide; and
4-(2-fluoro-6-methoxy-benzoylamino)-1H-pyrazole-3-carboxylic acid piperidin-4-ylamide;
or salts or tautomers or N-oxides or solvates thereof.

A further group of compounds of the invention is represented by the formla (VII):

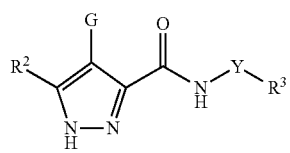

(VII)

or salts or tautomers or N-oxides or solvates thereof;
wherein $R^2$, $R^3$ and Y are as hereinbefore defined and G is a 5- or 6-membered carbocyclic or heterocyclic ring.

The group G can be an unsubstituted carbocyclic or heterocyclic ring or it can be a substituted carbocyclic or heterocyclic ring bearing one or more substituents selected from the groups $R^{10}$ and $R^{10a}$ as hereinbefore defined The carbocyclic or heterocyclic ring may be aromatic or non-aromatic and examples of such heterocyclic rings are set out above. In the context of the group G, preferred heterocyclic rings are those containing a nitrogen ring atom through which the group G is connected to the pyrazole ring. Particular heterocyclic rings are saturated heterocyclic rings containing up to 3 nitrogen atoms (more usually up to 2, for example 1) and optionally an oxygen atom. Particular examples of such rings are six membered rings such as piperidine, piperazine, N-methyl piperazine and morpholine.

When the group G is a carbocyclic group, it can be, for example a 6-membered aryl ring. For example, the group G can be an unsubstituted phenyl group or it can be a substituted phenyl group bearing one or more substituents selected from the groups $R^{10}$ and $R^{10a}$ as hereinbefore defined. The substituents, when present, are more typically small substituents such as hydroxyl, halogen (e.g. fluorine and chlorine), and $C_{1-4}$ hydrocarbyl(methyl, ethyl and cyclopropyl) optionally substituted by fluorine (e.g. trifluoromethyl) or hydroxy (e.g. hydroxymethyl).

In one general embodiment, when X is a non-aromatic heterocyclic group, then $R^3$ may be other than a six membered monocyclic aryl or heteroaryl group linked directly to a 5,6-fused bicyclic heteroaryl group.

A further group of compounds of the invention is represented by the formula (VIII):

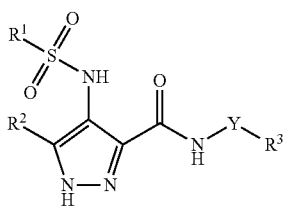

(VIII)

or salts or tautomers or N-oxides or solvates thereof;
wherein $R^1$, $R^2$, $R^3$ and Y are as defined herein.

Preferred groups $R^1$, $R^2$, Y and $R^3$ are as set out above in the section headed "General Preferences and Definitions" and in relation to compounds of the formulae (I) and (II) and sub-groups thereof as defined herein.

For the avoidance of doubt, it is to be understood that each general and specific preference, embodiment and example of the groups $R^1$ may be combined with each general and specific preference, embodiment and example of the groups $R^2$ and/or $R^3$ and/or $R^4$ and/or $R^{10}$ and/or Y and/or $R^g$ and/or sub-groups thereof as defined herein and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Particular compounds of the formulae (0), ($I^0$), (I), (Ia), (Ib), (II), (III), (IV), (IVa), (Va), (Vb), (VIa), (VIb), (VII) or (VIII) and sub-groups thereof are as illustrated in the examples below.

One particularly preferred compound is 4-(2,6-dichloro-benzoylamino)-1H-pyrazole-3-carboxylic acid piperidin-4-ylamide and salts thereof, particularly acid addition salts such as the methanesulphonic acid, acetic acid and hydrochloric acid salts.

Salts, Solvates, Tautomers, Isomers, N-Oxides, Esters, Prodrugs and Isotopes

A reference to a particular cytotoxic compound or signalling inhibitor or compound of the formulae (0), ($I^0$), (I), (Ia), (Ib), (II), (III), (IV), (IVa), (Va), (Vb), (VIa), (VIb), (VII) or (VIII) and sub-groups thereof also includes ionic, salt, solvate, isomers, tautomers, N-oxides, ester, prodrugs, isotopes and protected forms thereof, for example, as discussed below. Preferably, the salts or tautomers or isomers or N-oxides or solvates thereof. More preferably, the salts or tautomers or N-oxides or solvates thereof.

Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. As in the preceding sections of this application, all references to formula (I) should be taken to refer also to formulae (0), ($I^0$), (I), (Ia), (Ib), (II), (III), (IV), (IVa), (Va), (Vb), (VIa), (VIb), (VII) or (VIII) and sub-groups thereof unless the context indicates otherwise.

Salt forms may be selected and prepared according to methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, carbonic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

One particular group of salts includes salts formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, hydrochloric, isethionic, isobutyric, lactic (e.g. (+)-L-lactic and (±)-DL-lactic), lactobionic, laurylsulphonic, maleic, malic, (−)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

Another particular group of salts consists of salts formed from hydrochloric, hydriodic, phosphoric, nitric, sulphuric, citric, lactic, succinic, maleic, malic, isethionic, fumaric, benzenesulphonic, toluenesulphonic, methanesulphonic, ethanesulphonic, naphthalenesulphonic, valeric, acetic, propanoic, butanoic, malonic, glucuronic and lactobionic acids.

One preferred group of salts consists of salts formed from methanesulphonic, hydrochloric, acetic, adipic, L-aspartic and DL-lactic acids.

Particular salts are salts formed with hydrochloric, methanesulphonic and acetic acids.

One preferred salt is the salt formed with methanesulphonic acid.

Another preferred salt is the salt formed with acetic acid.

A further preferred salt is the salt formed with hydrochloric acid.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al³⁺. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

Where the compounds of the invention contain an amine function, these may form quaternary ammonium salts, for example by reaction with an alkylating agent according to methods well known to the skilled person. Such quaternary ammonium compounds are within the scope of formula (0), (I⁰), (I), (Ia), (Ib), (II), (III), (IV), (IVa), (Va), (Vb), (VIa), (VIb), (VII) or (VIII) and sub-groups thereof as defined herein.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Particular salts for use in the preparation of liquid (e.g. aqueous) compositions of the compounds of formulae (I) and sub-groups and examples thereof as described herein are salts having a solubility in a given liquid carrier (e.g. water) of greater than 25 mg/ml of the liquid carrier (e.g. water), more typically greater than 50 mg/ml and preferably greater than 100 mg/ml.

In one embodiment of the invention, the compound of the formula (I) as defined herein is provided in the form of a pharmaceutical composition comprising an aqueous solution containing the said compound in the form of a salt in a concentration of greater than 25 mg/ml, typically greater than 50 mg/ml and preferably greater than 100 mg/ml.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, in compounds of the formula (I) the pyrazole group may take either of the following two tautomeric forms A and B. For simplicity, the general formula (I) illustrates form A but the formula is to be taken as embracing both tautomeric forms.

A

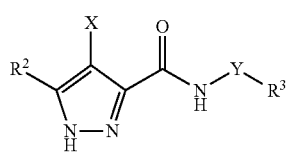

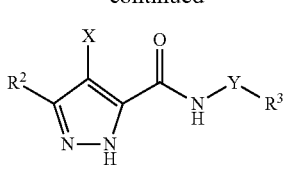

Other examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

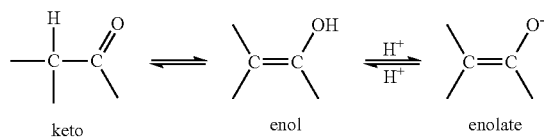

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (0), (I$^0$), (I), (Ia), (Ib), (II), (III), (IV), (IVa), (Va), (Vb), (VIa), (VIb), (VII) or (VIII) and sub-groups thereof as defined herein bearing a carboxylic acid group or a hydroxyl group are also embraced by Formula (I). Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of esters are groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl
(e.g., -Me, -Et, -nPr, -iPr, -nBu, -sBu, -iBu, -tBu);
$C_{1-7}$aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy)carbonyloxymethyl;
1-(4-tetrahydropyranyloxy)carbonyloxyethyl;

(4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Methanesulphonic acid and acetic acid addition salts of compound 4-(2,6-dichloro-benzoylamino)-1H-pyrazole-3-carboxylic acid piperidin-4-ylamide The combinations of the invention may comprise any of the compounds, salts, solvates, tautomers and isotopes thereof and, where the context admits, N-oxides, other ionic forms and prodrugs, as described below.

References to the compound 4-(2,6-dichloro-benzoylamino)-1H-pyrazole-3-carboxylic acid piperidin-4-ylamide and its acid addition salts include within their scope all solvates, tautomers and isotopes thereof and, where the context admits, N-oxides, other ionic forms and prodrugs.

The acid addition salt may be selected from salts formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, isethionic, isobutyric, lactic (e.g. (+)-L-lactic and (±)-DL-lactic), lactobionic, laurylsulphonic, maleic, malic, (−)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

One sub-group of acid addition salts includes salts formed with an acid selected from the group consisting of acetic, adipic, ascorbic (e.g. L-ascorbic), aspartic (e.g. L-aspartic), caproic, carbonic, citric, dodecanoic, fumaric, galactaric, glucoheptonic, gluconic (e.g. D-gluconic), glucuronic (e.g. D-glucuronic), glutamic (e.g. L-glutamic), glycolic, hippuric, lactic (e.g. (+)-L-lactic and (±)-DL-lactic), maleic, palmitic, phosphoric, sebacic, stearic, succinic, sulphuric, tartaric (e.g. (+)-L-tartaric) and thiocyanic acids.

More particularly the salts are acid addition salts formed with an acid selected from methanesulphonic acid and acetic acid, and mixtures thereof.

In one embodiment, the salt is an acid addition salt formed with methanesulphonic acid.

In another embodiment, the salt is an acid addition salt formed with acetic acid.

For convenience the salts formed from methanesulphonic acid and acetic acid may be referred to herein as the methanesulphonate or mesylate salts and acetate salts respectively.

In the solid state, the salts can be crystalline or amorphous or a mixture thereof.

In one embodiment, the salts are amorphous.

In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

In another embodiment, the salts are substantially crystalline; i.e. they are from 50% to 100% crystalline, and more particularly they may be at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

In a further embodiment, the salts are selected from the group consisting of salts that are from 50% to 100% crystalline, salts that are at least 50% crystalline, salts that are at least 60% crystalline, salts that are at least 70% crystalline, salts that are at least 80% crystalline, salts that are at least 90% crystalline, salts that are at least 95% crystalline, salts that are at least 98% crystalline, salts that are at least 99% crystalline, salts that are at least 99.5% crystalline, and salts that are at least 99.9% crystalline, for example 100% crystalline.

More preferably the salts may be those (or may be selected from the group consisting of those) that are 95% to 100% crystalline, for example at least 98% crystalline, or at least 99% crystalline, or at least 99.5% crystalline, or at least 99.6% crystalline or at least 99.7% crystalline or at least 99.8% crystalline or at least 99.9% crystalline, for example 100% crystalline.

One example of a substantially crystalline salt is a crystalline salt formed with methanesulphonic acid.

Another example of a substantially crystalline salt is a crystalline salt formed with acetic acid.

The salts, in the solid state, can be solvated (e.g. hydrated) or non-solvated (e.g. anhydrous).

In one embodiment, the salts are non-solvated (e.g. anhydrous). An example of a non-solvated salt is the crystalline salt formed with methanesulphonic acid as defined herein.

The term "anhydrous" as used herein does not exclude the possibility of the presence of some water on or in the salt (e.g a crystal of the salt). For example, there may be some water present on the surface of the salt (e.g. salt crystal), or minor amounts within the body of the salt (e.g. crystal). Typically, an anhydrous form contains fewer than 0.4 molecules of water per molecule of compound, and more preferably contains fewer than 0.1 molecules of water per molecule of compound, for example 0 molecules of water.

In another embodiment, the salts are solvated. Where the salts are hydrated, they can contain, for example, up to three molecules of water of crystallisation, more usually up to two molecules of water, e.g. one molecule of water or two molecules of water. Non-stoichiometric hydrates may also be formed in which the number of molecules of water present is less than one or is otherwise a non-integer. For example, where there is less than one molecule of water present, there may be for example 0.4, or 0.5, or 0.6, or 0.7, or 0.8, or 0.9 molecules of water present per molecule of compound.

Other solvates include alcoholates such as ethanolates and isopropanolates.

The salts can be synthesized from the parent compound 4-(2,6-dichloro-benzoylamino)-1H-pyrazole-3-carboxylic acid piperidin-4-ylamide by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the parent compound 4-(2,6-dichloro-benzoylamino)-1H-pyrazole-3-carboxylic acid piperidin-4-ylamide with the appropriate acid in water or in an organic solvent, or in a mixture of the two; generally, nonaqueous media such as ether, ethyl acetate, ethanol, isopropanol, or acetonitrile are used.

One method of preparing an acid addition salt of 4-(2,6-dichloro-benzoylamino)-1H-pyrazole-3-carboxylic acid piperidin-4-ylamide comprises forming a solution of 4-(2,6-dichloro-benzoylamino)-1H-pyrazole-3-carboxylic acid piperidin-4-ylamide free base in a solvent (typically an organic solvent) or mixture of solvents, and treating the solution with an acid to form a precipitate of the acid addition salt.

The acid may be added as a solution in a solvent which is miscible with the solvent in which the free base is dissolved. The solvent in which the free base is initially dissolved may be one in which the acid addition salt thereof is insoluble. Alternatively, the solvent in which the free base is initially dissolved may be one in which the acid addition salt is at least partially soluble, a different solvent in which the acid addition salt is less soluble subsequently being added such that the salt precipitates out of solution.

In an alternative method of forming an acid addition salt, 4-(2,6-dichloro-benzoylamino)-1H-pyrazole-3-carboxylic acid piperidin-4-ylamide is dissolved in a solvent comprising a volatile acid and optionally a co-solvent, thereby to form a solution of the acid addition salt with the volatile acid, and the resulting solution is then concentrated or evaporated to isolate the salt. An example of an acid addition salt that can be made in this way is the acetate salt.

In another aspect, the combination of the invention includes an acid addition salt of 4-(2,6-dichloro-benzoylamino)-1H-pyrazole-3-carboxylic acid piperidin-4-ylamide as defined herein, obtained (or obtainable) by treating a compound of the formula (X):

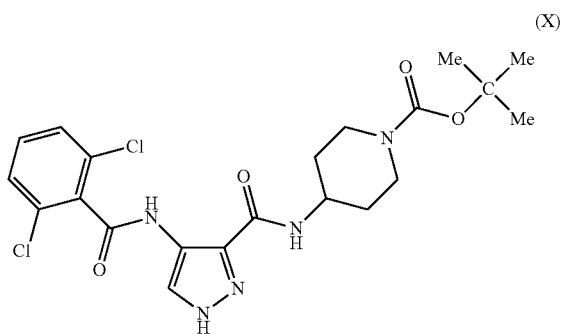 [SMILES: CC(C)(C)OC(=O)N1CCC(NC(=O)c2n[nH]cc2NC(=O)c2c(Cl)cccc2Cl)CC1]

(X)

with an organic or inorganic acid as defined herein, other than hydrochloric acid, in an organic solvent to remove the tert-butyloxycarbonyl group and form an acid addition salt of 4-(2,6-dichloro-benzoylamino)-1H-pyrazole-3-carboxylic acid piperidin-4-ylamide with the organic or inorganic acid, and optionally isolating the acid addition salt thus formed.

The salt is typically precipitated from the organic solvent as it is formed and hence can be isolated by separation of the solid from the solution, e.g. by filtration.

One salt form can be converted to the free base and optionally to another salt form by methods well known to the skilled person. For example, the free base can be formed by passing the salt solution through a column containing an amine stationary phase (e.g. a Strata-$NH_2$ column). Alternatively, a solution of the salt in water can be treated with sodium bicarbonate to decompose the salt and precipitate out the free base. The free base may then be combined with another acid by one of the methods described above or elsewhere herein.

The methanesulphonate salt form is particularly advantageous because of its good stability at elevated temperatures and in conditions of high relative humidity, its non-hygroscopicity (as defined herein), absence of polymorph and hydrate formation, and stability in aqueous conditions. Moreover, it has excellent water solubility and has better physiochemical properties (such as a high melting point) relative to other salts.

The term 'stable' or 'stability' as used herein includes chemical stability and solid state (physical) stability. The term 'chemical stability' means that the compound can be stored in an isolated form, or in the form of a formulation in which it is provided in admixture with for example, pharmaceutically acceptable carriers, diluents or adjuvants as described herein, under normal storage conditions, with little or no chemical degradation or decomposition. 'Solid-state stability' means the compound can be stored in an isolated solid form, or the form of a solid formulation in which it is provided in admixture with, for example, pharmaceutically acceptable carriers, diluents or adjuvants as described herein, under normal storage conditions, with little or no solid-state transformation (e.g. hydration, dehydration, solvatisation, desolvatisation, crystallisation, recrystallisation or solid-state phase transition).

The terms "non-hygroscopic" and "non-hygroscopicity" and related terms as used herein refer to substances that absorb less than 5% by weight (relative to their own weight) of water when exposed to conditions of high relative humidity, for example 90% relative humidity, and/or do not undergo changes in crystalline form in conditions of high humidity and/or do not absorb water into the body of the crystal (internal water) in conditions of high relative humidity.

Preferred salts for use in the combinations of the invention are acid addition salts (such as the mesylate and acetate and mixtures thereof as defined herein) having a solubility in a given liquid carrier (e.g. water) of greater than 15 mg/ml of the liquid carrier (e.g. water), more typically greater than 20 mg/ml, preferably greater than 25 mg/ml, and more preferably greater than 30 mg/ml.

In another aspect, there is provided a combination comprising an aqueous solution containing an acid addition salt of 4-(2,6-dichloro-benzoylamino)-1H-pyrazole-3-carboxylic acid piperidin-4-ylamide (such as the mesylate and acetate and mixtures thereof as defined herein, and preferably the mesylate) in a concentration of greater than 15 mg/ml, typically greater than 20 mg/ml, preferably greater than 25 mg/ml, and more preferably greater than 30 mg/ml.

In a preferred embodiment, the combination comprises an aqueous solution containing an acid addition salt of 4-(2,6-dichloro-benzoylamino)-1H-pyrazole-3-carboxylic acid piperidin-4-ylamide selected from an acetate or methanesulphonate salt or a mixture thereof in a concentration of greater than 15 mg/ml, typically greater than 20 mg/ml, preferably greater than 25 mg/ml, and more preferably greater than 30 mg/ml.

In another aspect, the combination of the invention includes an aqueous solution of an acid addition salt of 4-(2,6-dichloro-benzoylamino)-1H-pyrazole-3-carboxylic acid piperidin-4-ylamide (such as the mesylate and acetate and mixtures thereof as defined herein), wherein the aqueous solution has a pH of 2 to 12, for example 2 to 9, and more particularly 4 to 7.

In the aqueous solutions defined above, the acid addition salt may be any of the salts described herein but, in one preferred embodiment, is a mesylate or acetate salt as defined herein, and in particular the mesylate salt.

The combinations of the invention may include an aqueous solution of 4-(2,6-dichloro-benzoylamino)-1H-pyrazole-3-carboxylic acid piperidin-4-ylamide in protonated form together with one or more counter ions and optionally one or more further counter ions. In one embodiment one of the counter ions is selected from methanesulphonate and acetate.

In another embodiment one of the counter ions is from the formulation buffer as described herein such as acetate. In a further embodiment there may be one or more further counter ions such as a chloride ion (e.g. from saline).

The combinations of the invention may include an aqueous solution of 4-(2,6-dichloro-benzoylamino)-1H-pyrazole-3-carboxylic acid piperidin-4-ylamide in protonated form together with one or more counter ions selected from methanesulphonate and acetate and optionally one or more further counter ions such as a chloride ion.

In the situation where there is more than one counter ion the aqueous solution of 4-(2,6-dichloro-benzoylamino)-1H-pyrazole-3-carboxylic acid piperidin-4-ylamide in protonated form will potentially contain a mixture of counter ions for example a mixture of methanesulphonate and acetate counter ions and optionally one or more further counter ions such as a chloride ion.

The combinations of the invention may include an aqueous solution of 4-(2,6-dichloro-benzoylamino)-1H-pyrazole-3-carboxylic acid piperidin-4-ylamide in protonated form together with one or more counter ions selected from methanesulphonate and acetate and optionally one or more further counter ions such as a chloride ion, and a mixture thereof.

The aqueous solutions can be formed inter alia by dissolving a mesylate salt in a solution of acetate ions (e.g an acetate buffer) or by dissolving an acetate salt in a solution of mesylate ions. The mesylate and acetate ions may be present in the solution in a mesylate:acetate ratio of from 10:1 or less, for example 10:1 to 1:10, more preferably less then 8:1, or less than 7:1, or less than 6:1, or less than 5:1 or less than 4:1 or less than 3:1 or less than 2:1 or less than 1:1, more particularly from 1:1 to 1:10. In one embodiment, the mesylate and acetate ions are present in the solution in a mesylate:acetate ratio of from 1:1 to 1:10, for example 1:1 to 1:8, or 1:1 to 1:7 or 1:1 to 1:6 or 1:1 to 1:5, e.g. approximately 1:4.8.

The aqueous solutions of the salts may be buffered or unbuffered but in one embodiment are buffered.

In the context of the acid addition salt formed with methanesulphonic acid, a preferred buffer is a buffer formed from acetic acid and sodium acetate, for example at a solution pH of approximately 4.6. At this pH and in the acetate buffer, the methanesulphonic acid salt has a solubility of about 35 mg/ml.

The salts for use in the combinations of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms therefore also form part of the invention.

Biological Activity

The cytotoxic compounds and signalling inhibitors of the combinations of the invention interfere with metabolic processes vital to the physiology and proliferation of cancer cells as described above and have activity against various cancers.

The compounds of the formulae (0), (I$^0$), (I), (Ia), (Ib), (II), (III), (IV), (IVa), (Va), (Vb), (VIa), (VIb), (VII) or (VIII) and sub-groups thereof are inhibitors or modulators (in particular inhibitors) of one or more cyclin dependent kinases and/or glycogen synthase kinases, and in particular one or more cyclin dependent kinases selected from CDK1, CDK2, CDK3, CDK4, CDK5, CDK6 and CDK9, and more particularly selected from CDK1, CDK2, CDK3, CDK4, CDK5 and CDK9.

Preferred compounds of the formulae (0), (I$^0$), (I), (Ia), (Ib), (II), (III), (IV), (IVa), (Va), (Vb), (VIa), (VIb), (VII) or (VIII) and sub-groups thereof are compounds that inhibit one or more CDK kinases selected from CDK1, CDK2, CDK4 and CDK9, for example CDK1 and/or CDK2.

The compounds of the formulae (0), (I$^0$), (I), (Ia), (Ib), (II), (III), (IV), (IVa), (Va), (Vb), (VIa), (VIb), (VII) or (VIII) and sub-groups thereof may modulate or inhibit GSKs such as glycogen synthase kinase-3 (GSK3).

As a consequence of their activity in modulating or inhibiting CDK kinases and/or glycogen synthase kinases, and the activity of the cytotoxic agents and signalling inhibitors described herein, the combinations of the invention are expected to be useful in providing a means of arresting, or recovering control of, the cell cycle in abnormally dividing cells. It is therefore anticipated that the compounds will prove useful in treating or preventing proliferative disorders such as cancers.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. In particular RB+ve tumours may be particularly sensitive to CDK inhibitors. RB-ve tumours may also be sensitive to CDK inhibitors.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma, a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; Kaposi's sarcoma, B-cell lymphoma and chronic lymphocytic leukaemia.

The cancers may be cancers which are sensitive to inhibition of any one or more cyclin dependent kinases selected from CDK1, CDK2, CDK3, CDK4, CDK5 and CDK6, for example, one or more CDK kinases selected from CDK1, CDK2, CDK4 and CDK5, e.g. CDK1 and/or CDK2.

Whether or not a particular cancer is one which is sensitive to inhibition by a cyclin dependent kinase may be determined by means of a cell growth assay as set out in the examples below or by a method as set out in the section headed "Methods of Diagnosis".

Thus, in the pharmaceutical compositions, uses or methods of this invention for treating a disease or condition comprising abnormal cell growth, the disease or condition comprising abnormal cell growth in one embodiment is a cancer.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes breast cancer, ovarian cancer, colon cancer, prostate cancer, oesophageal cancer, squamous cancer and non-small cell lung carcinomas.

A further sub-set of cancers includes non small cell lung cancer, colon cancer, breast cancer, non-hodgkin's lymphoma, multiple myeloma and chromic lymphocytic leukemia.

A yet further sub-set of cancers includes breast cancer, colorectal cancer, ovarian cancer and non-small cell lung carcinoma.

A yet further sub-set of cancers includes colorectal cancer, ovarian cancer and non-small cell lung carcinoma.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma).

One particular cancer is chronic lymphocytic leukaemia.

Another particular cancer is mantle cell lymphoma.

Another particular cancer is diffuse large B cell lymphoma.

The activity of the compounds of the invention as inhibitors or modulators of cyclin dependent kinases and/or glycogen synthase kinases (e.g. GSK-3) can be measured using the assays set forth in the examples below and the level of activity exhibited by a given compound can be defined in terms of the 1050 value. Preferred compounds of the present invention are compounds having an 1050 value of less than 1 micromole, more preferably less than 0.1 micromole.

Methods for the Preparation of Compounds of Formula (I) of the Invention

Compounds of the formula (I) and the various sub-groups thereof can be prepared in accordance with synthetic methods well known to the skilled person. Unless stated otherwise, $R^1$, $R^2$, $R^3$, Y, X and A are as hereinbefore defined.

In this section, as in all the other sections of this application, references to formula (I) should be taken to refer also to formulae (0), ($I^0$), (I), (Ia), (Ib), (II), (III), (IV), (IVa), (Va), (Vb), (VIa), (VIb), (VII) or (VIII) and sub-groups thereof unless the context indicates otherwise.

Compounds of the formula (I) wherein $R^1$-A- forms an acyl group $R^1$—CO— can be prepared by reacting a carboxylic acid of the formula $R^1$—$CO_2H$ or an activated derivative thereof with an appropriately substituted 4-amino-pyrazole as shown in Scheme 1.

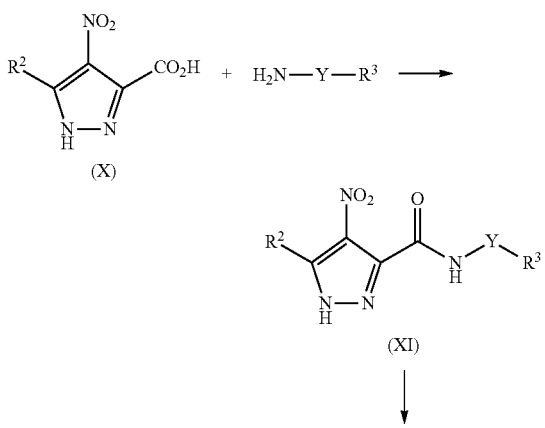

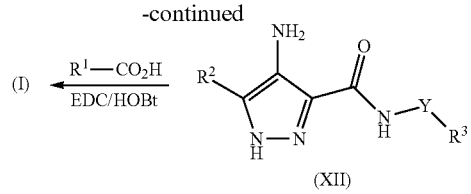

The starting material for the synthetic route shown in Scheme 1 is the 4-nitro-pyrazole-3-carboxylic acid (X) which can either be obtained commercially or can be prepared by nitration of the corresponding 4-unsubstituted pyrazole carboxy compound.

The 4-nitro-pyrazole carboxylic acid (X), or a reactive derivative thereof, is reacted with the amine $H_2N$—Y—$R^3$ to give the 4-nitro-amide (XI). The coupling reaction between the carboxylic acid (X) and the amine is preferably carried out in the presence of a reagent of the type commonly used in the formation of peptide linkages. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC but also known in the art as EDCI and WSCDI) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Preferred coupling reagents include EDC (EDAC) and DCC in combination with HOAt or HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

As an alternative, a reactive derivative of the carboxylic acid, e.g. an anhydride or acid chloride, may be used. Reaction with a reactive derivative such an anhydride is typically accomplished by stirring the amine and anhydride at room temperature in the presence of a base such as pyridine.

Amines of the formula $H_2N$—Y—$R^3$ can be obtained from commercial sources or can be prepared by any of a large number of standard synthetic methods well known those skilled in the art, see for example see *Advanced Organic Chemistry* by Jerry March, $4^{th}$ Edition, John Wiley & Sons, 1992, and Organic Syntheses, Volumes 1-8, John Wiley, edited by Jeremiah P. Freeman (ISBN: 0-471-31192-8), 1995, and see also the methods described in the experimental section below.

The nitro-pyrazole amide (XI) is reduced to give the corresponding 4-amino-compound of the formula (XII). The reduction may be carried out by standard methods such as catalytic hydrogenation, for example in the presence of palladium on carbon in a polar solvent such as ethanol or dimethylformamide at room temperature. As an alternative, reduction may be effected using a reducing agent such as tin (II) chloride in ethanol, typically with heating, for example to the reflux temperature of the solvent.

The 4-amino-pyrazole compound (XII) is then reacted with a carboxylic acid of the formula $R^1$—$CO_2H$, or a reactive derivative thereof, using the methods and conditions described above for the formation of the amide (XI), to give a compound of the formula (I).

Carboxylic acids of the formula $R^1$—$CO_2H$ can be obtained commercially or can be synthesised according to methods well known to the skilled person, see for example *Advanced Organic Chemistry and Organic Syntheses*, the details for which are given above.

Compounds of the formula (I) in which X is a group $R^1$-A-$NR^4$, where A is a bond, can be prepared from the 4-amino compounds of the formula (XII) by a number of methods. Reductive amination with an appropriately substituted aldehyde or ketone can be carried out in the presence of variety of reducing agents (see *Advanced Organic Chemistry* by Jerry March, $4^{th}$ Edition, John Wiley & Sons, 1992, pp 898-900. For example, reductive amination can be carried out in the presence of sodium triacetoxyborohydride in the presence of an aprotic solvent such as dichloromethane at or near ambient temperatures.

Compounds in which X is a group $R^1$-A-$NR^4$ where A is a bond can also be prepared by the reaction of the 4-amino pyrazole compound (XII) with a compound of the formula $R^1$-L in a nucleophilic displacement reaction where L is a leaving group such as a halogen.

In an alternative synthetic route, compounds of the formula (I) can be prepared by reaction of a compound of the formula (XIII) with a compound of the formula $R^3$—Y—$NH_2$. The reaction can be carried out using the amide coupling conditions described above.

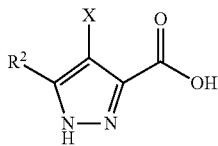

(XIII)

Compounds of the formula (I) where A is NH(C=O) can be prepared using standard methods for the synthesis of ureas. For example, such compounds can be prepared by reacting an aminopyrazole compound of the formula (XII) with a suitably substituted phenylisocyanate in a polar solvent such as DMF. The reaction is conveniently carried out at room temperature.

Compounds of the formula (I) where A is O(C=O) can be made using standard methods for the synthesis of carbamates, for example by reaction of an amino pyrazole compound of the formula (XII) with a chloroformate derivative of the formula $R^1$—O—C(O)—Cl under conditions well known to the skilled person.

Compounds of the formula (I), wherein A is $SO_2$, can be prepared from amino-compounds of the formula (XII) by standard methods for the formation of sulphonamides. For example, compounds of the formula XII) can be reacted with sulphonyl chlorides of the formula $R^1SO_2Cl$ or anhydrides of the formula $(R^1SO_2)_2O$. The reaction is typically carried out in an aprotic solvent such as acetonitrile or a chlorinated hydrocarbon (for example dichloromethane) in the presence of a non-interfering base such as a tertiary amine (e.g. triethylamine) or pyridine, or diisopropylethyl amine (Hunigs base). Alternatively, where the base is a liquid, as is the case with pyridine, the base itself may be used as the solvent for the reaction.

Compounds wherein X is a 5- or 6-membered ring containing a carbon atom ring member linked to the pyrazole group can be prepared by the sequence of reactions set out in Scheme 2.

As shown in Scheme 2, an aldehyde (XIV) (in which X is a C-linked aryl or heteroaryl group such as phenyl) is condensed with malononitrile to give the alkyne (XVI). The reaction is typically carried out in a polar solvent such as ethanol in the presence of a base such as piperidine, usually with heating. The alkyne (XVI) is then reacted with trimethylsilyldiazomethane in the presence an alkyl lithium such as butyl lithium to give the 5-trimethylsilyl pyrazole-3-nitrile (XVII). The reaction is carried out in a dry aprotic solvent such as THF under a protective atmosphere (e.g. nitrogen) at a reduced temperature (e.g. –78° C.).

The nitrile (XVII) is hydrolysed with an alkali metal hydroxide such as potassium hydroxide to give the acid (XIX) and/or the amide (XVII). Where a mixture of acid and amide are formed, they may be separated according to standard methods such as chromatography. The acid (XIX) can then be coupled with an amine of the formula $R^3$—Y—$NH_2$ under typical amide coupling conditions of the type described above to give the compound of the formula (I).

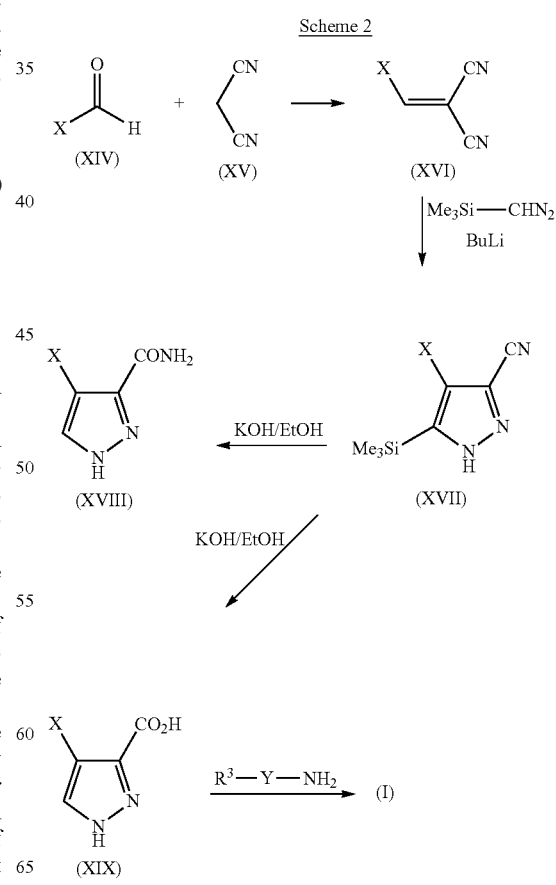

Scheme 2

Alternatively, compounds of the formula (I) in which X is a C-linked aryl or heteroaryl group such as phenyl can be prepared from compounds of the formula (XX):

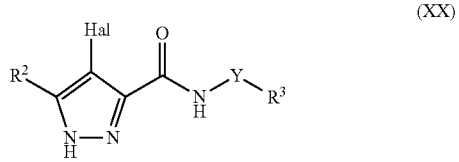

(XX)

where "Hal" is a halogen such as chlorine, bromine or iodine, by means of a Suzuki coupling reaction with the appropriate aryl or heteroaryl boronate. The reaction can be carried out under typical Suzuki Coupling conditions in the presence of a palladium catalyst such as bis(tri-t-butylphosphine)palladium and a base (e.g. a carbonate such as potassium carbonate). The reaction may be carried out in an aqueous solvent system, for example aqueous ethanol, and the reaction mixture is typically subjected to heating, for example to a temperature in excess of 100° C.

Compounds of the formula (XX) can be prepared from amino-pyrazole compounds of the formula (XII) by means of the Sandmeyer reaction (see *Advanced Organic Chemistry*, 4th edition, by Jerry March, John Wiley & Sons, 1992, page 723) in which the amino group is converted to a diazonium group by reaction with nitrous acid, and the diazonium compound is then reacted with a copper (I) halide such as Cu(I)Cl or Cu(I)I.

Once formed, one compound of the formula (I) may be transformed into another compound of the formula (I) using standard chemistry procedures well known in the art. For examples of functional group interconversions, see for example, *Fiesers' Reagents for Organic Synthesis*, Volumes 1-17, John Wiley, edited by Mary Fieser (ISBN: 0-471-58283-2), and *Organic Syntheses*, Volumes 1-8, John Wiley, edited by Jeremiah P. Freeman (ISBN: 0-471-31192-8), 1995.

The starting materials for the synthetic routes shown in the Schemes above, e.g. the pyrazoles of formula (X), can either be obtained commercially or can be prepared by methods known to those skilled in the art. They can be obtained using known methods e.g. from ketones, such as in a process described in EP308020 (Merck), or the methods discussed by Schmidt in *Helv. Chim. Acta.,* 1956, 39, 986-991 and *Helv. Chim. Acta.,* 1958, 41, 306-309. Alternatively they can be obtained by conversion of a commercially available pyrazole, for example those containing halogen, nitro, ester, or amide functionalities, to pyrazoles containing the desired functionality by standard methods known to a person skilled in the art. For example, in 3-carboxy-4-nitropyrazole, the nitro group can be reduced to an amine by standard methods. 4-Nitropyrazole-3-carboxylic acid (XII) can either be obtained commercially or can be prepared by nitration of the corresponding 4-unsubstituted pyrazole carboxy compound, and pyrazoles containing a halogen, may be utilized in coupling reactions with tin or palladium chemistry.

Protecting Groups

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a tetrahydropyranyl (THP) ether; a benzyl, benzhydryl(diphenylmethyl), or trityl(triphenylmethyl)ether; a trimethylsilyl or t-butyldimethylsilyl ether; or an acetyl ester (—OC(=O)CH$_3$, —OAc).

An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz or NH—Z); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec).

For example, in Scheme 1 above, when the moiety R$^3$ in the amine H$_2$N—Y—R$^3$ contains a second amino group, such as a cyclic amino group (e.g. a piperidine or pyrrolidine group), the second amino group can be protected by means of a protecting group as hereinbefore defined, one preferred group being the tert-butyloxycarbonyl (Boc) group. Where no subsequent modification of the second amino group is required, the protecting group can be carried through the reaction sequence to give an N-protected form of a compound of the formula (I) which can then be de-protected by standard methods (e.g. treatment with acid in the case of the Boc group) to give the compound of formula (0), (I$^0$), (I), (Ia), (Ib), (II), (III), (IV), (IVa), (Va), (Vb), (VIa), (VIb), (VII) or (VIII) and sub-groups thereof as defined herein.

Other protecting groups for amines, such as cyclic amines and heterocyclic N—H groups, include toluenesulphonyl (tosyl) and methanesulphonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$alkylsilyl-C$_{1-7}$alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

An example of such a system for purifying compounds via preparative LC-MS is described below in the Examples section of this application (under the heading "Mass Directed Purification LC-MS System"). However, it will be appreciated that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described below could alternatively be used to purify the compounds.

Cytotoxic Compounds and Signalling Inhibitors for use According to the Invention Any of a wide variety of cytotoxic compounds and signalling inhibitors may be used in the combinations of the invention. Cytotoxicity may be assayed or determined using any of a wide variety of techniques well-known to those skilled in the art. The cytotoxic compounds and signalling inhibitors of the combinations of the invention have activity against various cancers.

Preferably, the cytotoxic compounds for use in the combinations of the invention as described herein are selected from the following classes:

1. camptothecin compounds;
2. antimetabolites;
3. vinca alkaloids;
4. taxanes;
5. platinum compounds;
6. DNA binders and Topo II inhibitors (including anthracycline derivatives);
7. a combination of two or more of the foregoing classes.

Suitable signalling inhibitors are discussed in section 7, below.

A reference to a particular cytotoxic compound or signalling inhibitor herein (for example, a reference to a camptothecin compound, antimetabolite, vinca alkaloid, taxane, platinum compound, DNA binder, Topo II inhibitor (including anthracycline derivatives)) is intended to include ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof).

1. Camptothecin Compounds

In one embodiment of the invention, the cytotoxic compound is a camptothecin compound.

Definition: The term "camptothecin compound" as used herein refers to camptothecin per se or analogues of camptothecin as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: Camptothecin compounds are compounds related to or derived from the parent compound camptothecin which is a water-insoluble alkaloid derived from the Chinese tree Camptothecin acuminata and the Indian tree *Nothapodytes foetida*. Camptothecin has a potent inhibitory activity against DNA biosynthesis and has shown high activity against tumour cell growth in various experimental systems. Its clinical use in anti-cancer therapy is, however, limited significantly by its high toxicity, and various analogues have been developed in attempts to reduce the toxicity of camptothecin while retaining the potency of its anti-tumour effect. Examples of such analogues include irinotecan and topotecan.

These compounds have been found to be specific inhibitors of DNA topoisomerase I. Topoisomerases are enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme having a molecular weight of approximately 100,000. The enzyme binds to DNA and introduces a transient single-strand break, unwinds the double helix (or allows it to unwind) and subsequently reseals the break before dissociating from the DNA strand.

Irinotecan, namely 7-ethyl-10-(4-(1-piperidino)-1-piperidino)carbonyloxy-(20S)-camptothecin, and its hydrochloride, also known as CPT 11, have been found to have improved potency and reduced toxicity, and superior water-solubility. Irinotecan has been found to have clinical efficacy in the treatment of various cancers especially colorectal cancer. Another important camptothecin compound is topotecan, namely (S)-9-dimethylaminomethyl-10-hydroxy-camptothecin which, in clinical trials, has shown efficacy against several solid tumours, particularly ovarian cancer and non-small cell lung carcinoma.

Exemplary formulations: A parenteral pharmaceutical formulation for administration by injection and containing a camptothecin compound can be prepared by dissolving 100 mg of a water soluble salt of the camptothecin compound (for example a compound as described in EP 0321122 and in particular the examples therein) in 10 ml of sterile 0.9% saline and then sterilising the solution and filling the solution into a suitable container.

Biological activity: The camptothecin compounds of the combinations of the invention are specific inhibitors of DNA topoisomerase I are described above and have activity against various cancers.

Prior art references: WO 01/64194 (Janssen) discloses combinations of farnesyl transferase inhibitors and camptothecin compounds. EP 137145 (Rhone Poulenc Rorer) discloses camptothecin compounds including irinotecan. EP 321122 (SmithKline Beecham) discloses camptothecin compounds including topotecan.

Problems: Although camptothecin compounds have widely used as chemotherapeutic agents in humans, they are not therapeutically effective in all patients or against all types of tumours. There is therefore a need to increase the inhibitory efficacy of camptothecin compounds against tumour growth and also to provide a means for the use of lower dosages of camptothecin compounds to reduce the potential for adverse toxic side effects to the patient.

Preferences: Preferred camptothecin compounds for use in accordance with the invention include irinotecan and topotecan referred to above. Irinotecan is commercially available for example from Rhone-Poulenc Rorer under the trade name "Campto" and may be prepared for example as described in European patent specification No. 137145 or by processes analogous thereto. Topotecan is commercially available for example from SmithKline Beecham under the trade name "Hycamtin" and may be prepared for example as described in European patent number 321122 or by processes analogous thereto. Other camptothecin compounds may be prepared in conventional manner for example by processes analogous to those described above for irinotecan and topotecan.

Specific embodiments: In one embodiment, the camptothecin compound is irinotecan. In another embodiment, the camptothecin compound is a camptothecin compound other than irinotecan, for example a camptothecin compound such as topotecan.

Posology: The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment. These dosage may be administered for example once, twice or more per course of treatment, which may be repeated for example every 7, 14, 21 or 28 days.

2. Antimetabolites

In another embodiment of the invention, the cytotoxic compound is an antimetabolite.

Definition: The terms "antimetabolic compound" and "antimetabolite" are used as synonyms and define antimetabolic compounds or analogues of antimetabolic compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. Thus, the antimetabolic compounds, otherwise known as antimetabolites, referred to herein consitute a large group of anticancer drugs that interfere with metabolic processes vital to the physiology and proliferation of cancer cells. Such compounds include nucleoside derivatives, either pyrimidine or purine nucleoside analogs, that inhibit DNA synthesis, and inhibitors of thymidylate synthase and/or dihydrofolate reductase enzymes.

Technical background: Antimetabolites (or antimetabolic compounds), constitute a large group of anticancer drugs that interfere with metabolic processes vital to the physiology and proliferation of cancer cells. Such compounds include nucleoside derivatives, either pyrimidine or purine nucleoside analogues, that inhibit DNA synthesis, and inhibitors of thymidylate synthase and/or dihydrofolate reductase enzymes. Anti-tumour nucleoside derivatives have been used for many years for the treatment of various cancers. Among the oldest and most widely used of these derivatives is 5-fluorouracil (5-FU) which has been used to treat a number of cancers such as colorectal, breast, hepatic and head and neck tumours.

In order to enhance the cytotoxic effect of 5-FU, leucovorin has been used with the drug to modulate levels of thymidylate synthase which are critical to ensure that malignant cells are sensitive to the effect of 5-FU.

However, various factors limit the use of 5-FU, for example tumour resistance, toxicities, including gastrointestinal and haematological effects, and the need for intravenous administration. Various approaches have been taken to overcome these disadvantages including proposals to overcome the poor bioavailability of 5-FU and also to increase the therapeutic index of 5-FU, either by reducing systemic toxicity or by increasing the amount of active drug reaching the tumour.

One such compound which provides improved therapeutic advantage over 5-FU is capecitabine, which has the chemical name [1-(5-deoxy-β-D-ribofuranosyl)-5-fluoro-1,2-dihydro-2-oxo-4-pyrimidinyl]-carbamic acid pentyl ester. Capecitabine is a pro-drug of 5-FU which is well absorbed after oral dosing and delivers pharmacologically-active concentrations of 5-FU to tumours, with little systemic exposure to the active drug. As well as offering potentially superior activity to 5-FU, it can also be used for oral therapy with prolonged administration. Another anti-tumour nucleoside derivative is gemcitabine which has the chemical name 2'-deoxy-2',2'-difluoro-cytidine, and which has been used in the treatment of various cancers including non-small cell lung cancer and pancreatic cancer. Further anti-tumour nucleosides include cytarabine and fludarabine. Cytarabine, also known as ara-C, which has the chemical name 1-β-D-arabinofuranosylcytosine, has been found useful in the treatment of acute myelocytic leukemia, chronic myelocytic leukemia (blast phase), acute lymphocytic leukemia and erythroleukemia.

Fludarabine is a DNA synthesis inhibitor, which has the chemical name 9-β-D-arabinofuranosyl-2-fluoro-adenine, and is used for the treatment of refractory B-cell chronic lymphocytic leukaemia. Other antimetabolites used in anti-cancer chemotherapy include the enzyme inhibitors raltitrexed, pemetrexed, and methotrexate.

Raltitrexed is a folate-based thymidylate synthase inhibitor, which has the chemical name N-[5-[N-[(3,4-dihydro-2-methyl-4-oxo-6-quinazolinyl)-methyl-N-methylamino]-2-thenoyl]-L-glutamic acid, and is used in the treatment of advanced colorectal cancer.

Pemetrexed is a thymidylate synthase and transferase inhibitor, which has the chemical name N-[4-[2-(2-amino-4,7-dihydro-4-oxo-1H-pyrrolo[2,3-d]pyrimidin-5-yl)ethyl]benzoyl]-L-glutamic acid, disodium salt, and is used for the treatment of mesothelioma and locally advanced or metastatic non-small-cell lung cancer (SCLC) in previously treated patients.

Methotrexate is an antimetabolite which interrupts cell division by inhibiting DNA replication through dihydrofolate reductase inhibition, resulting in cell death, and has the chemical name is N-[4-[[(2,4-diamino-6-pteridinyl)methyl]-ethylamino]benzoyl]-L-glutamic acid, and is used for the treatment of acute lymphocytic leukemia, and also in the treatment of breast cancer, epidermoid cancers of the head and neck, and lung cancer, particularly squamous cell and small cell types, and advanced stage non-Hodgkin's lymphomas.

Biological activity: The antimetabolic compounds of the combinations of the invention interfere with metabolic processes vital to the physiology and proliferation of cancer cells as described above and have activity against various cancers.

Problems: These anticancer agents have a number of side-effects especially myelosuppression and in some cases nausea and diarrhoea. There is therefore a need to provide a means for the use of lower dosages to reduce the potential of adverse toxic side effects to the patient.

Preferences: Preferred antimetabolic compounds for use in accordance with the invention include anti-tumour nucleosides such as 5-fluorouracil, gemcitabine, capecitabine, cytarabine and fludarabine and enzyme inhibitors such as raltitrexed, pemetrexed and methotrexate referred to herein. Thus, preferred antimetabolic compounds for use in accordance with the invention are anti-tumour nucleoside derivatives including 5-fluorouracil, gemcitabine, capecitabine, cytarabine and fludarabine referred to herein. Other preferred antimetabolic compounds for use in accordance with the invention are enzyme inhibitors including ralitrexed, pemetrexed and methotrexate.

5-Fluorouracil is widely available commercially, or may be prepared for example as described in U.S. Pat. No. 2,802,005. Gemcitabine is commercially available for example from Eli Lilly and Company under the trade name Gemzar, or may be prepared for example as described in European patent specification No. 122707, or by processes analogous thereto. Capecitabine is commercially available for example from Hoffman-La Roche Inc under the trade name Xeloda, or may be prepared for example as described in European patent specification No. 698611, or by processes analogous thereto. Cytarabine is commercially available for example from Pharmacia and Upjohn Co under the trade name Cytosar, or may be prepared for example as described in U.S. Pat. No. 3,116,282, or by processes analogous thereto. Fludarabine is commercially available for example from Schering AG under the trade name Fludara, or may be prepared for example as described in U.S. Pat. No. 4,357,324, or by processes analogous thereto. Ralitrexed is commercially available for example from AstraZeneca plc under the trade name Tomudex, or may be prepared for example as described in European patent specification No. 239632, or by processes analogous thereto. Pemetrexed is commercially available for example from Eli Lilly and Company under the trade name Alimta, or may be prepared for example as described in European patent specification No. 432677, or by processes analogous thereto. Methotrexate is commercially available for example from Lederle Laboratories under the trade name Methotrexate-Lederle, or may be prepared for example as described in U.S. Pat. No. 2,512,572, or by processes analogous thereto. Other antimetabolites for use in the combinations of the invention include 6-mercapto purine, 6-thioguanine, cladribine, 2'-deoxycoformycin and hydroxyurea.

Specific embodiments: In one embodiment, the antimetabolic compound is gemcitabine. In another embodiment, the antimetabolic compound is a antimetabolic compound other than 5-fluorouracil or fludarabine, for example an antimetabolic compound such as gemcitabine, capecitabine, cytarabine, ralitrexed, pemetrexed or methotrexate.

Posology: The antimetabolite compound will be administered in a dosage that will depend on the factors noted above. Examples of dosages for particular preferred antimetabolites are given below by way of example. With regard to anti-tumour nucleosides, these are advantageously administered in a daily dosage of 10 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of 800 to 1200 mg/m$^2$, for capecitabine in a dosage of 1000 to 1200 mg/m$^2$, for cytarabine in a dosage of 100-200 mg/m$^2$ and for fludarabine in a dosage of 10 to 50 mg/m$^2$.

For the following enzyme inhibitors, examples are given of possible doses. Thus, raltitrexed can be administered in a dosage of about 3 mg/m$^2$, pemetrexed in a dosage of 500 mg/m$^2$ and methotrexate in a dosage of 30-40 mg/m$^2$.

The dosages noted above may generally be administered for example once, twice or more per course of treatment, which may be repeated for example every 7, 14, 21 or 28 days.

3. Vinca Alkaloids

In another embodiment of the invention, the cytotoxic compound is a vinca alkaloid.

Definition: The term "vinca alkaloid" as used herein refers to vinca alkaloid compounds or analogues of vinca alkaloid compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: The vinca alkaloids for use in the combinations of the invention are anti-tumour vinca alkaloids related to or derived from extracts of the periwinkle plant (*Vinca rosea*). Among these compounds, vinblastine and vincristine are important clinical agents for the treatment of leukaemias, lymphomas and testicular cancer, and vinorelbine has activity against lung cancer and breast cancer.

Biological activity: The vinca alkaloid compounds of the combinations of the invention are tubulin targeting agents and have activity against various cancers, particularly a sub-set of cancers including leukaemias, lymphomas, testicular cancer, lung cancer and breast cancer.

Problems: Vinca alkaloids suffer from toxicological effects. For example, vinblastine causes leukopenia which reaches a nadir in 7 to 10 days following drug administration, after which recovery ensues within 7 days, while vincristine demonstrates some neurological toxicity for example numbness and trembling of the extremities, loss of deep tendon reflexes and weakness of distal limb musculature. Vinorelbine has some toxicity in the form of granulocytopenia but with only modest thrombocytopenia and less neurotoxicity than other vinca alkaloids. There is therefore a need to increase the inhibitory efficacy of anti-tumour vinca alkaloids against tumour growth and also to provide a means for the use of lower dosages of anti-tumour vinca alkaloids to reduce the potential of adverse toxic side effects to the patient.

Preferences: Preferred anti-tumour vinca alkaloids for use in accordance with the invention include vindesine, vinvesir, vinblastine, vincristine and vinorelbine. Particularly preferred anti-tumour vinca alkaloids for use in accordance with the invention include vinblastine, vincristine and vinorelbine referred to above. Vinblastine is commercially available for example as the sulphate salt for injection from Eli Lilly and Co under the trade name Velban, and may be prepared for example as described in German patent specification No. 2124023 or by processes analogous thereto. Vincristine is commercially available for example as the sulphate salt for injection from Eli Lilly and Co under the trade name Oncovin and may be prepared for example as described in the above German patent specification No. 2124023 or by processes analogous thereto. Vincristine is also available as a liposomal formulation under the name Onco-TCS™. Vinorelbine is commercially available for example as the tartrate salt for injection from Glaxo Wellcome under the trade name Navelbine and may be prepared for example as described in U.S. Pat. No. 4,307,100, or by processes analogous thereto. Other anti-tumour vinca alkaloids may be prepared in conventional manner for example by processes analogous to those described above for vinoblastine, vincristine and vinorelbine.

Another preferred vinca alkaloid is vindesine. Vindesine is a synthetic derivative of the dimeric catharanthus alkaloid vinblastine, is available from Lilly under the tradename Eldisine and from Shionogi under the tradename Fildesin. Details of the synthesis of Vindesine are described in Lilly Pat. DE2415980 (1974) and by C. J. Burnett et al., J. Med. Chem. 21, 88 (1978).

Specific embodiments: In one embodiment, the vinca alkaloid compound is selected from vinoblastine, vincristine and vinorelbine. In another embodiment, the vinca alkaloid compound is vinoblastine.

Posology: The anti-tumour vinca alkaloid is advantageously administered in a dosage of 2 to 30 mg pr square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment. These dosages may be administered for example once, twice or more per course of treatment, which may be repeated for example every 1, 14, 21 or 28 days.

4. Taxanes

In another embodiment of the invention, the cytotoxic compound is a taxane.

Definition: The term "taxane compound" as used herein refers to taxane compounds or analogues of taxane compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: The taxanes are a class of compounds having the taxane ring system and related to or derived from extracts from certain species of yew (*Taxus*) trees. These compounds have been found to have activity against tumour cell growth and certain compounds in this class have been used in the clinic for the treatment of various cancers. Thus, for example, paclitaxel is a diterpene isolated from the bark of the yew tree, *Taxus brevifolia*, and can be produced by partial synthesis from 10-acetylbacctin, a precursor obtained from yew needles and twigs or by total synthesis, see Holton et al, J. Am. Chem. Soc. 116; 1597-1601 (1994) and Nicholau et al, Nature 367:630 (1994). Paclitaxel has shown anti-neoplastic activity and more recently it has been established that its antitumour activity is due to the promotion of microtubule polymerisation, Kumar N. J., Biol. Chem. 256: 1035-1041 (1981); Rowinsky et al, J. Natl. Cancer Inst. 82: 1247-1259 (1990); and Schiff et al, Nature 277: 655-667 (1979). Paclitaxel has now demonstrated efficacy in several human tumours in clinical trials, McGuire et al, Ann. Int. Med., 111:273-279 (1989); Holmes et al, J. Natl. Cancer Inst. 83: 1797-1805 (1991); Kohn et al J. Natl. Cancer Inst. 86: 18-24 (1994); and Kohn et al, American Society for Clinical Oncology, 12 (1993). Paclitaxel has for example been used for the treatment of ovarian cancer and also breast cancer.

Another taxane compound which has been used in the clinic is docetaxel which has been shown to have particular efficacy in the treatment of advanced breast cancer. Docetaxel has shown a better solubility in excipient systems than paclitaxel, therefore increasing the ease with which it can be handled and used in pharmaceutical compositions.

Biological activity: The taxane compounds of the combinations of the invention are tubulin targeting agents and have activity against various cancers.

Problems: Clinical use of taxanes has demonstrated a narrow therapeutic index with many patients unable to tolerate the side effects associated with its use. There is therefore a need to increase the inhibitory efficacy of taxane compounds against tumour growth and also to provide a means for the use of lower dosages of taxane compounds to reduce the potential of adverse toxic side effects to the patient.

Preferences: Preferred taxane compounds for use in accordance with the invention include paclitaxel or docetaxel referred to herein. Paclitaxel is available commercially for example under the trade name Taxol from Bristol Myers Squibb and docetaxel is available commercially under the trade name Taxotere from Rhone-Poulenc Rorer. Both compounds and other taxane compounds may be prepared in conventional manner for example as described in EP 253738, EP 253739 and WO 92/09589 or by processes analogous thereto.

Specific embodiments: In one embodiment, the taxane compound is paclitaxel. In another embodiment, the taxane compound is docetaxel.

Posology: The taxane compound is advantageously administered in a dosage of 50 to 400 mg per square metere (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment. These dosage may be administered for example once, twice or more per course of treatment, which may be repeated for example every 7, 14, 21 or 28 days.

5. Platinum Compounds

In another embodiment of the invention, the cytotoxic compound is a platinum compound.

Definition: The term "platinum compounds" as used herein refers to any tumour cell growth inhibiting platinum compound including platinum coordination compounds, compounds which provide platinum in the form of an ion and analogues of platinum compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: In the chemotherapeutic treatment of cancers, cisplatin (cis-diaminodichloroplatinum (II)) has been used successfully for many years in the treatment of various human solid malignant tumours for example testicular cancer, ovarian cancer and cancers of the head and neck, bladder, oesophagus and lung.

More recently, other diamino-platinum complexes, for example carboplatin (diamino(1,1-cyclobutane-dicarboxylato)platinum (II)), have also shown efficacy as chemotherapeutic agents in the treatment of various human solid malignant tumours, carboplatin being approved for the treatment of ovarian cancer. A further antitumour platinum compound is oxaliplatin (L-OHP), a third generation diamino-cyclohexane platinum-based cytotoxic drug, which has the chemical name (1,2-diaminocyclohexane)oxalato-platinum (II). Oxaliplatin is used, for example, for the treatment of metastatic colorectal cancer, based on its lack of renal toxicity and higher efficacy in preclinical models of cancer in comparison to cisplatin.

Biological activity: The platinum compounds of the combinations of the invention have activity against various cancers, in particular against a sub-set of cancers including solid malignant tumours (for example testicular cancer), ovarian cancer, metastatic colorectal cancer and cancers of the head and neck, bladder, oesophagus and lung.

Problems: Although cisplatin and other platinum compounds have been widely used as chemotherapeutic agents in humans, they are not therapeutically effective in all patients or against all types of tumours. Moreover, such compounds need to be administered at relatively high dosage levels which can lead to toxicity problems such as kidney damage. Also, and especially with cisplatin, the compounds cause nausea and vomiting in patients to a varying extent, as well as leucopenia, anemia and thrombocytopenia. There is therefore a need to increase efficacy and also to provide a means for the use of lower dosages to reduce the potential of adverse toxic side effects to the patient.

Preferences: Preferred platinum compounds for use in accordance with the invention include cisplatin, carboplatin and oxaliplatin. Other platinum compounds include chloro (diethylenediamino)-platinum (II) chloride; dichloro(ethylenediamino)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; and tetraplatin. Cisplatin is commercially available for example under the trade name Platinol from Bristol-Myers Squibb Corporation as a powder for constitution with water, sterile saline or other suitable vehicle. Cisplatin may also be prepared for example as described by G. B. Kauffman and D. O. Cowan, Inorg. Synth. 7, 239 (1963), or by processes analogous thereto. Carboplatin is commercially available for example from Bristol-Myers Squibb Corporation under the trade name Paraplatin, or may be prepared for example as described in U.S. Pat. No. 4,140,707, or by processes analogous thereto. Oxaliplatin is commercially available for example from Sanofi-Synthelabo Inc under the trade name Eloxatin, or may be prepared for example as described in U.S. Pat. No. 4,169,846, or by processes analogous thereto. Other platinum compounds and their pharmaceutical compositions are commercially available and/or can be prepared by conventional techniques.

Specific embodiments: In one embodiment, the platinum compound is selected from chloro(diethylenediamino)-platinum (II) chloride; dichloro(ethylenediamino)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; tetraplatin, cisplatin, carboplatin and oxaliplatin. In another embodiment, the platinum compound is a platinum compound other than cisplatin, for example a platinum compound such as chloro(diethylenediamino)-platinum (II) chloride; dichloro(ethylenediamino)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; tetraplatin, carboplatin or oxaliplatin, preferably selected from carboplatin and oxaliplatin.

Posology: The platinum coordination compound is advantageously administered in a dosage of 1 to 500 mg per square meter (mg/m$^2$) of body surface area, for example 50 to 400 mg/m$^2$ particularly for cisplatin in a dosage of about 75 mg/m$^2$, for carboplatin in about 300 mg/m$^2$ and for oxaliplatin in about 50-100 mg/m$^2$. These dosages may be administered for example once, twice or more per course of treatment, which may be repeated for example every 7, 14, 21 or 28 days.

6. Topoisomerase 2 Inhibitors

In another embodiment of the invention, the cytotoxic compound is a topoisomerase 2 inhibitor.

Definition: The term "topoisomerase 2 inhibitor" as used herein refers to topoisomerase 2 inhibitor or analogues of topoisomerase 2 inhibitor as described above, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: An important class of anticancer drugs are the inhibitors of the enzyme topoisomerase 2 which causes double-strand breaks to release stress build-up during DNA transcription and translation. Compounds that inhibit the function of this enzyme are therefore cytotoxic and useful as anti-cancer agents.

Among the topoisomerase 2 inhibitors which have been developed and used in cancer chemotherapy are the podophyllotoxins. These drugs act by a mechanism of action which involves the induction of DNA strand breaks by an interaction with DNA topoisomerase 2 or the formation of free radicals. Podophyllotoxin, which is extracted from the mandrake plant, is the parent compound from which two glycosides have been developed which show significant therapeutic activity in several human neoplasms, including pediatric leukemia, small cell carcinomas of the lung, testicular tumours, Hodgkin's disease, and large cell lymphomas. These derivatives are etoposide (VP-16), which has the chemical name 4'-demethylepipodophyllotoxin 9-[4,6-O—(R)-ethylidene-β-D-glucopyranoside], and teniposide (VM-26), which has the chemical name 4'-demethylepipodophyllotoxin 9-[4,6-0-(R)-2-thenylidene-β-D-glucopyranoside].

Both etoposide and teniposide, however, suffer from certain toxic side-effects especially myelosuppression. Another important class of topoisomerase 2 inhibitors are the anthracycline derivatives which are important anti-tumour agents and comprise antibiotics obtained from the fungus *Streptomyces peuticus* var. *caesius* and their derivatives, characterized by having a tetracycline ring structure with an unusual sugar, daunosamine, attached by a glycosidic linkage. Among these compounds, the most widely used include daunorubicin, which has the chemical name 7-(3-amino-2,3,6-trideoxy-L-lyxohexosyloxy)-9-acetyl-7,8,9,10-tetrahydro-6,9,11-trihydroxy-4-methoxy-5,12-naphthacenequinone, doxorubicin, which has the chemical name 10-[(3-amino-2,3,6-trideoxy-α-L-lyxohexopyranosyl)oxy]-7,8,9,10-tetrahydro-6,8,11-trihydroxy-8-(hydroxylacetyl)-I-methoxy-5,12-naphthacenedione, and idarubicin, which has the chemical name 9-acetyl-[(3-amino-2,3,6-trideoxy-α-L-lyxohexopyranosyl)oxy]-7,8,9,10-tetrahydro-6,9,11-trihydroxy-5,12-naphthacenedione.

Daunorubicin and idarubicin have been used primarily for the treatment of acute leukaemias whereas doxorubicin displays broader activity against human neoplasms, including a variety of solid tumours particularly breast cancer. Another anthracycline derivatives which is useful in cancer chemotherapy is epirubicin. Epirubicin, which has the chemical name (8S-cis)-10-[(3-amino-2,3,6-trideoxy-α-L-arabinohexopyranosyl)oxy]-7,8,9,10-tetrahydro-6,8,11-trihydroxy-8-(hydroxyacetyl)-1-methoxy-5,12-naphthacenedione, is a doxorubicin analog having a catabolic pathway that involves glucuronidation, by uridine diphosphate-glucuronosyl transferase in the liver (unlike that for doxorubicin), which is believed to account for its shorter half-life and reduced cardiotoxicity. The compound has been used for the treatment of various cancers including cervical cancer, endometrial cancer, advanced breast cancer and carcinoma of the bladder but suffers from the side-effects of myelosuppression and cardiotoxicity. The latter side-effect is typical of anthracycline derivatives which generally display a serious cardiomyopathy at higher doses, which limits the doses at which these compounds can be administered. A further type of topoisomerase 2 inhibitor is represented by mitoxantrone, which has the chemical name 1,4-dihydroxy-5,8-bis[[2-[(2-hydroxyethyl)amino]ethyl]amino]-9,10-anthracenedione, and is used for the treatment of multiple sclerosis, non-Hodgkin's lymphoma, acute myelogenous leukaemia, and breast, prostate and liver tumours. Others include losoxantrone and actinomycin D.

Side-effects from administration of mitoxantrone include myelosuppression, nausea, vomiting, stomatitis, alopecia but less cardiotoxicity than anthracyclines.

Biological activity: The topoisomerase 2 inhibitors of the combinations of the invention have activity against various cancers as described above. In particular, they have activity against a sub-set of cancers including leukemia (e.g. acute leukaemias), small cell carcinomas of the lung, testicular tumours, Hodgkin's disease, large cell lymphomas, breast cancer, cervical cancer, endometrial cancer, advanced breast cancer and carcinoma of the bladder.

Problems: This class of cytotoxic compound is associated with side effects, as mentioned above. Thus, there is a need to provide a means for the use of lower dosages to reduce the potential of adverse toxic side effects to the patient.

Preferences: Preferred topoisomerase 2 inhibitor compounds for use in accordance with the invention include anthracycline derivatives, mitoxantrone and podophyllotoxin derivatives as defined to herein.

Preferred anti-tumour anthracycline derivatives for use in accordance with the invention include daunorubicin, doxorubicin, idarubicin and epirubicin referred to above. Daunorubicin is commercially available for example as the hydrochloride salt from Bedford Laboratories under the trade name Cerubidine, or may be prepared for example as described in U.S. Pat. No. 4,020,270, or by processes analogous thereto. Doxorubicin is commercially available for example from Pharmacia and Upjohn Co under the trade name Adriamycin, or may be prepared for example as described in U.S. Pat. No. 3,803,124, or by processes analogous thereto. Doxorubicin derivatives include pegylated doxorubicin hydrochloride and liposome-encapsulated doxorubicin citrate. Pegylated doxorubicin hydrochloride is commercially available from Schering-Plough Pharmaceuticals under the trade name Caeylx; liposome-encapsulated doxorubicin citrate is commercially available for example from Elan Corporation under the trade name Myocet. Idarubicin is commercially available for example as the hydrochloride salt from Pharmacia & Upjohn under the trade name Idamycin, or may be prepared for example as described in U.S. Pat. No. 4,046,878, or by processes analogous thereto. Epirubicin is commercially available for example from Pharmacia and Upjohn Co under the trade name Pharmorubicin, or may be prepared for example as described in U.S. Pat. No. 4,058,519, or by processes analogous thereto. Mitoxantrone is commercially available for example of OSI Pharmaceuticals, under the trade name Novantrone, or may be prepared for example as described in U.S. Pat. No. 4,197,249, or by processes analogous thereto.

Other anti-tumour anthracycline derivatives may be prepared in conventional manner for example by processes analogous to those described above for the specific anthracycline derivatives.

Preferred anti-tumour podophyllotoxin derivatives for use in accordance with the invention include etoposide and teniposide referred to above. Etoposide is commercially available for example from Bristol-Myers Squibb Co under the trade name VePesid, or may be prepared for example as described in European patent specification No 111058, or by processes analogous thereto. Teniposide is commercially available for example from Bristol-Myers Squibb Co under the trade name Vumon, or may be prepared for example as described in PCT patent specification No. WO 93/02094, or by processes analogous thereto. Other anti-tumour podophyllotoxin derivatives may be prepared in conventional manner for example by processes analogous to those described above for etoposide and teniposide.

Specific embodiments: In one embodiment, the topoisomerase 2 inhibitor is an anthracycline derivative, mitoxantrone or a podophyllotoxin derivative. In another embodiment, the topoisomerase 2 inhibitor is selected from daunorubicin, doxorubicin, idarubicin and epirubicin. In a further embodiment, the topoisomerase 2 inhibitor is selected from etoposide and teniposide. Thus, in a preferred embodiment, the topoisomerase 2 inhibitor is etoposide. In another embodiment, the topoisomerase 2 inhibitor is an anthracycline derivative other than doxorubicin, for example a topoisomerase 2 inhibitor such as daunorubicin, idarubicin and epirubicin.

Posology: The anti-tumour anthracycline derivative is advantageously administered in a dosage of 10 to 150 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, for idarubicin in a dosage of about 10 to 15 $mg/m^2$ and for epirubicin in a dosage of about 100-120 $mg/m^2$.

Mitoxantrone is advantageously administered in a dosage of about 12 to 14 $mg/m^2$ as a short intravenous infusion about every 21 days.

The anti-tumour podophyllotoxin derivative is advantageously administered in a dosage of 30 to 300 $mg/m^2$ of body surface area, for example 50 to 250 mg/m particularly for etoposide in a dosage of about 35 to 100 mg/m, and for teniposide in about 50 to 250 $mg/m^2$.

The dosages noted above may generally be administered for example once, twice or more per course of treatment, which may be repeated for example every 7, 14, 21 or 28 days.

The antibiotic bleomycin may also be used as a cytotoxic agent as an ancillary compound according to the invention.

7. Signalling Inhibitors

In another embodiment of the invention, the combination comprises a signaling inhibitor.

Definition: The term "signalling inhibitor" as used herein refers to signalling inhibitors or analogues of signalling inhibitors as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs.

One driver for growth is the epidermal growth factor (EGF), and the receptor for EGF (EGFR) has been implicated in the development and progression of a number of human solid tumours including those of the lung, breast, prostate, colon, ovary, head and neck. EGFR is a member of a family of four receptors, namely EGFR (HER1 or ErbB1), ErbB2 (HER2/neu), ErbB3 (HER3), and ErbB4 (HER4). These receptors are large proteins that reside in the cell membrane, each having a specific external ligand binding domain, a transmembrane domain and an internal domain which has tyrosine kinase enzyme activity. When EGF attaches to EGFR, it activates the tyrosine kinase, triggering reactions that cause the cells to grow and multiply. EGFR is found at abnormally high levels on the surface of many types of cancer cells, which may divide excessively in the presence of EGF. Inhibition of EGFR activity has therefore been a target for chemotherapeutic research in the treatment of cancer. Such inhibition can be effected by direct interference with the target EGFR on the cell surface, for example by the use of antibodies, or by inhibiting the tyrosine kinase activity associated with the activated receptor.

Examples of antibodies which target EGFR are the monoclonal antibodies trastuzumab and cetuximab. Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor. In vitro and in vivo preclinical studies have shown that administration of trastuzumab alone or in combination with paclitaxel or carboplatin significantly inhibits the growth of breast tumour-derived cell lines that over-express the HER2 gene product. In clinical studies trastuzumab has been shown to have clinical activity in the treatment of breast cancer. The most common adverse effects of trastuzumab are fever and chills, pain, asthenia, nausea, vomiting, diarrhea, headache, dyspnea, rhinitis, and insomnia. Trastuzumab has been approved for the treatment of metastatic breast cancer involving over-expression of the HER2 protein in patients who have received one or more chemotherapy regimes.

Cetuximab has been used for the treatment of irotecan-refractory colorectal cancer. It is also being evaluated both as a single agent and in combination with other agents for use in the treatment of a variety of other cancers for example head and neck cancer, metastatic pancreatic carcinoma, and non-small-cell lung cancer. The administration of cetuximab can cause serious side effects, which may include difficulty in breathing and low blood pressure.

Examples of agents which target EGFR tyrosine kinase activity include the tyrosine kinase inhibitors gefitinib and erlotinib. Gefitinib which has the chemical name 4-(3-chloro-4-fluoroanilino)-7-methoxy-6-(3-morpholinopropoxy) quinazoline, is used for the treatment of non-small-cell lung cancer, and is also under development for other solid tumours that over-express EGF receptors such as breast and colorectal cancer. It has been found that patients receiving gefitinib may develop interstitial lung disease that causes inflammation within the lung. Eye irritation has also been observed in patients receiving gefitinib. Erlotinib, which has the chemical name N-(3-ethynyl-phenyl)-6,7-bis(2-methoxyethoxy)-4-quinazoline, has also been used for the treatment of non-small-cell lung cancer, and is being developed for the treatment of various other solid tumours such as pancreatic cancer, the most common side effects being rash, loss of appetite and fatigue; a more serious side effect which has been reported is interstitial lung disease.

Another growth factor which has received attention as a target for anticancer research is the vascular endothelial growth factor (VEGF). VEGF acts via association with a family of cell surface receptors and is a key regulator of vasculogenesis during angiogenic processes including wound healing, retinopathy, psoriasis, inflammatory disorders, tumour growth and metastasis. Studies have shown that over-expression of VEGF is strongly associated with invasion and metastasis in human malignant disease.

An example of an antibody that targets the VEGF/VEGF receptor system is the monoclonal antibody bevacizumab which is a recombinant humanised monoclonal IgG1 antibody that binds to and inhibits the growth factor VEGF. Bevacizumab has been used for the treatment of colorectal cancer, for example in combination with 5-fluorouracil. Bevacizumab is also being developed as a potential treatment for other solid tumours such as metastatic breast cancer, metastatic non-small-cell lung cancer and renal cell carcinoma. The most serious adverse events associated with bevacizumab include gastrointestinal perforations, hypertensive crises, nephrotic syndrome and congestive heart failure. Other therapeutic agents in development which target the action of VEGF at alternate points in the signal transduction cascade intiated by this growth factor include sunitinib which is marketed under the trade name Sutent by Sugen/Pfizer and inhibits the kinase activity of the VEGF receptor. Sutent has demonstrated efficacy in Phase III trials in gastrointestinal tumours.

Another growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment on chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. The most frequently reported drug-related adverse events were edema, nausea, vomiting, cramps and musculoskeletal pain.

A further growth factor target for cancer chemotherapy is inhibition of Raf which is a key enzyme in the signal transduction pathway that triggers cell growth. Abnormal activation of this pathway is a common factor in the development of most cancers, including two-thirds of melanomas. By blocking the action of Raf kinase, it may be possible to reverse the progression of these tumours. One such inhibitor is sorafenib (BAY 43-9006) which has the chemical name 4-(4-(3-(4-chloro-3-(trifluoromethyl)phenyl)ureido)phenoxy)-N2-methylpyridine-2-carboxamide. Sorafenib targets both the Raf signalling pathway to inhibit cell proliferation and the VEGFR/PDGFR signalling cascades to inhibit tumour angiogenesis. Raf kinase is a specific enzyme in the Ras pathway. Mutations in the Ras gene occur in approximately 20 percent of all human cancers, including 90 percent of pancreatic cancers, 50 percent of colon cancers and 30 percent of non-small cell lung cancers. Sorafenib is being investigated for the treatment of a number of cancers including liver and kidney cancer. The most common side effects of sorafenib are pain, swelling, redness of the hands and/or feet, and also rash, fatigue and diarrhea.

Biological activity: The signalling inhibitors of the combinations of the invention are specific inhibitors of cell signalling proteins as described above and have activity against various cancers. Combinations of compounds of Formula I with signalling inhibitors may be beneficial in the treatment and diagnosis of many types of cancer. Combination with a molecularly targeted agent such as a signalling inhibitor (e.g. Iressa, Avastin, herceptin, or Gleevec™) would find particular application in relation to cancers which express or have activated the relevant molecular target such as EGF receptor, VEGF receptor, ErbB2, BCRabl, c-kit, PDGF. Diagnosis of such tumours could be performed using techniques known to a person skilled in the art and as described herein such as RTPCR and FISH.

Problems: There is a need to increase the inhibitory efficacy of signalling inhibitors against tumour growth and also to provide a means for the use of lower dosages of signaling inhibitors to reduce the potential for adverse toxic side effects to the patient.

Preferences: Preferred signalling inhibitors for use in accordance with the invention include antibodies targeting EGFR such as monoclonal antibodies trastuzumab and cetuximab, EGFR tyrosine kinase inhibitors such as gefitinib and erlotinib, VEGF targeting antibody is bevacizumab, PDGFR inhibitor such as imatinib mesylate and Raf inhibitor such as sorafenib referred to herein.

Preferred antibodies targeting EGFR include the monoclonal antibodies trastuzumab and cetuximab. Trastuzumab is commercially available from Genentech Inc under the trade name Herceptin, or may be obtained as described in U.S. Pat. No. 5,821,337. Cetuximab is commercially available from Bristol-Myers Squibb Corporation under the trade name Erbitux, or may be obtained as described in PCT patent specification No. WO 96/40210.

Preferred EGFR tyrosine kinase inhibitors include gefitinib and erlotinib. Gefitinib is commercially available from AstraZeneca plc under the trade name Iressa, or may be obtained as described in PCT patent specification No. WO 96/33980. Erlotinib is commercially available from Pfizer Inc under the trade name Tarceva, or may be obtained as described in PCT patent specification No. WO 96/30347.

A preferred antibody targeting VEGF is bevacizumab which is commercially available from Genentech Inc under the trade name Avastin, or may be obtained as described in PCT patent specification No. WO 94/10202.

A preferred PDGFR inhibitor is imatinib mesylate which is commercially available from Novartis AG under the trade name Gleevec™ (a.k.a. Glivec®), or may be obtained as described in European patent specification No 564409.

A preferred Raf inhibitor is sorafenib which is available from Bayer AG, or may be obtained as described in PCT patent specification No. WO 00/42012.

Specific embodiments: In one embodiment, the signalling inhibitor is gefitinib (Iressa). In other embodiments the signalling inhibitor is selected from trastuzumab, cetuximab, gefitinib, erlotinib, bevacizumab, imatinib mesylate and sorafenib.

Posology: With regard to the EGFR antibodies, these are generally administered in a dosage of 1 to 500 mg per square meter (mg/m$^2$) of body surface area, trastuzumab being advantageously administered in a dosage of 1 to 5 mg/m$^2$ of body surface area, particularly 2 to 4 mg/m$^2$; cetuxumab is advantageously administered in a dosage of about 200 to 400 mg/m$^2$, preferably about 250 mg/m$^2$.

With regard to the EGFR tyrosine kinase inhibitors, these are generally administered in a daily oral dosage of 100 to 500 mg, for example gefitinib in a dosage of about 250 mg and erlotinib in a dosage of about 150 mg.

With regard to the VEGF monoclonal antibody bevacizumab, this is generally administered in a dosage of about 1 to 10 mg/kg for example about 5 mg/kg.

With regard to the PDGF inhibitor imatinib, this is generally administered in a dosage of about 400 to 800 mg per day preferably about 400 mg per day.

With regard to the Raf inhibitor sorfenib, this is still under evaluation but a possible dosage is about 800 mg daily.

These dosages may be administered for example once, twice or more per course of treatment, which may be repeated for example every 7, 14, 21 or 28 days.

PKB Pathway Inhibitors

Another preferred class of signaling inhibitor for use in the combinations of the invention are PKB pathway inhibitors. PKB pathway inhibitors are those that inhibit the activation of PKB, the activity of the kinase itself or modulate downstream targets, blocking the proliferative and cell survival effects of the pathway. Target enzymes in the pathway include Phosphatidyl inositol-3 kinase (PI3K), PKB itself, Mammalian target of rapamycin (MTOR), PDK-1 and p70 S6 kinase and forkhead translocation.

Several components of the PI 3-kinase/PKB/PTEN pathway are implicated in oncogenesis. In addition to growth factor receptor tyrosine kinases, integrin-dependent cell adhesion and G-protein coupled receptors activate PI 3-kinase both directly and indirectly through adaptor molecules. Functional loss of PTEN (the most commonly mutated tumour-suppressor gene in cancer after p53), oncogenic mutations in PI 3-kinase, amplification of PI 3-kinase and overexpression of PKB have been established in many malignancies. In addition, persistent signaling through the PI 3-kinase/PKB pathway by stimulation of the insulin-like growth factor receptor is a mechanism of resistance to epidermal growth factor receptor inhibitors.

The discovery of non-random, somatic mutations in the gene encoding p110α in a range of human tumours suggests an oncogenic role for the mutated PI 3-kinase enzyme (Samuels, et al., Science, 304 554, April 2004). Mutations in p110α have since been detected in the following human tumours: colon (32%), hepatocellular (36%) and endometroid and clear cell cancer (20%). p110α is now the most commonly mutated gene in breast tumours (25-40%). Forkhead family translocations often occur in acute leukemia.

The PI 3-kinase/PKB/PTEN pathway is thus an attractive target for cancer drug development since such agents would be expected to inhibit proliferation and surmount resistance to cytotoxic agents in cancer cells. Examples of PKB pathway inhibitors include PI3K Inhibitors such as Semaphore, SF1126 and MTOR inhibitors such as Rapamycin Analogues. RAD 001 (everolimus) from Novartis is an orally available derivative of the compound rapamycin. The compound is a novel macrolide, which is being developed as an antiproliferative drug with applications as an immunosuppressant and anticancer agent. RAD001 exerts its activity on growth-factor dependent proliferation of cells through its high affinity for an intracellular receptor protein, FKBP-12. The resulting FKBP-12/RAD001 complex then binds with mTOR to inhibit downstream signaling events. The compound is currently in clinical development for a wide variety of oncology indications. CCI 779 (temsirolemus) from Wyeth Pharmaceuticals and AP23573 from Ariad Pharmaceuticals are also rapamycin analogues. AP23841 and AP23573 from Ariad Pharmaceutical also target mTOR. Calmodulin inhibitors from Harvard are forkhead translocation inhibitors. (Nature Reviews drug discovery, Exploiting the PI3K/AKT Pathway for Cancer Drug Discovery; Bryan T. Hennessy, Debra L. Smith, Prahlad T. Ram, Yiling Lu and Gordon B. Mills; December 2005, Volume 4; pages 988-1004).

Preferred PKB pathway inhibitors for use in the combinations of the invention include PKB inhibitors, as described in more detail below:

Definition: The term "PKB inhibitor" is used herein to define a compound which inhibits or modulates protein kinase B (PKB), including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: KRX-0401 (Perifosine/NSC 639966) is a synthetic substituted heterocyclic alkylphosphocholine that acts primarily at the cell membrane targeting signal transduction pathways, including inhibition of PKB phosphorylation. KRX-0401 has been evaluated in phase 1 studies as a potential oral anticancer drug. Dose limiting toxicities included nausea, vomiting and fatigue. Gastrointestinal toxicities increased at higher doses. A phase II trial in refractory sarcoma is planned.

API-2/TCN is a small molecule inhibitor of PKB signaling pathway in tumour cells. Phase I and II clinical trials of API-2/TCN have been conducted on advanced tumours. API-2/TCN exhibited some side effects, which include hepatotoxicity, hypertriglyceridemia, thrombocytopenia, and hyperglycemia. Due to its severe side effects at high doses, API-2/TCN has been limited in the clinic.

RX-0201 is being developed as an AKT protein kinase inhibitor for the treatment of solid tumours. In July 2004, a phase I trial was initiated in patients with advanced or metastasized cancers. Data from this showed RX-0201 inhibited overexpression of Akt and suppressed cancer growth in brain, breast, cervix, liver, lung, ovary, prostate and stomach tumours, and was well tolerated. By March 2005, US Orphan Drug status had been granted to RX-0201 for several solid tumour types.

Enzastaurin HCl (LY317615) suppresses angiogenesis and was advanced for clinical development based upon anti-angiogenic activity. It is described as a selective PKCβ inhibitor. It also has a direct anti-tumour effect, and suppresses GSK3β phosphorylation.

SR-13668 is claimed to be an orally active specific AKT inhibitor that significantly inhibits phospho-AKT in breast cancer cells both in vitro and in vivo. In vivo assessment in mice showed no adverse effects at doses 10 times more than were needed for antitumour activity.

PX-316 is a D-3-deoxy-phosphatidyl-myo-inositol that binds to the PH domain of PKB, trapping it in the cytoplasm and thus preventing PKB activation. Anti-tumour activity was seen in early xenografts and was well tolerated.

Allosteric, selective inhibitors of PKB based on a 2,3-diphenylquinoxaline core or a 5,6-diphenylpyrazin-2(1H)-one core have been developed (Merck).

KRX-0401: In a Phase I weekly dosing study conducted in Europe, the recommended Phase II dose was 600/mg/week. Subsequent studies conducted in the U.S. have shown that much higher doses are well tolerated when the doses are divided and administered at 4 to 6 hour intervals. In addition, it has been shown that KRX-0401 has a very long half-life in the range of 100 hours. This makes the possibility of a relative non-toxic, intermittent dosing schedule very plausible.

A phase I trial of API-2 was conducted using a 5-day continuous infusion schedule. Dose levels ranged from 10 mg/sq m/day×5 days to 40 mg/sq m/day×5 days. Initially, courses were repeated every 3 to 4 weeks. As cumulative toxicity became manifested, the interval between courses was changed to every 6 weeks. Recommended schedule for Phase II studies is 20 mg/sq m/day for 5 days every 6 weeks. A Phase II trial of TCN-P was conducted in metastatic or recurrent squamous cell carcinoma of the cervix using a 5-day continuous infusion schedule. The starting dose was 35 mg/m$^{2 \times 5}$ days and courses were repeated every 6 weeks.

Further PKB inhibitors include Perifosine from Keryx Biopharmaceuticals. Perifosine is an oral Akt inhibitor which exerts a marked cytotoxic effect on human tumour cell lines, and is currently being tested in several phase II trials for treatment of major human cancers. KRX-0401 (Perifosine/NSC 639966) has the structure:

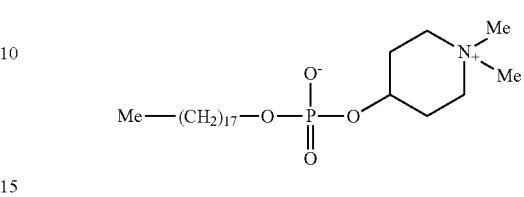

It can be prepared according to Aste Medica patent publication DE4222910 or Xenoport patent publication US2003171303.

API-2/TCN (Triciribine) has the structure:

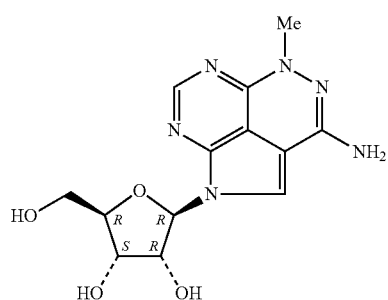

It can be prepared according to Bodor patent publication WO9200988 or Ribapharm patent publication WO2003061385.

Enzastaurin hydrochloride has the structure:

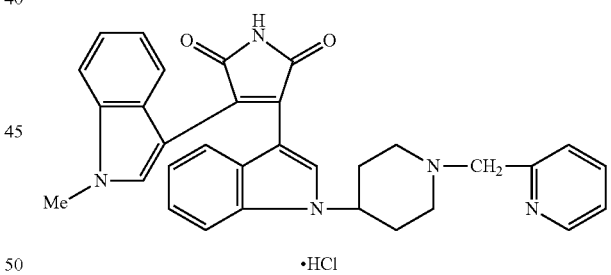

It can be prepared according to Eli Lilly patent publication WO2004006928.

SR 13668 has the structure:

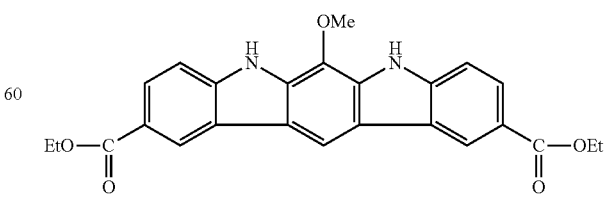

It can be prepared according to SRI International patent publication US2004043965.

NL-71-101 has the structure:

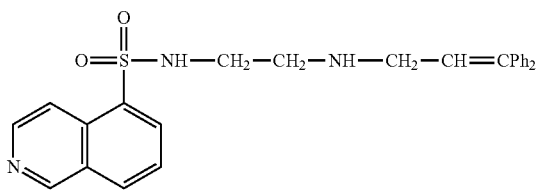

It can be prepared according to Biochemistry (2002), 41(32), 10304-10314 or Peptor patent publication WO2001091754.

DeveloGen (formerly Peptor) is investigating NL-71-101, a protein kinase B (PKB) inhibitor, for the potential treatment of cancer [466579], [539004]. At the beginning of 2003, the compound was undergoing lead optimization [495463]. By February 2004, the company was seeking to outlicense certain development rights to its protein kinase B program [523638].

In 2002, data were published showing that NL-71-101 inhibited the activity of PKB over PKA, PKG and PKC with IC50 values of 3.7, 9, 36 and 104 microM, respectively. NL-71-101 induced apoptosis in OVCAR-3 tumour cells, in which PKB is amplified at concentrations of 50 and 100 microM [466579]. This compound has the structure:

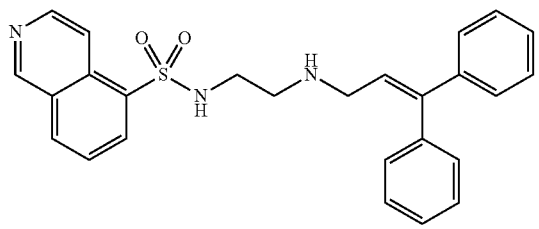 [SMILES: O=S(=O)(NCCNCC=C(c1ccccc1)c1ccccc1)c1cccc2cnccc12]

Specific embodiments: Embodiments contemplated include combinations in which the anti-cancer agent is a PKB inhibitor selected from one or more of the specific compounds described above.

Pharmaceutical Formulations

While it is possible for the active compounds in the combinations of the invention to be administered without any accompanying pharmaceutical excipients or carriers, it is preferable to present them in the form of pharmaceutical compositions (e.g. formulations). As such, they may be formulated for simultaneous or sequential administration.

Where they are intended for sequential administration, they will typically be formulated in separate compositions which may be of the same type or a different type. Thus, for example, the components of the combination may be formulated for delivery by the same route (e.g. both by the oral route or both by injection) or they may be formulated for administration by different routes (e.g. one by the oral route and another by a parenteral route such as by i.v. injection or infusion). In a preferred embodiment the compound 4-(2,6-dichloro-benzoylamino)-1H-pyrazole-3-carboxylic acid piperidin-4-ylamide and salts thereof, particularly acid addition salts such as the methanesulphonic acid, acetic acid and hydrochloric acid salts is administered sequentially (either before or after) or simultaneously with the ancillary compound. Preferably the compound 4-(2,6-dichloro-benzoylamino)-1H-pyrazole-3-carboxylic acid piperidin-4-ylamide and salts thereof, particularly acid addition salts such as the methanesulphonic acid, acetic acid and hydrochloric acid salts is administered using an i.v. formulation as defined herein.

When they are intended for simultaneous administration, they may be formulated together or separately and, as above, may be formulated for administration by the same route or by different routes.

The compositions typically comprise at least one active compound of the combination together with one or more pharmaceutically acceptable carriers, adjuvants, excipients, diluents, fillers, buffers, stabilisers, preservatives, lubricants, or other materials well known to those skilled in the art. The compositions may also include other therapeutic or prophylactic agents, for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF).

Also included are agents that inhibit bone resorption such as bisphosphonate agents e.g. zoledronate, pamidronate and ibandronate, as well as agents that suppress inflammatory responses (such as dexamethazone, prednisone, and prednisolone). Also included are agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self. In one particular embodiment is the combination of 5FU and leucovorin or 5FU and folinic acid. In addition megestrol acetate can be used for the treatment of side-effects including oedema and thromoembolic episodes.

Therefore in one embodiment the combinations further include an additional agent selected from erythropoietin (EPO), granulocyte macrophage-colony stimulating factor (GM-CSF), granulocyte-colony stimulating factor (G-CSF), zoledronate, pamidronate, ibandronate, dexamethazone, prednisone, prednisolone, leucovorin, folinic acid and megestrol acetate.

In particular the combinations further include an additional agent selected from erythropoietin (EPO), granulocyte macrophage-colony stimulating factor (GM-CSF), granulocyte-colony stimulating factor (G-CSF), zoledronate, pamidronate, dexamethazone, prednisone, prednisolone, leucovorin, and folinic acid such as erythropoietin (EPO), granulocyte macrophage-colony stimulating factor (GM-CSF) and granulocyte-colony stimulating factor (G-CSF).

Zoledronic acid is available from Novartis under the Tradename Zometa®. It is used in the treatment of bone metastasis in a variety of tumor types and for the treatment of hypercalcemia.

Pamidronate disodium (APD) available from Novartis under the tradename Aredia is a bone-resorption inhibitor and is used in the treatment of moderate or severe hypercalcemia. Pamidronate disodium is for i.v. injection.

Octreotide acetate is available from Novartis as Sandostatin LAR® (octreotide acetate for injectable suspension) and Sandostatin® (octreotide acetate for injection ampuls or for vials). Octreotide is known chemically as L-Cysteinamide, D-phenylalanyl-L-cysteinyl-L-phenylalanyl-D-tryptophyl- L-lysyl-L-threonyl-N-[2-hydroxy-1-(hydroxy-methyl)propyl]-, cyclic (2,7)-disulfide; [R—(R*,R*)]. Synthetic forms of the brain hormone somatostatin, such as octreotide, work at the site of the tumour. They bind to sst-2/sst-5 receptors to regulate gastrointestinal hormone secretion and affect tumour growth.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides combinations of a cytotoxic compound or signalling inhibitor and a compound of the formula (0) or a sub-group thereof such as formulae ($I^0$), (I), (Ia), (Ib), (II), (III) (IV), (IVa), (Va), (Vb), (VIa), (VIb), (VII) or (VIII) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris (hydroxymethyl)aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at ~5-20 mg/ml, an isotonicifier, a pH 5-8 buffer, and optionally cholesterol.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of formula (0), ($I^0$), (I), (Ia), (Ib), (II), (III), (IV), (IVa), (Va), (Vb), (VIa), (VIb), (VII) or (VIII) and sub-groups thereof as defined herein or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediamietetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; poly-alcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

Pharmaceutical compositions of the present invention for parenteral injection can also comprise pharmaceutically acceptable sterile aqueous or nonaqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If a compound is not stable in aqueous media or has low solubility in aqueous media, it can be formulated as a concentrate in organic solvents. The concentrate can then be diluted to a lower concentration in an aqueous system, and can be sufficiently stable for the short period of time during dosing. Therefore in another aspect, there is provided a pharmaceutical composition comprising a non aqueous solution composed entirely of one or more organic solvents, which can be dosed as is or more commonly diluted with a suitable IV excipient (saline, dextrose; buffered or not buffered) before administration (Solubilizing excipients in oral and injectable formulations, Pharmaceutical Research, 21(2), 2004, p 201-230). Examples of solvents and surfactants are propylene glycol, PEG300, PEG400, ethanol, dimethylacetamide (DMA), N-methyl-2-pyrrolidone (NMP, Pharmasolve), Glycerin, Cremophor EL, Cremophor RH 60 and polysorbate. Particular non aqueous solutions are composed of 70-80% propylene glycol, and 20-30% ethanol. One particular non aqueous solution is composed of 70% propylene glycol, and 30% ethanol. Another is 80% propylene glycol and 20% ethanol. Normally these solvents are used in combination and usually diluted at least 2-fold before IV bolus or IV infusion. The typical amounts for bolus IV formulations are ~50% for Glycerin, propylene glycol, PEG300, PEG400, and ~20% for ethanol. The typical amounts for IV infusion formulations are ~15% for Glycerin, 3% for DMA, and ~10% for propylene glycol, PEG300, PEG400 and ethanol.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are, or 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will be administered to a patient in need thereof (for example a human or animal patient) in an amount sufficient to achieve the desired therapeutic effect.

Where the compounds of the combination of the invention are presented together, they can be formulated together as tablets, capsules, solutions for infusion or injection or any of the other solid or liquid dosage forms described above. For example, where they are formulated together, they may be intimately mixed, or physically separated within the same formulation, for example by virtue of being present in different layers or granules within a tablet, or a separate beads or granules within a capsule. More typically, however, they are formulated separately for separate or concurrent administration.

In one embodiment, the individual components of the combination may be formulated separately and presented together in the form of a kit, optionally under common outer packaging and optionally with instructions for their use.

More commonly these days, pharmaceutical formulations are prescribed to a patient in "patient packs" containing the whole course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physicians instructions.

Accordingly, in a further embodiment, the invention provides a package containing separate dosage units, one or more of which contain a compound of the formula (0), ($I^0$), (I), (Ia), (Ib), (II), (III), (IV), (IVa), (Va), (Vb), (VIa), (VIb), (VII) or (VIII) and sub-groups thereof as defined herein, and one or more of which contain a cytotoxic compound or signalling inhibitor. Dosage units containing a compound of the formula (0), ($I^0$), (I), (Ia), (Ib), (II), (III), (IV), (IVa), (Va), (Vb), (VIa), (VIb), (VII) or (VIII) and sub-groups thereof as defined herein and a cytotoxic compound or signalling inhibitor have suitable amounts of active ingredient as defined herein. A package contains enough tablets, capsules or the like to treat a patient for a pre-determined period of time, for instance for 2 weeks, 1 month or 3 months.

Methods of Treatment

It is envisaged that the combinations containing a cytotoxic compound or signalling inhibitor and compounds of the formula (0) and sub-groups thereof such as formulae ($I^0$), (I), (Ia), (Ib), (II), (III), (IV), (IVa), (Va), (Vb), (VIa), (VIb), (VII) or (VIII) and sub-groups thereof as defined herein will be useful in the prophylaxis or treatment of a range of disease states or conditions mediated by cyclin dependent kinases and/or GSKs (e.g. GSK-3). Examples of such disease states and conditions are set out herein.

The combinations are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

The compounds of the combination can be administered simultaneously or sequentially. When administered sequentially, they can be administered at closely spaced intervals (for example over a period of 5-10 minutes) or at longer intervals (for example 1, 2, 3, 4 or more hours apart, or even longer periods, e.g. 1, 2, 3, 4, 5, 6, or 7 days, apart where required), the precise dosage regimen being commensurate with the properties of the therapeutic agent(s). With sequential administration, the delay in administering the second (or additional) active ingredient should not be such as to lose the advantageous benefit of the efficacious effect of the combination of the active ingredients. In addition, the delay in administering the second (or additional) active ingredient is typically timed so as to allow for any adverse side effects of the first compound to subside to an acceptable level before administration of the second compound, whilst not losing the advantageous benefit of the efficacious effect of the combination of the active ingredients.

The two or more treatments may be given in individually varying dose schedules and via the same or different routes.

For example, one compound may be administered by the oral route and the other compound administered by parenteral administration such as administration by injection (e.g. i.v.) or infusion. In an alternative, both compounds may be administered by injection or infusion. In a further alternative, both compounds may be given orally. In one particular embodiment, the compound of the formula (I) is administered by injection or infusion and the cytotoxic compound or signalling inhibitor is administered orally.

When administered at different times, the administration of one component of the combination may alternate with or interleaf with administration of the other component or the components of the combination may be administered in sequential blocks of therapy. As indicated above, the administration of the components of the combination may be spaced apart in time, for example by one or more hours, or days, or even weeks, provided that they form part of the same overall treatment. In one embodiment of the invention, the compound of the formula (0), ($I^0$), (I), (Ia), (Ib), (II), (III), (IV), (IVa), (Va), (Vb), (VIa), (VIb), (VII) or (VIII) and sub-groups thereof as defined herein is administered sequentially or simultaneously with the cytotoxic compound or signalling inhibitor.

In another embodiment of the invention, the compound of the formula (0), ($I^0$), (I), (Ia), (Ib), (II), (III), (IV), (IVa) (Va), (Vb), (VIa), (VIb), (VII) or (VIII) and sub-groups thereof as defined herein is administered sequentially with the cytotoxic compound or signalling inhibitor in either order.

In a further embodiment, the cytotoxic compound or signalling inhibitor is administered prior to the compound of the formula (0), ($I^0$), (I), (Ia), (Ib), (II), (III), (IV), (IVa), (Va), (Vb), (VIa), (VIb), (VII) or (VIII) and sub-groups thereof as defined herein.

In a further embodiment, the taxane compound e.g. paclitaxel is administered prior to the compound of the formula (0), ($I^0$), (I), (Ia), (Ib), (II), (III), (IV), (IVa), (Va), (Vb), (VIa), (VIb), (VII) or (VIII) and sub-groups thereof as defined herein.

In another embodiment, the cytotoxic compound or signalling inhibitor is administered after the compound of the formula (0), ($I^0$), (I), (Ia), (Ib), (II), (III), (IV), (IVa), (Va), (Vb), (VIa), (VIb), (VII) or (VIII) and sub-groups thereof as defined herein.

In another embodiment of the invention, the compound of the formula (0), ($I^0$), (I), (Ia), (Ib), (II), (III), (IV), (IVa), (Va), (Vb), (VIa), (VIb), (VII) or (VIII) and sub-groups thereof as defined herein and the cytotoxic compound or signalling inhibitor are administered simultaneously.

In another embodiment of the invention, the compound of the formula (0), ($I^0$), (I), (Ia), (Ib), (II), (III), (IV), (IVa), (Va), (Vb), (VIa), (VIb), (VII) or (VIII) and sub-groups thereof as defined herein and the signalling inhibitor are administered simultaneously.

In another embodiment of the invention, the compound of the formula (0), ($I^0$), (I), (Ia), (Ib), (II), (III), (IV), (IVa), (Va), (Vb), (VIa), (VIb), (VII) or (VIII) and sub-groups thereof as defined herein and the cytotoxic compound or signalling inhibitor are administered simultaneously.

In another embodiment, the compound of the formula (0), ($I^0$), (I), (Ia), (Ib), (II), (III), (IV), (IVa), (Va), (Vb), (VIa), (VIb), (VII) or (VIII) and sub-groups thereof as defined herein and the cytotoxic compound or signalling inhibitor are each administered in a therapeutically effective amount with respect to the individual components; in other words, the compound of the formula (0), ($I^0$), (I), (Ia), (Ib), (II), (III), (IV), (IVa), (Va), (Vb), (VIa), (VIb), (VII) or (VIII) and sub-groups thereof as defined herein and the cytotoxic compound or signalling inhibitor are administered in amounts that would be therapeutically effective even if the components were administered other than in combination.

In another embodiment, the compound of the formula (0), ($I^0$), (I), (Ia), (Ib), (II), (III), (IV), (IVa), (Va), (Vb), (VIa), (VIb), (VII) or (VIII) and sub-groups thereof as defined herein and the cytotoxic compound or signalling inhibitor are each administered in a sub-therapeutic amount with respect to the individual components; in other words, the compound of the formula (0), ($I^0$), (I), (Ia), (Ib), (II), (III), (IV), (IVa), (Va), (Vb), (VIa), (VIb), (VII) or (VIII) and sub-groups thereof as defined herein and the cytotoxic compound or signalling inhibitor are administered in amounts that would be therapeutically ineffective if the components were administered other than in combination.

Preferably, the cytotoxic compound or signalling inhibitor and the compound of the formula (0), ($I^0$), (I), (Ia), (Ib), (II), (III), (IV), (IVa), (Va), (Vb), (VIa), (VIb), (VII) or (VIII) and sub-groups thereof as defined herein interact in a synergistic or additive manner.

Preferably, the cytotoxic compound or signalling inhibitor e.g. gemcitabine and the compound of the formula (0), ($I^0$), (I), (Ia), (Ib), (II), (III), (IV), (IVa), (Va), (Vb), (VIa), (VIb), (VII) or (VIII) and sub-groups thereof as defined herein interact in a synergistic or additive manner.

Preferably, the taxane compound e.g. paclitaxel and the compound of the formula (0), ($I^0$), (I), (Ia), (Ib), (II), (III), (IV), (IVa), (Va), (Vb), (VIa), (VIb), (VII) or (VIII) and sub-groups thereof as defined herein interact in a synergistic or additive manner, and in particular a synergistic manner.

Preferably, the signalling inhibitor e.g. Iressa and the compound of the formula (0), ($I^0$), (I), (Ia), (Ib), (II), (III), (IV), (IVa), (Va), (Vb), (VIa), (VIb), (VII) or (VIII) and sub-groups thereof as defined herein interact in a synergistic or additive manner, and in particular a synergistic manner.

A typical daily dose of the compound of the formula (0), ($I^0$), (I), (Ia), (Ib), (II), (III), (IV), (IVa), (Va), (Vb), (VIa), (VIb), (VII) or (VIII) and sub-groups thereof as defined herein can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

An example of a dosage for a 60 kilogram person comprises administering a compound of the formula (I) as defined herein, for example the free base of compound 4-(2,6-dichloro-benzoylamino)-1H-pyrazole-3-carboxylic acid piperidin-4-ylamide at a starting dosage of 4.5-10.8 mg/60 kg/day (equivalent to 75-180 ug/kg/day) and subsequently by an efficacious dose of 44-97 mg/60 kg/day (equivalent to 0.7-1.6 mg/kg/day) or an efficacious dose of 72-274 mg/60 kg/day (equivalent to 1.2-4.6 mg/kg/day). The mg/kg dose would scale pro-rata for any given body weight.

An example of a dosage for the mesylate salt is, at a starting dosage of 5.6-13.5 mg/60 kg/day (equivalent to 93-225

μg/kg/day/person) and subsequently by an efficacious dose of 55-122 mg/60 kg/day (equivalent to 0.9-2.0 mg/kg/day/person) or an efficacious dose of 90-345 mg/60 kg/day (equivalent to 1.5-5.8 mg/kg/day/person).

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered, the type of composition used, and the timing and frequency of the administration of the two components will be commensurate with the nature of the disease or physiological condition being treated and will be at the discretion of the physician.

Accordingly, a person skilled in the art would know through their common general knowledge the dosing regimes and combination therapies to use. It will be appreciated that the preferred method and order of administration and the respective dosage amounts and regimes for each component of the combination will depend on the particular cytotoxic compound or signalling inhibitor and compounds of formula (0), (I$^0$), (I), (Ia), (Ib), (II), (III), (IV), (IVa), (Va), (Vb), (VIa), (VIb), (VII) or (VIII) and sub-groups thereof as defined herein being administered, their route of administration, the particular tumour being treated and the particular host being treated. The optimum method and order of administration and dosage amounts and regime can be readily determined by those skilled in the art using conventional methods and in view of the information set out herein.

As described infra, the compounds of the formula (I) are administered in combination therapy with one of more other cytotoxic compounds, for example in the treatment of a particular disease state (for example a neoplastic disease such as a cancer as hereinbefore defined). Examples of suitable cytotoxic compounds that may be used in the combinations of the invention are described in detail above.

However, the combinations of the invention may also be further combined with other classes of therapeutic agents or treatments that may be administered together (whether concurrently or at different time intervals) with the combinations of the invention, including (but not limited to):

1. hormones, hormone agonists, hormone antagonists and hormone modulating agents (including antiandrogens, antiestrogens and GNRAs);
2. monoclonal antibodies (e.g. monoclonal antibodies to cell surface antigen(s));
3. alkylating agents (including aziridine, nitrogen mustard and nitrosourea alkylating agents);
4. CDK inhibitors;
5. COX-2 inhibitors;
6. HDAC inhibitors;
7. DNA methylase inhibitors;
8. proteasome inhibitors;
9. Other therapeutic or prophylactic agents, for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), granulocyte-colony stimulating factor (G-CSF). In other embodiments, the other therapeutic or prophylactic agents can be as described below.

Alternatively, the combinations of the invention may also be further combined with other classes of therapeutic agents or treatments that may be administered together (whether concurrently or at different time intervals) with the combinations of the invention, including (but not limited to):

1. hormones, hormone agonists, hormone antagonists and hormone modulating agents (including antiandrogens, antiestrogens and GNRAs);
2. monoclonal antibodies (e.g. monoclonal antibodies to cell surface antigen(s));
3. camptothecin compounds;
4. antimetabolites;
5. vinca alkaloids;
6. taxanes;
7. platinum compounds;
8. DNA binders and Topo II inhibitors (including anthracycline derivatives);
9. alkylating agents (including aziridine, nitrogen mustard and nitrosourea alkylating agents);
10. a combination of two or more of the foregoing classes (1)-(9).
11. signalling inhibitors (including PKB signalling pathway inhibitors);
12. CDK inhibitors;
13. COX-2 inhibitors;
14. HDAC inhibitors;
15. DNA methylase inhibitors;
16. proteasome inhibitors;
17. a combination of two or more of the foregoing classes (11)-(16);
18. a combination of two or more of the foregoing classes (1)-(17);
19. Other therapeutic or prophylactic agents, for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), granulocyte-colony stimulating factor (G-CSF). In other embodiments, the other therapeutic or prophylactic agents can be as described below.

Other Therapeutic or Prophylactic Agents

The compositions may also include other therapeutic or prophylactic agents, for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF).

Also included are agents that inhibit bone resorption such as bisphosphonate agents e.g. zoledronate, pamidronate and ibandronate, as well as agents that suppress inflammatory responses (such as dexamethazone, prednisone, and prednisolone). Also included are agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self. In one particular embodiment is the combination of 5FU and leucovorin or 5FU and folinic acid. In addition megestrol acetate can be used for the treatment of side-effects including oedema and thromoembolic episodes.

Therefore in one embodiment the combinations further include an additional agent selected from erythropoietin (EPO), granulocyte macrophage-colony stimulating factor (GM-CSF), granulocyte-colony stimulating factor (G-CSF), zoledronate, pamidronate, ibandronate, dexamethazone, prednisone, prednisolone, leucovorin, folinic acid and megestrol acetate.

In particular the combinations further include an additional agent selected from erythropoietin (EPO), granulocyte macrophage-colony stimulating factor (GM-CSF), granulocyte-colony stimulating factor (G-CSF), zoledronate, pamidronate, dexamethazone, prednisone, prednisolone, leucovorin, and folinic acid such as erythropoietin (EPO), granulocyte macrophage-colony stimulating factor (GM-CSF) and granulocyte-colony stimulating factor (G-CSF).

Zoledronic acid is available from Novartis under the Tradename Zometa®. It is used in the treatment of bone metastasis in a variety of tumor types and for the treatment of hypercalcemia.

Pamidronate disodium (APD) available from Novartis under the tradename Aredia is a bone-resorption inhibitor and is used in the treatment of moderate or severe hypercalcemia. Pamidronate disodium is for i.v. injection.

Octreotide acetate is available from Novartis as Sandostatin LAR® (octreotide acetate for injectable suspension) and Sandostatin® (octreotide acetate for injection ampuls or for vials). Octreotide is known chemically as L-Cysteinamide, D-phenylalanyl-L-cysteinyl-L-phenylalanyl-D-tryptophyl-L-lysyl-L-threonyl-N-[2-hydroxy-1-(hydroxy-methyl) propyl]-, cyclic (2,7)-disulfide; [R—(R*,R*)]. Synthetic forms of the brain hormone somatostatin, such as octreotide, work at the site of the tumour. They bind to sst-2/sst-5 receptors to regulate gastrointestinal hormone secretion and affect tumour growth.

Each of the compounds present in the combinations of the invention may be given in individually varying dose schedules and via different routes.

Thus, administration of the compound of the formula (I) in combination therapy with one or more cytotoxic compounds may comprise simultaneous or sequential administration. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The combinations of the invention may also be administered in conjunction with non-chemotherapeutic treatments such as radiotherapy, photodynamic therapy, gene therapy, surgery and controlled diets.

The combination therapy may therefore involve the formulation of the compound of the formula (I) with one, two, three, four or more other therapeutic agents (including at least one cytotoxic compound or signalling inhibitor). Such formulations can be, for example, a dosage form containing two, three, four or more therapeutic agents. In an alternative, the individual therapeutic agents may be formulated separately and presented together in the form of a kit, optionally with instructions for their use.

A person skilled in the art would know through their common general knowledge the dosing regimes and combination therapies to use.

Methods of Diagnosis

Prior to administration of a compound of the formula (I), a patient may be screened to determine whether a disease or condition from which the patient is or may be suffering is one which would be susceptible to treatment with a compound having activity against cyclin dependent kinase(s) and/or GSK (e.g. GSK-3) or treatment with a cytotoxic compound or signalling inhibitor.

For example, a biological sample taken from a patient may be analysed to determine whether a condition or disease, such as cancer, that the patient is or may be suffering from is one which is characterised by a genetic abnormality or abnormal protein expression which leads to over-activation of CDKs or to sensitisation of a pathway to normal CDK activity. Examples of such abnormalities that result in activation or sensitisation of the CDK2 signal include up-regulation of cyclin E, (Harwell R M, Mull B B, Porter D C, Keyomarsi K.; J Biol Chem. 2004 Mar. 26; 279(13):12695-705) or loss of p21 or p27, or presence of CDC4 variants (Rajagopalan H, Jallepalli P V, Rago C, Velculescu V E, Kinzler K W, Vogelstein B, Lengauer C.; Nature. 2004 Mar. 4; 428(6978):77-81). The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of cyclin E, or loss of p21 or p27, or presence of CDC4 variants. The term diagnosis includes screening. By marker we include genetic markers including, for example, the measurement of DNA composition to identify mutations of CDC4. The term marker also includes markers which are characteristic of up regulation of cyclin E, including enzyme activity, enzyme levels, enzyme state (e.g. phosphorylated or not) and mRNA levels of the aforementioned proteins.

Tumours with upregulation of cyclin E, or loss of p21 or p27 may be particularly sensitive to CDK inhibitors. Tumours may preferentially be screened for upregulation of cyclin E, or loss of p21 or p27 prior to treatment. Thus, the patient may be subjected to a diagnostic test to detect a marker characteristic of up-regulation of cyclin E, or loss of p21 or p27. The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

It has been found, Rajagopalan et al (Nature. 2004 Mar. 4; 428(6978):77-81), that there were mutations present in CDC4 (also known as Fbw7 or Archipelago) in human colorectal cancers and endometrial cancers (Spruck et al, Cancer Res. 2002 Aug. 15; 62(16):4535-9). Identification of individual carrying a mutation in CDC4 may mean that the patient would be particularly suitable for treatment with a CDK inhibitor. Tumours may preferentially be screened for presence of a CDC4 variant prior to treatment. The screening process will typically involve direct sequencing, oligonucleotide microarray analysis, or a mutant specific antibody.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of cyclin E, or loss of p21 or p27, or detection of CDC4 variants could be applicable in the present case.

Therefore all of these techniques could also be used to identify tumours particularly suitable for treatment with combinations of CDK inhibitors and cytotoxic compounds or signalling inhibitors. Patients with mantle cell lymphoma (MCL) could be selected for treatment with a CDK inhibitor using diagnostic tests outlined herein. MCL is a distinct clinicopathologic entity of non-Hodgkin's lymphoma, characterized by proliferation of small to medium-sized lymphocytes with co-expression of CD5 and CD20, an aggressive and incurable clinical course, and frequent t(11; 14)(q13; q32) translocation. Over-expression of cyclin D1 mRNA, found in mantle cell lymphoma (MCL), is a critical diagnostic marker. Yatabe et al (Blood. 2000 Apr. 1; 95(7):2253-61) proposed that cyclin D1-positivity should be included as one of the standard criteria for MCL, and that innovative therapies for this incurable disease should be explored on the basis of the new criteria. Jones et al (J Mol Diagn. 2004 May; 6(2):84-9) developed a real-time, quantitative, reverse transcription PCR assay for cyclin D1 (CCND1) expression to aid in the diagnosis of mantle cell lymphoma (MCL). Howe et al (Clin Chem. 2004 January; 50(1):80-7) used real-time quantitative RT-PCR to evaluate cyclin D1 mRNA expression and found that quantitative RT-PCR for cyclin D1 mRNA normalized to CD19 mRNA can be used in the diagnosis of MCL in blood, marrow, and tissue. Alternatively, patients with breast cancer could be selected for treatment with a CDK inhibitor using diagnostic tests outline above. Tumour cells commonly over-express cyclin E and it has been shown that cyclin E is over-expressed in breast cancer (Harwell et al, Cancer Res, 2000, 60, 481-489). Therefore breast cancer may in particular be treated with a CDK inhibitor.

Examples

The invention will now be illustrated, but not limited, by reference to the specific embodiments described in the following examples.

In the examples, the compounds prepared were characterised by liquid chromatography and mass spectroscopy (LC-MS) using the system and operating conditions set out below. Where chlorine is present and a single mass is quoted, the mass quoted for the compound is for $^{35}Cl$. The two systems were equipped with identical chromatography columns and were set up to run under the same operating conditions. The operating conditions used are also described below. In the examples, the retention times are given in minutes.

Platform System
System: Waters 2790/Platform LC
Mass Spec Detector: Micromass Platform LC
PDA Detector: Waters 996 PDA
Analytical Conditions:
Eluent A: 5% CH3CN in 95% $H_2O$ (0.1% Formic Acid)
Eluent B: $CH_3CN$ (0.1% Formic Acid)
Gradient: 10-95% eluent B
Flow: 1.2 ml/min
Column: Synergi 4 μm Max-RP $C_{12}$, 80A, 50×4.6 mm (Phenomenex)
MS Conditions:
Capillary voltage: 3.5 kV
Cone voltage: 30 V
Source Temperature: 120° C.
FractionLynx System
System: Waters FractionLynx (dual analytical/prep)
Mass Spec Detector: Waters-Micromass ZQ
PDA Detector: Waters 2996 PDA
Analytical Conditions:
Eluent A: $H_2O$ (0.1% Formic Acid)
Eluent B: $CH_3CN$ (0.1% Formic Acid)
Gradient: 5-95% eluent B
Flow: 1.5 ml/min
Column: Synergi 4 μm Max-RP $C_{12}$, 80A, 50×4.6 mm (Phenomenex)
MS Conditions:
Capillary voltage: 3.5 kV
Cone voltage: 30 V Source Temperature: 120° C.
Desolvation Temperature: 300° C.
Analytical LC-MS System Several systems were used, as described below, and these were equipped with were set up to run under closely similar operating conditions. The operating conditions used are also described below.

HPLC System: Waters 2795
Mass Spec Detector: Micromass Platform LC
PDA Detector: Waters 2996 PDA
Acidic Analytical Conditions:
Eluent A: $H_2O$ (0.1% Formic Acid)
Eluent B: $CH_3CN$ (0.1% Formic Acid)
Gradient: 5-95% eluent B over 3.5 minutes
Flow: 0.8 ml/min
Column: Phenomenex Synergi 4μ MAX-RP 80A, 2.0×50 mm
Basic Analytical Conditions:
Eluent A: $H_2O$ (10 mM $NH_4HCO_3$ buffer adjusted to pH=9.5 with $NH_4OH$)
Eluent B: $CH_3CN$
Gradient: 05-95% eluent B over 3.5 minutes
Flow: 0.8 ml/min
Column: Thermo Hypersil-Keystone BetaBasic-18 5 μm 2.1×50 mm
or
Column: Phenomenex Luna C18(2) 5 μm 2.0×50 mm
Polar Analytical Conditions:
Eluent A: $H_2O$ (0.1% Formic Acid)
Eluent B: $CH_3CN$ (0.1% Formic Acid)
Gradient: 00-50% eluent B over 3 minutes
Flow: 0.8 ml/min
Column: Thermo Hypersil-Keystone HyPurity Aquastar, 5μ, 2.1×50 mm
or
Column: Phenomenex Synergi 4μ MAX-RP 80A, 2.0×50 mm or
Longer Analytical Conditions:
Eluent A: $H_2O$ (0.1% Formic Acid)
Eluent B: $CH_3CN$ (0.1% Formic Acid)
Gradient: 05-95% eluent B over 15 minutes
Flow: 0.4 ml/min
Column: Phenomenex Synergi 4μ MAX-RP 80A, 2.0×150 mm
MS Conditions:
Capillary voltage: 3.6 kV
Cone voltage: 30 V
Source Temperature: 120° C.
Scan Range: 165-700 amu
Ionisation Mode: ElectroSpray Positive or
ElectroSpray Negative or
ElectroSpray Positive & Negative
Mass Directed Purification LC-MS System The following preparative chromatography systems can be used to purify the compounds of the invention.
Hardware:
Waters Fractionlynx System:
2767 Dual Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Software: Masslynx 4.0
Columns:

1. Low pH chromatography: Phenomenex Synergy MAX-RP, 10μ, 150×15 mm (alternatively used same column type with 100×21.2 mm dimensions).

2. High pH chromatography: Phenomenex Luna C18 (2), 10μ, 100×21.2 mm (alternatively used Thermo Hypersil Keystone BetaBasic C18, 5μ, 100×21.2 mm)

Eluents:
1. Low pH chromatography:
Solvent A: $H_2O$+0.1% Formic Acid, pH 1.5
Solvent B: $CH_3CN$+0.1% Formic Acid
2. High pH chromatography:
Solvent A: $H_2O$+10 mM $NH_4HCO_3$+$NH_4OH$, pH 9.5
Solvent B: $CH_3CN$
3. Make up solvent: MeOH+0.1% formic acid (for both chromatography type)

Methods:

Prior to using preparative chromatography to isolate and purify the product compounds, analytical LC-MS (see above) can first be used to determine the most appropriate conditions for preparative chromatography. A typical routine is to run an analytical LC-MS using the type of chromatography (low or high pH) most suited for compound structure. Once the analytical trace shows good chromatography, a suitable preparative method of the same type can be chosen. Typical running condition for both low and high pH chromatography methods are:

Flow rate: 24 ml/min

Gradient: Generally all gradients have an initial 0.4 min step with 95% A+5% B. Then according to analytical trace a 3.6 min gradient is chosen in order to achieve good separation (e.g. from 5% to 50% B for early retaining compounds; from 35% to 80% B for middle retaining compounds and so on)

Wash: 1 minute wash step is performed at the end of the gradient

Re-equilibration: A 2.1 minute re-equilibration step is carried out to prepare the system for the next run Make Up flow rate: 1 ml/min Solvent:

All compounds were usually dissolved in 100% MeOH or 100% DMSO

MS Running Conditions:
Capillary voltage: 3.2 kV
Cone voltage: 25 V
Source Temperature: 120° C.
Multiplier: 500 V
Scan Range: 125-800 amu
Ionisation Mode: ElectroSpray Positive The starting materials for each of the Examples are commercially available unless otherwise specified.

Example 1

4-Amino-1H-pyrazole-3-carboxylic acid phenylamide

1A. 4-Nitro-1H-pyrazole-3-carboxylic acid phenylamide

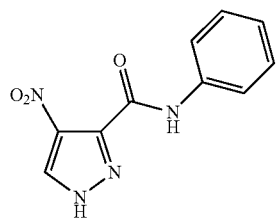 [SMILES: O=C(Nc1ccccc1)c1n[nH]cc1[N+](=O)[O-]]

4-Nitropyrazole-3-carboxylic acid (2.5 g; 15.9 mmol) was added to a stirred solution of aniline (1.6 ml; 17.5 mmol), EDC (3.7 g; 19.1 mmol), and HOBt (2.6 g; 19.1 mmol) in N,N-dimethylformamide (DMF) (25 ml), then stirred at room temperature overnight. The solvent was removed by evaporation under reduced pressure and the residue triturated with ethyl acetate/saturated $NaHCO_3$ solution. The resultant solid was collected by filtration, washed with water and diethyl ether then dried under vacuum to give 2.85 g of the title compound (sodium salt) as a yellow/brown solid. (LC/MS: $R_t$ 2.78, $[M+H]^+$ 232.95).

1B. 4-Amino-1H-pyrazole-3-carboxylic acid phenylamide

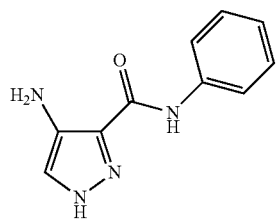

4-Nitro-1H-pyrazole-3-carboxylic acid phenylamide (100 mg; 0.43 mmol) was dissolved in ethanol (5 ml), treated with tin (II) chloride dihydrate (500 mg; 2.15 mmol) then heated at reflux overnight. The reaction mixture was cooled and evaporated. The residue was partitioned between ethyl acetate and brine, and the ethyl acetate layer was separated, dried ($MgSO_4$), filtered and evaporated. The crude product was purified by flash column chromatography eluting with 1:1 ethyl acetate/petroleum ether then 5% methanol/dichloromethane. Evaporation of product containing fractions followed by preparative LC/MS gave 15 mg of the product as an off white solid. (LC/MS: $R_t$ 1.40, $[M+H]^+$ 202.95).

Example 2

4-Acetylamino-1H-pyrazole-3-carboxylic acid (4-fluoro-phenyl)-amide

2A. 4-Nitro-1H-pyrazole-3-carboxylic acid (4-fluoro-phenyl)-amide

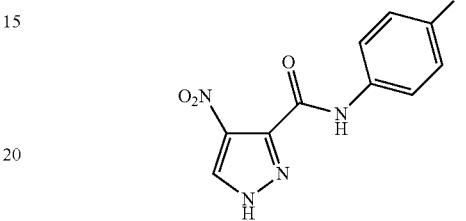

4-Nitropyrazole-3-carboxylic acid (10 g; 63.66 mmol) was added to a stirred solution of 4-fluoroaniline (6.7 ml; 70 mmol), EDC (14.6 g; 76.4 mmol), and HOBt (10.3 g; 76.4 mmol) in DMF (25 ml), then stirred at room temperature overnight. The solvent was removed by evaporation under reduced pressure and the residue triturated with ethyl acetate/saturated brine solution. The resultant yellow solid was collected by filtration, washed with 2M hydrochloric acid, then dried under vacuum to give 15.5 g of the title compound. (LC/MS: $R_t$ 2.92 $[M+H]^+$ 250.89).

2B. 4-Amino-1H-pyrazole-3-carboxylic acid (4-fluoro-phenyl)-amide

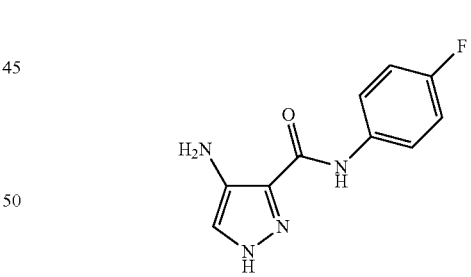

4-Nitro-1H-pyrazole-3-carboxylic acid (4-fluorophenyl)-amide (15 g) was dissolved in 200 ml of ethanol, treated with 1.5 g of 10% palladium on carbon under a nitrogen atmosphere, then hydrogenated at room temperature and pressure overnight. The catalyst was removed by filtration through Celite and the filtrate evaporated. The crude product was dissolved in acetone/water (100 ml:100 ml) and after slow evaporation of the acetone the product was collected by filtration as a brown crystalline solid (8.1 g). (LC/MS: $R_t$ 1.58, $[M+H]^+$ 220.95).

2C. 4-Acetylamino-1H-pyrazole-3-carboxylic acid (4-fluoro-phenyl)-amide

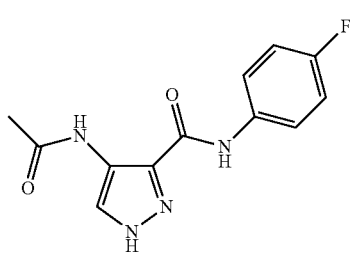 [SMILES: CC(=O)Nc1c[nH]nc1C(=O)Nc1ccc(F)cc1]

4-Amino-1H-pyrazole-3-carboxylic acid (4-fluorophenyl)-amide (500 mg; 2.27 mmol) was dissolved in 5 ml of pyridine, treated with acetic anhydride (240 μl, 2.5 mmol) then stirred at room temperature overnight. The solvent was removed by evaporation then dichloromethane (20 ml) and 2M hydrochloric acid (20 ml) were added. The undissolved solid was collected by filtration, washed with more dichloromethane and water then dried under vacuum. The product was isolated as an off white solid (275 mg). (LC/MS: $R_t$ 2.96, [M+H]$^+$ 262.91).

Example 3

4-(2,2,2-Trifluoro-acetylamino)-1H-pyrazole-3-carboxylic acid (4-fluoro-phenyl)-amide

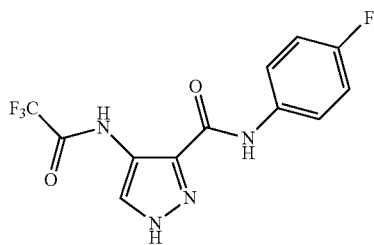 [SMILES: O=C(Nc1ccc(F)cc1)c1n[nH]cc1NC(=O)C(F)(F)F]

4-Amino-1H-pyrazole-3-carboxylic acid (4-fluorophenyl)-amide (Example 2B) (500 mg; 2.27 mmol) was dissolved in 5 ml of pyridine, treated with trifluoroacetic anhydride (320 μl, 2.5 mmol) then stirred at room temperature overnight. The solvent was removed by evaporation, the residue was partitioned between ethyl acetate (50 ml) and 2 M hydrochloric acid (50 ml), and the ethyl acetate layer was separated, washed with brine (50 ml), dried (MgSO$_4$), filtered and evaporated to give 560 mg of product as a brown solid. (LC/MS: [M+H]$^+$ 317).

Example 4

4-[(5-Oxo-pyrrolidine-2-carbonyl)-amino]-1H-pyrazole-3-carboxylic acid (4-fluoro-phenyl)-amide

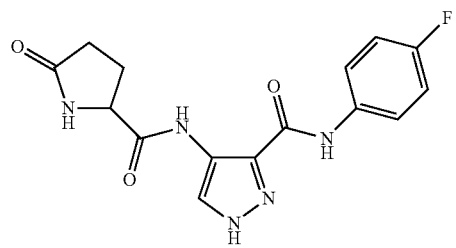 [SMILES: O=C1CCC(C(=O)Nc2c[nH]nc2C(=O)Nc2ccc(F)cc2)N1]

To a stirred solution of 4-amino-1H-pyrazole-3-carboxylic acid (4-fluorophenyl)-amide (Example 2B) (50 mg; 0.23 mmol), EDAC (52 mg; 0.27 mmol) and HOBt (37 mg; 0.27 mmol) in 5 ml of DMF was added 2-oxoproline (33 mg; 0.25 mmol), and the mixture was then left at room temperature overnight. The reaction mixture was evaporated and the residue purified by preparative LC/MS, to give 24 mg of the product as a white solid. (LC/MS: $R_t$ 2.27 [M+H]$^+$ 332).

Example 5

4-Phenylacetylamino-1H-pyrazole-3-carboxylic acid (4-fluoro-phenyl)-amide

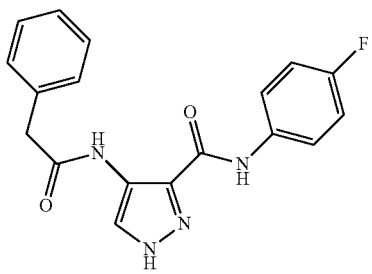 [SMILES: O=C(Cc1ccccc1)Nc1c[nH]nc1C(=O)Nc1ccc(F)cc1]

The reaction was carried out in a manner analogous to Example 4 but using phenylacetic acid (34 mg; 0.23 mmol) as the starting material. The title compound (14 mg) was isolated as a white solid. (LC/MS: $R_t$ 3.24 [M+H]$^+$ 339).

Example 6

4-(2-1H-Indol-3-yl-acetylamino)-1H-pyrazole-3-carboxylic acid (4-fluoro-phenyl)-amide

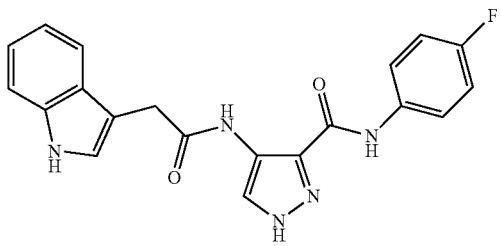 [SMILES: O=C(Cc1c[nH]c2ccccc12)Nc1c[nH]nc1C(=O)Nc1ccc(F)cc1]

The reaction was carried out in a manner analogous to Example 4, but using indole-3-acetic acid (44 mg; 0.23 mmol) as the starting material. The title product (14 mg) was isolated as a white solid. (LC/MS: $R_t$ 3.05 [M+H]$^+$ 378).

Example 7

4-(2-Benzenesulphonyl-acetylamino)-1H-pyrazole-3-carboxylic acid (4-fluoro-phenyl)-amie

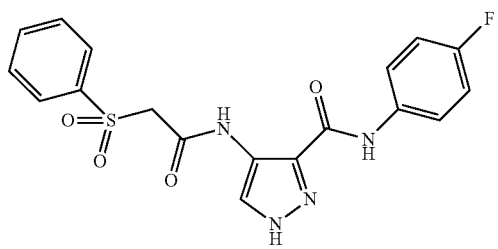 [SMILES: O=C(CS(=O)(=O)c1ccccc1)Nc1c[nH]nc1C(=O)Nc1ccc(F)cc1]

The reaction was carried out in a manner analogous to Example 4, but using 2-(phenylsulphonyl) acetic acid (50 mg; 0.23 mmol) as the starting material. The title compound (29 mg) was isolated as a white solid. (LC/MS: $R_t$ 3.00 [M+H]$^+$ 403).

Example 8

4-[2-(5-Amino-tetrazol-1-yl)-acetylamino]-1H-pyrazole-3-carboxylic acid (4-fluoro-phenyl)-amide

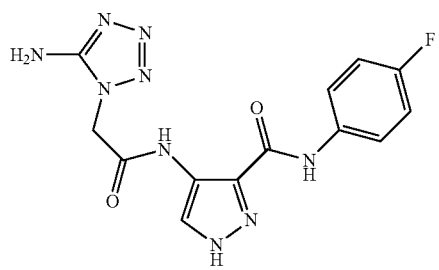 [SMILES: Nc1nnnn1CC(=O)Nc1c[nH]nc1C(=O)Nc1ccc(F)cc1]

The reaction was carried out in a manner analogous to Example 4, but 5-aminotetrazole-1-acetic acid (36 mg; 0.23 mmol) was used as the starting material. The title compound (23 mg) was isolated as a white solid. (LC/MS: $R_t$ 2.37 [M+H]$^+$ 346).

Example 9

N-[3-(4-Fluoro-phenylcarbamoyl)-1H-pyrazol-4-yl]-6-hydroxy-nicotinamide

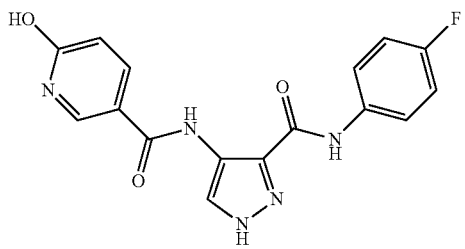 [SMILES: O=C(Nc1c[nH]nc1C(=O)Nc1ccc(F)cc1)c1ccc(O)nc1]

The reaction was carried out in a manner analogous to Example 4, but using 6-hydroxynicotinic acid (38 mg; 0.23 mmol) as the starting material. The title compound (17 mg) was isolated as a white solid. (LC/MS: $R_t$ 2.32 [M+H]$^+$ 342).

Example 10

4-[3-(4-Chloro-phenyl)-propionylamino]-1H-pyrazole-3-carboxylic acid (4-fluoro-phenyl)-amide

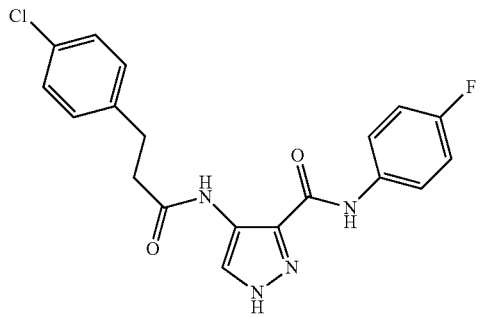 [SMILES: O=C(CCc1ccc(Cl)cc1)Nc1c[nH]nc1C(=O)Nc1ccc(F)cc1]

The reaction was carried out in a manner analogous to Example 4, but using 3-(4-chlorophenyl)propionic acid (46 mg; 0.23 mmol) as the starting material. The title compound (40 mg) was isolated as a white solid. (LC/MS: $R_t$ 3.60 [M+H]$^+$ 388).

Example 11

4-(3-4H-[1,2,4]Triazol-3-yl-propionylamino)-1H-pyrazole-3-carboxylic acid (4-fluoro-phenyl)-amide

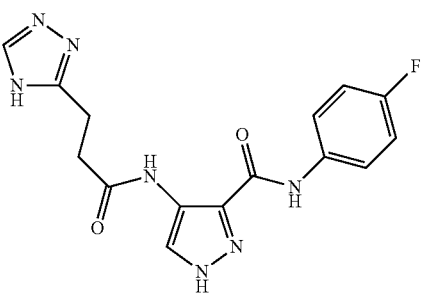 [SMILES: O=C(CCc1nnc[nH]1)Nc1c[nH]nc1C(=O)Nc1ccc(F)cc1]

The reaction was carried out in a manner analogous to Example 4, but using 3-triazol-3-yl propionic acid (36 mg; 0.23 mmol) as the starting material. The title compound (18 mg) was isolated as a white solid. (LC/MS: $R_t$ 2.39 [M+H]$^+$ 344).

Example 12

4-[2-(1-Methyl-1H-indol-3-yl)-acetylamino]-1H-pyrazole-3-carboxylic acid (4-fluoro-phenyl)-amide

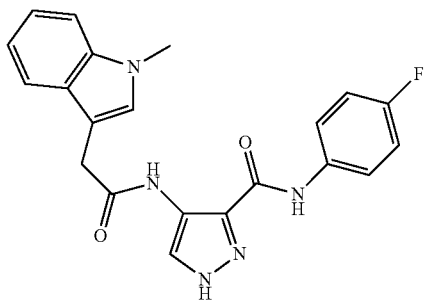 [SMILES: Cn1cc(CC(=O)Nc2c[nH]nc2C(=O)Nc2ccc(F)cc2)c2ccccc21]

The reaction was carried out in a manner analogous to Example 4, but using N-methyl indole-3-acetic acid (48 mg; 0.23 mmol) as the starting material. The title compound (20 mg) was isolated as a white solid. (LC/MS: $R_t$ 3.34 [M+H]$^+$ 392).

Example 13

4-[(1-Hydroxy-cyclopropanecarbonyl)-amino]-1H-pyrazole-3-carboxylic acid (4-fluoro-phenyl)-amide

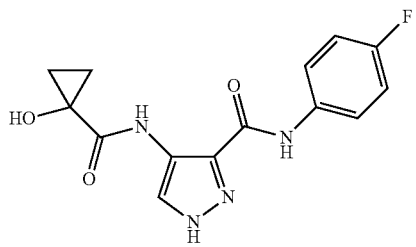 [SMILES: O=C(Nc1ccc(F)cc1)c1n[nH]cc1NC(=O)C1(O)CC1]

The reaction was carried out in a manner analogous to Example 4, but using 1-hydroxycyclopropane carboxylic acid (26 mg; 0.23 mmol) as the starting material. The title compound (24 mg) was isolated as a white solid. (LC/MS: $R_t$ 2.55 [M+H]$^+$ 305).

Example 14

1-Acetyl-piperidine-4-carboxylic acid [3-(4-fluoro-phenylcarbamoyl)-1H-pyrazol-4-yl]-amide

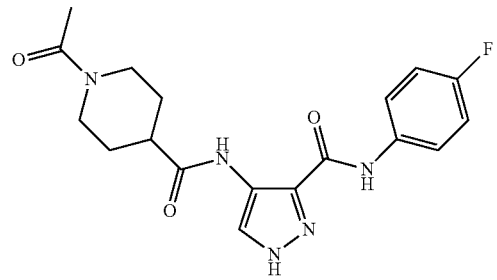 [SMILES: CC(=O)N1CCC(C(=O)Nc2c[nH]nc2C(=O)Nc2ccc(F)cc2)CC1]

The reaction was carried out in a manner analogous to Example 4, but using N-acetylpiperidine acetic acid (43 mg; 0.23 mmol) as the starting material. The title compound (19 mg) was isolated as a white solid. (LC/MS: $R_t$ 2.49 [M+H]$^+$ 374).

Example 15

4-[3-(4-Methyl-piperazin-1-yl)-propionylamino]-1H-pyrazole-3-carboxylic acid (4-fluoro-phenyl)-amide

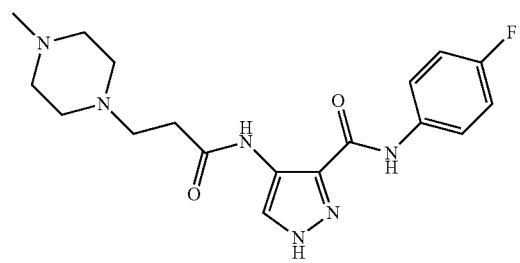 [SMILES: CN1CCN(CCC(=O)Nc2c[nH]nc2C(=O)Nc2ccc(F)cc2)CC1]

The reaction was carried out in a manner analogous to Example 4, but using 4-N-methylpiperazine-1-N-propionic acid (31 mg; 0.23 mmol) as the starting material. The title compound (19 mg) was isolated as a white solid. (LC/MS: $R_t$ 1.77 [M+H]$^+$ 375).

Example 16

4-(2-1H-Imidazol-4-yl-acetylamino)-1H-pyrazole-3-carboxylic acid (4-fluorophenyl)-amide

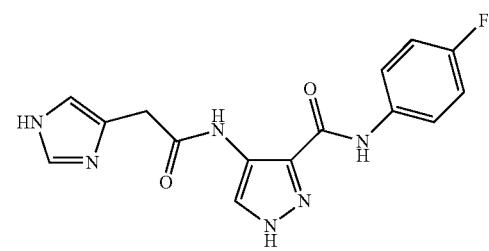 [SMILES: O=C(Cc1c[nH]cn1)Nc1c[nH]nc1C(=O)Nc1ccc(F)cc1]

The reaction was carried out in a manner analogous to Example 4, but using imidazole-4-acetic acid (32 mg; 0.23 mmol) as the starting material. The title compound (35 mg) was isolated as a white solid. (LC/MS: $R_t$ 1.82 [M+H]$^+$ 329).

Example 17

4-(3-Morpholin-4-yl-propionylamino)-1H-pyrazole-3-carboxylic acid (4-fluorophenyl)-amide

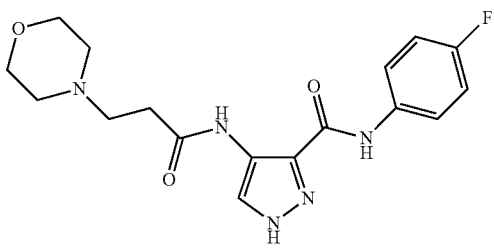 [SMILES: O=C(CCN1CCOCC1)Nc1c[nH]nc1C(=O)Nc1ccc(F)cc1]

The reaction was carried out in a manner analogous to Example 4, but using 3-morpholin-4-yl-propionic acid (40 mg; 0.23 mmol) as the starting material. The title compound (15 mg) was isolated as a white solid. (LC/MS: $R_t$ 1.84 [M+H]$^+$ 362).

Example 18

4-(3-Piperidin-1-yl-propionylamino)-1H-pyrazole-3-carboxylic acid (4-fluoro-phenyl)-amide

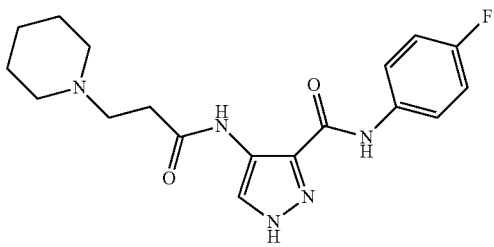 [SMILES: O=C(CCN1CCCCC1)Nc1c[nH]nc1C(=O)Nc1ccc(F)cc1]

The reaction was carried out in a manner analogous to Example 4, but using 3-piperidine-4-yl-propionic acid (39 mg; 0.23 mmol) as the starting material. The title compound (19 mg) was isolated as a white solid. (LC/MS: $R_t$ 1.92 [M+H]$^+$ 360).

Example 19

4-Cyclohexylamino-1H-pyrazole-3-carboxylic acid (4-fluoro-phenyl)-amide

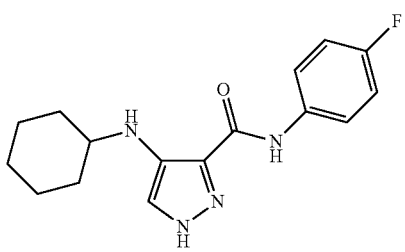 [SMILES: O=C(Nc1ccc(F)cc1)c1n[nH]cc1NC1CCCCC1]

To a solution of 4-amino-1H-pyrazole-3-carboxylic acid (4-fluoro-phenyl)-amide (200 mg; 1 mmol) and cyclohexanone (107 mg; 1.1 mmol) in dichloromethane (10 ml) were added 3A molecular sieves (1 g) and sodium triacetoxyborohydride (315 mg; 1.5 mmol), and the mixture was then stirred at room temperature over the weekend. The reaction mixture was filtered through Celite®, diluted with ethyl acetate, washed with brine, dried (MgSO$_4$) and evaporated to give the 48 mg of the product as a grey gum. (LC/MS: $R_t$ 2.95, [M+H]$^+$ 285).

Example 20

4-Isopropylamino-1H-pyrazole-3-carboxylic acid (4-fluoro-phenyl)-amide

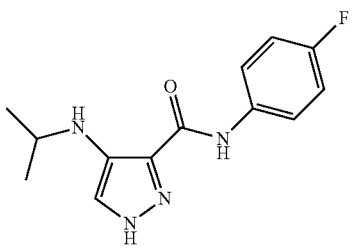 [SMILES: CC(C)Nc1c[nH]nc1C(=O)Nc1ccc(F)cc1]

The title compound was prepared in a manner analogous to Example 19, but using acetone in place of cyclohexanone. (LC/MS: $R_t$ 2.08, [M+H]$^+$ 245).

Example 21

4-(2-Hydroxy-1-methyl-ethylamino)-1H-pyrazole-3-carboxylic acid (4-fluorophenyl)-amide

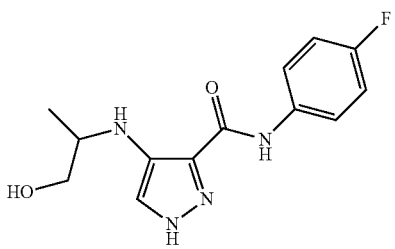 [SMILES: CC(CO)Nc1c[nH]nc1C(=O)Nc1ccc(F)cc1]

The compound was prepared in a manner analogous to Example 19, but using hydroxyacetone in place of cyclohexanone. $^1$HNMR (400 MHz, D6-DMSO): 9.9 (1H, br s), 7.8 (2H, dd), 7.3 (1H, s), 7.15 (2H, t), 5.15 (1H, d), 4.7 (1H, br s), 3.4 (2H, m), 3.2 (1H, m), 1.1 (3H, d).

Example 22

4-(1-Ethyl-propylamino)-1H-pyrazole-3-carboxylic acid (4-fluoro-phenyl)-amide

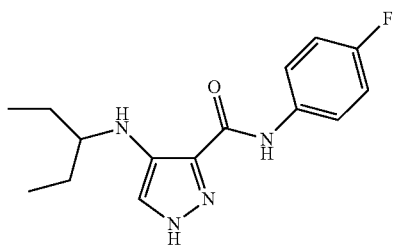 [SMILES: CCC(CC)Nc1c[nH]nc1C(=O)Nc1ccc(F)cc1]

The compound was prepared in a manner analogous to Example 19, but using 3-pentanone in place of cyclohexanone. $^1$HNMR (400 MHz, D6-DMSO): 12.85 (1h, br s), 9.9 (1H, br s), 7.8 (2H, br t), 7.3 (1H, s), 7.15 (2H, t), 5.0 (1H, d), 2.9 (1H, br m), 1.5 (4H, m), 3.2 (1H, m), 0.9 (6H, t).

Example 23

4-(3-Chloro-pyrazin-2-ylamino)-1H-pyrazole-3-carboxylic acid (4-fluoro-phenyl)-amide

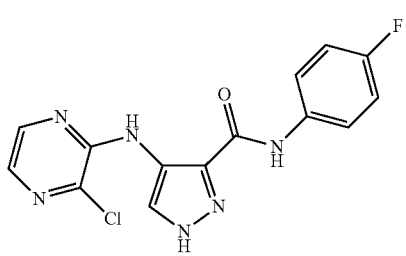 [SMILES: O=C(Nc1ccc(F)cc1)c1n[nH]cc1Nc1nccnc1Cl]

A mixture of 4-amino-1H-pyrazole-3-carboxylic acid (4-fluoro-phenyl)-amide (50 mg; 0.23 mmol) and 2,3-dichloropyrazine (140 mg; 0.92 mmol) was heated at 150° C. (50W) for 20 minutes in a CEM Discover™ microwave synthesiser. The crude reaction mixture was purified by flash column chromatography eluting with ethyl acetate/hexane (1:3 then 1:2). Product containing fractions were combined and evaporated to give 15 mg of the title compound as a white solid. (LC/MS: $R_t$ 4.06 M+H]$^+$ 332).

Example 24

4-(Pyrazin-2-ylamino)-1H-pyrazole-3-carboxylic acid (4-fluoro-phenyl)-amide

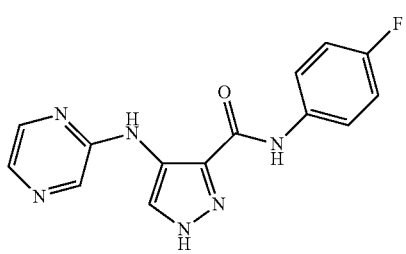 [SMILES: O=C(Nc1ccc(F)cc1)c1n[nH]cc1Nc1cnccn1]

The compound was prepared in a manner analogous to Example 23, but using 2-chloropyrazine in place of 2,3-dichloropyrazine. (LC/MS: $R_t$ 3.28 [M+H]$^+$ 299).

Example 25

Synthesis of 4-(2-Methoxy-benzoylamino)-1H-pyrazole-3-carboxylic acid (4-fluoro-phenyl)-amide

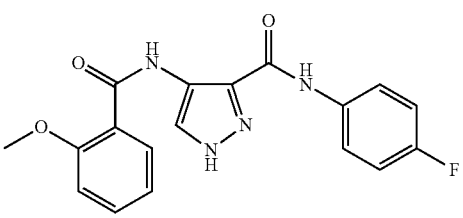 [SMILES: COc1ccccc1C(=O)Nc1c[nH]nc1C(=O)Nc1ccc(F)cc1]

2-Methoxy-benzoic acid (38 mg, 0.25 mmol) was added to a solution of 4-amino-1H-pyrazole-3-carboxylic acid (4-fluoro-phenyl)-amide (50 mg, 0.23 mmol), EDC (53 mg, 0.27 mmol), and HOBt (37 mg, 0.27 mmol) in DMF (5 ml). The reaction mixture was stirred at room temperature for 24 hours. The solvent was removed under reduced pressure. The residue was purified by preparative LC/MS and, after evapoartion of product-containing fractions, yielded the product as a pinkish solid (12 mg, 15%). (LC/MS: $R_t$ 4.00, [M+H]$^+$ 354.67).

Example 26

Synthesis of 4-Benzoylamino-1H-pyrazole-3-carboxylic acid (4-fluoro-phenyl)-amide

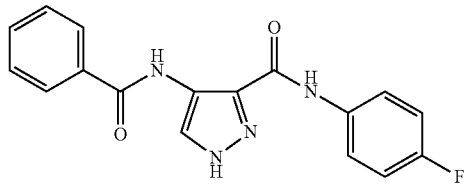 [SMILES: O=C(Nc1c[nH]nc1C(=O)Nc1ccc(F)cc1)c1ccccc1]

The experiment was carried out in a manner analogous to that of Example 25 using benzoic acid (31 mg, 0.25 mmol) as starting acid. The product was isolated as a pink solid (26 mg, 35%). (LC/MS: $R_t$ 3.96, [M+H]$^+$ 324.65).

Example 27

Synthesis of 4-(Cyclohexanecarbonyl-amino)-1H-pyrazole-3-carboxylic acid (4-fluoro-phenyl)-amide

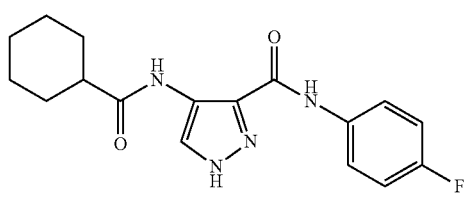 [SMILES: O=C(Nc1ccc(F)cc1)c1n[nH]cc1NC(=O)C1CCCCC1]

The experiment was carried out in a manner analogous to that of Example 25 using cyclohexanecarboxylic acid (32 mg, 0.25 mmol) as starting acid. The product was isolated as a pink solid (28 mg, 37%). (LC/MS: $R_t$ 4.16, $[M+H]^+$ 330.70).

Example 28

Synthesis of 4-[(1-Methyl-cyclopropanecarbonyl)-amino]-1H-pyrazole-3-carboxylic acid (4-fluoro-phenyl)-amide

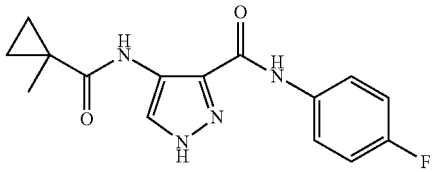 [SMILES: CC1(C(=O)Nc2c[nH]nc2C(=O)Nc2ccc(F)cc2)CC1]

The experiment was carried out in a manner analogous to that of Example 25 using 1-methyl-cyclopropanecarboxylic acid (25 mg, 0.25 mmol) as starting acid. The product was isolated as a pink solid (24 mg, 35%). (LC/MS: $R_t$ 3.72, $[M+H]^+$ 302.68).

Example 29

Synthesis of 4-(2-Hydroxy-acetylamino)-1H-pyrazole-3-carboxylic acid (4-fluoro-phenyl)-amide

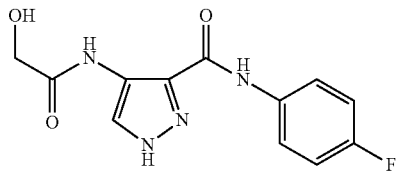 [SMILES: O=C(CO)Nc1c[nH]nc1C(=O)Nc1ccc(F)cc1]

The experiment was carried out in a manner analogous to that of Example 25 using hydroxy-acetic acid (19 mg, 0.25 mmol) as starting acid. The product was isolated as a white solid (26 mg, 41%). (LC/MS: $R_t$ 2.65, $[M+H]^+$ 278.61).

Example 30

Synthesis of 4-(2,2-Dimethyl-propionylamino)-1H-pyrazole-3-carboxylic acid (4-fluoro-phenyl)-amide

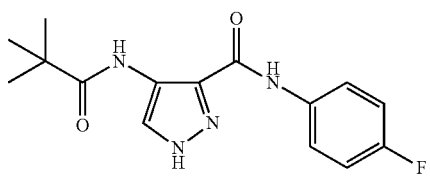 [SMILES: CC(C)(C)C(=O)Nc1c[nH]nc1C(=O)Nc1ccc(F)cc1]

The experiment was carried out in a manner analogous to that of Example 25 using 2,2-dimethyl-propionic acid (26 mg, 0.25 mmol) as starting acid. The product was isolated as a pink solid (21 mg, 30%). (LC/MS: $R_t$ 3.83, $[M+H]^+$ 304.68).

Example 31

Synthesis of 4-(3-Hydroxy-propionylamino)-1H-pyrazole-3-carboxylic acid (4-fluoro-phenyl)-amide

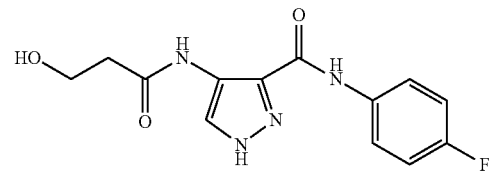 [SMILES: O=C(CCO)Nc1c[nH]nc1C(=O)Nc1ccc(F)cc1]

The experiment was carried out in a manner analogous to that of Example 25 using 3-hydroxy-propionic acid (75.1 mg, 0.25 mmol) as starting acid. The product was isolated as a beige solid (5 mg, 8%). (LC/MS: $R_t$ 2.58, $[M+H]^+$ 292.65).

Example 32

Synthesis of 4-(2-Fluoro-benzoylamino)-1H-pyrazole-3-carboxylic acid (4-fluoro-phenyl)-amide

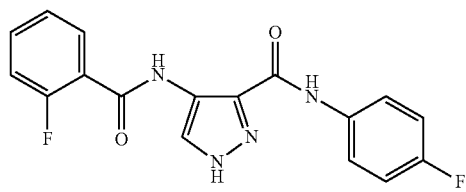 [SMILES: O=C(Nc1c[nH]nc1C(=O)Nc1ccc(F)cc1)c1ccccc1F]

2-Fluorobenzoic acid (36 mg, 0.25 mmol) was added to a solution of 4-amino-1H-pyrazole-3-carboxylic acid (4-fluoro-phenyl)-amide (50 mg, 0.23 mmol), EDC (53 mg, 0.27 mmol) and HOBt (37 mg, 0.27 mmol) in DMSO (1 ml). The reaction mixture was stirred at room temperature for 24 hours and purified by preparative LC/MS. Evaporation of product-containing fractions yielded the product as a white solid (15 mg, 19%). (LC/MS: $R_t$ 3.91, $[M+H]^+$ 342.66).

Example 33

Synthesis of 4-(3-Fluoro-benzoylamino)-1H-pyrazole-3-carboxylic acid (4-fluoro-phenyl)-amide

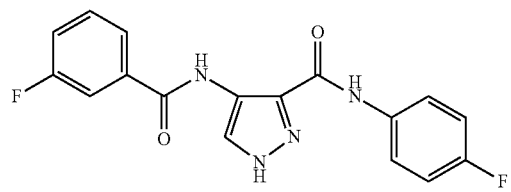 [SMILES: O=C(Nc1c[nH]nc1C(=O)Nc1ccc(F)cc1)c1cccc(F)c1]

The experiment was carried out in a manner analogous to that of Example 32 using 3-fluorobenzoic acid (36 mg, 0.25 mmol) as starting acid. The product was isolated as a white solid (19 mg, 24%). (LC/MS: R$_t$ 4.03, [M+H]$^+$ 342.67).

Example 34

Synthesis of 4-(3-Methoxy-benzoylamino)-1H-pyrazole-3-carboxylic acid (4-fluoro-phenyl)-amide

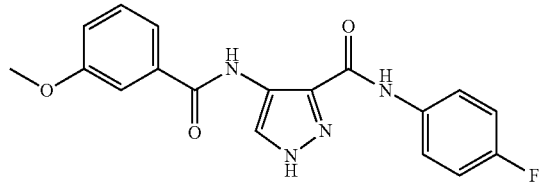 [SMILES: COc1cccc(C(=O)Nc2c[nH]nc2C(=O)Nc2ccc(F)cc2)c1]

The experiment was carried out in a manner analogous to that of Example 32 using 3-methoxy-benzoic acid (39 mg, 0.25 mmol) as starting acid. The product was isolated as a white solid (20 mg, 25%). (LC/MS: R$_t$ 3.97, [M+H]$^+$ 354.68).

Example 35

Synthesis of 4-(2-Nitro-benzoylamino)-1H-pyrazole-3-carboxylic acid (4-fluoro-phenyl)-amide

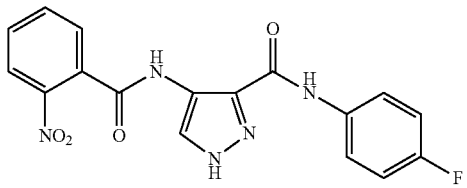 [SMILES: O=C(Nc1c[nH]nc1C(=O)Nc1ccc(F)cc1)c1ccccc1[N+](=O)[O-]]

The experiment was carried out in a manner analogous to that of Example 32 using 2-nitrobenzoic acid (43 mg, 0.25 mmol) as starting acid. The product was isolated as a white solid (17 mg, 20%). (LC/MS: R$_t$ 3.67, [M+H]$^+$ 369.66).

Example 36

Synthesis of 4-(4-Nitro-benzoylamino)-1H-pyrazole-3-carboxylic acid (4-fluoro-phenyl)-amide

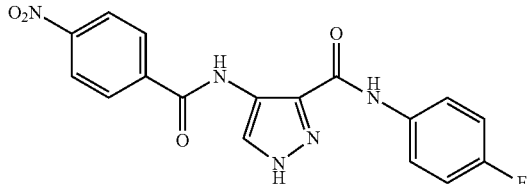

The experiment was carried out in a manner analogous to that of Example 32 using 4-nitrobenzoic acid (43 mg, 0.25 mmol) as starting acid. The product was isolated as a white solid (15 mg, 18%). (LC/MS: R$_t$ 3.98, [M+H]$^+$ 369.63).

Example 37

Synthesis of 4-[(3-Methyl-furan-2-carbonyl)-amino]-1H-pyrazole-3-carboxylic acid (4-fluoro-phenyl)-amide

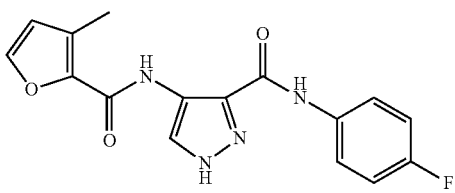 [SMILES: Cc1ccoc1C(=O)Nc1c[nH]nc1C(=O)Nc1ccc(F)cc1]

The experiment was carried out in a manner analogous to that of Example 32 using 3-methyl-2-furoic acid (32 mg, 0.25 mmol) as starting acid. The product was isolated as a white solid (15 mg, 20%). (LC/MS: R$_t$ 3.86, [M+H]$^+$ 328.68).

Example 38

Synthesis of 4-[(Furan-2-carbonyl)-amino]-1H-pyrazole-3-carboxylic acid (4-fluoro-phenyl)-amide

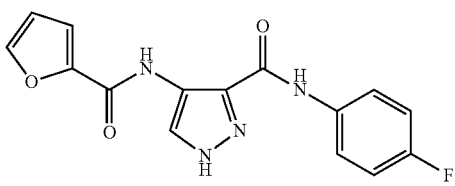 [SMILES: O=C(Nc1c[nH]nc1C(=O)Nc1ccc(F)cc1)c1ccco1]

The experiment was carried out in a manner analogous to that of Example 32 using 2-furoic acid (29 mg, 0.25 mmol) as starting acid. The product was isolated as a white solid (18 mg, 25%). (LC/MS: R$_t$ 3.56, [M+H]$^+$ 314.64).

Example 39

Synthesis of 4-[(3H-Imidazole-4-carbonyl)-amino]-1H-pyrazole-3-carboxylic acid (4-fluoro-phenyl)-amide

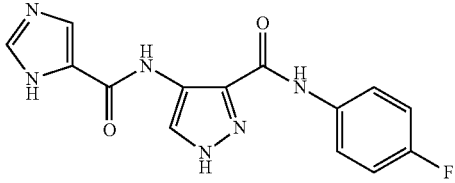 [SMILES: O=C(Nc1c[nH]nc1C(=O)Nc1ccc(F)cc1)c1cnc[nH]1]

The experiment was carried out in a manner analogous to that of Example 32 using 1H-imidazole-4-carboxylic acid (29 mg, 0.25 mmol) as starting acid. The product was isolated as a white solid (16 mg, 22%). (LC/MS: $R_t$ 2.59, $[M+H]^+$ 314.65).

Example 40

Synthesis of 4-(4-Fluoro-benzoylamino)-1H-pyrazole-3-carboxylic acid (4-fluoro-phenyl)-amide

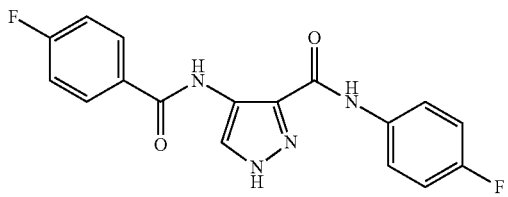 [SMILES: O=C(Nc1c[nH]nc1C(=O)Nc1ccc(F)cc1)c1ccc(F)cc1]

The experiment was carried out in a manner analogous to that of Example 32 using 4-fluorobenzoic acid (36 mg, 0.25 mmol) as starting acid. The product was isolated as a cream coloured solid (23 mg, 29%). (LC/MS: $R_t$ 4.00, $[M+H]^+$ 342.67).

Example 41

Synthesis of 4-(2,6-Difluoro-benzoylamino)-1H-pyrazole-3-carboxylic acid (4-fluoro-phenyl)-amide

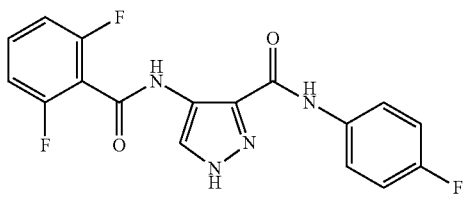 [SMILES: O=C(Nc1ccc(F)cc1)c1n[nH]cc1NC(=O)c1c(F)cccc1F]

The experiment was carried out in a manner analogous to that of Example 32 using 2,6-difluorobenzoic acid (40 mg, 0.25 mmol) as starting acid. The product was isolated as a cream coloured solid (25 mg, 30%). (LC/MS: $R_t$ 3.76, $[M+H]^+$ 360.66).

Example 42

Synthesis of 4-(3-Nitro-benzoylamino)-1H-pyrazole-3-carboxylic acid (4-fluoro-phenyl)-amide

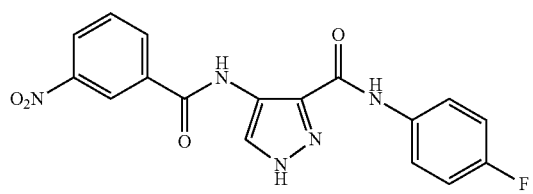 [SMILES: O=C(Nc1c[nH]nc1C(=O)Nc1ccc(F)cc1)c1cccc([N+](=O)[O-])c1]

The experiment was carried out in a manner analogous to that of Example 32 using 3-nitrobenzoic acid (43 mg, 0.25 mmol) as starting acid. The product was isolated as a cream coloured solid (15 mg, 18%). (LC/MS: $R_t$ 3.94, $[M+H]^+$ 369.65).

Example 43

Synthesis of 1H-Indole-3-carboxylic acid [3-(4-fluoro-phenylcarbamoyl)-1H-pyrazol-4-yl]-amide

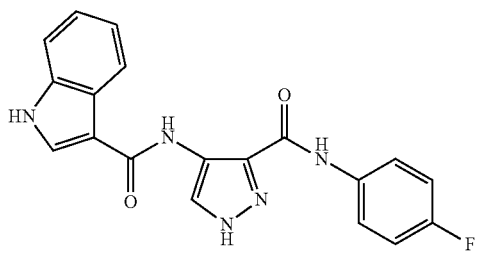 [SMILES: O=C(Nc1ccc(F)cc1)c1n[nH]cc1NC(=O)c1c[nH]c2ccccc12]

The experiment was carried out in a manner analogous to that of Example 32 using indole-3-carboxylic acid (41 mg, 0.25 mmol) as starting acid. The product was isolated as a rust coloured solid (14 mg, 17%). (LC/MS: $R_t$ 3.60, $[M+H]^+$ 363.66).

Example 44

Synthesis of 4-(4-Hydroxymethyl-benzoylamino)-1H-pyrazole-3-carboxylic acid (4-fluoro-phenyl)-amide

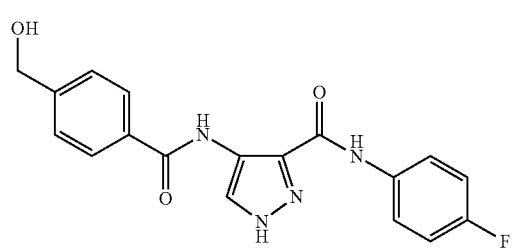 [SMILES: O=C(Nc1c[nH]nc1C(=O)Nc1ccc(F)cc1)c1ccc(CO)cc1]

The experiment was carried out in a manner analogous to that of Example 32 using 4-hydroxymethylbenzoic acid (39 mg, 0.25 mmol) as starting acid. The product was isolated as a white solid (19 mg, 23%). (LC/MS: $R_t$ 3.12, $[M+H]^+$ 354.68).

Example 45

Synthesis of 4-(3-Methyl-benzoylamino)-1H-pyrazole-3-carboxylic acid (4-fluoro-phenyl)-amide

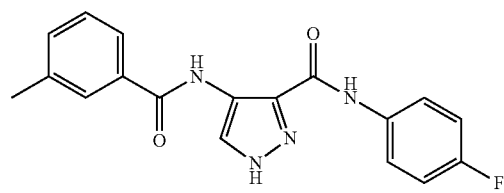 [SMILES: Cc1cccc(C(=O)Nc2c[nH]nc2C(=O)Nc2ccc(F)cc2)c1]

The experiment was carried out in a manner analogous to that of Example 32 using 3-methylbenzoic acid (35 mg, 0.25 mmol) as starting acid. The product was isolated as an off-white solid (21 mg, 27%). (LC/MS: $R_t$ 4.13, [M+H]$^+$ 338.71).

Example 46

Synthesis of 4-(2-Methyl-benzoylamino)-1H-pyrazole-3-carboxylic acid (4-fluoro-phenyl)-amide

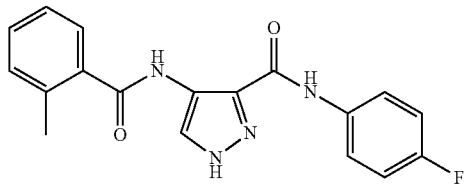 [SMILES: Cc1ccccc1C(=O)Nc1c[nH]nc1C(=O)Nc1ccc(F)cc1]

The experiment was carried out in a manner analogous to that of Example 32 using 2-methylbenzoic acid (35 mg, 0.25 mmol) as starting acid. The product was isolated as an off-white solid (20 mg, 26%). (LC/MS: $R_t$ 4.05, [M+H]$^+$ 338.69).

Example 47

Synthesis of 4-(4-Methyl-benzoylamino)-1H-pyrazole-3-carboxylic acid (4-fluoro-phenyl)-amide

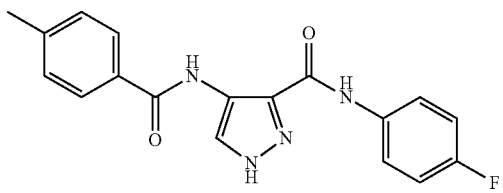 [SMILES: Cc1ccc(C(=O)Nc2c[nH]nc2C(=O)Nc2ccc(F)cc2)cc1]

The experiment was carried out in a manner analogous to that of Example 32 using 4-methylbenzoic acid (35 mg, 0.25 mmol) as starting acid. The product was isolated as an off-white solid (19 mg, 24%). (LC/MS: $R_t$ 4.16, [M+H]$^+$ 338.70).

Example 48

Synthesis of 4-[(2-Methyl-thiophene-3-carbonyl)-amino]-1H-pyrazole-3-carboxylic acid (4-fluoro-phenyl)-amide

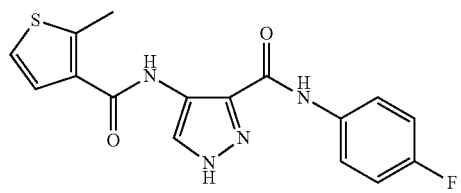 [SMILES: Cc1sccc1C(=O)Nc1c[nH]nc1C(=O)Nc1ccc(F)cc1]

2-Methyl-3-thiophenecarboxylic acid (36 mg, 0.25 mmol) was added to a solution of 4-amino-1H-pyrazole-3-carboxylic acid (4-fluoro-phenyl)-amide (Example 2B) (50 mg, 0.23 mmol), EDC (53 mg, 0.27 mmol), and HOBt (37 mg, 0.27 mmol) in DMSO (1 ml). The reaction mixture was stirred at room temperature for 24 hours. The reaction mixture was added dropwise to water (30 ml) and the resultant solid was collected by filtration, washed with water and sucked dry. The title compound was obtained as a beige solid (15 mg, 19%). (LC/MS: $R_t$ 4.08, [M+H]$^+$ 344.67).

Example 49

Synthesis of Quinoline-2-carboxylic acid[3-(4-fluoro-phenylcarbamoyl)-1H-pyrazol-4-yl]-amide

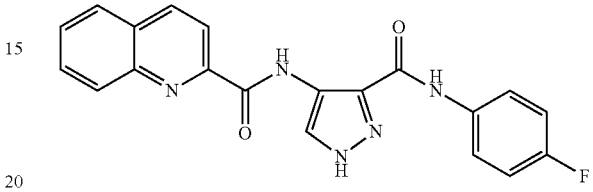

The experiment was carried out in a manner analogous to that of Example 48 using quinaldic acid (44 mg, 0.25 mmol) as starting acid. The product was isolated as a brown solid (16 mg, 19%). (LC/MS: $R_t$ 4.29, [M+H]$^+$ 375.66).

Example 50

Synthesis of 4-[(Thiophene-3-carbonyl)-amino]-1H-pyrazole-3-carboxylic acid (4-fluoro-phenyl)-amide

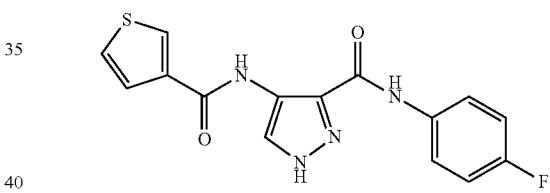

The experiment was carried out in a manner analogous to that of Example 48 using thiophene-3-carboxylic acid (33 mg, 0.25 mmol) as starting acid. The product was isolated as a beige solid (15 mg, 20%). (LC/MS: $R_t$ 3.77, [M+H]$^+$ 330.61).

Example 51

4-(2-fluoro-3-methoxy-benzoylamino)-1H-pyrazole-3-carboxylic acid (4-fluoro-phenyl)-amide

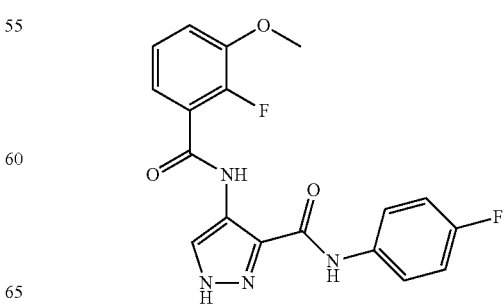

2-Fluoro-3-methoxybenzoic acid (0.047 g, 0.28 mmol), 4-amino-1H-pyrazole-3-carboxylic acid (4-fluoro-phenyl)-amide (Example 2B) (0.055 g, 0.25 mmol), EDC (0.58 g, 0.30 mmol) and HOBt (0.041 g, 0.30 mmol) were stirred at room temperature in DMSO (1.25 ml) for 5 hours. The reaction mixture was poured into water (30 ml) and the resultant solid was collected by filtration and dried in a vacuum oven to give the title compound as a grey solid (0.058 g, 63%). (LC/MS: $R_t$ 3.99, [MH]$^+$ 372.98).

Example 52

Synthesis of 4-[2-(2-Pyrrolidin-1-yl-ethoxy)-benzoylamino]-1H-pyrazole-3-carboxylic acid 4-fluorophenylamide 52A 2-(2-Pyrrolidin-1-yl-ethoxy)-benzoic acid methyl ester

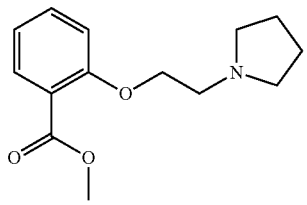 [SMILES: COC(=O)c1ccccc1OCCN1CCCC1]

Diisopropylazodicarboxylate (0.404 g, 2 mmol) was added dropwise to a solution of triphenylphosphine (0.524 g, 2 mmol) in THF (10 ml). Methyl salicylate (0.304 g, 2 mmol) was added dropwise and the resultant mixture was stirred at room temperature for 1 hour. 1,2-Hydroxyethyl pyrrolidine (0.230 g, 2 mmol) was added dropwise and the reaction mixture was left stirring at room temperature for a further 1.5 hours. The resulting solution was reduced in vacuo and subject to flash column chromatography, eluting with hexane:ethyl acetate (5:1, 1:1) then ethyl acetate:methanol (4:1) to give the product as a clear yellow oil (0.104 g, 21%). (LC/MS: $R_t$ 0.69, 1.62, [MH]$^+$ 250.02).

52B. 4-[2-(2-Pyrrolidin-1-yl-ethoxy)-benzoylamino]-1H-pyrazole-3-carboxylic acid 4-fluorophenylamide

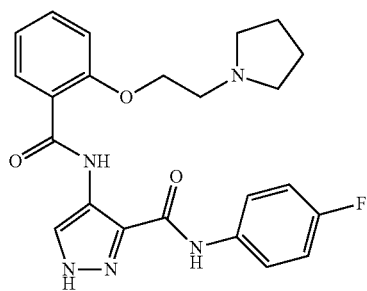 [SMILES: O=C(Nc1c[nH]nc1C(=O)Nc1ccc(F)cc1)c1ccccc1OCCN1CCCC1]

2-(2-Pyrrolidin-1-yl-ethoxy)-benzoic acid methyl ester (0.104 g, 0.42 mmol) was treated with 2 M aqueous NaOH (20 ml) and water (20 ml). The reaction mixture was stirred at room temperature for 20 hours, then reduced in vacuo and azeotroped with toluene (3×5 ml). Water (50 ml) was added and the mixture taken to pH 5 using 1M aqueous HCl. The resulting solution was reduced in vacuo and azeotroped with toluene (3×5 ml) to give a white solid, which was combined with 4-amino-1H-pyrazole-3-carboxylic acid (4-fluoro-phenyl)-amide (Example 2B) (0.055 g, 0.25 mmol), EDC (0.058 g, 0.3 mmol) and HOBt (0.041 g, 0.3 mmol) and stirred at room temperature in DMSO (3 ml) for 20 hours. The reaction mixture was poured into water (30 ml) and the resultant solid was collected by filtration and dried in a vacuum oven to give the title compound as a grey solid (0.015 g, 14%). (LC/MS: $R_t$ 2.18, [MH]$^+$ 438.06).

Example 53

Synthesis of 4-(2,6-Difluoro-benzoylamino)-1H-pyrazole-3-carboxylic acid (1-methyl-piperidin-4-yl)-amide

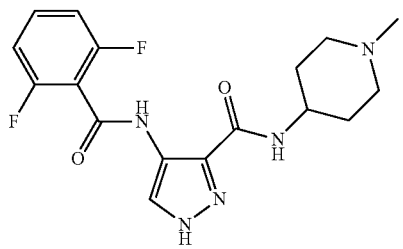 [SMILES: CN1CCC(NC(=O)c2n[nH]cc2NC(=O)c2c(F)cccc2F)CC1]

A mixture of 4-(2,6-difluoro-benzoylamino)-1H-pyrazole-3-carboxylic acid (134 mg, 0.50 mmol), 4-amino-N-methylpiperidine (50.0 µl, 0.45 mmol), EDAC (104 mg, 0.54 mmol) and HOBt (73.0 mg, 0.54 mmol) in DMF (3 ml) was stirred at ambient temperature for 16 hours. The mixture was reduced in vacuo, the residue taken up in EtOAc and washed successively with saturated aqueous sodium bicarbonate, water and brine. The organic portion was dried (MgSO$_4$) and reduced in vacuo to give 4-(2,6-difluoro-benzoylamino)-1H-pyrazole-3-carboxylic acid (1-methyl-piperidin-4-yl)-amide as a white solid (113 mg, 69%). (LC/MS: $R_t$ 2.52, [M+H]$^+$ 364.19).

Example 54

Synthesis of 4-(Cyclohexyl-methyl-amino)-1H-pyrazole-3-carboxylic acid (4-fluoro-phenyl)-amide

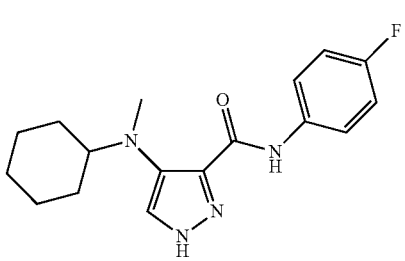 [SMILES: CN(c1c[nH]nc1C(=O)Nc1ccc(F)cc1)C1CCCCC1]

This compound was prepared in a manner analogous to the compound of Example 19 by successive reductive alkylations using firstly cyclohexanone and then formaldehyde. (LC/MS: $R_t$ 2.77 [MH]$^+$ 316.71).

Example 55

4-(Pyridin-2-ylamino)-1H-pyrazole-3-carboxylic acid (4-fluoro-phenyl)-amide

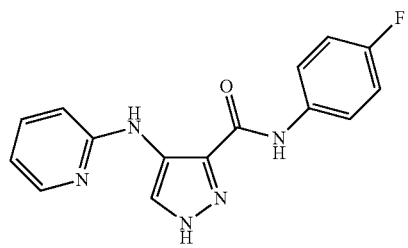 [SMILES: O=C(Nc1ccc(F)cc1)c1n[nH]cc1Nc1ccccn1]

The title compound was prepared in a manner analogous to the compound of Example 23. (LC/MS: $R_t$ 2.07 [MH]$^+$ 298.03).

Examples 56-81

By following the procedures described in the foregoing examples or methods analogous thereto, or by carrying out chemical transformations using the compounds described in the above examples and synthetic methods well known to the skilled person, the compounds set out in Table 3 were prepared.

TABLE 3

| Example No. | Structure | Prepared using method analogous to Example No | Differences to Example? | LCMS |
| --- | --- | --- | --- | --- |
| 56 | 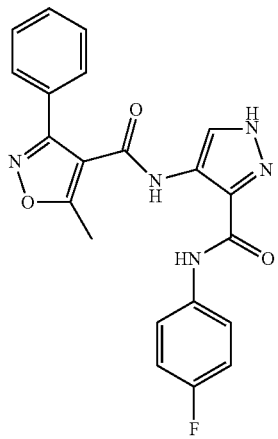 [SMILES: Cc1onc(-c2ccccc2)c1C(=O)Nc1c[nH]nc1C(=O)Nc1ccc(F)cc1] | 4 | | $R_t$ 3.20 min [M + H]$^+$ 406.07 |
| 57 | 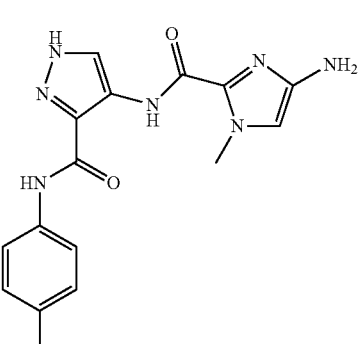 | 4 | Then removal of t-Boc protecting group with TFA as described in Example 82 | $R_t$ 2.35 min m/z 343.72 |

TABLE 3-continued

| Example No. | Structure | Prepared using method analogous to Example No | Differences to Example? | LCMS |
|---|---|---|---|---|
| 58 | 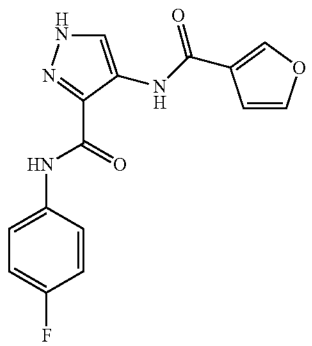 [SMILES: O=C(Nc1c[nH]nc1C(=O)Nc1ccc(F)cc1)c1ccoc1] | 4 | Used DMSO instead of DMF as solvent | $R_t$ 3.51 min m/z 314.62 |
| 59 | 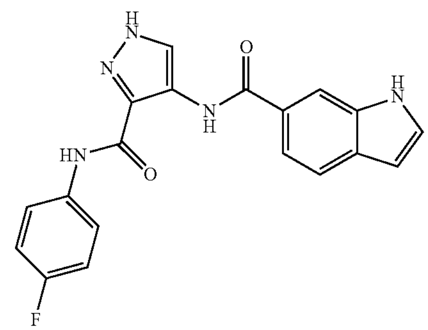 [SMILES: O=C(Nc1c[nH]nc1C(=O)Nc1ccc(F)cc1)c1ccc2cc[nH]c2c1] | 4 | Used DMSO instead of DMF as solvent | $R_t$ 3.79 min m/z 363.67 |
| 60 | 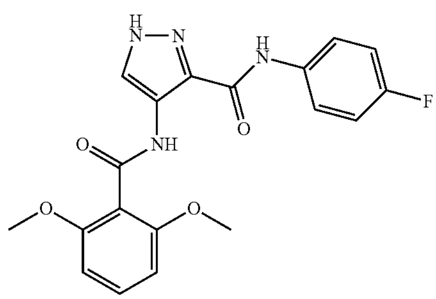 [SMILES: COc1cccc(OC)c1C(=O)Nc1c[nH]nc1C(=O)Nc1ccc(F)cc1] | 48 | Purified by column chromatography using EtOAC: Petroleum ether eluent | $R_t$ 3.68 min m/z 384.69 |
| 61 | 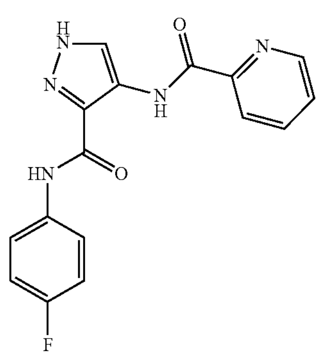 [SMILES: O=C(Nc1c[nH]nc1C(=O)Nc1ccc(F)cc1)c1ccccn1] | 48 | Purified by column chromatography using EtOAC: Petroleum ether eluent | $R_t$ 3.61 min m/z 326.10 |

TABLE 3-continued

| Example No. | Structure | Prepared using method analogous to Example No | Differences to Example? | LCMS |
|---|---|---|---|---|
| 62 | 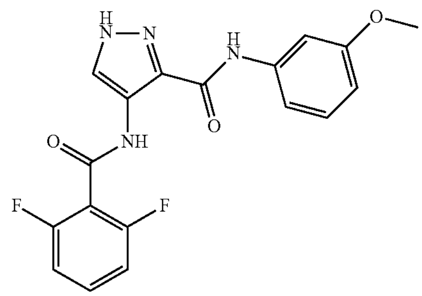 | 48 | Purified by column chromatography using EtOAC: Petroleum ether eluent | R_t 3.51 min m/z 387.11 |
| 63 | 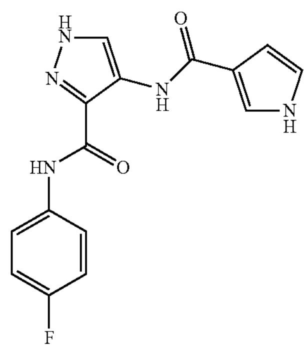 [SMILES: O=C(Nc1c[nH]nc1C(=O)Nc1ccc(F)cc1)c1cc[nH]c1] | 48 | | R_t 3.11 min m/z 313.65 |
| 64 | 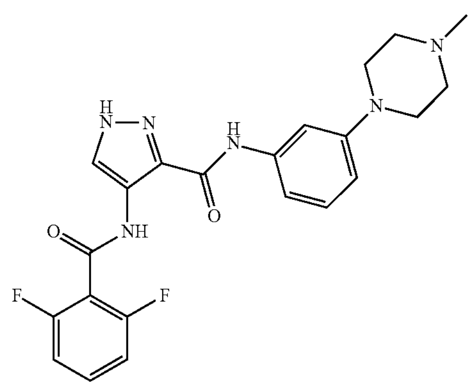 | 48 | Purified by column chromatography using EtOAC: Petroleum ether eluent | R_t 2.20 min m/z 455.19 |
| 65 | 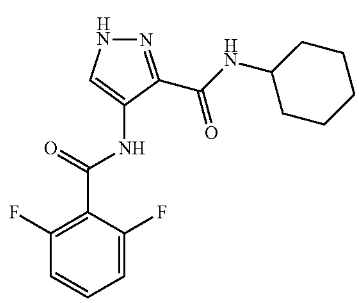 [SMILES: O=C(NC1CCCCC1)c1n[nH]cc1NC(=O)c1c(F)cccc1F] | 53 | | R_t 3.95 min m/z 349.09 |

TABLE 3-continued

| Example No. | Structure | Prepared using method analogous to Example No | Differences to Example? | LCMS |
|---|---|---|---|---|
| 66 | 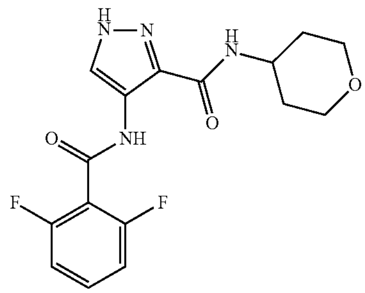 [SMILES: O=C(NC1CCOCC1)c1n[nH]cc1NC(=O)c1c(F)cccc1F] | 48 | Purified by column chromatography using EtOAC: Petroleum ether eluent | R_t 2.39 min m/z 351.07 |
| 67 | 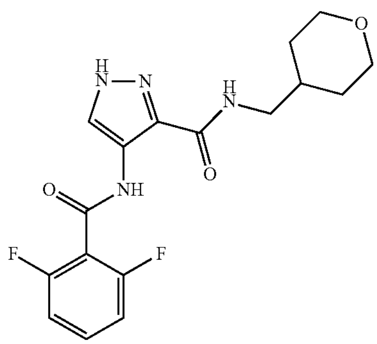 [SMILES: O=C(NCC1CCOCC1)c1n[nH]cc1NC(=O)c1c(F)cccc1F] | 48 | Purified by column chromatography using EtOAC: Petroleum ether eluent | R_t 2.83 min m/z 365.13 |
| 68 | 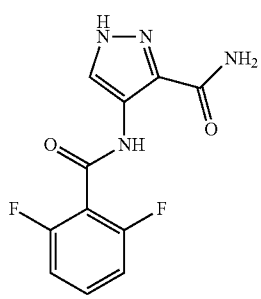 [SMILES: NC(=O)c1n[nH]cc1NC(=O)c1c(F)cccc1F] | | Removal of PMB group from the compound of Example 62 using TFA-anisole | R_t 2.10 min m/z 266.97 |
| 69 | 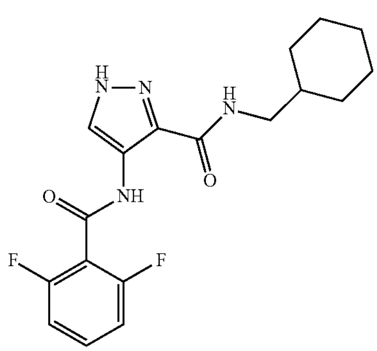 [SMILES: O=C(NCC1CCCCC1)c1n[nH]cc1NC(=O)c1c(F)cccc1F] | 48 | Used DMF instead of DMSO as solvent | R_t 3.22 min m/z 363.10 |

| Example No. | Structure | Prepared using method analogous to Example No | Differences to Example? | LCMS |
|---|---|---|---|---|
| 70 | 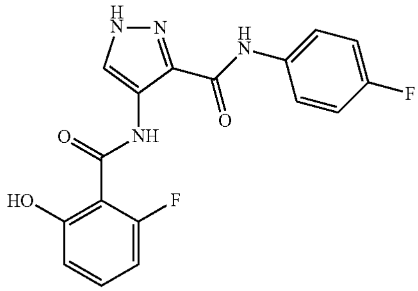 [SMILES: O=C(Nc1ccc(F)cc1)c1n[nH]cc1NC(=O)c1c(O)cccc1F] | 48 | | R$_t$ 4.48 min m/z 358.96 |
| 71 | 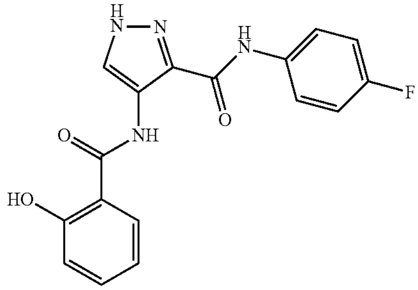 [SMILES: O=C(Nc1c[nH]nc1C(=O)Nc1ccc(F)cc1)c1ccccc1O] | 48 | | R$_t$ 3.93 min m/z 340.96 |
| 72 | 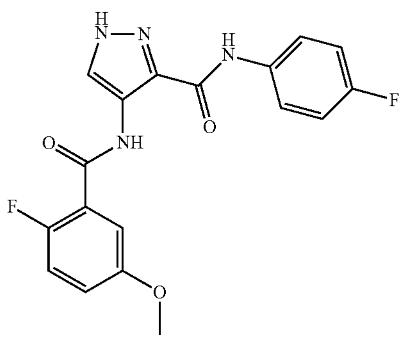 [SMILES: COc1ccc(F)c(C(=O)Nc2c[nH]nc2C(=O)Nc2ccc(F)cc2)c1] | 48 | | R$_t$ 4.11 min m/z 373.01 |
| 73 | 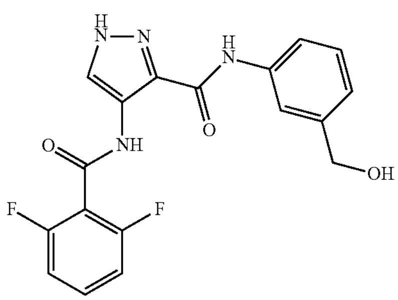 [SMILES: O=C(Nc1cccc(CO)c1)c1n[nH]cc1NC(=O)c1c(F)cccc1F] | 48 | Used DMF instead of DMSO as solvent | R$_t$ 2.56 min m/z 373.05 |
| 74 | 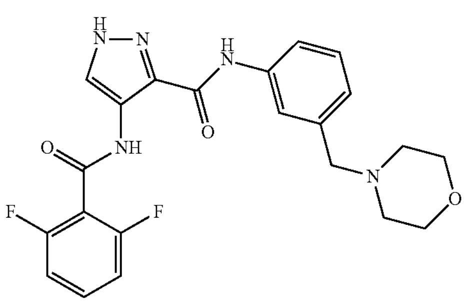 [SMILES: O=C(Nc1cccc(CN2CCOCC2)c1)c1n[nH]cc1NC(=O)c1c(F)cccc1F] | | Obtained by oxidation and then reductive amination of Example 73 | R$_t$ 1.99 min m/z 442.09 |

TABLE 3-continued

| Example No. | Structure | Prepared using method analogous to Example No | Differences to Example? | LCMS |
|---|---|---|---|---|
| 75 | 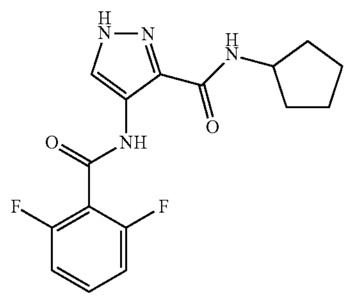 [SMILES: O=C(NC1CCCC1)c1n[nH]cc1NC(=O)c1c(F)cccc1F] | 53 | Purified by column chromatography using DCM:MeOH (1:0 to 19:1) eluent | R$_t$ 3.65 min m/z 335.03 |
| 76 | 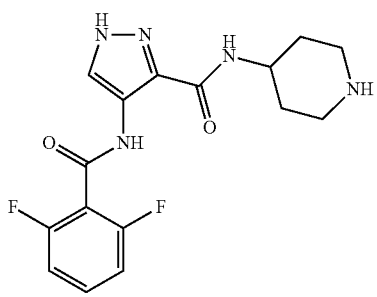 [SMILES: O=C(NC1CCNCC1)c1n[nH]cc1NC(=O)c1c(F)cccc1F] | 25 | Purified by column chromatography. Then removal of t-Boc protecting group with saturated ethyl acetate/HCl | R$_t$ 1.57 min m/z 350.10 |
| 77 | 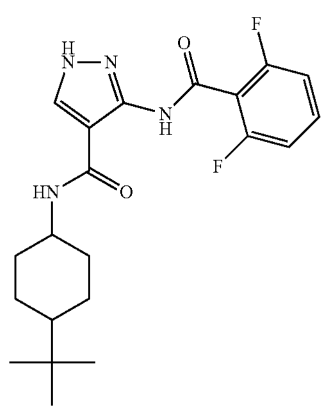 [SMILES: CC(C)(C)C1CCC(NC(=O)c2c[nH]nc2NC(=O)c2c(F)cccc2F)CC1] | 53 | | R$_t$ 5.05 min m/z 405.14 |
| 78 | 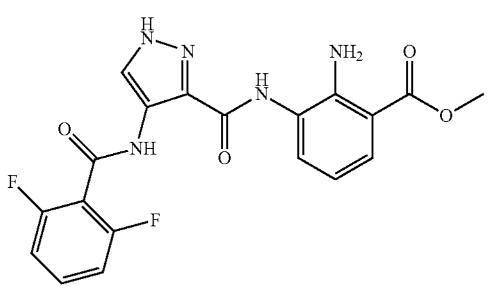 [SMILES: COC(=O)c1cccc(NC(=O)c2n[nH]cc2NC(=O)c2c(F)cccc2F)c1N] | 53 | | R$_t$ 2.87 min m/z 416.07 |

TABLE 3-continued

| Example No. | Structure | Prepared using method analogous to Example No | Differences to Example? | LCMS |
|---|---|---|---|---|
| 79 | 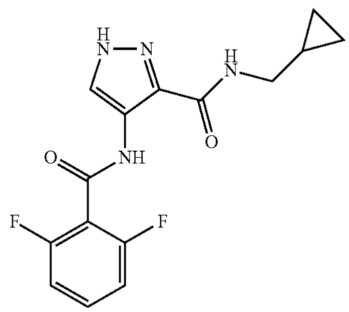 [SMILES: O=C(NCC1CC1)c1n[nH]cc1NC(=O)c1c(F)cccc1F] | 53 | Purified by column chromatography using EtOAC: Petroleum ether eluent (1:1) | $R_t$ 3.41 min m/z 321.03 |
| 80 | 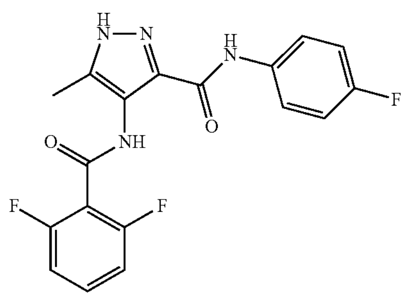 [SMILES: Cc1[nH]nc(C(=O)Nc2ccc(F)cc2)c1NC(=O)c1c(F)cccc1F] | 2A, 2B & 53 | Commercially available 5-methyl-pyrazole-1H-3-carboxylic acid used as starting material. Purified by column chromatography using EtOAc: Hexane eluent (1:3 to 1:1) | $R_t$ 3.42 min m/z 375.05 |
| 81 | 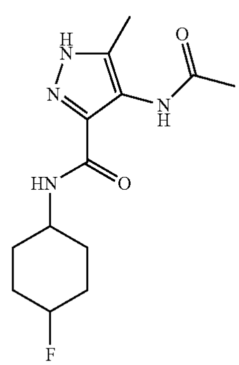 | 2C | Purified by column chromatography using EtOAC: Hexane eluent (1:1 to 1:0) | $R_t$ 2.37 min m/z 277.04 |

Example 82

4-[(4-Amino-1-methyl-1H-imidazole-2-carbonyl)-amino]-1H-pyrazole-3-carboxylic acid (4-fluoro-phenyl)-amide

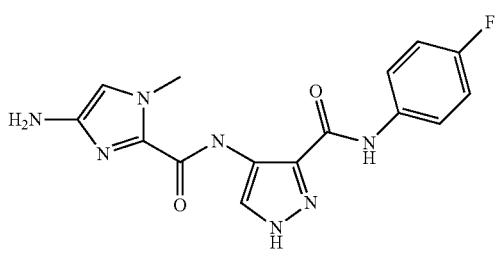 [SMILES: Cn1cc(N)nc1C(=O)Nc1c[nH]nc1C(=O)Nc1ccc(F)cc1]

Trifluoroacetic acid (200 μl) was added to a stirred suspension of {2-[3-(4-fluoro-phenylcarbamoyl)-1H-pyrazol-4-yl-carbamoyl]-1-methyl-1H-imidazol-4-yl}-carbamic acid tert-butyl ester (30 mg) in dichloromethane (5 ml), then stirred at room temperature for 2 hours. The solvent was evaporated then re-evaporated with toluene (2×10 ml). The residue was triturated with diethyl ether and the resultant solid collected by filtration. The solid was washed with diethyl ether then dried under vacuum to give 15 mg of 4-[(4-amino-1-methyl-1H-imidazole-2-carbonyl)-amino]-1H-pyrazole-3-carboxylic acid (4-fluoro-phenyl)-amide as an off-white solid. (LC/MS: [M+H]+ 343.72).

Example 83

Synthesis of 4-{[4-(2,6-Difluoro-benzoylamino)-1H-pyrazole-3-carbonyl]-amino}-cyclohexanecarboxylic acid 83A. 4-{[4-(2,6-difluoro-benzoylamino)-1H-pyrazole-3-carbonyl]-amino}-cyclohexanecarboxylic acid ethyl ester

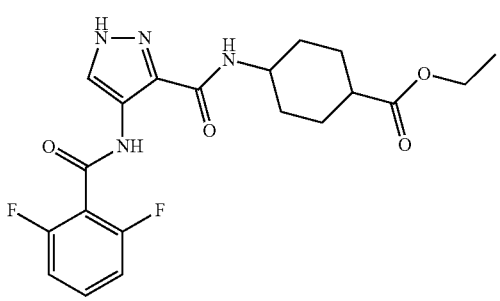 [SMILES: CCOC(=O)C1CCC(NC(=O)c2n[nH]cc2NC(=O)c2c(F)cccc2F)CC1]

Thionyl chloride (0.32 ml, 4.40 mmol) was slowly added to a mixture of 4-aminocyclohexanecarboxylic acid (572 mg, 4.00 mmol) in EtOH (10 ml) and stirred at ambient temperature for 16 hours. The mixture was reduced in vacuo, azeotroping with toluene, to give the corresponding ethyl ester (650 mg) as a pale solid.

A mixture of the ethyl ester (103 mg, 0.60 mmol), 4-(2,6-difluoro-benzoylamino)-1H-pyrazole-3-carboxylic acid (134 mg, 0.50 mmol), EDC (115 mg, 0.60 mmol) and HOBt (81 mg, 0.60 mmol) in DMF (5 ml) was stirred at ambient temperature for 16 hours. The mixture was reduced in vacuo, the residue taken up in EtOAc and washed successively with saturated aqueous sodium bicarbonate, water and brine. The organic portion was dried (MgSO$_4$) and reduced in vacuo to give 4-{[4-(2,6-difluoro-benzoylamino)-1H-pyrazole-3-carbonyl]-amino}-cyclohexanecarboxylic acid ethyl ester (112 mg).

83B. 4-{[4-(2,6-difluoro-benzoylamino)-1H-pyrazole-3-carbonyl]-amino}-cyclohexanecarboxylic acid

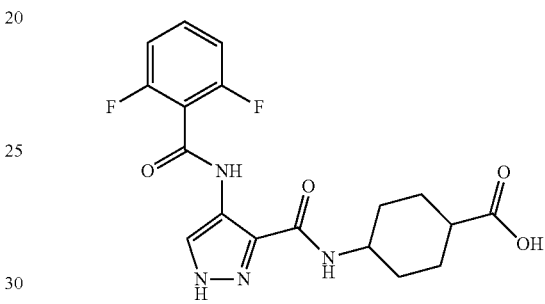

A mixture of the ester (45 mg) (from 83A) in MeOH (2.5 ml) and 2M aqueous NaOH (2.5 ml) was stirred at ambient temperature for 16 hours. The volatiles were removed in vacuo, water (10 ml) added and the mixture taken to pH 5 using 1M aqueous HCl. The precipitate formed was collected by filtration and purified by column chromatography using EtOAc/MeOH (1:0-9:1) to give 4-{[4-(2,6-difluoro-benzoylamino)-1H-pyrazole-3-carbonyl]-amino}-cyclohexanecarboxylic acid (11 mg) as a white solid and mixture of cis-/trans-isomers.

(LC/MS: R$_t$ 2.78 and 2.96, [M+H]+ 393.09).

Examples 84-152

General Procedure A

Preparation of Amide from Pyrazole Carboxylic Acid

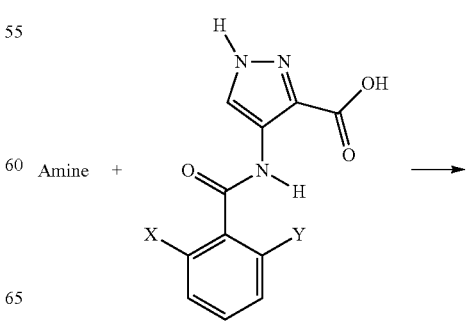

-continued

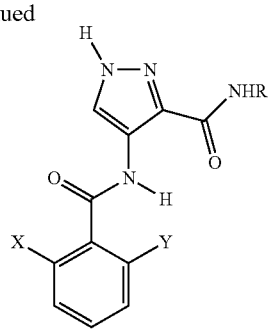

A mixture of the appropriate benzoylamino-1H-pyrazole-3-carboxylic acid (0.50 mmol), EDAC (104 mg, 0.54 mmol), HOBt (73.0 mg, 0.54 mmol) and the corresponding amine (0.45 mmol) in DMF (3 ml) was stirred at ambient temperature for 16 hours. The mixture was reduced in vacuo, the residue taken up in EtOAc and washed successively with saturated aqueous sodium bicarbonate, water and brine. The organic portion was dried (MgSO$_4$) and reduced in vacuo to give the desired product.

General Procedure B

Preparation of Amide from Amino-Pyrazole

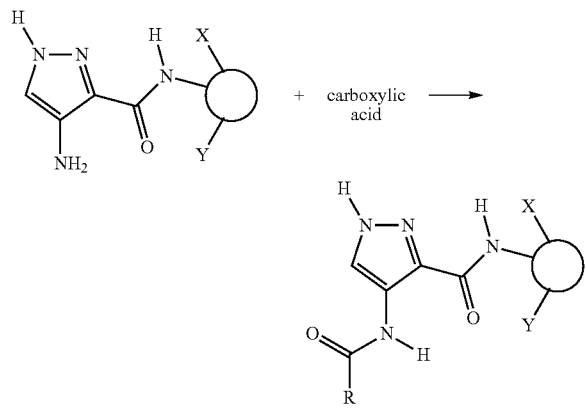

To a stirred solution of the appropriate 4-amino-1H-pyrazole-3-carboxylic acid amide (0.23 mmol), EDAC (52 mg; 0.27 mmol) and HOBt (37 mg; 0.27 mmol) in 5 ml of N,N-dimethylformamide was added the corresponding carboxylic acid (0.25 mmol), and the mixture was then left at room temperature overnight. The reaction mixture was evaporated and the residue purified by preparative LC/MS, to give the product.

General Procedure C

Deprotection of Piperidine Ring Nitrogen by Removal of tert-Butoxycarbonyl Group A product of Procedure A or Procedure B containing a piperidine group bearing an N-tert-butoxycarbonyl (t-Boc) protecting group (40 mg) was treated with saturated ethyl acetate/HCl, and stirred at room temperature for 1 hour. A solid precipitated out of the reaction mixture, which was filtered off, washed with ether, and then dried to give 25 mg product (LC/MS: [M+H]$^+$ 364).

Procedure L

Preparation of Amine Starting Materials

The following method was used to prepare the following amines:
4-thiomorpholine-4-yl-cyclohexylamine;
4-(1,1-dioxo-thiomorpholine-4-yl)-cyclohexylamine;
N-(tetrahydro-pyran-4-yl)-cyclohexane-1,4-diamine;
4-(4-methyl-piperazin-1-yl)-cyclohexylamine;
1'-methyl-[1,4']bipiperidinyl-4-ylamine; and
4-morpholin-4-yl-cyclohexylamine.

A solution of N-4-Boc-aminocyclohexanone (0.5 g, 2.3 mmol) in THF (10 ml) was treated with the appropriate amine, e.g. thiomorpholine (0.236 g, 2.3 mmol), and sodium triacetoxyborohydride (0.715 g, 2.76 mmol) and acetic acid (0.182 ml). The reaction was stirred overnight at room temperature, then diluted with CH$_2$Cl$_2$ and washed with saturated sodium carbonate. The organic layer was dried over MgSO$_4$ and evaporated to give a white solid which was used without further purification in the next step. The white solid was treated with saturated HCl/EtOAc, stirred at room temperature for 1 hour, evaporated to dryness and then re-evaporated with toluene. The resulting amines were isolated as the hydrochloride salt. (LC/MS: R$_t$ 1.75, [M+H]$^+$ 201).

By following General Procedures A, B, C and L, modified where stated, the compounds set out in Table 4 were prepared.

TABLE 4

| Example No. | | Method of Preparation | LCMS |
| --- | --- | --- | --- |
| 84 |  | Procedure A | [M + H]$^+$ 380 R$_t$ 1.42 |

TABLE 4-continued

| Example No. | | Method of Preparation | LCMS |
|---|---|---|---|
| 85 | | Procedure A | [M + H]+ 426 R, 1.93 |
| 86 | | Procedure A | [M + H]+ 440 R, 1.87 |
| 87 | | Procedure A | [M + H]+ 406 R, 2.78 |
| 88 | | Procedure A | [M + H]+ 406 R, 2.55 |
| 89 | | Procedure A DMSO instead of DMF | [M + H]+ 358 R, 1.98 |

TABLE 4-continued

| Example No. | Method of Preparation | LCMS |
|---|---|---|
| 90 | Procedure A<br>DMSO instead of DMF | [M + H]⁺ 357<br>R$_t$ 3.37 |
| 91 | Procedure A<br>DMSO instead of DMF | [M + H]⁺ 391<br>R$_t$ 3.16 |
| 92 | Procedure A<br>DMSO instead of DMF | [M + H]⁺ 375<br>R$_t$ 3.02 |
| 93 | Procedure A<br>DMSO instead of DMF | [M + H]⁺ 425<br>R$_t$ 3.27 |

TABLE 4-continued

| Example No. | Method of Preparation | LCMS |
|---|---|---|
| 94 | Procedure A<br>DMSO instead of DMF | [M + H]+ 393<br>R$_t$ 3.01 |
| 95 | Procedure A<br>DMSO instead of DMF | [M + H]+ 365<br>R$_t$ 2.22 |
| 96 | Procedure A<br>DMSO instead of DMF | [M + H]+ 387<br>R$_t$ 3.05 |
| 97 | Procedure A<br>DMSO instead of DMF | [M + H]+ 4 |

TABLE 4-continued

| Example No. | Method of Preparation | LCMS |
|---|---|---|
| 98 | Procedure C using the product of Example 97 as starting material | [M + H]⁺ 364, R, 1.76 |
| 99 | Procedure A DMSO instead of DMF | [M + H]⁺ 389, R, 2.36 |
| 100 | Procedure A DMSO instead of DMF | [M + H]⁺ 351, R, 2.55 |
| 101 | Procedure A DMSO instead of DMF | [M + H]⁺ 362, R, 2.63 |

TABLE 4-continued

| Example No. | | Method of Preparation | LCMS |
|---|---|---|---|
| 102 | | Procedure A<br>DMSO instead of DMF<br>Starting amine prepared according to Procedure L | [M + H]⁺ 364<br>R$_t$ 1.75 |
| 103 | | Procedure A<br>DMSO instead of DMF | [M + H]⁺ 358<br>R$_t$ 3.2 |
| 104 | | Procedure A<br>DMSO instead of DMF | [M + H]⁺ 358<br>R$_t$ 1.77 |
| 105 | | Procedure A<br>DMSO instead of DMF | [M + H]⁺ 344<br>R$_t$ 2.71 |
| 106 | | Procedure A<br>DMSO instead of DMF | [M + H]⁺ 392<br>R$_t$ 2.57 |

TABLE 4-continued

| Example No. | | Method of Preparation | LCMS |
|---|---|---|---|
| 107 | | Procedure A<br>DMSO instead of DMF | [M + H]⁺ 347<br>R$_t$ 2.8 |
| 108 | | Procedure A<br>DMSO instead of DMF | [M + H]⁺ 371<br>R$_t$ 3.1 |
| 109 | | Procedure A<br>Et$_3$N 1 equiv., DMSO instead of DMF | [M + H]⁺ 404<br>R$_t$ 2.7 |
| 110 | | Procedure A<br>Et$_3$N 2 equiv., HOAt instead of HOBt,<br>DMSO instead of DMF | [M + H]⁺ 428<br>R$_t$ 2.63 |

TABLE 4-continued

| Example No. | | Method of Preparation | LCMS |
|---|---|---|---|
| 111 | | Procedure Procedure A followed by Procedure C Et$_3$N 2 equiv., HOAt instead of HOBt, DMSO instead of DMF | [M + H]$^+$ 364 R$_t$ 1.75 |
| 112 | | Procedure A Et$_3$N 2 equiv., HOAt instead of HOBt, DMSO instead of DMF | [M + H]$^+$ 427 R$_t$ 2.71 |
| 113 | | Procedure A HOAt instead of HOBt, DMSO instead of DMF | [M + H]$^+$ 363 R$_t$ 3.34 |
| 114 | | Procedure A Et$_3$N 2 equiv., HOAt instead of HOBt, DMSO instead of DMF | [M + H]$^+$ 432 R$_t$ 2.63 |

TABLE 4-continued
| Example No. | | | Method of Preparation | LCMS |
|---|---|---|---|---|
| 115 | 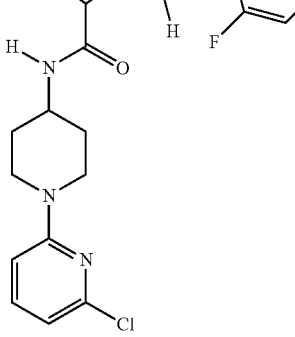 | | Procedure A | [M + H]+ 461<br>R, 3.3 |
| 116 | 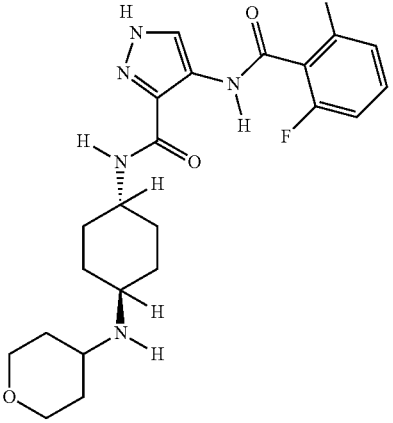 | Chiral | Procedure A<br>DMSO instead of DMF, Et₃N 2 equiv<br>Starting amine prepared according to Procedure L | [M + H]+ 448<br>R, 1.87 |
| 117 | 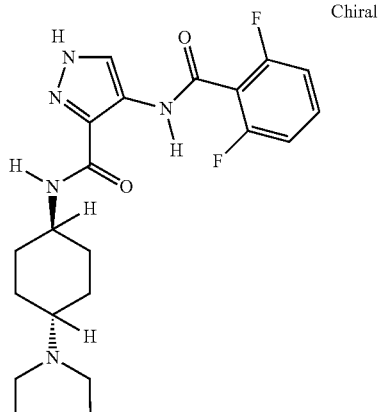 | Chiral | Procedure A<br>DMSO instead of DMF, Et₃N 2 equiv<br>Starting amine prepared according to Procedure L | [M + H]+ 447<br>R, 1.65 |

TABLE 4-continued
| Example No. | | Method of Preparation | LCMS |
|---|---|---|---|
| 118 | 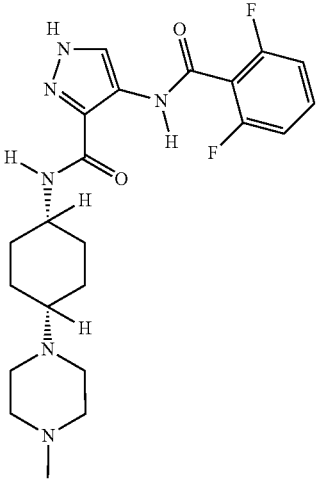 Chiral | Procedure A<br>DMSO instead of DMF, Et₃N 2 equiv<br>Starting amine prepared according to Procedure L | [M + H]⁺ 447<br>R, 1.72 |
| 119 | 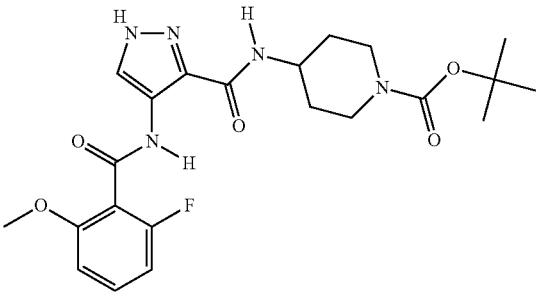 | Procedure B | [M + H]⁺ 462<br>R, 2.97 |
| 120 | 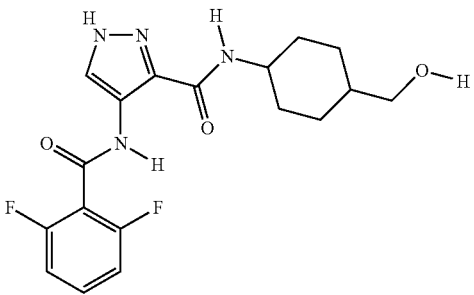 | Procedure A<br>N-ethyl-morpholine (NEM) 2 equiv | [M + H]⁺ 379<br>R, 2.45 |
| 121 | 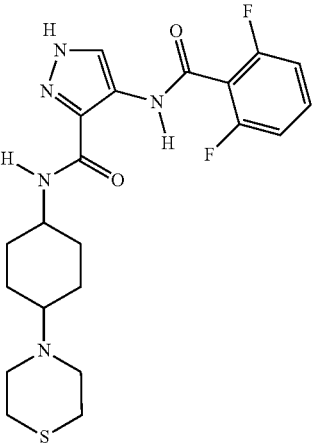 | Procedure A<br>HOAt instead of HOBt, Et₃N 2 equiv<br>Starting amine prepared according to Procedure L | [M + H]⁺ 450<br>R, 1.97 |

TABLE 4-continued

| Example No. | | Method of Preparation | LCMS |
| --- | --- | --- | --- |
| 122 | (structure) | Procedure B | [M + H]+ 387<br>R, 3.83 |
| 123 | (structure) | Procedure B | [M + H]+ 417<br>R, 3.65 |
| 124 | (structure) Chiral | Procedure A<br>HOAt instead of HOBt, Et₃N 2 equiv | [M + H]+ 392<br>R, 1.85 |
| 125 | (structure) | Procedure A<br>HOAt instead of HOBt, Et₃N 2 equiv | [M + H]+ 408<br>R, 1.82 |

TABLE 4-continued
| Example No. | | Method of Preparation | LCMS |
|---|---|---|---|
| 126 | 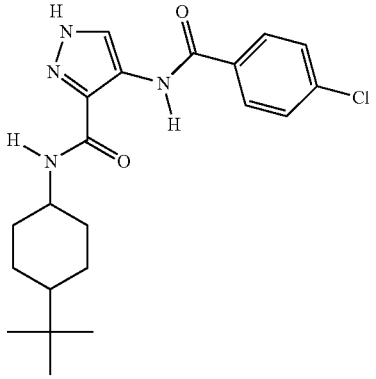 | Procedure B | [M + H]+ 403<br>R_t 4.02 |
| 127 | 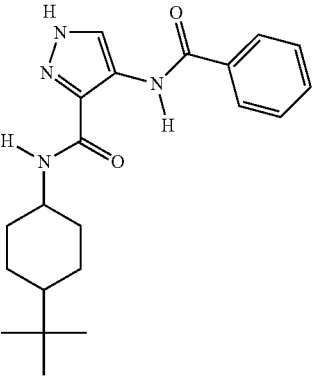 | Procedure B | [M + H]+ 369<br>R_t 3.78 |
| 128 | 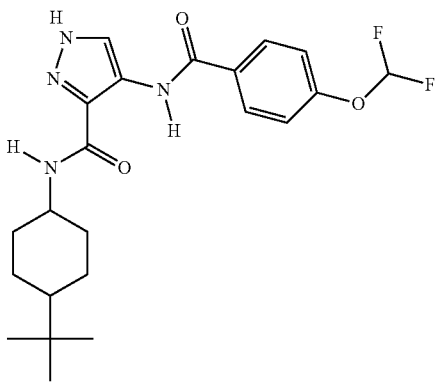 | Procedure B | [M + H]+ 435<br>R_t 3.83 |
| 129 | 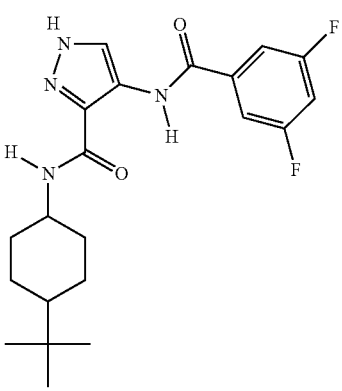 | Procedure B | [M + H]+ 405<br>R_t 3.96 |

TABLE 4-continued
| Example No. | | Method of Preparation | LCMS |
|---|---|---|---|
| 130 | 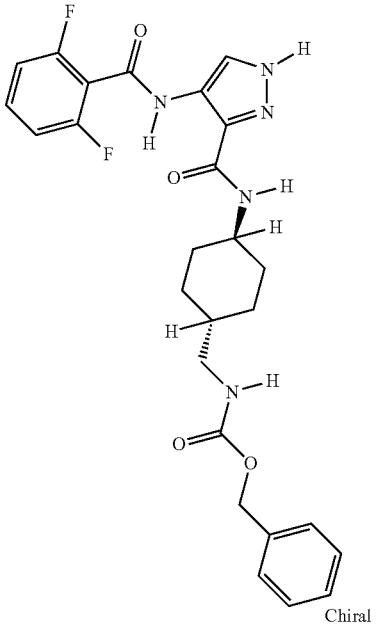 [SMILES: O=C(NC[C@H]1CC[C@H](NC(=O)c2n[nH]cc2NC(=O)c2c(F)cccc2F)CC1)OCc1ccccc1] Chiral | Procedure A HOAt instead of HOBt | [M + H]+ 512 R, 3.1 |
| 131 | 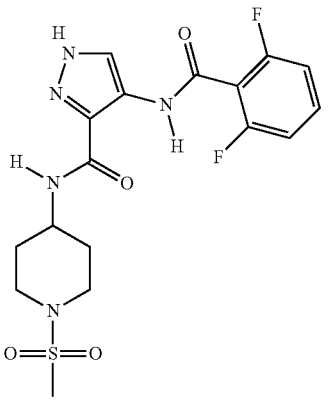 | Procedure A HOAt instead of HOBt, | [M + H]+ 428 R, 2.45 |
| 132 | 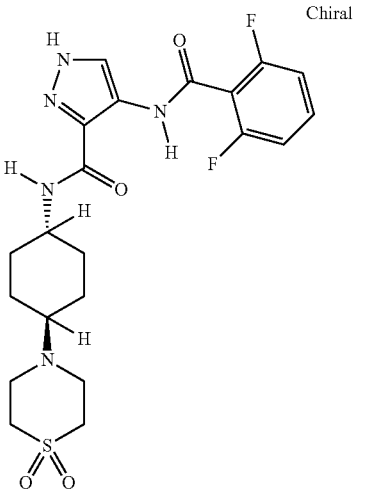 Chiral | Procedure A HOAt instead of HOBt, Et3N 2 equiv. Cis and trans isomers separated after amide coupling step Starting amine prepared according to Procedure L | [M + H]+ 482 R, 1.96 |

TABLE 4-continued
| Example No. | | Method of Preparation | LCMS |
|---|---|---|---|
| 133 | 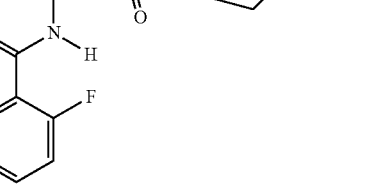 | Procedure A<br>HOAt instead of HOBt,<br>DMSO instead of DMF | [M + H]⁺ 434<br>R$_t$ 2.3 |
| 134 | 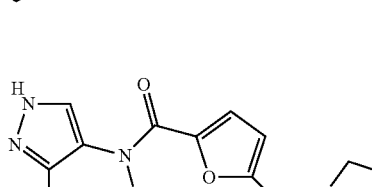 | Procedure B | [M + H]⁺ 442<br>R$_t$ 2.39 |
| 135 | 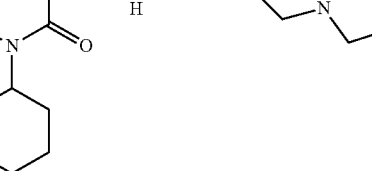 | Procedure B | [M + H]⁺ 458<br>R$_t$ 2.26 |
| 136 | 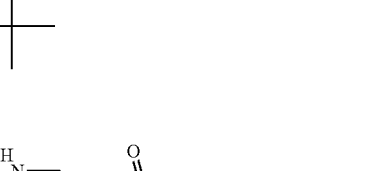 | Procedure B<br>HOAt instead of HOBt, | [M + H]⁺ 468<br>R$_t$ 3.07 |

TABLE 4-continued
| Example No. | | | Method of Preparation | LCMS |
|---|---|---|---|---|
| 137 | 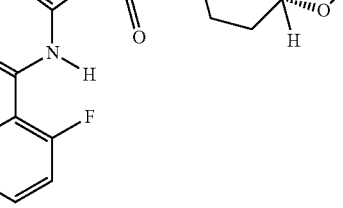 | Chiral | Procedure A
Et₃N 2 equiv., HOAt instead of HOBt, | [M + H]⁺ 379
R, 2.6 |
| 138 | 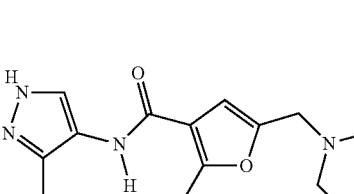 | | Procedure B | [M + H]⁺ 472
R, 2.40 |
| 139 |  | Chiral | Procedure A
Et₃N 2 equiv., HOAt instead of HOBt,
DMSO instead of DMF | [M + H]⁺ 364
R, 2.1 |
| 140 | 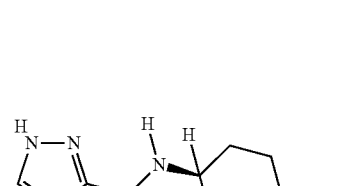 | | Procedure B followed by Procedure C | [M + H]⁺ 314
R, 1.78 |

TABLE 4-continued

| Example No. | | Method of Preparation | LCMS |
|---|---|---|---|
| 141 | *structure* | Procedure B followed by Procedure C | [M + H]⁺ 332<br>R, 1.89 |
| 142 | *structure* | Procedure B followed by Procedure C | [M + H]⁺ 362<br>R, 1.78 |
| 143 | *structure* | Procedure B followed by Procedure C | [M + H]⁺ 348<br>R, 2.01 |
| 144 | *structure* | Procedure B followed by Procedure C | [M + H]⁺ 350<br>R, 1.97 |

TABLE 4-continued

| Example No. | | Method of Preparation | LCMS |
|---|---|---|---|
| 145 | | Procedure B followed by Procedure C | [M + H]+ 380<br>R_t 2.01 |
| 146 | | Procedure B followed by Procedure C | [M + H]+ 395<br>R_t 1.94 |
| 147 | | Procedure B followed by Procedure C | [M + H]+ 396<br>R_t 2.11 |
| 148 | | Procedure B followed by Procedure C<br>HOAt instead of HOBt | [M + H]+ 368<br>R_t 1.76 |

TABLE 4-continued

| Example No. | | Method of Preparation | LCMS |
|---|---|---|---|
| 149 | (structure) | Procedure B followed by Procedure C | [M + H]⁺ 366 R$_t$ 1.78 |
| 150 | (structure) | Procedure B followed by Procedure C | [M + H]⁺ 383 R$_t$ 1.87 |
| 151 | (structure) | Procedure B followed by Procedure C | [M + H]⁺ 433 R$_t$ 1.89 |
| 152 | (structure, Chiral) | Procedure A followed by Procedure C HOAt instead of HOBt | [M + H]⁺ 350 R$_t$ 1.76 |

Examples 153-165

General Procedure D

Preparation of Protected 4-Amino-pyrazol-3-yl carboxylic acid 4-hydroxy-cyclohexylamide

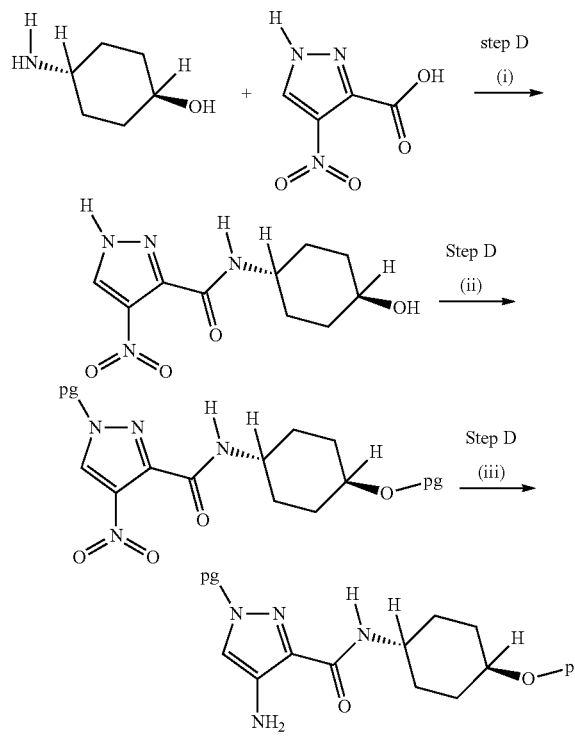

pg = protecting group

Step D (i):

A mixture of 4-nitro-3-pyrazolecarboxylic acid (4.98 g, 31.7 mmol), trans 4-aminocyclohexanol (3.65 g, 31.7 mmol), EDAC (6.68 g, 34.8 mmol) and HOBt (4.7 g, 34.8 mmol) in DMF (120 ml) was stirred at ambient temperature for 16 hours. The mixture was reduced in vacuo, the residue taken up in $CH_2Cl_2$ and washed successively with 5% citric acid, saturated aqueous sodium bicarbonate, water and brine. The product was found to be mainly in the citric acid wash, which was basified and extracted with EtOAc. The organic layer was dried over $MgSO_4$, filtered and evaporated to give a white solid, which was triturated with $CHCl_3$ to give 1.95 g of 4-nitro-1H-pyrazole-3-carboxylic acid 4-hydroxy-cyclohexylamide. (LC/MS: $R_t$ 1.62, [M+H]$^+$ 255).

Step D (ii):

Introduction of Tetrahydro-pyran-2-yl Protecting Group

A solution of 4-nitro-1H-pyrazole-3-carboxylic acid 4-hydroxy-cyclohexylamide (1.95 g; 7.67 mmol) in a mix of THF (50 ml) and chloroform (100 ml), was treated with 3,4-dihydro-2H-pyran (1.54 ml, 15.34 mmol) and p-toluenesulphonic acid monohydrate (100 mg). The reaction mixture was stirred at room temperature overnight, and then excess pyran (0.9 ml) was added in total to bring reaction to completion. The reaction mixture was diluted with $CH_2Cl_2$ and washed successively with saturated aqueous sodium bicarbonate, water and brine. The resulting solution was reduced in vacuo and subject to Biotage column chromatography, eluting with hexane (2 column lengths) followed by 30% ethyl acetate:hexane (10 column lengths), 70% ethyl acetate:hexane (10 column lengths) to give 1.25 g of 4-nitro-1-(tetrahydro-pyran-2-yl-1H-pyrazole-3-carboxylic acid[4-(tetrahydro-pyran-2-yloxy)-cyclohexyl]-amide. (LC/MS: $R_t$ 2.97, [M+H]$^+$ 423).

Step D (iii):

A solution of 4-nitro-1-(tetrahydro-pyran-2-yl)-1H-pyrazole-3-carboxylic acid[4-(tetrahydro-pyran-2-yloxy)-cyclohexyl]-amide (0.3 g; 0.71 mmol) in methanol (25 ml), was treated with 10% palladium on carbon (30 mg) then hydrogenated at room temperature and pressure overnight. The catalyst was removed by filtration and washed three times with methanol. The filtrate was evaporated to give 0.264 g of the required product. (LC/MS: $R_t$ 2.39, [M+H]$^+$ 393).

General Procedure E

Procedure for Removal of a Tetrahydropyran-2-yl Protecting Group

To a suspension of 4-(2-methoxy-benzoylamino)-1-(tetrahydro-pyran-2-yl-1H-pyrazole-3-carboxylic acid[4-(tetrahydro-pyran-2-yloxy)-cyclohexyl]-amide (0.125 g, 0.23 mmol) in EtOH (10 ml) was added p-toluene sulphonic acid hydrate (90 mg, 0.46 mmol). The reaction mixture was heated at 70° C. for 30 mins. The reaction was diluted with EtOAc and washed successively with saturated aqueous sodium bicarbonate, water and brine. The resulting solution was reduced in vacuo to give a white solid, which contained traces of p-toluene sulphonic acid hydrate. The solid was then taken up in EtOAc and washed with 1M NaOH and then brine. The resulting solution was reduced in vacuo and then triturated with ether/hexane to give 10 mg of required product. (LC/MS: $R_t$ 2.29, [M+H]$^+$ 359)

General Procedure F

Preparation of a Urea from a 4-Amino-pyrazole-3-carboxylic acid amide

To a solution of 4-amino-1-(tetrahydro-pyran-2-yl-1H-pyrazole-3-carboxylic acid[4-(tetrahydro-pyran-2-yloxy)-cyclohexyl]-amide (80 mg, 0.2 mmol) in toluene (2 ml) was added phenyl isocyanate (929 mg, 0.24 mmol). The reaction mixture was heated at 70° C. for 1 hour. The reaction was diluted with EtOAc and washed successively with water and brine. The resulting solution was reduced in vacuo to give yellow oil. This was used without further purification. (LC/MS: $R_t$ 2.28, [M+H]$^+$ 344).

General Procedure G

Conversion of a 4-Amino-pyrazole Group to a 4-(Morpholine-4-carbonylamino)-Pyrazole Group To a solution of 4-amino-1-(tetrahydro-pyran-2-yl-1H-pyrazole-3-carboxylic acid[4-(tetrahydro-pyran-2-yloxy)-cyclohexyl]-amide (0.1 g, 0.255 mmol) in $CH_2Cl_2$ (5 ml) at −10° C. was added in a dropwise manner a 20% solution of phosgene in toluene. The reaction mixture was stirred at −10° C. for 15 mins and then morpholine (0.765 mmol) was added. The reaction mixture was allowed to warm up to room temperature over 1 hour then stirred at room temperature overnight. The reaction was diluted with $CH_2Cl_2$ and washed General Procedure H Preparation of N-Oxides To a suspension of the compound of Example 53 (7.7 mg, 0.02 mmol) in $CH_2Cl_2$ (0.5 ml) was added meta-chloroperbenzoic acid (MCPBA) (3.6 mg, 0.02 mmol). The reaction mixture was stirred at room temperature overnight, and then evaporated. The residue was purified by preparative LC/MS, to give 3 mg of the required product. (LC/MS: $R_t$ 1.83, $[M+H]^+$ 380)

General Procedure I

Removal of a Benzyloxycarbonyl Protecting Group

A solution of the compound of Example 130 (0.2 g; 0.39 mmol) in EtOAc (40 ml) was treated with 10% palladium on carbon (20 mg) then hydrogenated at room temperature and pressure for 3 hours. The catalyst was removed by filtration and washed three times with EtOAc. The filtrate was evaporated and the residue was subjected to chromatography using 10% MeOH-$CH_2Cl_2$ then 20% MeOH—$CH_2Cl_2$ to give 80 mg of the required product. (LC/MS: $R_t$ 1.88, $[M+H]^+$ 378).

General Procedure J

Mesylation of an Amine

To a solution of the compound of Example 163 (20 mg, 0.05 mmol) in $CH_3CN$ (3 ml) added methane-sulphonyl chloride (0.0045 ml, 0.058 mmol) followed by Hunig's Base (0.018 ml, 0.1 mmol). The reaction mixture was stirred at room temperature for 2 hours and was then evaporated down. The residue was purified by preparative LC/MS to give 8 mg of the required product. (LC/MS: $R_t$ 2.54, $[M+H]^+$ 456).

By following Procedures A to L, the compounds set out in Table 5 were prepared.

TABLE 5

| Example No. | | Method of Preparation | LCMS |
|---|---|---|---|
| 153 | | Procedure D followed by B then E HOAt instead of HOBt, $CH_2Cl_2$ instead of DMF | $[M + H]^+$ 359 $R_t$ 2.29 |
| 154 | | Procedure D followed by B then E HOAt instead of HOBt, $CH_2Cl_2$ instead of DMF | $[M + H]^+$ 377 $R_t$ 2.22 |
| 155 | | Procedure D followed by B then E HOAt instead of HOBt, $CH_2Cl_2$ instead of DMF | $[M + H]^+$ 381 $R_t$ 2.34 |

TABLE 5-continued
| Example No. | | Method of Preparation | LCMS |
|---|---|---|---|
| 156 | 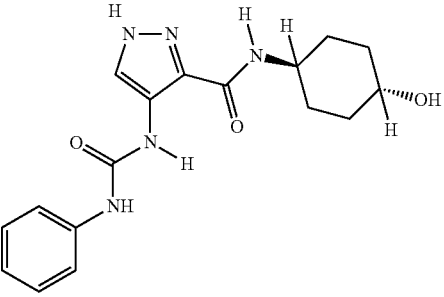 | Procedure D followed by F then E | [M + H]⁺ 344<br>R$_t$ 2.28 |
| 157 | 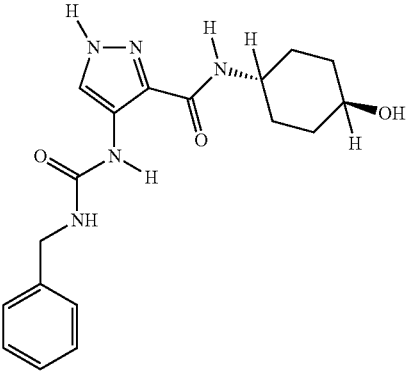 [SMILES: O=C(NCc1ccccc1)Nc1c[nH]nc1C(=O)N[C@H]1CC[C@H](O)CC1] | Procedure D followed by F then E | [M + H]⁺ 358<br>R$_t$ 2.22 |
| 158 | 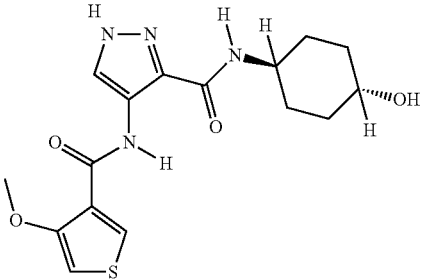 | Procedure D followed by B then E<br>HOAt instead of HOBt,<br>CH$_2$Cl$_2$ instead of DMF | [M + H]⁺ 365<br>R$_t$ 2.21 |
| 159 | 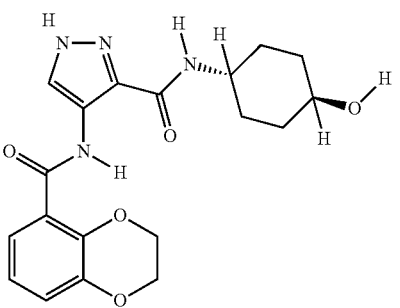 | Procedure D followed by B then E<br>HOAt instead of HOBt,<br>CH$_2$Cl$_2$ instead of DMF | [M + H]⁺ 387<br>R$_t$ 2.29 |

TABLE 5-continued

| Example No. | | Method of Preparation | LCMS |
|---|---|---|---|
| 160 | | Procedure D followed by F then E | [M + H]+ 380<br>R$_t$ 2.17 |
| 161 | | Procedure D followed by G then E | [M + H]+ 338<br>R$_t$ 1.68 |
| 162 | | Procedure H | [M + H]+ 380<br>R$_t$ 1.83 |
| 163 | | Procedure A (HOAt instead of HOBt) to give the compound of Example 130 followed by Procedure I. | [M + H]+ 378<br>R$_t$ 1.78 |

TABLE 5-continued

| Example No. | | Method of Preparation | LCMS |
|---|---|---|---|
| 164 | (structure) | Procedures A (HOAt instead of HOBt) and I to give the compound of Example 163 followed by Procedure J. | [M + H]⁺ 456 R, 2.54 |

General Procedure M

Formation of pyrazole 4-amide group

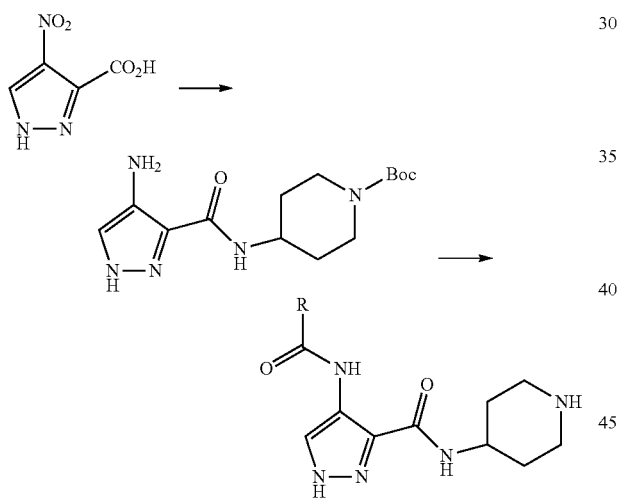

4-Nitropyrazole-3-carboxylic acid (7.3 g; 15.9 mmol) was added to a stirred solution of 4-amino-1-Boc-piperidine (10.2 mg; 51 mmol), EDC (10.7 g; 55.8 mmol), and HOAt (55.8 g; 19.1 mmol) in DMF (100 ml), and then stirred at room temperature overnight. The solvent was removed by evaporation under reduced pressure and the residue triturated with water (250 ml). The resultant cream solid was collected by filtration, washed with water then dried under vacuum to give 13.05 g of 4-[(4-nitro-1H-pyrazole-3-carbonyl)-amino]-piperidine-1-carboxylic acid tert-butyl ester (LC/MS: $R_t$ 2.50, [M+H]⁺ 340).

4-[(4-Nitro-1H-pyrazole-3-carbonyl)-amino]-piperidine-1-carboxylic acid tert-butyl ester (13.05 g) was dissolved in ethanol/DMF (300 ml/75 ml), treated with 10% palladium on carbon (500 mg) then hydrogenated at room temperature and pressure overnight. The catalyst was removed by filtration through Celite and the filtrate evaporated and re-evaporated with toluene. The crude material was purified by flash column chromatography eluting with EtOAc then 2% MeOH/EtOAc then 5% MeOH/EtOAc. Product containing fractions were combined and evaporated to give 8.78 g of 4-[(4-amino-1H-pyrazole-3-carbonyl)-amino]-piperidine-1-carboxylic acid tert-butyl ester as a brown foam. (LC/MS: $R_t$ 1.91, [M+H]⁺ 310).

To a stirred solution of 4-[(4-amino-1H-pyrazole-3-carbonyl)-amino]-piperidine-1-carboxylic acid tert-butyl ester (200 mg; 0.65 mmol), EDAC (150 mg; 0.78 mmol) and HOBt (105 mg; 0.78 mmol) in 5 ml of N,N-dimethylformamide was added the corresponding carboxylic acid (0.25 mmol), and the mixture was then left at room temperature overnight. The reaction mixture was diluted with saturated aqueous sodium bicarbonate solution and the product collected by filtration and dried under vacuum. The Boc-protected compound was dissolved in saturated HCl/EtOAc and stirred at room temperature for 3 hours. The product was collected by filtration, washed with diethyl ether and dried under vacuum.

General Procedure N

Preparation of 1-tert-Butyl-piperidin-4-ylamine

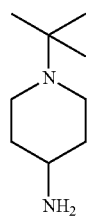

Step N (i)

To a solution of 1-ethyl-4-oxopiperidine (25 g, 0.197 mol) in acetone (250 ml) at RT in a water bath was added methyl iodide (15.5 ml, 0.25 mol) at such a rate to keep the temperature below 30° C. The mixture was filtered and the precipitate washed with acetone and dried to yield 1-ethyl-1-methyl-4-oxopiperidinium iodide (45 g) (LC/MS: $R_t$ 0.38, [M+H]⁺ 143).

Step N (ii)

To a solution of t-butylamine (78.2 ml, 0.74 mol) in toluene (400 ml) was added a solution of 1-ethyl-1-methyl-4-oxopiperidinium iodide (40 g, 0.148 mol) and sodium bicarbonate (1.245 g, 0.014 mol) in water (60 ml). The reaction mixture was heated at 78° C. for 6 hours and then allowed to cool to ambient temperature. The layers were separated and the aqueous layer was washed with EtOAc. The organics were combined and washed with brine, dried (MgSO$_4$), filtered and reduced in vacuo to yield 1-tert-butyl-4-oxopiperidine (14 g) (LC/MS: R$_t$ 0.39, [M+H]$^+$ 156).

Step N (iii)

A solution of 1-tert-butyl-4-oxopiperidine (3.6 g, 23.1), benzylamine (5.1 ml, 46.8 mmol), acetic acid (1.5 ml) and sodium triacetoxyborohydride (7.38 g, 34.8 mmol) was stirred at ambient for 2 days. Reaction mixture reduced in vacuo, residue partitioned between aqueous K$_2$CO$_3$ and EtOAc. The organic portion was dried (Na$_2$SO$_4$), filtered and reduced in vacuo. The residue was subjected to chromatography using CH$_2$Cl$_2$/MeOH/NH$_4$OH (87/12/1) as the eluent to yield N-benzyl-1-tert-butylpiperidin-4-amine (1.5 g) (LC/MS: R$_t$ 0.45, [M+H]$^+$ 247).

Step N (iv)

A solution of N-benzyl-1-tert-butylpiperidin-4-amine (1.56 g) and 10% palladium on carbon (2 g) in MeOH (250 ml) was hydrogenated in a Parr shaker at 50 psi for 16 hours. The solution was filtered and the reaction mixture reduced in vacuo, to yield 1-tert-butylpiperidin-4-amine (0.64 g) (LC/MS: R$_t$ 02.31, no [M+H]$^+$).

Example 165

Synthesis of 4-(2,6-difluoro-benzoylamino)-1H-pyrazole-3-carboxylic acid[5-fluoro-2-(1-methyl-piperidin-4-yloxy)-phenyl]-amide

165A. Synthesis of 4-nitro-1H-pyrazole-3-carboxylic acid ethyl ester

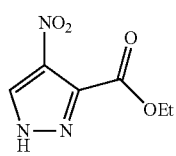 [SMILES: CCOC(=O)c1n[nH]cc1[N+](=O)[O-]]

Thionyl chloride (2.90 ml, 39.8 mmol) was slowly added to a mixture of 4-nitro-3-pyrazolecarboxylic acid (5.68 g, 36.2 mmol) in EtOH (100 ml) at ambient temperature and the mixture stirred for 48 h. The mixture was reduced in vacuo and dried through azeotrope with toluene to afford 4-nitro-1H-pyrazole-3-carboxylic acid ethyl ester as a white solid (6.42 g, 96%). ($^1$H NMR (400 MHz, DMSO-d$_6$) ☐ 14.4 (s, 1H), 9.0 (s, 1H), 4.4 (q, 2H), 1.3 (t, 3H)).

165B. Synthesis of 4-amino-1H-pyrazole-3-carboxylic acid ethyl ester

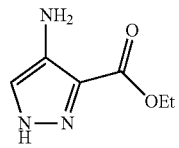 [SMILES: CCOC(=O)c1n[nH]cc1N]

A mixture of 4-nitro-1H-pyrazole-3-carboxylic acid ethyl ester (6.40 g, 34.6 mmol) and 10% Pd/C (650 mg) in EtOH (150 ml) was stirred under an atmosphere of hydrogen for 20 h. The mixture was filtered through a plug of Celite, reduced in vacuo and dried through azeotrope with toluene to afford 4-amino-1H-pyrazole-3-carboxylic acid ethyl ester as a pink solid (5.28 g, 98%). ($^1$H NMR (400 MHz, DMSO-d$_6$) ☐ 12.7 (s, 1H), 7.1 (s, 1H), 4.8 (s, 2H), 4.3 (q, 2H), 1.3 (t, 3H)).

165C. Synthesis of 4-(2,6-difluoro-benzoylamino)-1H-pyrazole-3-carboxylic acid ethyl ester

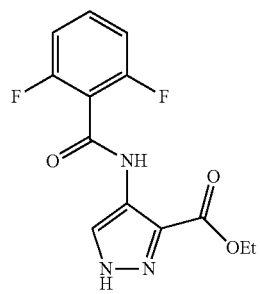 [SMILES: CCOC(=O)c1n[nH]cc1NC(=O)c1c(F)cccc1F]

A mixture of 2,6-difluorobenzoic acid (6.32 g, 40.0 mmol), 4-amino-1H-pyrazole-3-carboxylic acid ethyl ester (5.96 g, 38.4 mmol), EDC (8.83 g, 46.1 mmol) and HOBt (6.23 g, 46.1 mmol) in DMF (100 ml) was stirred at ambient temperature for 6 h. The mixture was reduced in vacuo, water added and the solid formed collected by filtration and air-dried to give 4-(2,6-difluoro-benzoylamino)-1H-pyrazole-3-carboxylic acid ethyl ester as the major component of a mixture (15.3 g). (LC/MS: R$_t$ 3.11, [M+H]$^+$ 295.99).

165D. Synthesis of 4-(2,6-difluoro-benzoylamino)-1H-pyrazole-3-carboxylic acid

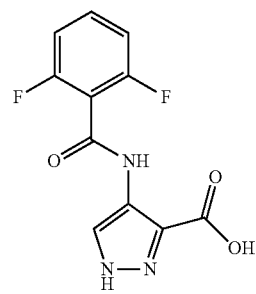

A mixture of 4-(2,6-difluoro-benzoylamino)-1H-pyrazole-3-carboxylic acid ethyl ester (10.2 g) in 2 M aqueous NaOH/MeOH (1:1, 250 ml) was stirred at ambient temperature for 14 h. Volatile materials were removed in vacuo, water (300 ml) added and the mixture taken to pH 5 using 1M aqueous HCl. The resultant precipitate was collected by filtration and dried through azeotrope with toluene to afford 4-(2,6-difluoro-benzoylamino)-1H-pyrazole-3-carboxylic acid as a pink solid (5.70 g). (LC/MS: $R_t$ 2.33, $[M+H]^+$ 267.96).

165E. Synthesis of 5-fluoro-2-(1-methyl-piperidin-4-yloxy)-phenylamine

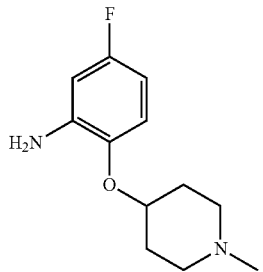 [SMILES: CN1CCC(Oc2ccc(F)cc2N)CC1]

3,4-Dinitrofluorobenzene (1.86 g, 10 mmol) and 4-hydroxy-1-methylpiperidine (1.38 g, 12 mmol) were dissolved in THF (20 ml) and stirred at ambient temperature while sodium hydride (60% dispersion in mineral oil, 0.40 g, 10 mmol) was added in several small portions. The reaction mixture was stirred for one hour and then reduced in vacuo, partitioned between ethyl acetate and water, and the organic phase washed with brine, dried (MgSO$_4$) and reduced in vacuo. The resulting residue was subject to column chromatography, eluting with 5% MeOH/DCM to give a yellow solid (1.76 g, 2:1 ratio of 4-(3,4-dinitro-phenoxy)-1-methyl-piperidine and a 4-(4-fluoro-2-nitro-phenoxy)-1-methyl-piperidine).

A sample of the mixture of products obtained (0.562 g) was dissolved in DMF (10 ml) under an atmosphere of nitrogen. Palladium on carbon (10%, 0.056 g) was added and the reaction mixture was shaken under a hydrogen atmosphere for 40 hours. The solids were removed by filtration and the filtrate reduced in vacuo, taken up in ethyl acetate, washed (saturated aqueous ammonium chloride solution, then saturated aqueous brine), dried (MgSO$_4$) and reduced in vacuo to give 5-fluoro-2-(1-methyl-piperidin-4-yloxy)-phenylamine) as a brown oil (0.049 g, 7%). ($^1$H NMR (400 MHz, MeOD-d$_4$) □ 6.6 (m, 2H), 6.4 (m, 1H), 4.3 (m, 1H), 2.7 (m, 2H), 2.3 (m, 2H), 1.9 (m, 2H), 1.7 (m, 2H)).

165F. Synthesis of 4-(2,6-Difluoro-benzoylamino)-1H-pyrazole-3-carboxylic acid[5-fluoro-2-(1-methyl-piperidin-4-yloxy)-phenyl]-amide

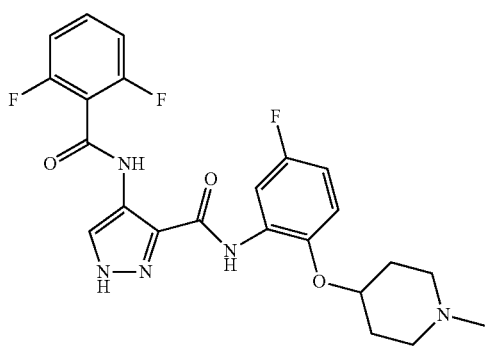 [SMILES: CN1CCC(Oc2ccc(F)cc2NC(=O)c2n[nH]cc2NC(=O)c2c(F)cccc2F)CC1]

5-fluoro-2-(1-methyl-piperidin-4-yloxy)-phenylamine) (0.049 g, 0.22 mmol) was combined with 4-(2,6-difluoro-benzoylamino)-1H-pyrazole-3-carboxylic acid (0.053 g, 0.20 mmol), EDC (0.048 g, 0.25 mmol), HOBt (0.034 g, 0.25 mmol) and DMF (1 ml) and the resulting reaction mixture was stirred at ambient temperature for 18 hours. The reaction mixture was reduced in vacuo and purified by preparative LC/MS to give 4-(2,6-Difluoro-benzoylamino)-1H-pyrazole-3-carboxylic acid[5-fluoro-2-(1-methyl-piperidin-4-yloxy)-phenyl]amide as a buff solid. (0.010 g, 11%) (LC/MS: $R_t$ 2.19, $[M+H]^+$ 474.27).

Example 166

Synthesis of 4-(2,6-Difluoro-benzoylamino)-1H-pyrazole-3-carboxylic acid[5-fluoro-2-(2-pyrrolidin-1-yl-ethoxy)-phenyl]-amide

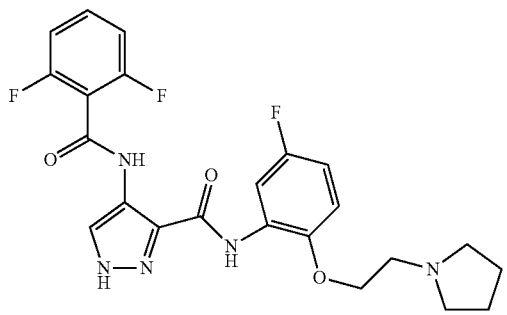 [SMILES: O=C(Nc1cc(F)ccc1OCCN1CCCC1)c1n[nH]cc1NC(=O)c1c(F)cccc1F]

3,4-Dinitrofluorobenzene (0.93 g, 5 mmol) and 1-(2-hydroxyethylpyrrolidine) (0.69 g, 6 mmol) were dissolved in THF (10 ml) and stirred at ambient temperature while sodium hydride (60% dispersion in mineral oil, 0.24 g, 6 mmol) was added in several small portions. The reaction mixture was stirred for 5 hours, diluted with ethyl acetate and the combined organics washed with water and brine, dried (MgSO$_4$) and reduced in vacuo. The resulting residue was subject to column chromatography, eluting with 5% MeOH/DCM to give an orange oil (0.94 g, 1:1 ratio of 1-[2-(3,4-dinitro-phenoxy)-ethyl]-pyrrolidine and 1-[2-(4-Fluoro-2-nitro-phenoxy)-ethyl]-pyrrolidine.

A sample of the mixture of products obtained (0.281 g) was dissolved in DMF (5 ml) under an atmosphere of nitrogen. Palladium on carbon (10%, 0.028 g) was added and the reaction mixture was shaken under a hydrogen atmosphere for 20 hours. The solids were removed by filtration and the filtrate reduced in vacuo and combined with 4-(2,6-difluoro-benzoylamino)-1H-pyrazole-3-carboxylic acid (0.134 g, 0.50 mmol), EDC (0.116 g, 0.60 mmol), HOBt (0.081 g, 0.60 mmol) and DMF (2.5 ml) and the resulting reaction mixture was stirred at ambient temperature for 18 hours. The reaction mixture was reduced in vacuo and the residue partitioned between ethyl acetate (50 ml) and saturated aqueous sodium bicarbonate solution (50 ml). The organic layer was washed with brine, dried (MgSO$_4$) and reduced in vacuo to give the intermediate amides. Acetic acid (10 ml) was added to the crude amide and the mixture was heated at reflux for 3 hours and then reduced in vacuo. 4-(2,6-Difluoro-benzoylamino)-1H-pyrazole-3-carboxylic acid[5-fluoro-2-(2-pyrrolidin-1-yl-ethoxy)-phenyl]amide was isolated from the residue by preparative LC/MS as an off white solid (0.040 g, 5.6%). (LC/MS: $R_t$ 2.38, $[M+H]^+$ 474.33).

Examples 167-223

By following the procedures described above, the compounds set out in Table 6 were prepared.

TABLE 6

| Example No. | Structure | Method | Differences | LCMS |
|---|---|---|---|---|
| 167 | 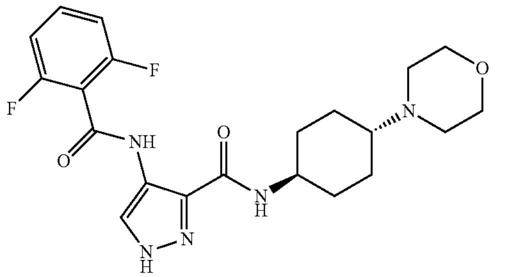 [SMILES: O=C(N[C@H]1CC[C@H](N2CCOCC2)CC1)c1n[nH]cc1NC(=O)c1c(F)cccc1F] | A Starting amine prepared according to Procedure L | HOAt instead of HOBt DMSO as solvent instead of DMF Et$_3$N 2 eq Purified by HPLC Cis/Trans Isomers separated after amine preparation (L) | [M + H]$^+$ 434 R$_t$ 1.97 |
| 168 | 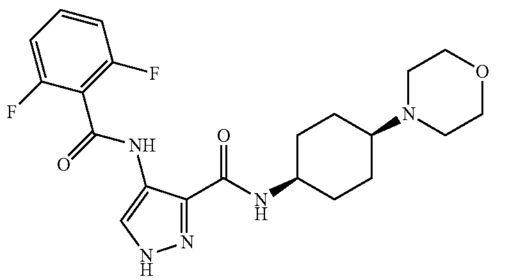 [SMILES: O=C(N[C@H]1CC[C@@H](N2CCOCC2)CC1)c1n[nH]cc1NC(=O)c1c(F)cccc1F] | A Starting amine prepared according to Procedure L | HOAt instead of HOBt DMSO as solvent instead of DMF Et$_3$N 2 eq Purified by chromatography 10% MeOH/CH$_2$Cl$_2$ Cis/Trans Isomers separated after amine preparation (L) | [M + H]$^+$ 434 R$_t$ 2.03 |
| 169 | 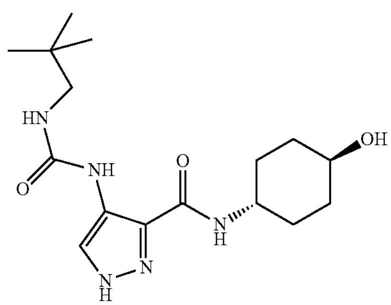 [SMILES: CC(C)(C)CNC(=O)Nc1c[nH]nc1C(=O)N[C@H]1CC[C@H](O)CC1] | Procedure D followed by G then E | | [M + H]$^+$ 338 R$_t$ 2.28 |
| 170 | 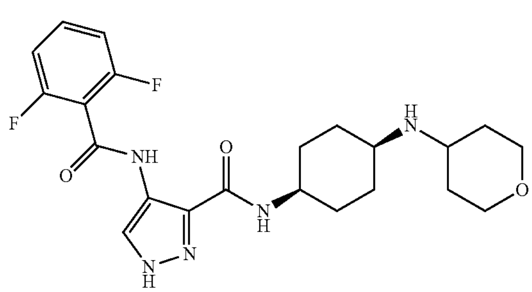 [SMILES: O=C(N[C@H]1CC[C@@H](NC2CCOCC2)CC1)c1n[nH]cc1NC(=O)c1c(F)cccc1F] | A Starting amine prepared according to Procedure L | DMSO as solvent instead of DMF Et$_3$N eq Heated 80° C. for 4 hours then RT O/N Purified by HPLC Cis/Trans isomers separated after final step | [M + H]$^+$ 448 R$_t$ 1.97 |
| 171 | 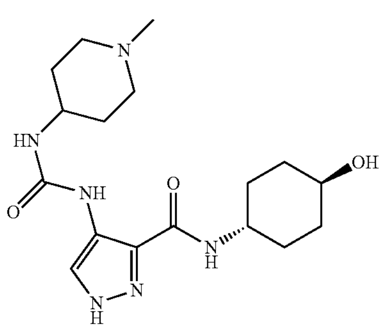 [SMILES: CN1CCC(NC(=O)Nc2c[nH]nc2C(=O)N[C@H]2CC[C@H](O)CC2)CC1] | Procedure D followed by G then E | | [M + H]$^+$ 365 R$_t$ 0.34 |

TABLE 6-continued

| Example No. | Structure | Method | Differences | LCMS |
|---|---|---|---|---|
| 172 | 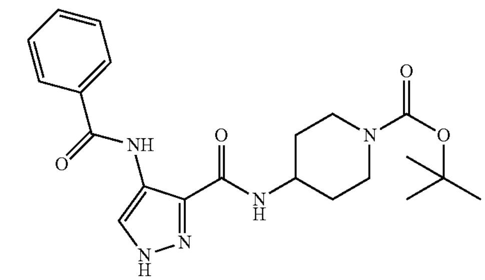 [SMILES: CC(C)(C)OC(=O)N1CCC(NC(=O)c2n[nH]cc2NC(=O)c2ccccc2)CC1] | B | Purified by column chromatography (pet. ether-EtOAc (1:1)) | [M + H]⁺ 414.13 R_t 3.05 |
| 173 | 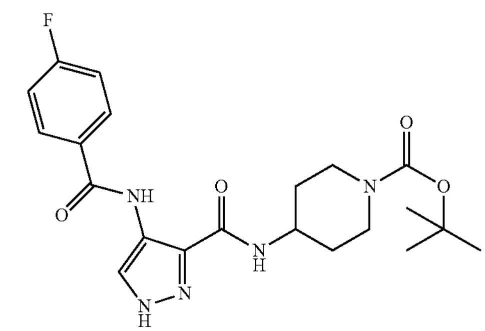 [SMILES: CC(C)(C)OC(=O)N1CCC(NC(=O)c2n[nH]cc2NC(=O)c2ccc(F)cc2)CC1] | B | Purified by column chromatography (pet. ether-EtOAc (1:1)) | [M + H]⁺ 432.12 R_t 3.12 |
| 174 | 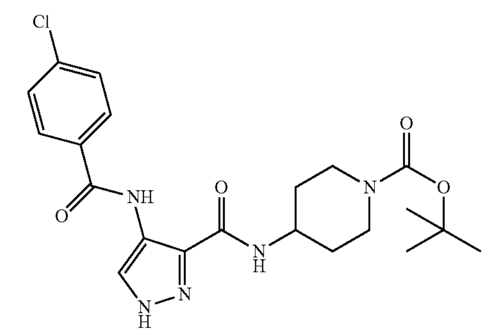 | B | Purified by column chromatography (pet. ether-EtOAc (1:1)) | [M + H]⁺ 448.06 R_t 3.33 |
| 175 | 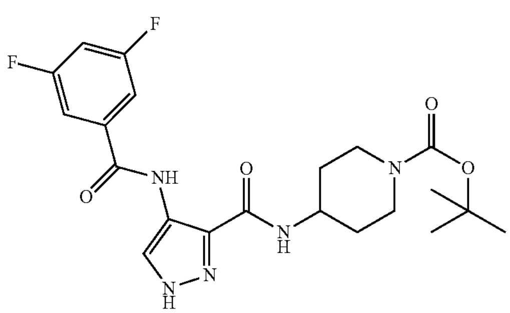 [SMILES: CC(C)(C)OC(=O)N1CCC(NC(=O)c2n[nH]cc2NC(=O)c2cc(F)cc(F)c2)CC1] | B | Purified by column chromatography (pet. ether-EtOAc (1:1)) | [M + H]⁺ 450.08 R_t 3.29 |

TABLE 6-continued

| Example No. | Structure | Method | Differences | LCMS |
|---|---|---|---|---|
| 176 | 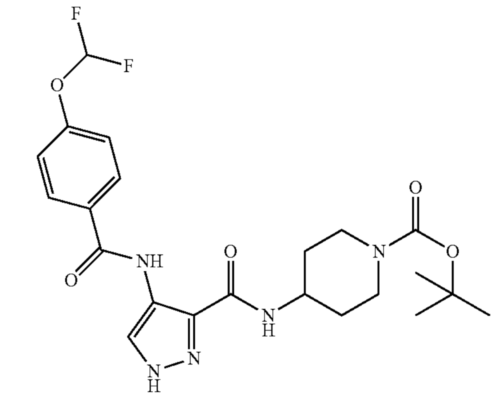 [SMILES: CC(C)(C)OC(=O)N1CCC(NC(=O)c2n[nH]cc2NC(=O)c2ccc(OC(F)F)cc2)CC1] | B | Purified by column chromatography (pet. ether-EtOAc (1:1)) | [M + H]⁺ 480.05 R_t 3.18 |
| 177 | 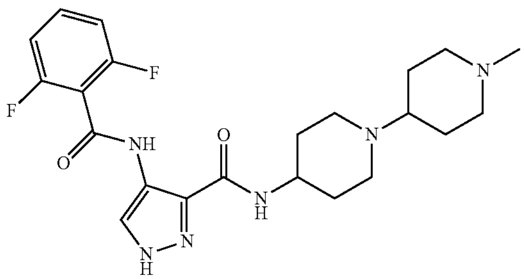 [SMILES: CN1CCC(N2CCC(NC(=O)c3n[nH]cc3NC(=O)c3c(F)cccc3F)CC2)CC1] | A Starting amine prepared according to Procedure L | HOAt instead of HOBt DMSO as solvent instead of DMF Et₃N 2 eq Purified by HPLC and formation of HCl salt | [M + H]⁺ 447 R_t 2.01 |
| 178 | 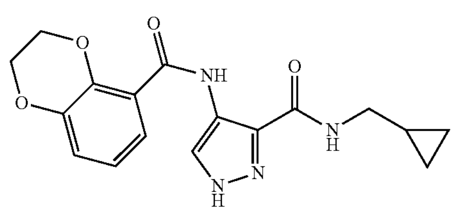 [SMILES: O=C(Nc1c[nH]nc1C(=O)NCC1CC1)c1cccc2c1OCCO2] | B | | [M + H]⁺ 343.05 R_t 3.38 (polar method) |
| 179 | 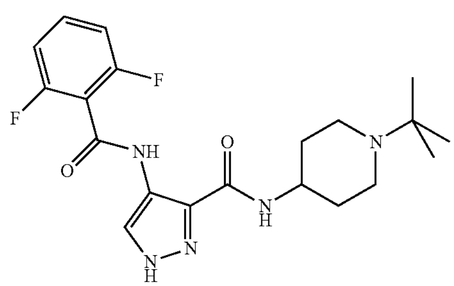 [SMILES: CC(C)(C)N1CCC(NC(=O)c2n[nH]cc2NC(=O)c2c(F)cccc2F)CC1] | A Butyl-piperidin-4-ylamine prepared by Procedure N | HOAt instead of HOBt Purified by trituration with MeOH | [M + H]⁺ 406 R_t 1.85 |
| 180 | 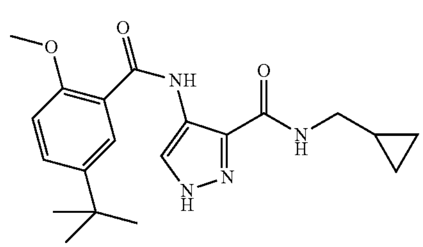 [SMILES: COc1ccc(C(C)(C)C)cc1C(=O)Nc1c[nH]nc1C(=O)NCC1CC1] | B | | [M + H]⁺ 371.09 R_t 3.27 (polar method) |

TABLE 6-continued

| Example No. | Structure | Method | Differences | LCMS |
|---|---|---|---|---|
| 181 | 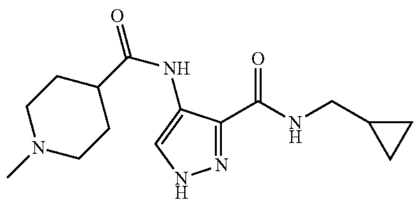 [SMILES: CN1CCC(C(=O)Nc2c[nH]nc2C(=O)NCC2CC2)CC1] | B | | [M + H]+ 306.06<br>R$_t$ 1.53 |
| 182 | 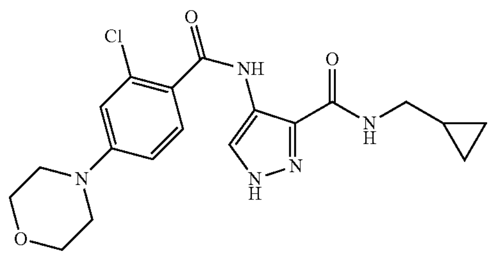 [SMILES: O=C(Nc1c[nH]nc1C(=O)NCC1CC1)c1ccc(N2CCOCC2)cc1Cl] | B | | [M + H]+ 403.98<br>R$_t$ 2.78 |
| 183 | 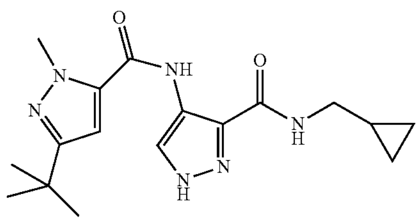 [SMILES: Cn1nc(C(C)(C)C)cc1C(=O)Nc1c[nH]nc1C(=O)NCC1CC1] | B | | [M + H]+ 345.05<br>R$_t$ 3.03 |
| 184 | 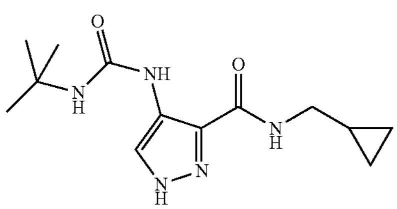 [SMILES: CC(C)(C)NC(=O)Nc1c[nH]nc1C(=O)NCC1CC1] | B | | [M + H]+ 280.05<br>R$_t$ 3.75<br>(basic method) |
| 185 | 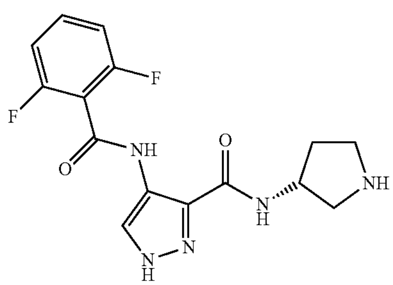 | A | HOAt instead of HOBt followed by EtOAc/HCl deprotection | [M + H]+ 336<br>R$_t$ 1.67 |
| 186 | 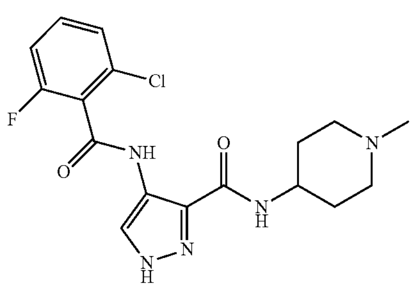 [SMILES: CN1CCC(NC(=O)c2n[nH]cc2NC(=O)c2c(F)cccc2Cl)CC1] | A | | [M + H]+ 380.05<br>R$_t$ 1.78 |

TABLE 6-continued

| Example No. | Structure | Method | Differences | LCMS |
| --- | --- | --- | --- | --- |
| 187 | 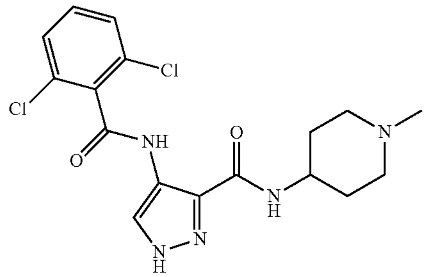 [SMILES: CN1CCC(NC(=O)c2n[nH]cc2NC(=O)c2c(Cl)cccc2Cl)CC1] | A | | [M + H]⁺ 396.02<br>R_t 1.86 |
| 188 | 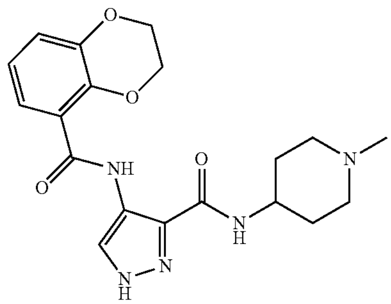 [SMILES: CN1CCC(NC(=O)c2n[nH]cc2NC(=O)c2cccc3c2OCCO3)CC1] | A | | [M + H]⁺ 386.10<br>R_t 1.88 |
| 189 | 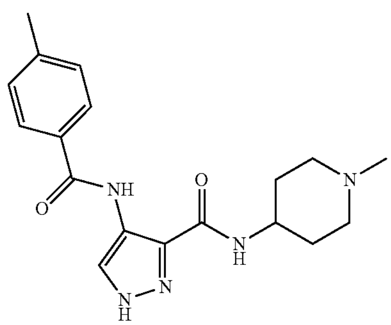 [SMILES: Cc1ccc(C(=O)Nc2c[nH]nc2C(=O)NC2CCN(C)CC2)cc1] | A | | [M + H]⁺ 342.10<br>R_t 1.95 |
| 190 | 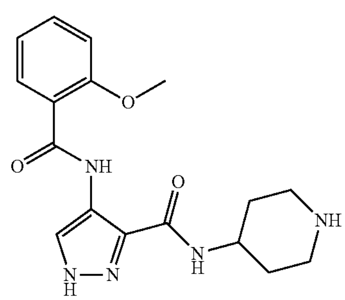 [SMILES: COc1ccccc1C(=O)Nc1c[nH]nc1C(=O)NC1CCNCC1] | M | | [M + H]⁺ = 344<br>R_t = 1.87 |
| 191 | 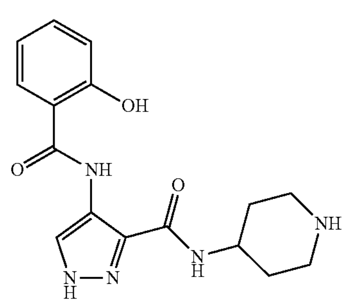 | M | | [M + H]⁺ = 330<br>R_t = 1.80 |

TABLE 6-continued

| Example No. | Structure | Method | Differences | LCMS |
|---|---|---|---|---|
| 192 | 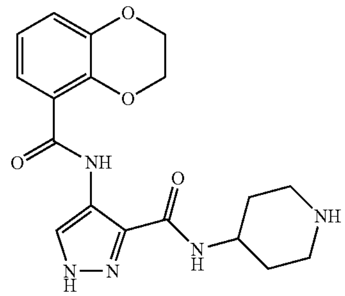 [SMILES: O=C(Nc1c[nH]nc1C(=O)NC1CCNCC1)c1cccc2c1OCCO2] | M | | [M + H]⁺ = 372<br>R$_t$ = 1.87 |
| 193 | 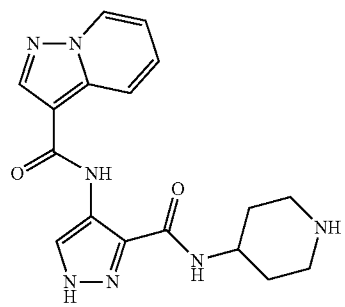 [SMILES: O=C(NC1CCNCC1)c1n[nH]cc1NC(=O)c1cnn2ccccc12] | M | | [M + H]⁺ = 354<br>R$_t$ = 1.77 |
| 194 | 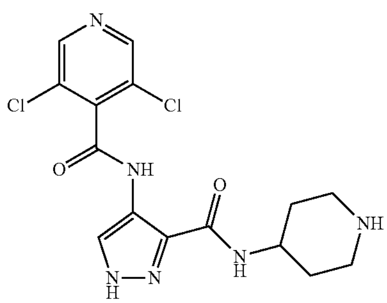 [SMILES: O=C(NC1CCNCC1)c1n[nH]cc1NC(=O)c1c(Cl)cncc1Cl] | M | Purified by flash chromatography eluting with dichloromethane 120 ml, methanol 15, acetic acid 3 ml, water 2 ml (DMAW 120) | [M + H]⁺ = 383/385<br>R$_t$ = 1.72 |
| 195 | 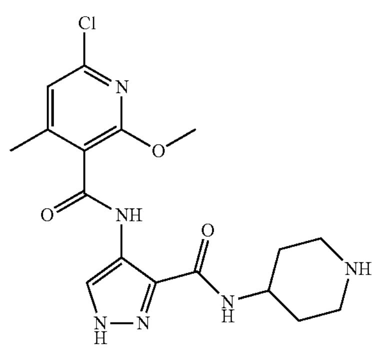 [SMILES: COc1nc(Cl)cc(C)c1C(=O)Nc1c[nH]nc1C(=O)NC1CCNCC1] | M | Purified by flash chromatography eluting with DMAW 120 | [M + H]⁺ = 393/395<br>R$_t$ = 1.86 |
| 196 | 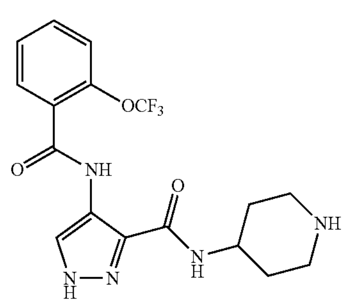 [SMILES: O=C(Nc1c[nH]nc1C(=O)NC1CCNCC1)c1ccccc1OC(F)(F)F] | M | | [M + H]⁺ = 398<br>R$_t$ = 1.94 |

TABLE 6-continued

| Example No. | Structure | Method | Differences | LCMS |
|---|---|---|---|---|
| 197 | (2-(difluoromethoxy)benzamide linked to 4-aminopyrazole-3-carboxamide with 4-aminopiperidine) | M | | [M + H]$^+$ = 330<br>R$_t$ = 1.80 |
| 198 | (2-ethoxybenzamide linked to 4-aminopyrazole-3-carboxamide with 4-aminopiperidine) | M | | [M + H]$^+$ = 358<br>R$_t$ = 1.89 |
| 199 | (2-morpholinobenzamide linked to 4-aminopyrazole-3-carboxamide with 4-aminopiperidine) | M | | [M + H]$^+$ = 399<br>R$_t$ = 1.88 |
| 200 | (2-(benzyloxy)benzamide linked to 4-aminopyrazole-3-carboxamide with 4-aminopiperidine) | M | | [M + H]$^+$ = 420<br>R$_t$ = 2.13 |
| 201 | (2-bromobenzamide linked to 4-aminopyrazole-3-carboxamide with 4-aminopiperidine) | M | | [M + H]$^+$ = 392/394<br>R$_t$ = 1.84 |

TABLE 6-continued

| Example No. | Structure | Method | Differences | LCMS |
|---|---|---|---|---|
| 202 | 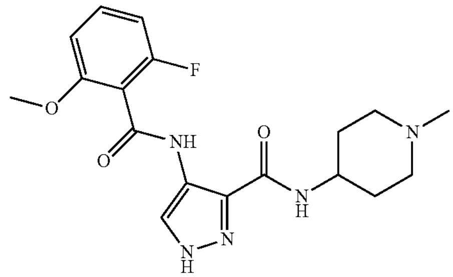 | B | Purified using flash chromatography (CH$_2$Cl$_2$—MeOH—AcOH—H$_2$O (90:18:3:2)) | [M + H]$^+$ 376.14 R$_t$ 1.78 |
| 203 | 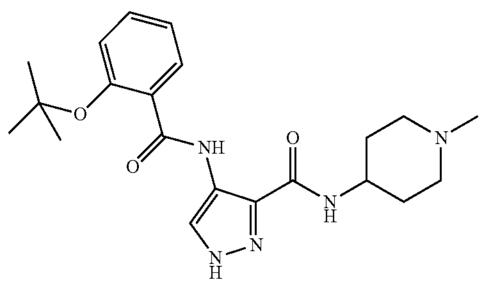 [SMILES: CN1CCC(NC(=O)c2n[nH]cc2NC(=O)c2ccccc2OC(C)(C)C)CC1] | B | Purified using flash chromatography (CH$_2$Cl$_2$—MeOH—AcOH—H$_2$O (90:18:3:2)) | [M + H]$^+$ 400.17 R$_t$ 2.08 |
| 204 | 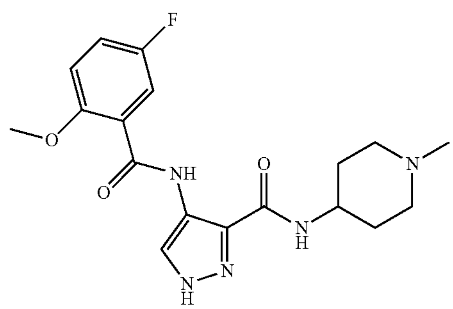 | B | Purified using flash chromatography (CH$_2$Cl$_2$—MeOH—AcOH—H$_2$O (90:18:3:2)) | [M + H]$^+$ 376.15 R$_t$ 1.92 |
| 205 | 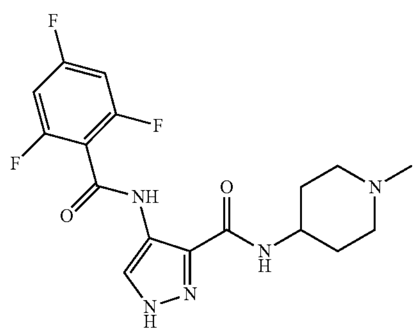 [SMILES: CN1CCC(NC(=O)c2n[nH]cc2NC(=O)c2c(F)cc(F)cc2F)CC1] | B | Purified using column chromatography (CH$_2$Cl$_2$—MeOH—AcOH—H$_2$O (90:18:3:2)) | [M + H]$^+$ 382.12 R$_t$ 1.77 |
| 206 | 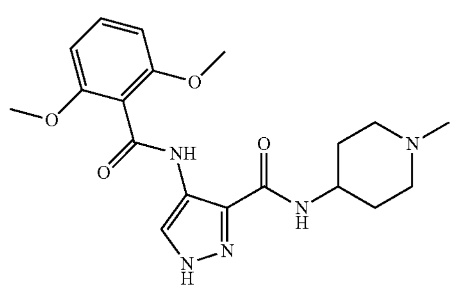 | B | Purified using column chromatography (CH$_2$Cl$_2$—MeOH—AcOH—H$_2$O (90:18:3:2)) | [M + H]$^+$ 388.18 R$_t$ 1.73 |

TABLE 6-continued

| Example No. | Structure | Method | Differences | LCMS |
|---|---|---|---|---|
| 207 | 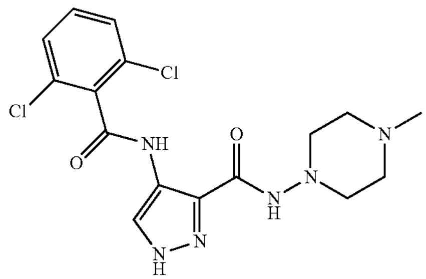 [SMILES: CN1CCN(NC(=O)c2n[nH]cc2NC(=O)c2c(Cl)cccc2Cl)CC1] | A | Purified by flash chromatography eluting with DMAW 120 | [M + H]⁺ = 397/399<br>R_t = 1.83 |
| 208 | 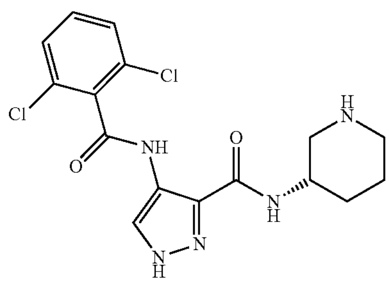 | A | Coupling using (S)-3-amino-1-N-BOC-piperidine. Deprotection as procedure M. Purified using column chromatography (CH₂Cl₂—MeOH—AcOH—H₂O (90:18:3:2)) | [M + H]⁺ 382.02<br>R_t 1.82 |
| 209 | 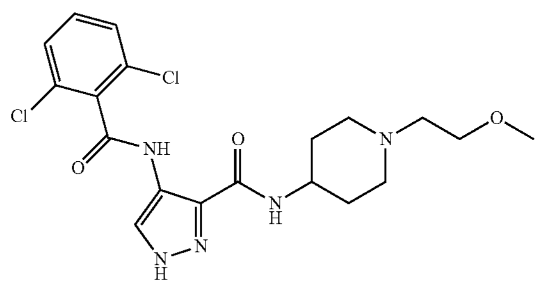 [SMILES: COCCN1CCC(NC(=O)c2n[nH]cc2NC(=O)c2c(Cl)cccc2Cl)CC1] | A | | [M + H]⁺ 440.22<br>R_t 1.92 |
| 210 | 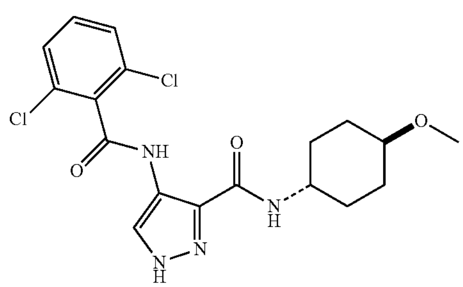 | A | | [M + H]⁺ 411.20<br>R_t 2.97 |
| 211 | 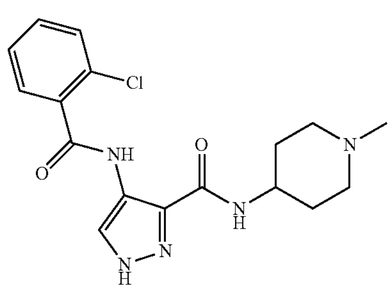 [SMILES: CN1CCC(NC(=O)c2n[nH]cc2NC(=O)c2ccccc2Cl)CC1] | A | Purified by prep. LCMS after work-up | [M + H]⁺ 362.11<br>R_t 1.91 |

TABLE 6-continued

| Example No. | Structure | Method | Differences | LCMS |
|---|---|---|---|---|
| 212 | 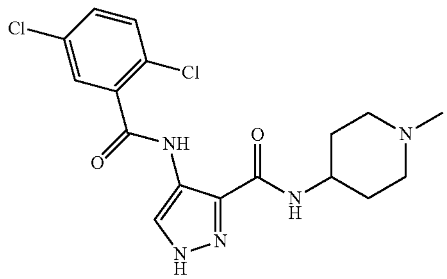 [SMILES: CN1CCC(NC(=O)c2n[nH]cc2NC(=O)c2cc(Cl)ccc2Cl)CC1] | A | Purified by prep. LCMS after work-up | [M + H]+ 396.08 R$_t$ 2.06 |
| 213 | 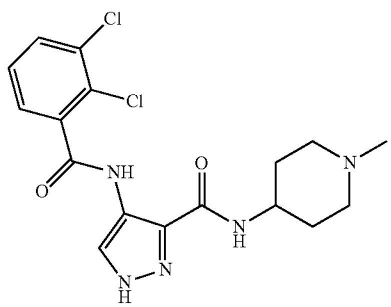 [SMILES: CN1CCC(NC(=O)c2n[nH]cc2NC(=O)c2cccc(Cl)c2Cl)CC1] | A | Purified by prep. LCMS after work-up | [M + H]+ 396.06 R$_t$ 2.04 |
| 214 | 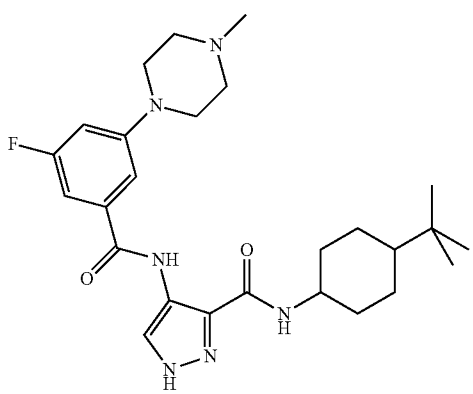 [SMILES: CN1CCN(c2cc(F)cc(C(=O)Nc3c[nH]nc3C(=O)NC3CCC(C(C)(C)C)CC3)c2)CC1] | B | The mixture was reduced in vacuo, the residue taken up in EtOAc and washed successively with saturated aqueous sodium bicarbonate, water and brine. The organic portion was dried (MgSO$_4$) and reduced in vacuo to give the desired product | [M + H]+ 485 R$_t$ 2.59 |
| 215 | 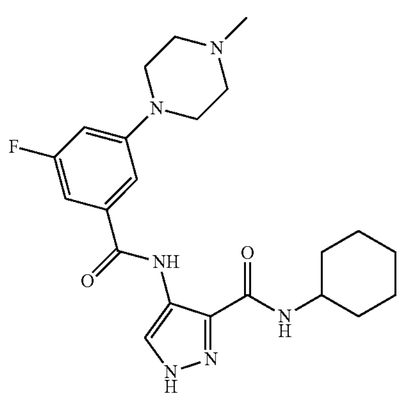 [SMILES: CN1CCN(c2cc(F)cc(C(=O)Nc3c[nH]nc3C(=O)NC3CCCCC3)c2)CC1] | B | The mixture was reduced in vacuo, the residue taken up in EtOAc and washed successively with saturated aqueous sodium bicarbonate, water and brine. The organic portion was dried (MgSO$_4$) and reduced in vacuo to give the desired product | [M + H]+ 429 R$_t$ 2.25 |

US 8,404,718 B2

TABLE 6-continued

| Example No. | Structure | Method | Differences | LCMS |
|---|---|---|---|---|
| 216 | 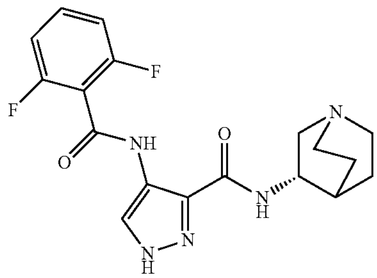 [SMILES: O=C(N[C@@H]1CN2CCC1CC2)c1n[nH]cc1NC(=O)c1c(F)cccc1F] | A | Purified by flash chromatography eluting with DMAW 120 | [M + H]⁺ = 376<br>R$_t$ = 1.85 |
| 217 | 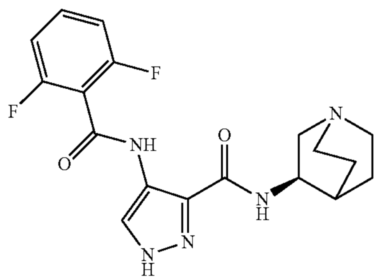 [SMILES: O=C(N[C@H]1CN2CCC1CC2)c1n[nH]cc1NC(=O)c1c(F)cccc1F] | A | Purified by flash chromatography eluting with DMAW 120 | [M + H]⁺ = 376<br>R$_t$ = 1.87 |
| 218 | 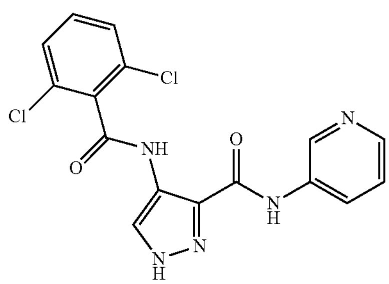 [SMILES: O=C(Nc1cccnc1)c1n[nH]cc1NC(=O)c1c(Cl)cccc1Cl] | A | Purified by flash chromatography eluting with 5% then 10% MeOH/DCM | [M + H]⁺ = 376/378<br>R$_t$ = 2.23 |
| 219 | 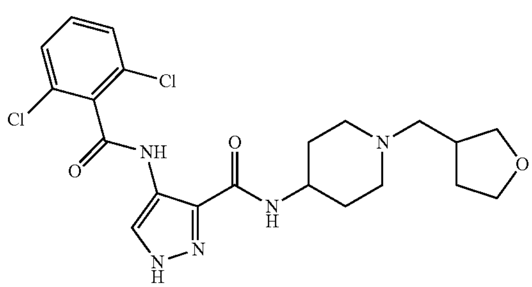 [SMILES: O=C(NC1CCN(CC2CCOC2)CC1)c1n[nH]cc1NC(=O)c1c(Cl)cccc1Cl] | A<br>Starting amine prepared according to Procedure L | Purified by flash chromatography eluting with DMAW 90 | [M + H]⁺ = 466/468<br>R$_t$ = 1.98 |
| 220 | 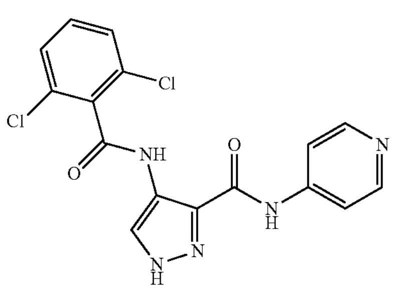 [SMILES: O=C(Nc1ccncc1)c1n[nH]cc1NC(=O)c1c(Cl)cccc1Cl] | A | Purified by flash chromatography eluting with 5% then 10% MeOH/DCM | [M + H]⁺ = 376/378<br>R$_t$ = 2.09 |

TABLE 6-continued

| Example No. | Structure | Method | Differences | LCMS |
|---|---|---|---|---|
| 221 | | A | Starting amine prepared according to Procedure L | Purified by flash chromatography eluting with DMAW 90 | $[M + H]^+ = 434$ $R_t = 1.82$ |
| 222 | 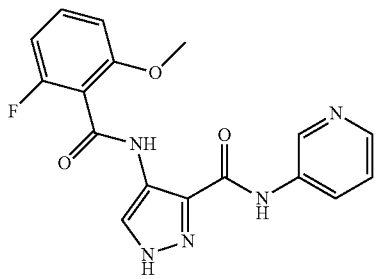 [SMILES: COc1cccc(F)c1C(=O)Nc1c[nH]nc1C(=O)Nc1cccnc1] | A | Purified by flash chromatography eluting with 5% then 10% MeOH/DCM | $[M + H]^+ = 356$ $R_t = 2.11$ |
| 223 | 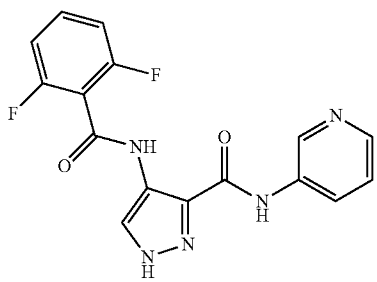 [SMILES: O=C(Nc1cccnc1)c1n[nH]cc1NC(=O)c1c(F)cccc1F] | A | Purified by flash chromatography eluting with 5% then 10% MeOH/DCM | $[M + H]^+ = 344$ $R_t = 2.09$ |

Example 224

4-(4-Methyl-piperazin-1-yl)-1H-pyrazole-3-carboxylic acid(4-fluoro-phenyl)-amide

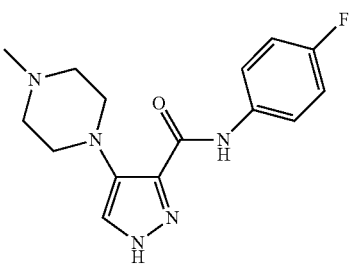 [SMILES: CN1CCN(c2c[nH]nc2C(=O)Nc2ccc(F)cc2)CC1]

Bis(2-chloroethyl)methylamine hydrochloride (97 mg; 0.5 mmol) was added to a stirred solution of 4-amino-1H-pyrazole-3-carboxylic acid(4-fluoro-phenyl)-amide (100 mg; 0.45 mmol), tetrabutylammonium iodide (20 mg; 0.045 mmol) and diisopropylethylamine (200 ul) 1.13 mmol) in DMF (5 ml), and the resulting mixture was heated at 200° C. (100 W) for 30 minutes in a CEM Discover™ microwave synthesiser. The DMF was removed under vacuum, then purified by flash column chromatography, eluting with dichloromethane/methanol/acetic acid/water (90:18:3:2). Product containing fractions were combined and evaporated, treated with HCl in ethyl acetate and then re-evaporated with toluene (2×20 ml) to give an off white solid (27 mg). (LC/MS: $R_t$ 1.64, $[M+H]^+$ 378).

Example 225

4-Morpholin-4-yl-1H-pyrazole-3-carboxylic acid(4-fluoro-phenyl)-amide

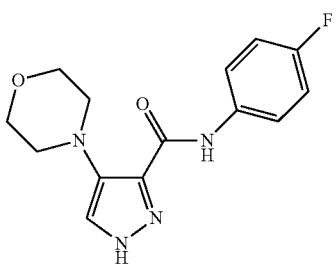 [SMILES: O=C(Nc1ccc(F)cc1)c1n[nH]cc1N1CCOCC1]

The compound was prepared in a manner analogous to Example 224, but using bis(2-chloroethyl)ether in place of bis(2-chloroethyl)methylamine hydrochloride. (LC/MS: R$_t$ 2.48 [M+H]$^+$ 291).

Example 226

4-(2,4-Dichloro-phenyl)-1H-pyrazole-3-carboxylic acid 4-(4-methyl-piperazin-1-yl)-benzylamide

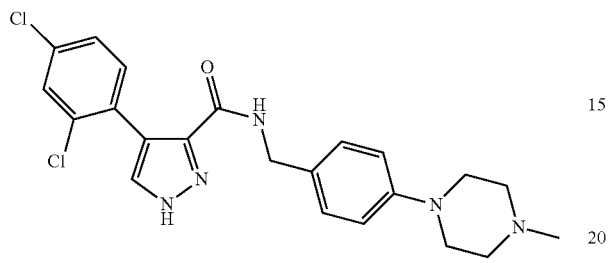

226A. Preparation of 4-(2,4-dichloro-phenyl)-1H-pyrazole-3-carboxylic acid

A solution of 4-(2,4-dichloro-phenyl)-1H-pyrazole-3-carboxylic acid ethyl ester (205 mg; 0.72 mmol) and lithium hydroxide monohydrate (125 mg; 2.9 mmol) in 1:1 THF/water (10 ml) was heated at 60° C. overnight. The THF was removed by evaporation, the aqueous phase acidified with 1M hydrochloric acid then extracted with ethyl acetate (20 ml). The ethyl acetate layer was dried (MgSO$_4$), filtered and evaporated to give 200 mg of 4-(2,4-dichloro-phenyl)-1H-pyrazole-3-carboxylic acid. (LC/MS: [M+H]$^+$ 256.85).

226B. Preparation of 4-(2,4-dichloro-phenyl)-1H-pyrazole-3-carboxylic acid 4-(4-methyl-piperazin-1-yl)-benzylamide A solution of 4-(2,4-dichloro-phenyl)-1H-pyrazole-3-carboxylic acid (70 mg; 0.27 mmol), 4-(4-methyl-piperazin-1-yl)-benzylamine (62 mg; 0.3 mmol), EDAC (63 mg; 0.33 mmol) and HOBt (45 mg; 0.33 mmol) in 5 ml of DMF was stirred at room temperature for 48 hours. The reaction was evaporated and the residue partitioned between ethyl acetate and brine. The ethyl acetate layer was separated, dried (MgSO$_4$), filtered, evaporated then dried further under vacuum to give 34 mg of 4-(2,4-dichloro-phenyl)-1H-pyrazole-3-carboxylic acid 4-(4-methyl-piperazin-1-yl)-benzylamide. (LC/MS: R$_t$ 2.42 [M+H]$^+$ 444).

Example 227

4-(2,4-Dichloro-phenyl)-1H-pyrazole-3-carboxylic acid 4-methylsulphamoylmethyl-benzylamide

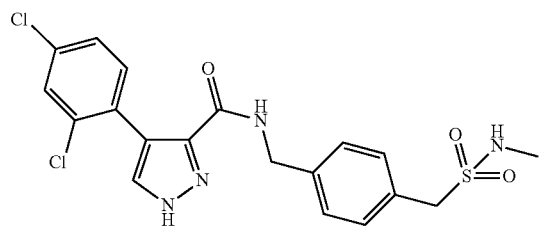 [SMILES: CNS(=O)(=O)Cc1ccc(CNC(=O)c2n[nH]cc2-c2ccc(Cl)cc2Cl)cc1]

The title compound was prepared in a manner analogous to Example 226, but using (4-aminomethyl-phenyl)-N-methyl-methanesulphonamide as the starting material. 6 mg of product were isolated as a white solid. (LC/MS: R$_t$ 3.56 [M+H]$^+$ 440).

Example 228

4-Phenyl-1H-pyrazole-3-carboxylic acid amide

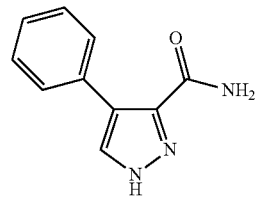 [SMILES: NC(=O)c1n[nH]cc1-c1ccccc1]

228A. 2-Benzylidene-but-3-yne nitrile

To a solution of benzaldehyde (2 g; 18.9 mmol) and malononitrile (1.37 g; 20.7 mmol) in ethanol (40 ml) was added 5 drops of piperidine and the mixture was heated at reflux overnight. The reaction was cooled, evaporated then purified by flash column chromatography eluting with 1:9 ethyl acetate/hexane and the product containing fractions combined and evaporated to give 930 mg of 2-benzylidene-but-3-yne nitrile.

228B. 4-phenyl-5-trimethylsilanyl-1H-pyrazole-3-carbonitrile n-Butyl lithium (2.7 M solution in heptane) (3.3 ml, 9 mmol) was added drop wise to a stirred solution of trimethylsilyl diazomethane (2 M solution in diethyl ether) (4.5 ml, 9 mmol) in anhydrous THF (10 ml) at −78° C. under a nitrogen atmosphere, then stirred for a further 30 minutes. To this was added drop wise a solution of 2-benzylidene-but-3-yne nitrile (920 mg; 6 mmol) in anhydrous THF (5 ml), the mixture stirred for 30 minutes at −78° C. then gradually allowed to warm to room temperature overnight. The reaction mixture was diluted with ethyl acetate (30 ml) then washed with saturated ammonium chloride solution followed by brine. The ethyl acetate layer was separated, dried (MgSO$_4$), filtered and evaporated. The crude product was purified by flash column chromatography eluting with 1:8 then 1:4 ethyl acetate/hexane and the product containing fractions combined and evaporated to give 1.0 g of 4-phenyl-5-trimethylsilanyl-1H-pyrazole-3-carbonitrile.

228C. 4-phenyl-1H-pyrazole-3-carboxylic acid amide

4-Phenyl-5-trimethylsilanyl-1H-pyrazole-3-carbonitrile (500 mg; 2.1 mmol) was dissolved in 1 ml of ethanol, treated with potassium hydroxide (600 mg) in water (3 ml) then heated at 150° C. (100 W) for 30 minutes then 170° C. (100 W) for 20 minutes in a CEM Discover™ microwave synthesiser. The reaction mixture was acidified to pH1 with concentrated hydrochloric acid, diluted with water (40 ml) then extracted with ethyl acetate (2×40 ml). The combined ethyl acetate layers were separated, dried (MgSO$_4$), filtered and evaporated to give a 3:1 mixture of 4-phenyl-1H-pyrazole-3-carboxylic acid and 4-phenyl-1H-pyrazole-3-carboxylic acid amide. A 50 mg batch of the crude material was purified by flash column chromatography eluting with 5% methanol/dichloromethane, and the product containing fractions combined and evaporated to give 15 mg of 4-phenyl-1H-pyrazole-3-carboxylic acid amide as a white solid. (LC/MS: $R_t$ 2.15 [M+H]$^+$ 188).

Example 229

4-phenyl-1H-pyrazole-3-carboxylic acid phenylamide

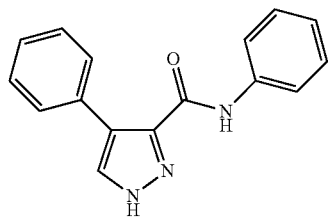 [SMILES: O=C(Nc1ccccc1)c1n[nH]cc1-c1ccccc1]

A solution of 4-phenyl-1H-pyrazole-3-carboxylic acid (75 mg; 0.4 mmol) (prepared according to Example 228C), aniline (45 ml; 0.48 mmol), EDAC (92 mg; 0.48 mmol) and HOBt (65 mg; 0.48 mmol) in 5 ml of DMF was stirred at room temperature overnight. The reaction was evaporated then purified by flash column chromatography eluting with 1:3 then 1:2 ethyl acetate/hexane. Product containing fractions were combined and evaporated to give 30 mg of 4-phenyl-1H-pyrazole-3-carboxylic acid phenylamide as a white solid. (LC/MS: $R_t$ 3.12 [M+H]$^+$ 264).

Example 230

4-Phenyl-1H-pyrazole-3-carboxylic acid 4-(4-methyl-piperazin-1-yl)-benzylamide

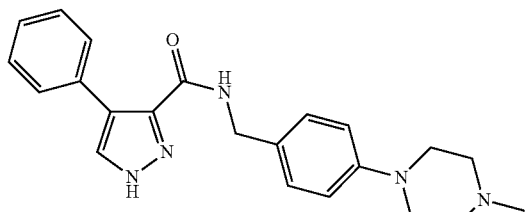

The compound was prepared in a manner analogous to Example 229, but using 4-(4-methyl-piperazin-1-yl)-benzylamine as the starting material. 6 mg of product were isolated as a white solid. (LC/MS: $R_t$ 2.05 [M+H]$^+$ 376).

Example 231

4-Phenyl-1H-pyrazole-3-carboxylic acid(6-methoxy-pyridin-3-yl) amide

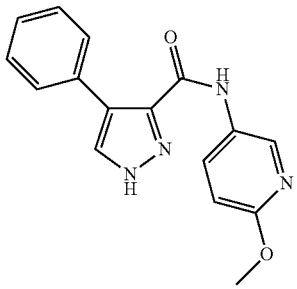 [SMILES: COc1ccc(NC(=O)c2n[nH]cc2-c2ccccc2)cn1]

The compound was prepared in a manner analogous to Example 230, but using 3-amino-6-methoxypyridine as the amine fragment. 100 mg of product were isolated as a pale brown solid. (LC/MS: $R_t$ 3.17 [M+H]$^+$ 295).

Example 232

4-(3-Benzyloxy-phenyl)-1H-pyrazole-3-carboxylic acid 4-(4-methyl-piperazin-1-yl)-benzylamide

The compound was prepared in a manner analogous to Example 226. The product was isolated as a white solid. (LC/MS: $R_t$ 2.65 [M+H]$^+$ 482).

Example 233

4-(3-Hydroxy-phenyl)-1H-pyrazole-3-carboxylic acid 4-(4-methyl-piperazin-1-yl)-benzylamide

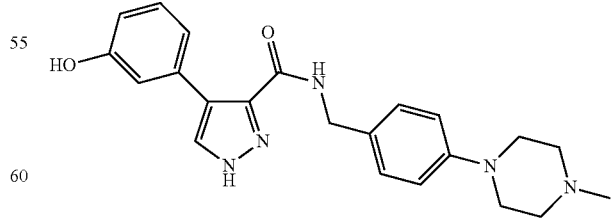

A solution of 4-(3-benzyloxy-phenyl)-1H-pyrazole-3-carboxylic acid 4-(4-methyl-piperazin-1-yl)-benzylamide (25 mg; 0.05 mmol) in methanol (5 ml), was treated with 10% palladium on carbon (10 mg) then hydrogenated at room temperature and pressure overnight. The catalyst was removed by filtration through Celite and the filtrate evaporated. Purification by preparative LC/MS gave 8 mg of the required product as a cream solid. (LC/MS: $R_t$ 1.67 [M+H]$^+$ 392).

Example 234

4-(5-Methyl-3H-imidazol-4-yl)-1H-pyrazole-3-carboxylic acid(4-fluoro-phenyl)-amide

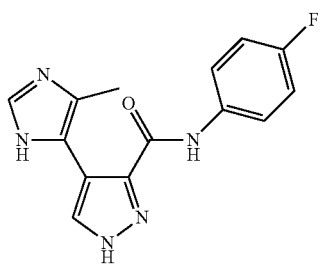 [SMILES: Cc1nc[nH]c1-c1c[nH]nc1C(=O)Nc1ccc(F)cc1]

The compound was prepared in a manner analogous to Example 226, but using 4-methyl-5-formylimidazole as the starting material in the condensation step. The product (6 mg) was isolated as a white solid. (LC/MS: $R_t$ 2.00 [M+H]$^+$ 286).

Example 235

4-(2,5-Dimethyl-pyrrol-1-yl)-1H-pyrazole-3-carboxylic acid(4-fluoro-phenyl)-amide

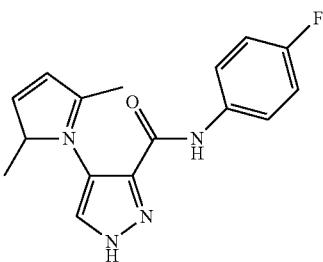

A mixture of 4-amino-1H-pyrazole-3-carboxylic acid(4-fluoro-phenyl)-amide (100 mg) and Montmorillonite KSF clay (100 mg) in acetonylacetone (1 ml) was heated at 120° C. (50 W) for 15 minutes in a CEM discover microwave synthesiser. The reaction mixture was diluted with 5% methanol/dichloromethane, filtered and evaporated. The crude product was purified by flash column chromatography eluting with 1:2 ethyl acetate/hexane, and the product containing fractions were combined and evaporated to give 65 mg of the target molecule as a pale brown solid. (LC/MS: $R_t$ 3.75 [M+H]$^+$ 299).

Example 236

4-(3-Hydroxymethyl-phenyl)-1H-pyrazole-3-carboxylic acid phenylamide

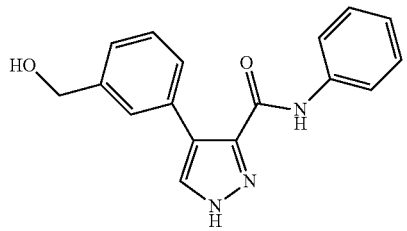 [SMILES: O=C(Nc1ccccc1)c1n[nH]cc1-c1cccc(CO)c1]

236A. 4-iodo-1H-pyrazole-3-carboxylic acid phenylamide

An aqueous solution of sodium nitrite (760 mg) in 2 ml of water was added drop wise to a stirred suspension of 4-amino-1H-pyrazole-3-carboxylic acid phenylamide (2 g; 10 mmol) in concentrated hydrochloric acid (20 ml) at 0° C., then stirred at 0° C. for a further 60 minutes. The reaction mixture was diluted with acetone (10 ml) then treated with potassium iodide (1.8 g) and copper (I) iodide (2.1 g) and stirred at room temperature for 90 minutes. The reaction mixture was diluted with brine and ethyl acetate then washed with saturated sodium thiosulphate solution. The ethyl acetate layer was separated, dried (MgSO$_4$), filtered and evaporated to give 680 mg of 4-iodo-1H-pyrazole-3-carboxylic acid phenylamide.

236B. 4-iodo-1-(4-methoxy-benzyl)-1H-pyrazole-3-carboxylic acid phenylamide

A solution of 4-iodo-1H-pyrazole-3-carboxylic acid phenylamide (670 mg; 2.14 mmol) in acetonitrile (10 ml) was treated with potassium carbonate (360 mg; 2.57 mmol)) followed by 4-methoxybenzyl chloride (320 μl; 2.35 mmol). The mixture was stirred at room temperature overnight then evaporated under reduced pressure. The residue was partitioned between ethyl acetate and brine; the ethyl acetate layer was separated, dried (MgSO$_4$), filtered and evaporated. The crude material was purified by flash column chromatography eluting with 1:3 ethyl acetate/hexane and the product containing fractions combined and evaporated to give 660 mg of 4-iodo-1-(4-methoxy-benzyl)-1H-pyrazole-3-carboxylic acid phenylamide.

236C. 4-(3-hydroxymethyl-phenyl)-1-(4-methoxy-benzyl)-1H-pyrazole-3-carboxylic acid phenylamide A mixture of 4-iodo-1-(4-methoxy-benzyl)-1H-pyrazole-3-carboxylic acid phenylamide (50 mg; 0.11 mmol), bis(tri-tert-butylphosphine)palladium (12 mg), potassium carbonate (100 mg; 0.66 mmol) and 3-(hydroxymethyl)benzene boronic acid (21 mg; 0.14 mmol) in ethanol/toluene/water (4 ml:1 ml:1 ml) was heated at 120° C. (50 W) for 15 minutes in a CEM Discover microwave synthesiser. The reaction was evaporated and the residue partitioned between ethyl acetate and brine. The ethyl acetate layer was separated, dried (MgSO$_4$), filtered and evaporated and the crude material purified by flash column chromatography eluting with 1:2 then 2:1 ethyl acetate/hexane. Product containing fractions were combined and evaporated to give 60 mg of 4-(3-hydroxymethyl-phenyl)-1-(4-methoxy-benzyl)-1H-pyrazole-3-carboxylic acid phenylamide.

236D. 4-(3-Hydroxymethyl-phenyl)-1H-pyrazole-3-carboxylic acid phenylamide

A mixture of 4-(3-hydroxymethyl-phenyl)-1-(4-methoxy-benzyl)-1H-pyrazole-3-carboxylic acid phenylamide (20 mg) and anisole (20 µl) in trifluoroacetic acid (1 ml) was heated at 120° C. (50 W) for 15 minutes in a CEM Discover microwave synthesiser. The reaction was evaporated then purified by flash column chromatography eluting with 2:1 ethyl acetate/hexane. Product containing fractions were combined and evaporated to give 5 mg of product. (LC/MS: R$_t$ 2.55 [M+H]$^+$ 294).

Example 237

Preparation of 4-(2,6-dichloro-benzoylamino)-1H-pyrazole-3-carboxylic acid piperidin-4-ylamide hydrochloride

237A. 4-(2,6-dichloro-benzoylamino)-1H-pyrazole-3-carboxylic acid 2,6-dichlorobenzoyl chloride (8.2 g; 39.05 mmol) was added cautiously to a solution of 4-amino-1H-pyrazole-3-carboxylic acid methyl ester (prepared in a manner analogous to 165B) (5 g; 35.5 mmol) and triethylamine (5.95 ml; 42.6 mmol) in dioxan (50 ml) then stirred at room temperature for 5 hours. The reaction mixture was filtered and the filtrate treated with methanol (50 ml) and 2M sodium hydroxide solution (100 ml), heated at 50° C. for 4 hours, and then evaporated. 100 ml of water was added to the residue then acidified with concentrated hydrochloric acid. The solid was collected by filtration, washed with water (100 ml) and sucked dry to give 10.05 g of 4-(2,6-dichloro-benzoylamino)-1H-pyrazole-3-carboxylic acid as a pale violet solid.

237B. 4-{[4-(2,6-dichloro-benzoylamino)-1H-pyrazole-3-carbonyl]-amino}-piperidine-1-carboxylic acid tert-butyl ester A mixture of 4-(2,6-dichloro-benzoylamino)-1H-pyrazole-3-carboxylic acid (6.5 g, 21.6 mmol), 4-amino-1-BOC-piperidine (4.76 g, 23.8 mmol), EDC (5.0 g, 25.9 mmol) and HOBt (3.5 g, 25.9 mmol) in DMF (75 ml) was stirred at room temperature for 20 hours. The reaction mixture was reduced in vacuo and the residue partitioned between ethyl acetate (100 ml) and saturated aqueous sodium bicarbonate solution (100 ml). The organic layer was washed with brine, dried (MgSO$_4$) and reduced in vacuo. The residue was taken up in 5% MeOH-DCM (~30 ml). The insoluble material was collected by filtration and, washed with DCM and dried in vacuo to give 4-{[4-(2,6-dichloro-benzoylamino)-1H-pyrazole-3-carbonyl]-amino}-piperidine-1-carboxylic acid tert-butyl ester (5.38 g) as a white solid. The filtrate was reduced in vacuo and the residue purified by column chromatography using gradient elution 1:2 EtOAc/hexane to EtOAc to give further 4-{[4-(2,6-dichloro-benzoylamino)-1H-pyrazole-3-carbonyl]-amino}-piperidine-1-carboxylic acid tert-butyl ester (2.54 g) as a white solid.

237C. 4-(2,6-dichloro-benzoylamino)-1H-pyrazole-3-carboxylic acid piperidin-4-ylamide A solution of 4-{[4-(2,6-dichloro-benzoylamino)-1H-pyrazole-3-carbonyl]-amino}-piperidine-1-carboxylic acid tert-butyl ester (7.9 g) in MeOH (50 mL) and EtOAc (50 ml) was treated with sat. HCl-EtOAc (40 mL) then stirred at r.t. overnight. The product did not crystallise due to the presence of methanol, and therefore the reaction mixture was evaporated and the residue triturated with EtOAc. The resulting off white solid was collected by filtration, washed with EtOAc and sucked dry on the sinter to give 6.3 g of 4-(2,6-dichloro-benzoylamino)-1H-pyrazole-3-carboxylic acid piperidin-4-ylamide as the hydrochloride salt. (LC/MS: R$_t$ 5.89, [M+H]$^+$ 382/384).

Example 238

4-Methanesulfonylamino-1H-pyrazole-3-carboxylic acid(4-fluoro-phenyl)-amide

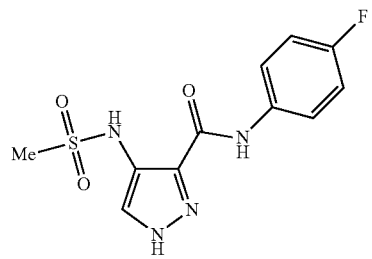 [SMILES: CS(=O)(=O)Nc1c[nH]nc1C(=O)Nc1ccc(F)cc1]

A solution of 4-amino-1H-pyrazole-3-carboxylic acid(4-fluorophenyl)-amide (50 mg) (Example 2B) and methanesulphonic anhydride (45 mg) in pyridine (1 ml) was stirred at room temperature overnight then evaporated and purified by flash column chromatography eluting with 2:1 EtOAc/hexane. Evaporation of product containing fractions gave 20 mg of the title compound. (LC/MS: R$_t$ 2.87; [M+H+] 299).

Examples 239 to 245

The compounds of Examples 239 to 245 were prepared using the methods described above or methods closely analogous thereto.

Example 239

4-(2,6-Difluoro-benzoylamino)-1H-pyrazole-3-carboxylic acid[1-(2-fluoro-ethyl)-piperidin-4-yl]-amide

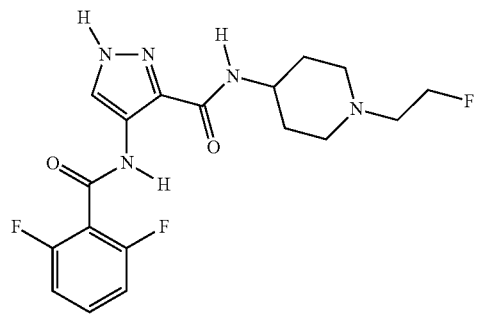 [SMILES: O=C(NC1CCN(CCF)CC1)c1n[nH]cc1NC(=O)c1c(F)cccc1F]

Example 240

4-(2,6-Dichloro-benzoylamino)-1H-pyrazole-3-carboxylic acid(6-chloro-pyridin-3-yl)-amide

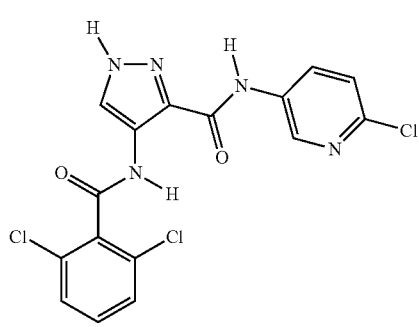 [SMILES: O=C(Nc1ccc(Cl)nc1)c1n[nH]cc1NC(=O)c1c(Cl)cccc1Cl]

Example 241

4-(2,6-Dichloro-benzoylamino)-1H-pyrazole-3-carboxylic acid(6-amino-pyridin-3-yl)-amide

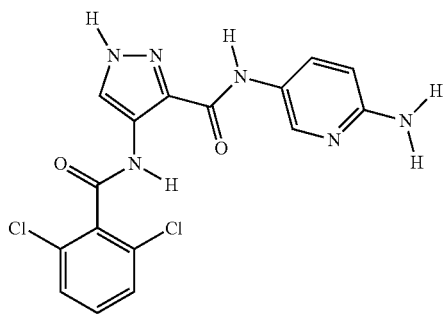 [SMILES: Nc1ccc(NC(=O)c2n[nH]cc2NC(=O)c2c(Cl)cccc2Cl)cn1]

Example 242

4-(2,6-Dichloro-benzoylamino)-1H-pyrazole-3-carboxylic acid(6-methoxy-pyridin-3-yl)-amide

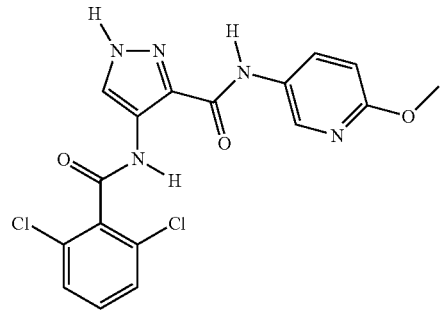 [SMILES: COc1ccc(NC(=O)c2n[nH]cc2NC(=O)c2c(Cl)cccc2Cl)cn1]

Example 243

4-[3-Chloro-5-(4-methyl-piperazin-1-yl)-benzoylamino]-1H-pyrazole-3-carboxylic acid cyclohexylamide

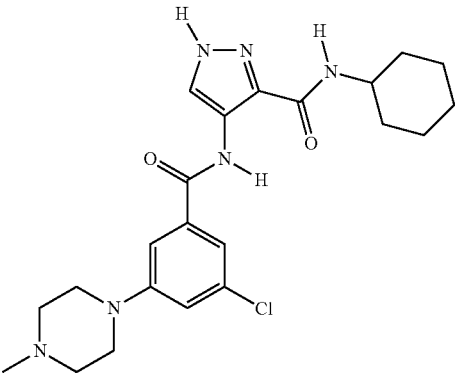 [SMILES: CN1CCN(c2cc(Cl)cc(C(=O)Nc3c[nH]nc3C(=O)NC3CCCCC3)c2)CC1]

Example 244

4-(2,6-Difluoro-benzoylamino)-1H-pyrazole-3-carboxylic acid[1-(2,2-difluoro-ethyl)-piperidin-4-yl]-amide

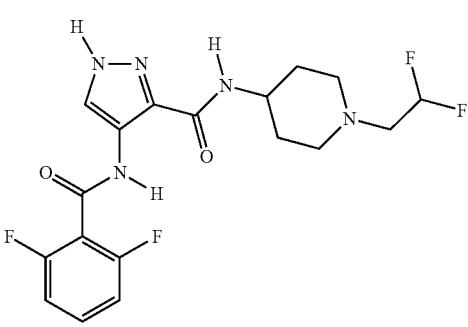 [SMILES: O=C(NC1CCN(CC(F)F)CC1)c1n[nH]cc1NC(=O)c1c(F)cccc1F]

Example 245

4-[3-(4-Methyl-piperazin-1-yl)-benzoylamino]-1H-pyrazole-3-carboxylic acid cyclohexylamide

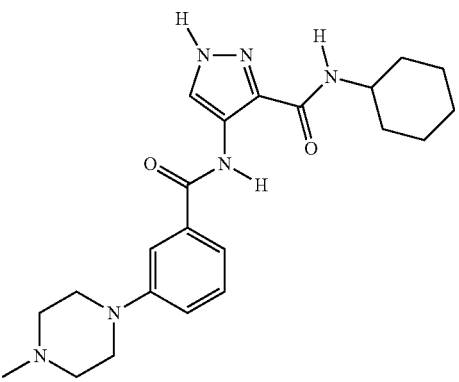 [SMILES: CN1CCN(c2cccc(C(=O)Nc3c[nH]nc3C(=O)NC3CCCCC3)c2)CC1]

Example 246

Preparation of 4-(2,6-dichloro-benzoylamino)-1H-pyrazole-3-carboxylic acid piperidin-4-ylamide acetic acid salt

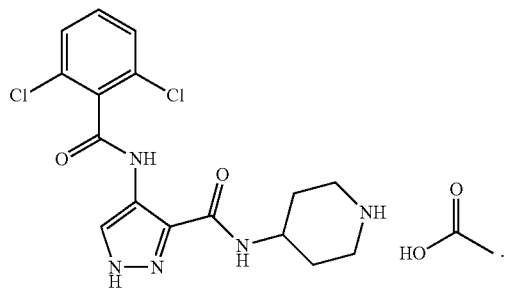

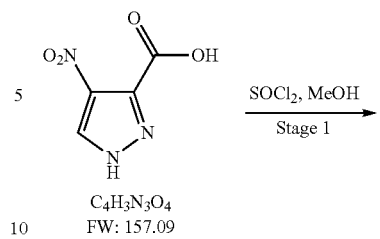

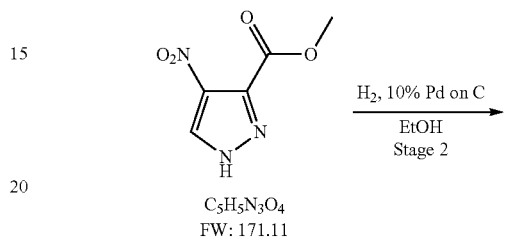

To a solution of 4-(2,6-dichloro-benzoylamino)-1H-pyrazole-3-carboxylic acid piperidin-4-ylamide hydrochloride salt (Example (237C) 20.6 g, 50 mmol) in water (500 ml) stirring at ambient temperature was added sodium bicarbonate (4.5 g, 53.5 mmol). The mixture was stirred for 1 hour and the solid formed collected by filtration and dried in vacuo azeotroping with toluene (×3) to give the corresponding free base of 4-(2,6-dichloro-benzoylamino)-1H-pyrazole-3-carboxylic acid piperidin-4-ylamide.

$^1$H NMR (400 MHz, DMSO-$d_6$) □ 10.20 (s, 1H), 8.30 (s, 1H), 8.25 (d, 1H), 7.60-7.50 (m, 3H), 3.70 (m, 1H), 3.00 (d, 2H), 2.50 (m, 2H), 1.70 (d, 2H), 1.50 (m, 2H).

To a stirred suspension of 4-(2,6-dichloro-benzoylamino)-1H-pyrazole-3-carboxylic acid piperidin-4-ylamide (10.0 g, 26.2 mmol) in methanol (150 ml) was added glacial acetic acid (15 ml, 262 mmol) at ambient temperature. After 1 h, a clear solution was obtained which was reduced in vacuo azeotroping with toluene (×2). The residue was then triturated with acetonitrile (2×100 ml) and the solid dried in vacuo to give 4-(2,6-dichloro-benzoylamino)-1H-pyrazole-3-carboxylic acid piperidin-4-ylamide acetic acid salt (10.3 g) as a white solid.

$^1$H NMR (400 MHz, DMSO-$d_6$) □ 10.20 (s, 1H), 8.40 (d, 1H), 8.35 (s, 1H), 7.60-7.50 (m, 3H), 3.85 (m, 1H), 3.00 (d, 2H), 2.60 (t, 2H), 1.85 (s, 3H), 1.70 (d, 2H), 1.55 (m, 2H)

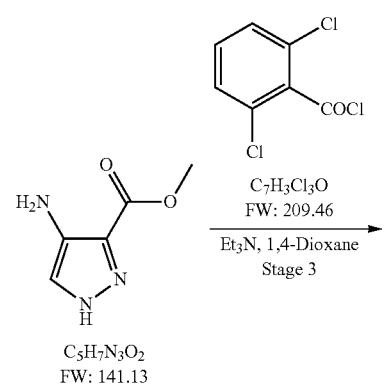

Example 247

Synthesis of the methanesulphonic acid salt of 4-(2,6-dichloro-benzoylamino)-1H-pyrazole-3-carboxylic acid piperidin-4-ylamide The methane sulphonic acid salt of 4-(2,6-dichloro-benzoylamino)-1H-pyrazole-3-carboxylic acid piperidin-4-ylamide may be prepared by the synthetic route shown in the Scheme below.

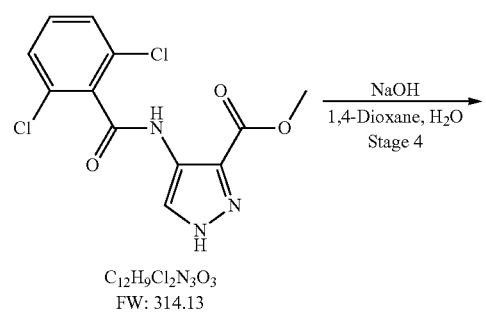

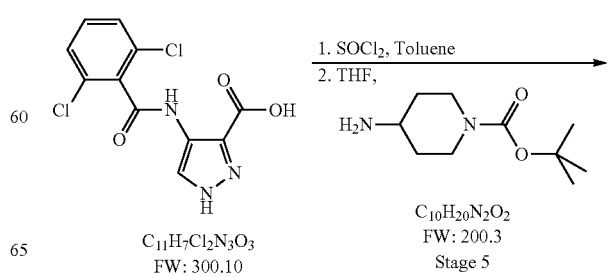

-continued

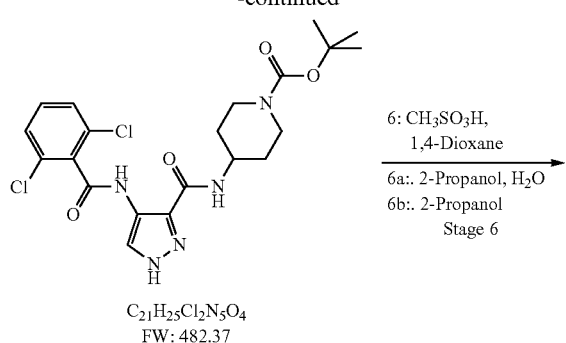

C₂₁H₂₅Cl₂N₅O₄
FW: 482.37

6: CH₃SO₃H, 1,4-Dioxane
6a:. 2-Propanol, H₂O
6b:. 2-Propanol
Stage 6

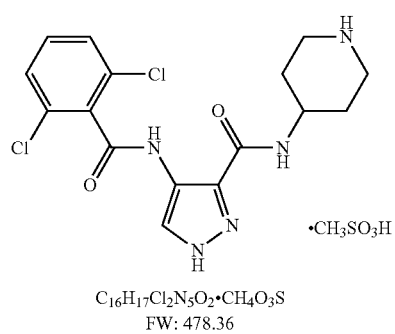

C₁₆H₁₇Cl₂N₅O₂·CH₄O₃S
FW: 478.36

Stage 1: Preparation of 4-nitro-1H-pyrazole-3-carboxylic acid methyl ester

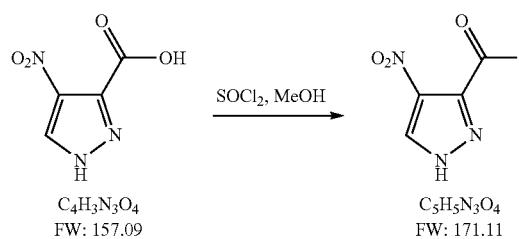

C₄H₃N₃O₄
FW: 157.09

SOCl₂, MeOH

C₅H₅N₃O₄
FW: 171.11

A 20 L reaction vessel equipped with a digital thermometer and stirrer was charged with 4-nitro-1H-pyrazole-3-carboxylic acid (1.117 Kg, 7.11 mol, 1 wt) and methanol (8.950 L, 8 vol). The reaction mixture was stirred under nitrogen, cooled to 0 to 5° C., thionyl chloride (0.581 L, 8.0 mol, 0.52 vol) added over 180 minutes and the resultant mixture allowed to warm to and stir at 18 to 22° C. overnight, after which time ¹H NMR analysis (d₆-DMSO) indicated reaction completion. The reaction mixture was concentrated under reduced pressure at 40 to 45° C., the residue treated with toluene and re-concentrated (3×2.250 L, 3×2 vol) under reduced pressure at 40 to 45° C. to give 4-nitro-1H-pyrazole-3-carboxylic acid methyl ester as an off-white solid (1.210 Kg, 99.5%).

Stage 2: Preparation of 4-amino-1H-pyrazole-3-carboxylic acid methyl ester

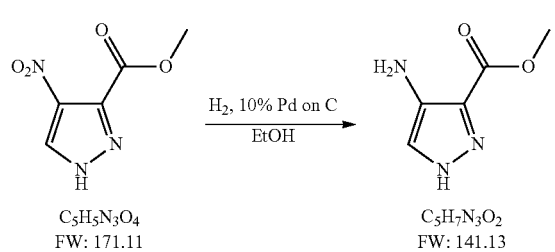

C₅H₅N₃O₄
FW: 171.11

H₂, 10% Pd on C
EtOH

C₅H₇N₃O₂
FW: 141.13

A 20 L reaction vessel equipped with a digital thermometer and stirrer was charged with palladium on carbon (10% wet paste, 0.170 Kg, 0.14 wt) under nitrogen. In a separate vessel a slurry of 4-nitro-1H-pyrazole-3-carboxylic acid methyl ester (1.210 Kg, 7.07 mol, 1 wt) in ethanol (12.10 L, 10 vol) was warmed to 30 to 35° C. to effect dissolution and the solution added to the catalyst under nitrogen. Following a nitrogen-hydrogen purge sequence an atmosphere of hydrogen was introduced and the reaction mixture maintained at 28 to 30° C. until reaction completion (5 to 10 hours) was noted by ¹H NMR analysis (d₆-DMSO). Following a purge cycle, the reaction mixture under nitrogen was filtered and the liquors concentrated under reduced pressure to give 4-amino-1H-pyrazole-3-carboxylic acid methyl ester (0.987 Kg, 98.9%).

Stage 3: Preparation of 4-(2,6-dichlorobenzoylamino)-1H-pyrazole-3-carboxylic acid methyl ester

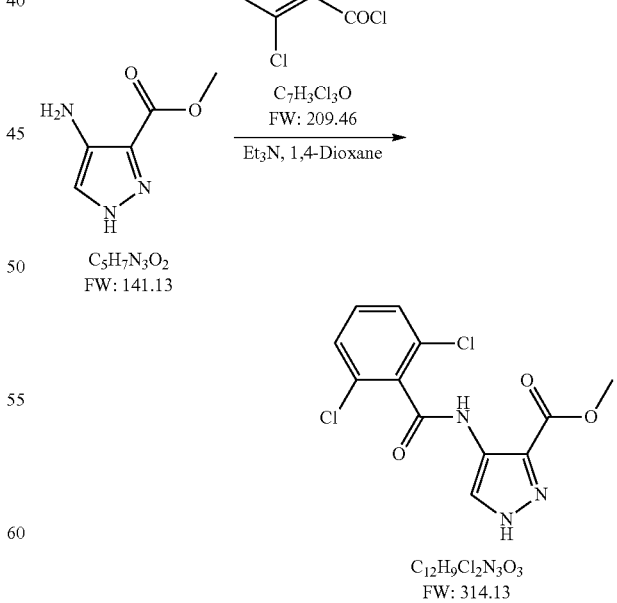

A solution of 4-amino-1H-pyrazole-3-carboxylic acid methyl ester (0.634 Kg, 4.49 mol, 1 wt) in 1,4-dioxane (8.90 L, 9 vol) under nitrogen was treated with triethylamine (0.761

L, 5.46 mol, 1.2 vol) followed by 2,6-dichlorobenzoyl chloride (0.710 L, 4.96 mol, 0.72 vol) such that the internal temperature was maintained in the range 20 to 25° C. Residual 2,6-dichlorobenzoyl chloride was washed in with a line rinse of 1,4-dioxane (0.990 L, 1 vol) and the reaction mixture stirred at 18 to 25° C. until complete (16 hours) by TLC analysis (eluent: ethyl acetate:heptanes 3:1; $R_{f\ amine}$ 0.25, $R_{f\ product}$ 0.65). The reaction mixture was filtered, the filter-cake washed with 1,4-dioxane (2×0.990 L, 2×1 vol) and the combined filtrates (red) progressed to Stage 4 without further isolation.

Stage 4: Preparation of 4-(2,6-dichlorobenzoylamino)-1H-pyrazole-3-carboxylic acid

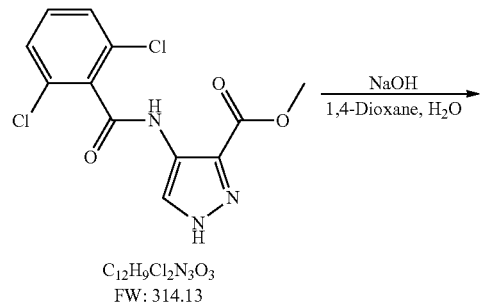

$C_{12}H_9Cl_2N_3O_3$
FW: 314.13

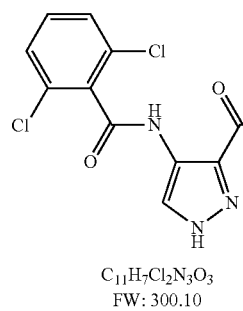

$C_{11}H_7Cl_2N_3O_3$
FW: 300.10

To a solution of sodium hydroxide (0.484 Kg, 12.1 mol) in water (6.05 L) was charged a solution of the Stage 3 ester in one portion: (1.099 Kg, 3.50 mol in 6.00 L). The reaction mixture was stirred to completion at 20 to 25° C. as determined by TLC analysis (eluent: ethyl acetate:heptanes 3:1; $R_{f\ ester}$ 0.65, $R_{f\ Stage}$ 4 baseline). The reaction mixture was concentrated under reduced pressure at 45 to 50° C., the oily residue diluted with water (9.90 L) and acidified to pH 1 with concentrated hydrochloric acid such that the temperature was maintained below 30° C. The resulting precipitate was collected by filtration, washed with water (5.00 L), pulled dry on the filter and subsequently washed with heptanes (5.00 L). The filter-cake was charged to a 20 L rotary evaporator flask and drying completed azeotropically with toluene (2×4.50 L) to afford 4-(2,6-dichlorobenzoylamino)-1H-pyrazole-3-carboxylic acid as a yellow solid (1.044 Kg, approx. 99.5%).

Stage 5: Preparation of 4-{[4-(2,6-dichlorobenzoylamino)-1H-pyrazole-3-carbonyl]amino}piperidine-1-carboxylic acid tert-butyl ester

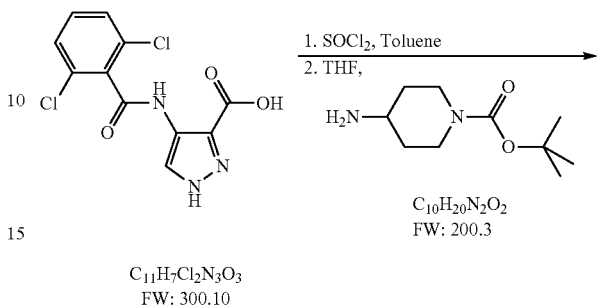

$C_{11}H_7Cl_2N_3O_3$
FW: 300.10

$C_{10}H_{20}N_2O_2$
FW: 200.3

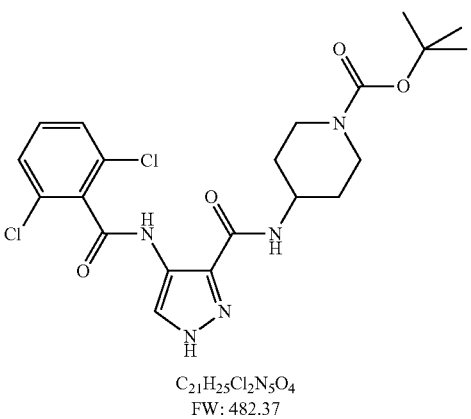

$C_{21}H_{25}Cl_2N_5O_4$
FW: 482.37

Stage 4 product (1.0 wt) and toluene (10.0 vol) were charged to a suitably sized flange flask equipped with a mechanical stirrer, dropping funnel and thermometer. The contents were stirred under nitrogen at 16 to 25° C. and thionyl chloride (0.3 vol) was added slowly. The contents were then heated to 80 to 100° C. and stirred at this temperature until the reaction was judged complete by $^1$H NMR. Further toluene (up to 10 vol) could be added at this stage if the contents were to become too thick to stir. Once complete, the mixture was cooled to between 40 and 50° C. and then concentrated under vacuum at 45 to 50° C. to dryness. The residue was then azeo-dried with toluene (3×2.0 vol).

The isolated solid was transferred to a suitably sized flask and tetrahydrofuran (5.0 vol) was charged. The contents were stirred under nitrogen at 16 to 25° C. and triethylamine (0.512 vol) was added. To a separate flask was charged 4-amino-piperidine-1-carboxylic acid tert-butyl ester (0.704 wt) and tetrahydrofuran (5.0 vol). The contents were agitated until complete dissolution was achieved and the solution was then charged to the reaction flask, maintaining the temperature between 16 and 30° C. The reaction mixture was then heated to between 45 and 50° C. and the contents stirred until judged complete by $^1$H NMR. The contents were then cooled to between 16 and 25° C. and water (5.0 vol) was charged. Mixed heptanes (0.5 vol) were added, the contents were stirred for up to 10 minutes and the layers were separated. The aqueous phase was then extracted with tetrahydrofuran:mixed heptanes [(9:1), 3×5.0 vol]. The organic phases were combined, washed with water (2.5 vol) and then concentrated under vacuum at 40 to 45° C. The residue was azeotroped with toluene (3×5.0 vol) and concentrated to dryness to yield the crude Stage 5 product.

The solid was then transferred to a suitably sized flask, methanol:toluene [(2.5:97.5), 5.0 vol] was added and the slurry was stirred under nitrogen for 3 to 18 hours. The contents were filtered, the filter-cake was washed with toluene (2×0.7 vol) and the solid was then dried under vacuum at 40 to 50° C. to yield 4-{[4-(2,6-dichlorobenzoylamino)-1H-pyrazole-3-carbonyl]amino}piperidine-1-carboxylic acid tert-butyl ester as an off-white solid.

Two batches of Stage 4 product (0.831 kg per batch) were processed in this way to give a total of 2.366 kg (88.6% yield) of 4-{[4-(2,6-dichlorobenzoylamino)-1H-pyrazole-3-carbonyl]amino}piperidine-1-carboxylic acid tert-butyl ester.

Stage 6: Preparation of 4-(2,6-dichlorobenzoylamino)-1H-pyrazole-3-carboxylic acid piperidin-4-ylamide methanesulphonate

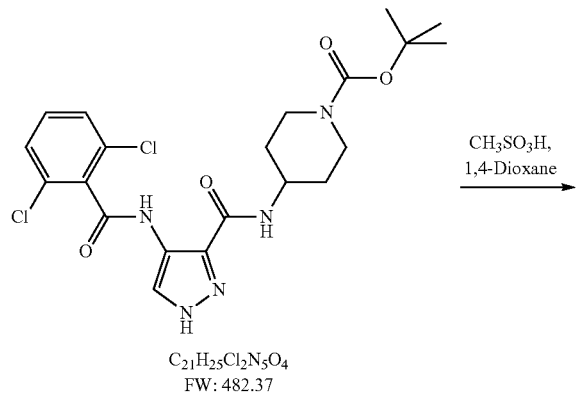

$C_{21}H_{25}Cl_2N_5O_4$
FW: 482.37

CH$_3$SO$_3$H,
1,4-Dioxane

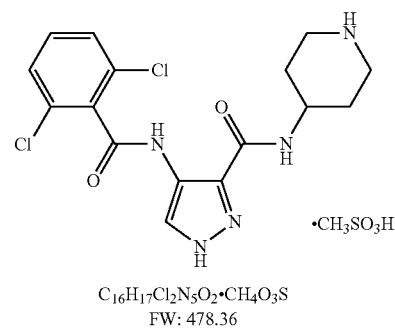

$C_{16}H_{17}Cl_2N_5O_2 \cdot CH_4O_3S$
FW: 478.36

Stage 5 product (1.0 wt) and 1,4-dioxane (30.0 vol) were charged to a suitably sized flange flask equipped with a mechanical stirrer, dropping funnel and thermometer. The contents were stirred under nitrogen and heated to between 80 and 90° C. Methanesulphonic acid (0.54 vol) was added over 30 to 60 minutes and the contents were then heated to 95 to 105° C. and stirred in this temperature range until the reaction was judged complete by $^1$H NMR. Once complete, the contents were cooled to between 20 and 30° C. and the resultant precipitate collected by filtration. The filter-cake was washed with 2-propanol (2×2.0 vol) and pulled dry on the filter for 3 to 24 hours to give crude 4-(2,6-dichlorobenzoylamino)-1H-pyrazole-3-carboxylic acid piperidin-4-ylamide methanesulphonate as a free-flowing off-white solid (80.0 to 120.0% w/w, uncorrected for impurities or solutes).

Several batches of Stage 5 product were processed in this way and the details of the quantities of starting material and product for each batch are set out in Table 1 below.

TABLE 1

| | Yields from the deprotection step - Stage 6 | | |
|---|---|---|---|
| Batch | Input (g) of (4-{[4-(2,6-Dichloro-benzoylamino)-1H-pyrazole-3-carbonyl]amino}-piperidine-1-carboxylic acid tert-butyl ester) | Output (g) of [4-(2,6-Dichlorobenzoyl-amino)-1H-pyrazole-3-carboxylic acid piperidin-4-ylamide methanesulphonate] | Chemical purity (HPLC % area) |
| 1 | 590.0 | 579.6 | 97.88 |
| | | 99.1% th, 98.2% w/w | |
| 2 | 521.0 | 532.7 | 98.09 |
| | | 103.1% th, 102.2% w/w | |
| 3 | 523.8 | 511.7 | 98.17 |
| | | 98.5% th, 97.7% w/w | |
| 4 | 518.4 | 596.3 | 98.24 |
| | | 116.0% th, 115.0% w/w | |
| 5 | 563.2 | 600.1 | 98.16 |
| | | 107.4% th, 106.6% w/w | |
| 6 | 563.1 | 565.2 | 98.49 |
| | | 101.2% th, 100.4% w/w | |
| 7 | 560.4 | 553.9 | 98.70 |
| | | 99.7% th, 98.8% w/w | |
| 8 | 569.7 | 560.6 | 98.41 |
| | | 99.2% th, 98.4% w/w | |

Stage 6a: Recrystallisation of 4-(2,6-dichlorobenzoy-lamino)-1H-pyrazole-3-carboxylic acid piperidin-4-ylamide methanesulphonate The product of Stage 6 was recrystallised to ensure that any residual levels of Boc-protected product of Stage 5 were no greater than 0.25%. Four batches of Stage 6 product were recrystallised using the following protocol.

Crude Stage 6 product and 2-propanol (10.0 vol) were charged to a suitably sized flask equipped with a mechanical stirrer, dropping funnel and thermometer. The contents were stirred under nitrogen and heated to between 75 and 85° C. Water (up to 2.5 vol) was then charged to the contents until a clear solution was obtained. The contents were then cooled to between 40 and 60° C. and concentrated under vacuum at 40 to 50° C. until the reaction volume was reduced by approximately 50%. 2-Propanol (3.0 vol) was charged to the flask and the contents were concentrated at 40 to 50° C. until approximately 3.0 vol of solvent was removed. This process was then repeated twice more with 2-propanol (2×3.0 vol) and the water content was checked. The resultant slurry was then cooled to between 0 and 5° C. and stirred at this temperature for 1 to 2 hours. The contents were filtered, the filter-cake was washed with 2-propanol (2×1.0 vol) and then pulled dry on the filter for up to 24 hours. The solid was transferred to drying trays and dried under vacuum at 45 to 50° C. to constant weight to give 4-(2,6-dichlorobenzoylamino)-1H-pyrazole-3-carboxylic acid piperidin-4-ylamide methanesulphonate as an off-white solid (60.0 to 100.0% w/w).

The recrystallisation yields for the four batches ranged between 85.6% and 90.4% and the purities of the recrystallised product ranged from 99.29% to 99.39%. A second recrystallisation increased the purity still further.

The 4-(2,6-dichlorobenzoylamino)-1H-pyrazole-3-carboxylic acid piperidin-4-ylamide methanesulphonate produced by this route had a melting point (by DSC) of 379.8° C.

Removal of Residual Boc-Protected Product of Stage 5

In some cases, when the methanesulphonate salt was dissolved in acetate buffer, a fine precipitate consisting of residual traces of the Boc-protected free base was observed. Several techniques may be used for removing or preventing the formation of the precipitate, as set out below.

(a) Filtration

A mixture of the methanesulphonate salt in 200 mM acetate buffer was drawn from a vial into a 20 mL single-use syringe using a sterile needle, and a clinical grade 0.2 μm filter (a Sartorius Minisart sterile single use filter unit) was then attached to the syringe. The plunger of the syringe was slowly depressed and the filtrate collected in a clean, clear glass vial. The content of the vial was a clear, colourless solution of the methanesulphonate salt free of particulate matter.

(b) Heating in Aqueous Acid

A mixture of the methanesulphonate salt and methanesulphonic acid (0.4 eq.) in water (10 vol) was heated at 100° C. for 4 hours, and then cooled to 60° C. Analysis by TLC indicates that the methanesulphonate salt was present as a single component. 2-Propanol (10 vol) was added and the mixture cooled to 40° C. The mixture was reduced in vacuo to approximately 10 volumes, then a further portion of 2-propanol added (10 vol) and the mixture again reduced to 10 volumes. This cycle was repeated a further three times. The mixture was cooled in an ice-bath and the solid formed collected by filtration, washed with 2-propanol (5 vol) and dried in vacuo to give the methanesulphonate salt as a white to off-white solid.

(c) Organic-Aqueous Extractions

A mixture of the methanesulphonate salt and methanesulphonic acid (0.4 eq.) in water (10 vol) was heated at 100° C. for 3 hours, and then cooled to ambient temperature. To this mixture was added THF-heptane (9:1, 10 vol) and the resultant mixture stirred vigorously to give a solution. The layers were separated and the aqueous phase washed with THF-heptane (9:1, 2×10 vol) then ethyl acetate (2×10 vol). To the aqueous phase was added 2-propanol (10 vol) and the solution was reduced in vacuo to approximately 5 volumes, then a further portion of 2-propanol added (10 vol) and the mixture again reduced to 5 volumes. This cycle was repeated a further three times. The solid formed was collected by filtration, washed with 2-propanol (5 vol) and dried in vacuo to give the methanesulphonate salt as a white to off-white solid.

(d) Chromatography

The use of chromatographic techniques may provide a route for removing non-polar impurities from the methanesulphonate salt. It is envisaged that the use of reverse-phase methods will be particularly useful.

Biological Activity

The biological activities of the compounds of (0), (I°), (I), (Ia), (Ib), (II), (III), (IV), (IVa), (Va), (Vb), (VIa), (VIb), (VII) or (VIII) and sub-groups thereof as defined herein as inhibitors of CDK kinases, GSK-3 kinase and as inhibitors of cell growth are demonstrated by the examples set out below.

Example 248

Measurement of CDK2 Kinase Inhibitory Activity ($IC_{50}$)

Compounds of the invention were tested for kinase inhibitory activity using either the following protocol or the activated CDK2/cyclin A kinase protocol described in Example 250.

1.7 μl of active CDK2/CyclinA (Upstate Biotechnology, 10 U/μl) is diluted in assay buffer (25.0 μl of 10× strength assay buffer (200 mM MOPS pH 7.2, 250 mM (3-glycerophosphate, 50 mM EDTA, 150 mM $MgCl_2$), 11.27 μl 10 mM ATP, 2.5 μl 1M DTT, 25 μl 100 mM sodium orthovanadate, 708.53 μl $H_2O$), and 10 μl mixed with 10 μl of histone substrate mix (60 μl bovine histone H1 (Upstate Biotechnology, 5 mg/ml), 940 μl $H_2O$, 35 μCi $\gamma^{33}$P-ATP) and added to 96 well plates along with 5 μl of various dilutions of the test compound in DMSO (up to 2.5%). The reaction is allowed to proceed for 5 hours before being stopped with an excess of ortho-phosphoric acid (30 μl at 2%).

$\gamma^{33}$P-ATP which remains unincorporated into the histone H1 is separated from phosphorylated histone H1 on a Millipore MAPH filter plate. The wells of the MAPH plate are wetted with 0.5% orthophosphoric acid, and then the results of the reaction are filtered with a Millipore vacuum filtration unit through the wells. Following filtration, the residue is washed twice with 200 μl of 0.5% orthophosphoric acid. Once the filters have dried, 25 μl of Microscint 20 scintillant is added, and then counted on a Packard Topcount for 30 seconds.

The % inhibition of the CDK2 activity is calculated and plotted in order to determine the concentration of test compound required to inhibit 50% of the CDK2 activity ($IC_{50}$).

By means of the protocol set out above, it was found that the compounds of Examples 2C to 87, 89-92, 94, 96-101, 104-105, 165, 166, 224, 225, 227, 229, 231, 233, 234 and 236 each have $IC_{50}$ values less than 20 μM or provide at least 50% inhibition of the CDK2 activity at a concentration of 10 μM. The compounds of Examples 88, 93, 226, 228, 230 and 235 each have $IC_{50}$ values less than 750 μM.

Example 249

CDK Selectivity Assays

Compounds of the invention are tested for kinase inhibitory activity against a number of different kinases using the general protocol described in Example 247, but modified as set out below.

Kinases are diluted to a 10× working stock in 20 mM MOPS pH 7.0, 1 mM EDTA, 0.1% γ-mercaptoethanol, 0.01% Brij-35, 5% glycerol, 1 mg/ml BSA. One unit equals the incorporation of 1 nmol of phosphate per minute into 0.1 mg/ml histone H1, or CDK7 substrate peptide at 30° C. with a final ATP concentration of 100 uM.

The substrate for all the CDK assays (except CDK7) is histone H1, diluted to 10× working stock in 20 mM MOPS pH 7.4 prior to use. The substrate for CDK7 is a specific peptide obtained from Upstate diluted to 10× working stock in deionised water.

Assay Procedure for CDK1/cyclinB, CDK2/cyclinA, CDK2/cyclinE, CDK3/cyclinE, CDK5/p35, CDK6/cyclinD3:

In a final reaction volume of 25 µl, the enzyme (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx 500 cpm/pmol, concentration as required). The reaction is initiated by the addition of $Mg^{2+}$ [γ-$^{33}$P-ATP]. After incubation for 40 minutes at room temperature the reaction is stopped by the addition of 5 µl of a 3% phosphoric acid solution. 10 ml of the reaction is spotted onto a P30 filter mat and washed 3 times for 5 minutes in 75 mM phosphoric acid and once in methanol prior to drying and counting.

In the CDK3/cyclinE assay, the compound of Example 150 had an $IC_{50}$ of less than 20 µM.

In the CDK5/p35 assay, the compounds of Examples 41 and 150 had an $IC_{50}$ of less than 20 µM.

In the CDK6/cyclinD3 assay, the compound of Example 150 had an $IC_{50}$ of less than 20 µM.

Assay Procedure for CDK7/cyclinH/MAT1

In a final reaction volume of 25 µl, the enzyme (5-10 mU) is incubated with 8 mM MOPS pH 7.0, 0.2 mM EDTA, 500 µM peptide, 10 mM MgAcetate and [γ-$^{33}$P-ATP] (specific activity approx 500 cpm/pmol, concentration as required). The reaction is initiated by the addition of $Mg^{2}$+[γ-$^{33}$P-ATP]. After incubation for 40 minutes at room temperature the reaction is stopped by the addition of 5 µl of a 3% phosphoric acid solution. 10 ml of the reaction is spotted onto a P30 filtermat and washed 3 times for 5 minutes in 75 mM phosphoric acid and once in methanol prior to drying and counting.

Example 250

A. Measurement of Activated CDK2/CyclinA Kinase Inhibitory Activity Assay ($IC_{50}$)

Compounds of the invention were tested for kinase inhibitory activity using the following protocol.

Activated CDK2/CyclinA (Brown et al, Nat. Cell Biol., 1, pp 438-443, 1999; Lowe, E. D., et al Biochemistry, 41, pp 15625-15634, 2002) is diluted to 125 pM in 2.5× strength assay buffer (50 mM MOPS pH 7.2, 62.5 mM (3-glycerophosphate, 12.5 mM EDTA, 37.5 mM $MgCl_2$, 112.5 mM ATP, 2.5 mM DTT, 2.5 mM sodium orthovanadate, 0.25 mg/ml bovine serum albumin), and 10 µl mixed with 10 µl of histone substrate mix (60 µl bovine histone H1 (Upstate Biotechnology, 5 mg/ml), 940 µl $H_2O$, 35 µCi γ$^{33}$ P-ATP) and added to 96 well plates along with 5 µl of various dilutions of the test compound in DMSO (up to 2.5%). The reaction is allowed to proceed for 2 to 4 hours before being stopped with an excess of ortho-phosphoric acid (5 µl at 2%).

γ$^{33}$P-ATP which remains unincorporated into the histone H1 is separated from phosphorylated histone H1 on a Millipore MAPH filter plate. The wells of the MAPH plate are wetted with 0.5% orthophosphoric acid, and then the results of the reaction are filtered with a Millipore vacuum filtration unit through the wells. Following filtration, the residue is washed twice with 200 µl of 0.5% orthophosphoric acid. Once the filters have dried, 20 µl of Microscint 20 scintillant is added, and then counted on a Packard Topcount for 30 seconds.

The % inhibition of the CDK2 activity is calculated and plotted in order to determine the concentration of test compound required to inhibit 50% of the CDK2 activity ($IC_{50}$).

By means of the foregoing protocol, it was found that the compounds of Examples 95, 96, 99-104, 106-121, 123-125, 130-137, 139, 142-145, 147-150, 152-156, 158-160, 162-164, 167-173, 177-179, 181-182, 184-190, 194, 196-204, 208-213 and 215 have $IC_{50}$ values less than 20 µM. The compounds of Examples 122, 126-129, 140, 141, 146, 157 and 161 each have $IC_{50}$ values less than 750 µM and most have $IC_{50}$ values of less than 100 µM.

B. CDK1/CyclinB Assay.

CDK1/CyclinB assay is identical to the CDK2/CyclinA above except that CDK1/CyclinB (Upstate Discovery) is used and the enzyme is diluted to 6.25 nM.

In the CDK1 assay carried out as described above or by means of the protocol set out in Example 240, the compounds of Examples 2C, 41, 48, 53, 64, 65, 66, 73, 76, 77, 91, 95, 102, 106, 117, 123, 125, 133, 137, 142, 150, 152, 154, 167, 186, 187, 189, 190, 193, 194, 196, 199, 202-204, 207, 208-213, 215 AND 218-223 were found to have $IC_{50}$ values less than 20 µM, and the compounds of Examples 188 and 206, were found to have $I_{50}$ values less than 100 µM.

Example 251

Assay Procedure for CDK4

Assays for CDK4 inhibitory activity were carried out by Proqinase GmbH, Freiburg, Germany using their proprietary 33PanQinase® Activity Assay. The assays were performed in 96 well FlashPlates™ (PerkinElmer). In each case, the reaction cocktail (50 µl final volume) is composed of; 20 µl assay buffer (final composition 60 mM HEPES-NaOH, pH 7.5, 3 mM $MgCl_2$, 3 µM Na-orthovanadate, 1.2 mM DTT, 50 µg/ml $PEG_{2000}$, 5 µl ATP solution (final concentration 1 µM [γ-33P]-ATP (approx 5×10$^5$ cpm per well)), 5 µl test compound (in 10% DMSO), 10 µl substrate/10 µl enzyme solution (premixed). The final amounts of enzyme and substrate were as below.

| Kinase | Kinase ng/50 µl | Substrate | Substrate ng/50 µl |
|---|---|---|---|
| CDK4/CycD1 | 50 | Poly (Ala, Glu, Lys, Tyr) 6:2:5:1 | 500 |

The reaction cocktail was incubated at 30° C. for 80 minutes. The reaction was stopped with 50 µl of 2% $H_3PO_4$, plates were aspirated and washed twice with 200 µl 0.9% NaCl. Incorporation of $^{33}$P was determined with a microplate scintillation counter. Background values were subtracted from the data before calculating the residual activities for each well. $IC_{50}$s were calculated using Prism 3.03.

The compound of Example 150 has an IC50 of less than 5 µM in this assay.

Example 252

Measurement of Inhibitory Activity Against Glycogen Synthase Kinase-3 (GSK-3)

The activities of the compounds of the invention as inhibitors of GSK-3 were determined using either Protocol A or Protocol B below.

Protocol A

Protocol A

GSK3-β (Upstate Discovery) is diluted to 7.5 nM in 25 mM MOPS, pH 7.00, 25 mg/ml BSA, 0.0025% Brij-35®, 1.25% glycerol, 0.5 mM EDTA, 25 mM $MgCl_2$, 0.025% β-mercaptoethanol, 37.5 mM ATP and 10 µl mixed with 10 µl of substrate mix. The substrate mix is 12.5 µM phospho-glycogen synthase peptide-2 (Upstate Discovery) in 1 ml of water with 35 µCi $\gamma^{33}$P-ATP. Enzyme and substrate are added to 96 well plates along with 5 µl of various dilutions of the test compound in DMSO (up to 2.5%). The reaction is allowed to proceed for 3 hours before being stopped with an excess of ortho-phosphoric acid (5 µl at 2%). The filtration procedure is as for Activated CDK2/CyclinA assay above.

Protocol B

GSK3β (human) is diluted to a 10× working stock in 50 mM Tris pH 7.5, 0.1 mM EGTA, 0.1 mM sodium vanadate, 0.1% β-mercaptoethanol, 1 mg/ml BSA. One unit equals the incorporation of 1 nmol of phosphate per minute phosphoglycogen synthase peptide 2 per minute.

In a final reaction volume of 25 µl, GSK3β (5-10 mU) is incubated with 8 mM MOPS 7.0, 0.2 mM EDTA, 20 µM YRRAAVPPSPSLSRHSSPHQS(p)EDEEE (phospho GS2 peptide), 10 mM MgAcetate and [Δ-$^{33}$P-ATP] (specific activity approx 500 cpm/pmol, concentration as required). The reaction is initiated by the addition of $Mg^{2+}$+[$\gamma$-$^{33}$P-ATP]. After incubation for 40 minutes at room temperature the reaction is stopped by the addition of 5 µl of a 3% phosphoric acid solution. 10 µl of the reaction is spotted onto a P30 filter mat and washed 3 times for 5 minutes in 50 mM phosphoric acid and once in methanol prior to drying and counting.

From the results of the GSK3-B assays carried out using either of the two protocols set out above, it was found that the compounds of Examples 2C, 26, 48, 53, 65, 76, 77, 84, 86, 95, 102, 106, 119, 122, 123, 126, 127, 128, 129, 131, 134, 135, 138, 140, 141, 142, 143, 144, 145, 146, 147, 149, 150 and 151 each have $IC_{50}$ values of less than 10 µM.

Example 253

Anti-Proliferative Activity

The anti-proliferative activities of the combinations of the invention, as well as the individual components of the combinations, are determined by measuring the ability of the compounds to inhibition of cell growth in a number of cell lines. Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. All cell lines are obtained from ECACC (European Collection of cell Cultures).

HCT-116 Cell Line

In assays against the human colon carcinoma cell line HCT 116 (ECACC No. 91091005), the compounds of Examples 10, 25-27, 41, 44, 46, 48, 50, 52, 53, 60, 62, 64-67, 69, 73-77, 79, 80, 83A, 86, 90-93, 95-98, 100-104, 106, 107, 109-121, 123-125, 131-134, 136-143, 147-155, 158, 159, 162-164, 166, 167, 178, 179, 185-190, 192-205, 207-215 and 218-223 have $IC_{50}$ values of less than 20 µM and the compounds of Examples 2C, 3, 29, 38, 39, 49, 51, 85, 89, 99, 108, 135, 160, 182, 183, 206 and 216 have $IC_{50}$ values of less than 100 µM.

Example 254

The effect of the compound 4-(2,6-dichloro-benzoylamino)-1H-pyrazole-3-carboxylic acid piperidin-4-ylamide ("Compound I") in combination with 5FU, Gemcitibine, Paclitaxel, and Iressa (Compound II) were assessed using the following technique:

$IC_{50}$ Shift Assay

Human colon carcinoma cell line HT29 (ECACC No. 91072201) cells were seeded onto 96-well tissue culture plates at a concentration of 5×10$^3$ cells/well. Cells were allowed to recover overnight prior to addition of compound(s) or vehicle control (0.2% DMSO) as follows;

|  | Compound I | | | | | | Compound I | | | | | |
|---|---|---|---|---|---|---|---|---|---|---|---|---|
| Conc | a | b | c | d | e | Control | a | b | c | d | e | Control |
| a |  |  |  |  |  |  |  |  |  |  |  |  |
| b |  |  |  |  |  |  |  |  |  |  |  |  |
| c |  |  |  |  |  |  |  |  |  |  |  |  |
| Compound II  d |  |  |  |  |  |  |  |  |  |  |  |  |
| e |  |  |  |  |  |  |  |  |  |  |  |  |
| f |  |  |  |  |  |  |  |  |  |  |  |  |
| g |  |  |  |  |  |  |  |  |  |  |  |  |
| Control |  |  |  |  |  |  |  |  |  |  |  |  |

Compounds were added according to one of the following schedules;
a) Concurrent for 72 hours.
b) Compound I for 24 hours followed by Compound II for 48 hours.
c) Compound II for 24 hours followed by Compound I for 48 hours.

Following a total of 72 hours compound incubation, Alamar Blue™ was added to a final concentration of 10% (v/v) and incubated at 37° C. for 6 hours. Fluorescent product was quantified by reading at d535/25x (excitation) and d590/20m (emission) on a Fusion Reader (Perkin Elmer). The $IC_{50}$ for Compound II in the presence of varying doses of Compound I was determined. Synergy was determined when the $IC_{50}$ shifted down in the presence of sub-effective doses of Compound I. Additivity was determined when the response to Compound II and Compound I together resulted in an effect equivalent to the sum of the two compounds individually. Antagonistic effects were defined as those causing the $IC_{50}$ to shift upwards, i.e. those where the response to the two compounds was less than the sum of the effect of the two compounds individually.

1. Gemcitibine

Figure 2:
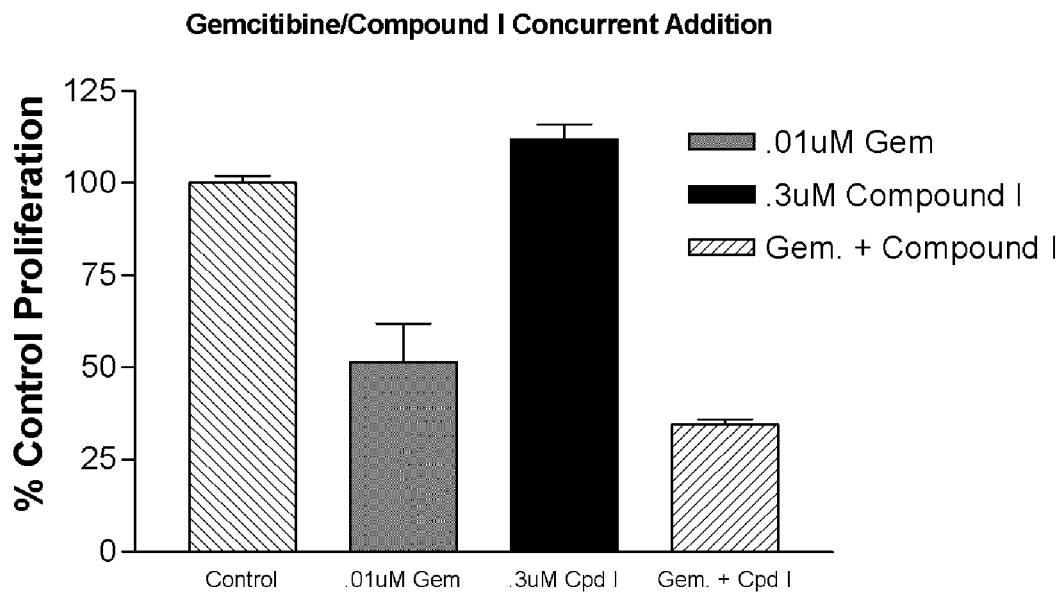
FIG. 2 depicts the percent control proliferation in A2780 cells in the presence and absence of either 0.01 uM Gemcitabine, 0.3 uM Compound I or both added concurrently using the example of percentage control proliferation following each treatment regimen.
Figure 3:
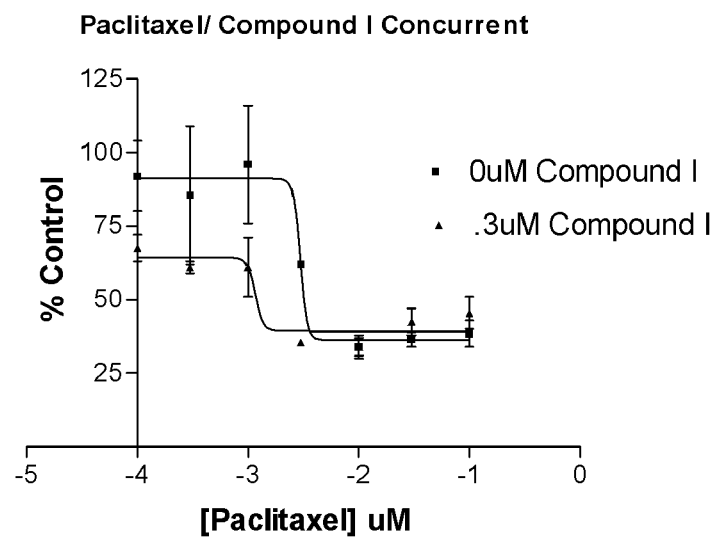
FIG. 3 depicts the percent control proliferation in A2780 cells for Paclitaxel in the presence and absence of 0.3 μM Compound I added concurrently, using the example of the $IC_{50}$ response curve to Paclitaxel.
Figure 4:
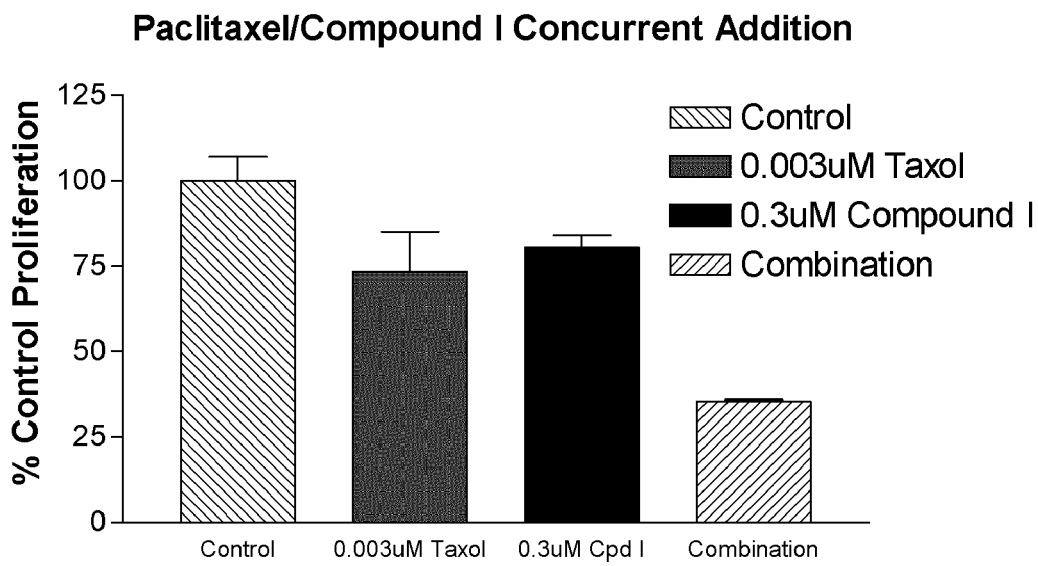
FIG. 4 depicts the percent control proliferation in A2780 cells for Paclitaxel in the presence and absence of either 0.003 uM Paclitaxel, 0.3 μM Compound I or both added concurrently using the example of percentage control proliferation following each treatment regimen.
Figure 5:
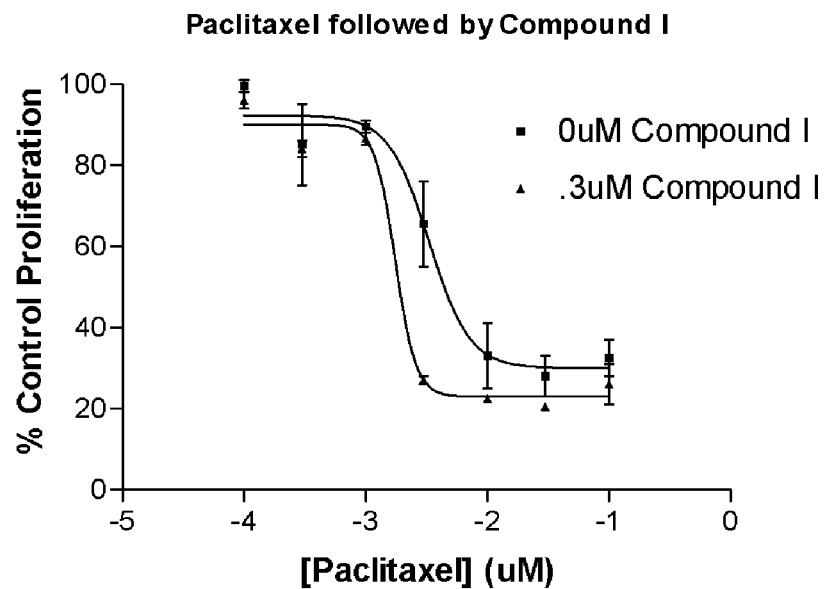
FIG. 5 depicts the percent control proliferation in A2780 cells for Paclitaxel in the absence of Compound I, and followed by addition of 0.3 μM Compound I, using the example of the $IC_{50}$ response curve to Paclitaxel.
Figure 6:
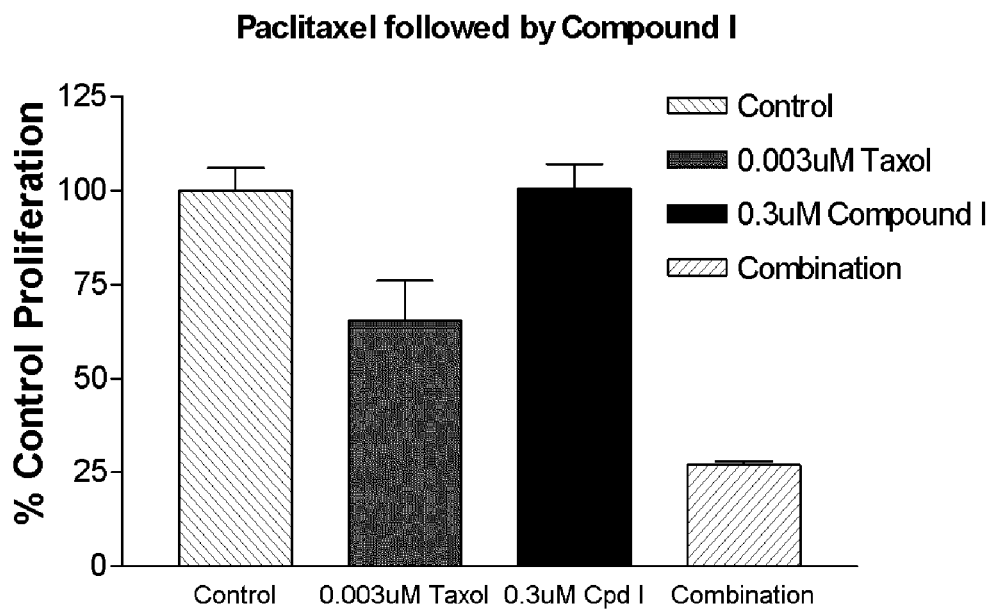
FIG. 6 depicts the percent control proliferation in A2780 cells for Paclitaxel in the absence of either 0.003 uM Paclitaxel, 0.3 uM Compound I or a combination where Paclitaxel is added 24 h prior to Compound I using the example of percentage control proliferation following each treatment regimen.

Combinations of Compound I and Gemcitibine were shown to be additive in the $IC_{50}$ shift assay performed in A2780 cells. This effect was observed when compounds were added concurrently for 72 h or when Gemcitibine was added for 24 h followed by Compound I for a further 48 h. The data obtained are summarised in FIGS. 1 and 2 below using the example of the $IC_{50}$ response curves to Gemcitibine in the presence and absence of 0.3 μM Compound I added concurrently.

2. Paclitaxel

Combinations of Compound I and Paclitaxel were shown to be additive or synergistic in the $IC_{50}$ shift assay dependent upon schedule. The studies were performed in A2780 cells. Additive effects were observed when compounds were added concurrently for 72 h and synergy when Paclitaxel was added for 24 h followed by Compound I for a further 48 h. The data obtained are summarised in FIGS. 3, 4, 5 and 6 below using examples of the $IC_{50}$ response curves to Paclitaxel in the presence and absence of 0.3 μM Compound I.

3. 5FU

Figure 7:
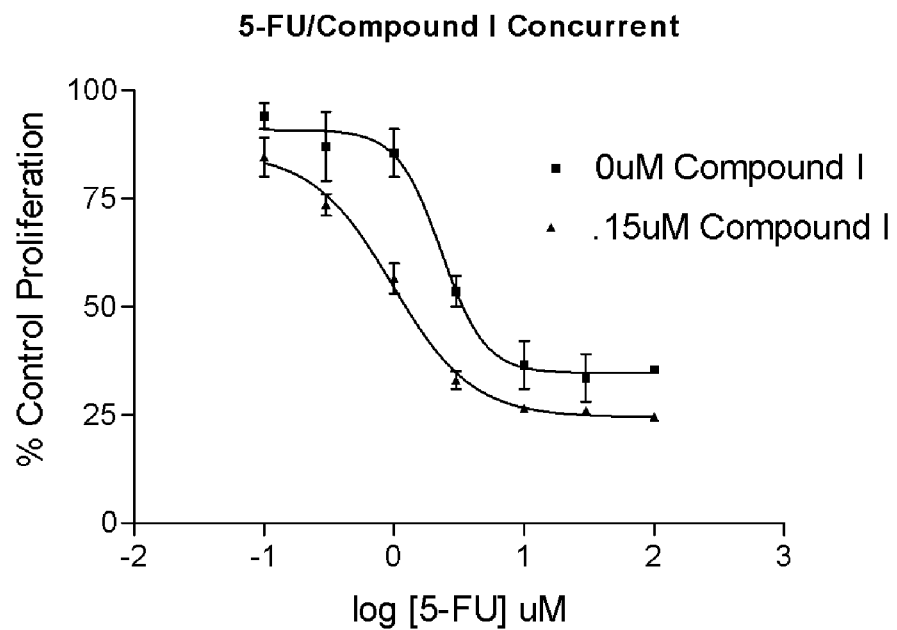
FIG. 7 depicts the percent control proliferation in A2780 cells for 5-FU in the presence and absence of 0.15 μM Compound I added concurrently, using the example of the $IC_{50}$ response curves to 5-FU.
Figure 8:
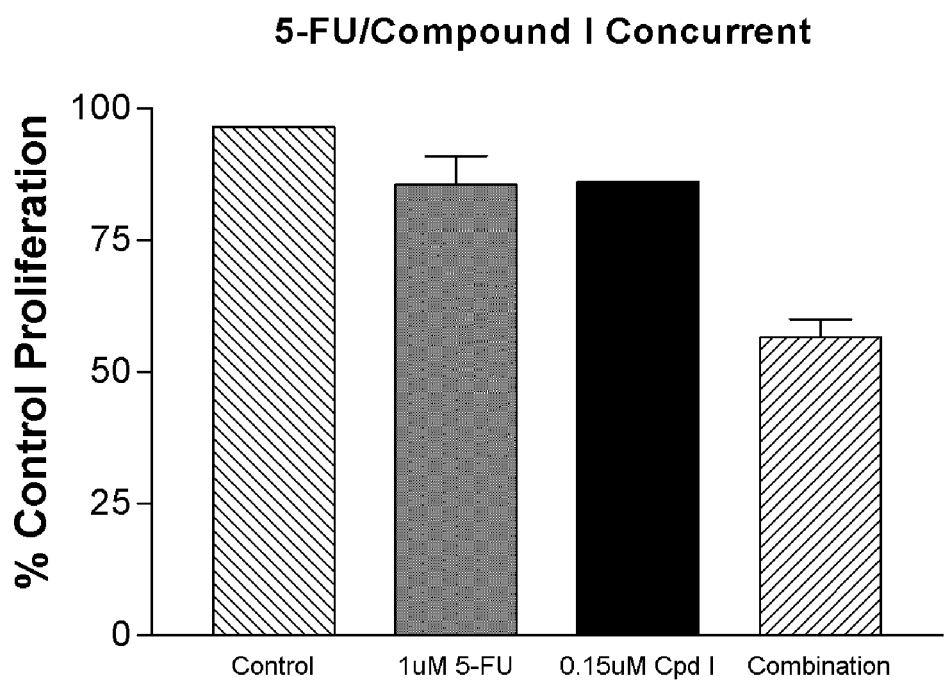
FIG. 8 depicts the percent control proliferation in A2780 cells for 5-FU in the presence and absence of either 1 uM 5-FU, 0.15 uM Compound I or both added concurrently using the example of percentage control proliferation following each treatment regimen.
Figure 9:
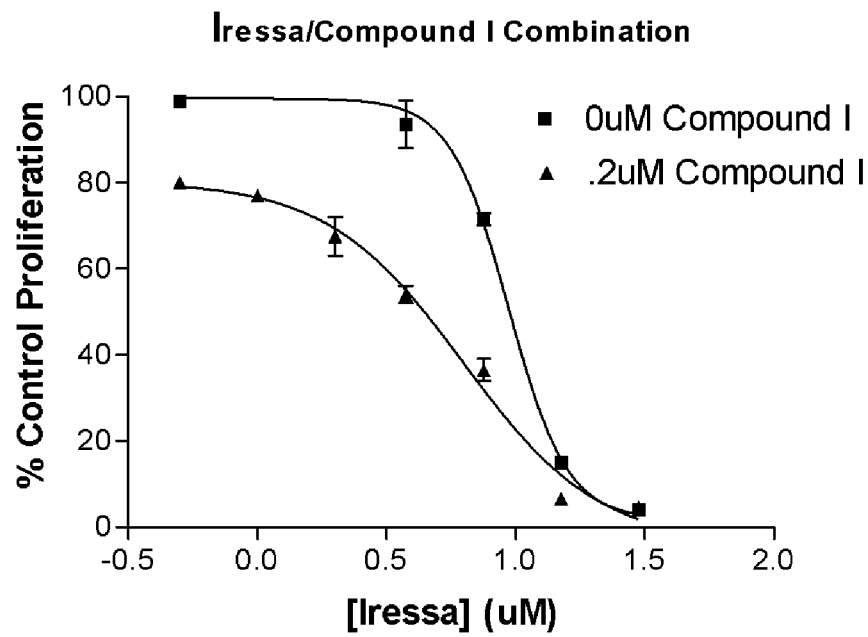
FIG. 9 depicts the percent control proliferation in A2780 cells for Iressa in the presence and absence of 0.2 μM Compound I added in combination therewith, using the example of the $IC_{50}$ response curves to Iressa.
Figure 10:
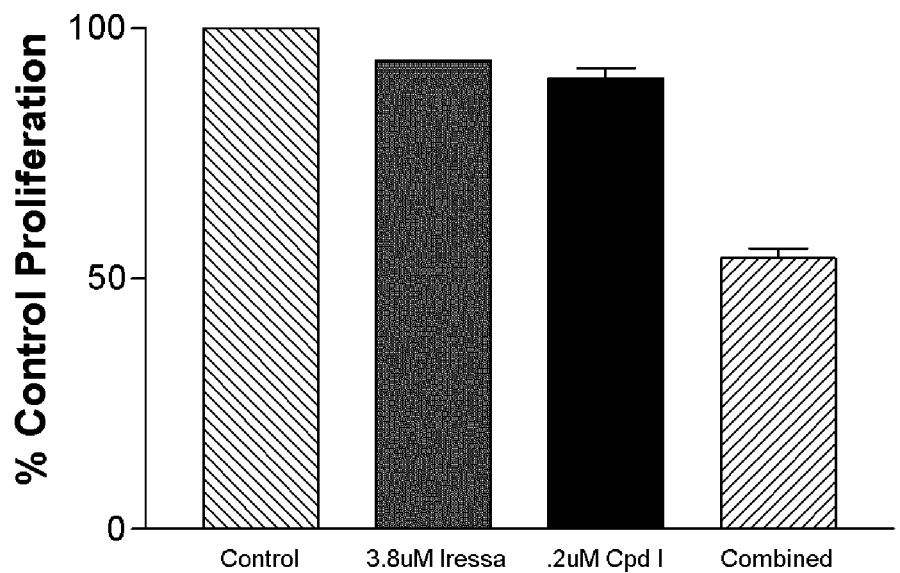
FIG. 10 depicts the percent control proliferation in A2780 cells for Iressa in the presence and absence of either 3.8 uM Iressa, 0.2 uM Compound I or both added concurrently using the example of percentage control proliferation following each treatment regimen.

Combinations of Compound I and 5-FU were shown to be mildly synergistic in the $IC_{50}$ shift assay performed in A2780 cells. This effect was observed when compounds were added concurrently for 72 h. The data obtained are summarised in FIGS. 7 and 8 below using the example of the $IC_{50}$ response curves to 5-FU in the presence and absence of 0.15 μM Compound I when added concurrently.

4. Iressa

Combinations of Compound I and Iressa were shown to be synergistic in the $IC_{50}$ shift assay performed in A2780 cells. This effect was observed when compounds were added concurrently for 72 h. The data obtained are summarised below using examples of the $IC_{50}$ response curves to Iressa in the presence and absence of 0.2 μM Compound I. These data were confirmed in the HCT116 and SkBR3 cell lines.

Example 255

The effect of the compound 4-(2,6-dichloro-benzoylamino)-1H-pyrazole-3-carboxylic acid piperidin-4-ylamide ("Compound I") in combination with camptothecin was assessed using the following technique:

1. $IC_{50}$ Shift Assay

Human colon carcinoma cell line HT29 (ECACC No. 91072201) cells were seeded onto 96-well tissue culture plates at a concentration of 5×10³ cells/well. Cells were allowed to recover overnight prior to addition of compound(s) or vehicle control (0.2% DMSO) as follows;

Compounds were added according to one of the following schedules;

a) Concurrent for 72 hours.

b) Compound I for 24 hours followed by camptothecin for 48 hours.

c) Camptothecin for 24 hours followed by Compound I for 48 hours.

Following a total of 72 hours compound incubation, Alamar Blue™ was added to a final concentration of 10% (v/v) and incubated at 37° C. for 6 hours. Fluorescent product was quantified by reading at d535/25x (excitation) and d590/20m (emission) on a Fusion Reader (Perkin Elmer). The $IC_{50}$ for camptothecin in the presence of varying doses of Compound I was determined. Synergy was determined when the $IC_{50}$ shifted down in the presence of sub-effective doses of Compound I. Additivity was determined when the response to camptothecin and Compound I together resulted in an effect equivalent to the sum of the two compounds individually. Antagonistic effects were defined as those causing the $IC_{50}$ to shift upwards, i.e. those where the response to the two compounds was less than the sum of the effect of the two compounds individually.

Figure 11:
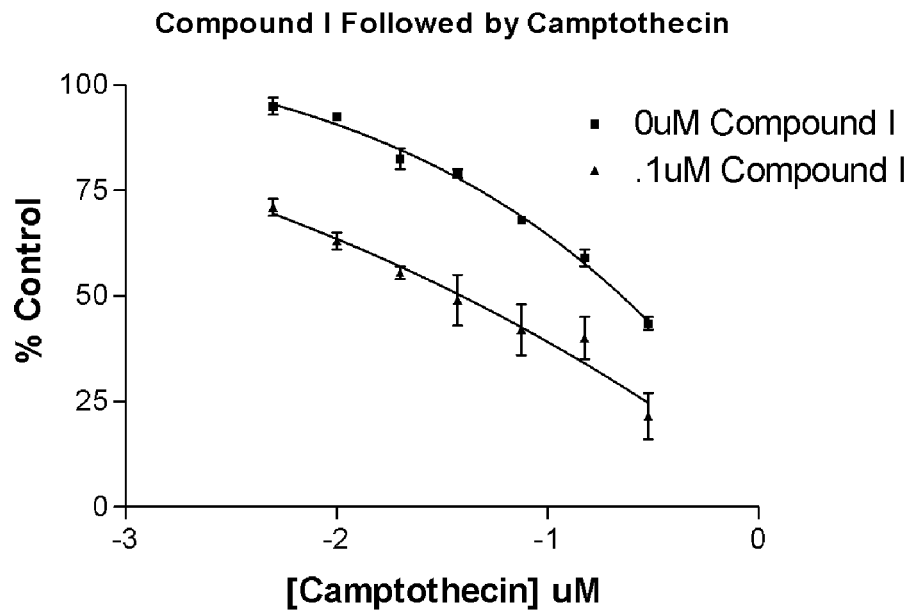
FIG. 11 depicts the percent control proliferation in HT29 cells for camptothecin in the absence of Compound I, and 0.1 μM Compound I added prior to camptothecin, using the example of the $IC_{50}$ response curve to camptothecin.
Figure 12:
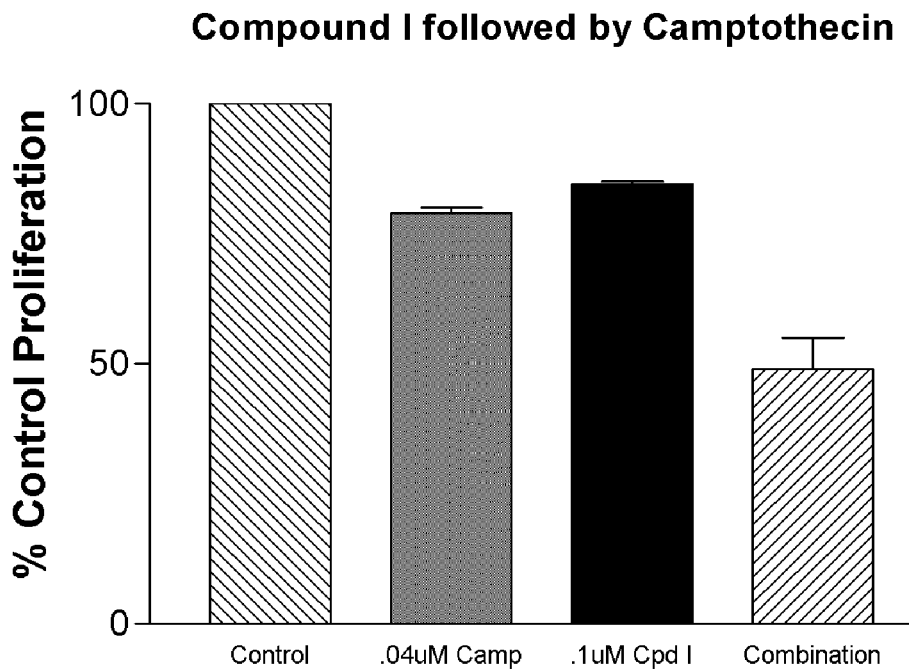
FIG. 12 depicts the percent control proliferation in HT29 cells for camptothecin in the absence of either 0.04 uM camptothecin, 1 uM Compound I or a combination where Compound I is added 24 h prior to camptothecin using the example of percentage control proliferation following each treatment regimen.

Combinations of Compound I and camptothecin were shown to be additive in the $IC_{50}$ shift assay performed in HT29 cells. This effect was observed when compounds were added concurrently for 72 hours or when camptothecin was added for 24 hours followed by Compound I for a further 48 hours. Similar additivity was observed when Compound I was added prior to camptothecin. The data obtained are summarised in FIGS. 11 and 12 below using the example of the $IC_{50}$ response curves to camptothecin in the presence and absence of 0.1 μM Compound I in Schedule (b) (Compound I added followed by camptothecin).

Example 256

The effect of the compound 4-(2,6-dichloro-benzoylamino)-1H-pyrazole-3-carboxylic acid piperidin-4-ylamide ("Compound I") in combination with vinblastine was assessed using the following technique:

1. $IC_{50}$ Shift Assay

Human colon carcinoma cell line HT29 (ECACC No. 91072201) cells were seeded onto 96-well tissue culture plates at a concentration of 5×10³ cells/well. Cells were allowed to recover overnight prior to addition of compound(s) or vehicle control (0.2% DMSO) as follows;

|  |  | | | Compound I | | | | | | Compound I | | | | |
|---|---|---|---|---|---|---|---|---|---|---|---|---|---|---|
|  | Conc | a | b | c | d | e | Control | a | b | c | d | e | Control |
| Campto-thecin | a |  |  |  |  |  |  |  |  |  |  |  |  |
|  | b |  |  |  |  |  |  |  |  |  |  |  |  |
|  | c |  |  |  |  |  |  |  |  |  |  |  |  |
|  | d |  |  |  |  |  |  |  |  |  |  |  |  |
|  | e |  |  |  |  |  |  |  |  |  |  |  |  |
|  | f |  |  |  |  |  |  |  |  |  |  |  |  |
|  | g |  |  |  |  |  |  |  |  |  |  |  |  |
|  | Control |  |  |  |  |  |  |  |  |  |  |  |  |

|  |  | | | Compound I | | | | | | Compound I | | | | |
|---|---|---|---|---|---|---|---|---|---|---|---|---|---|---|
|  | Conc | a | b | c | d | e | Control | a | b | c | d | e | Control |
| Vinblastine | a |  |  |  |  |  |  |  |  |  |  |  |  |
|  | b |  |  |  |  |  |  |  |  |  |  |  |  |
|  | c |  |  |  |  |  |  |  |  |  |  |  |  |
|  | d |  |  |  |  |  |  |  |  |  |  |  |  |
|  | e |  |  |  |  |  |  |  |  |  |  |  |  |
|  | f |  |  |  |  |  |  |  |  |  |  |  |  |
|  | g |  |  |  |  |  |  |  |  |  |  |  |  |
|  | Control |  |  |  |  |  |  |  |  |  |  |  |  |

Compounds were added according to one of the following schedules;
d) Concurrent for 72 hours.
e) Compound I for 24 hours followed by vinblastine for 48 hours.
f) Vinblastine for 24 hours followed by Compound I for 48 hours.

Following a total of 72 hours compound incubation, Alamar Blue™ was added to a final concentration of 10% (v/v) and incubated at 37° C. for 6 hours. Fluorescent product was quantified by reading at d535/25x (excitation) and d590/20m (emission) on a Fusion Reader (Perkin Elmer). The $IC_{50}$ for vinblastine in the presence of varying doses of Compound I was determined. Synergy was determined when the $IC_{50}$ shifted down in the presence of sub-effective doses of Compound I. Additivity was determined when the response to vinblastine and Compound I together resulted in an effect equivalent to the sum of the two compounds individually. Antagonistic effects were defined as those causing the $IC_{50}$ to shift upwards, i.e. those where the response to the two compounds was less than the sum of the effect of the two compounds individually.

Figure 13:
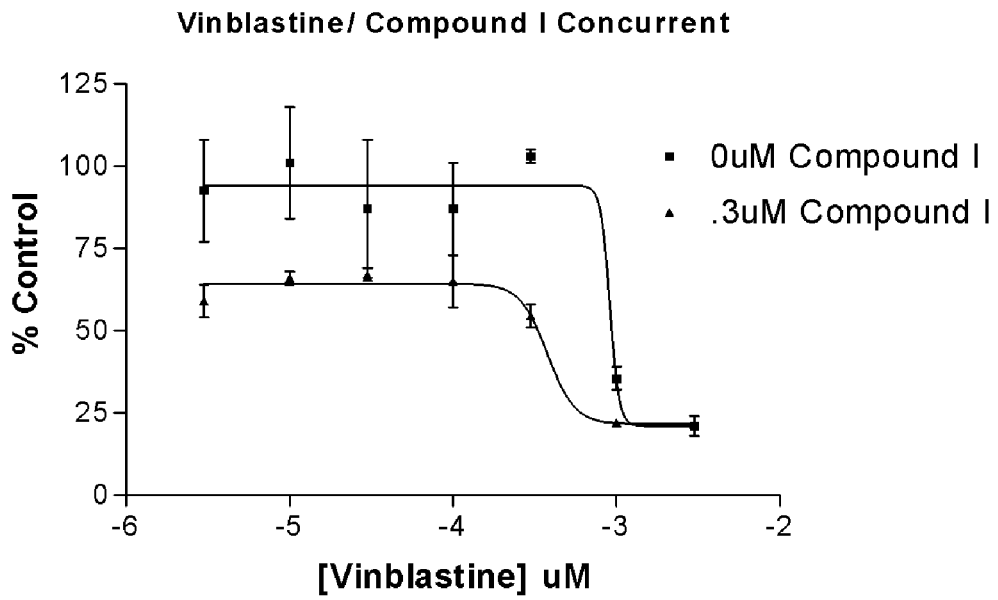
FIG. 13 depicts the percent control proliferation in A2780 cells for Vinblastine in the presence and absence of 0.3 μM Compound I added concurrently, using the example of the $IC_{50}$ response curves to Vinblastine.
Figure 14:
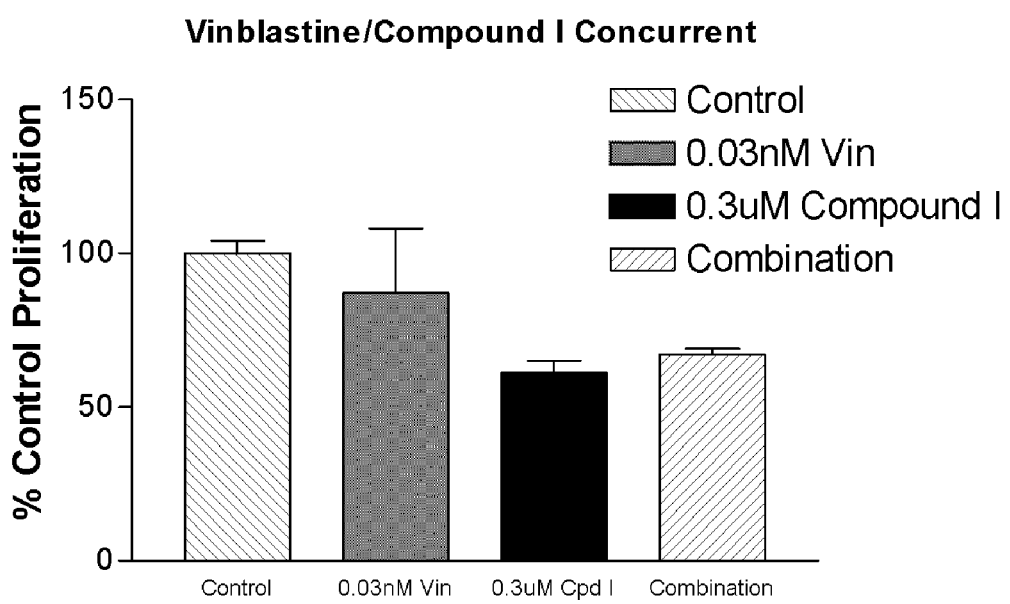
FIG. 14 depicts the percent control proliferation in A2780 cells for Vinblastine in the presence and absence of either 0.03 uM Vinblastine, 0.3 uM Compound I or both added concurrently using the example of percentage control proliferation following each treatment regimen.

Combinations of Compound I and Vinblastine were shown to be additive in the $IC_{50}$ shift assay performed in A2780 cells. This effect was observed when compounds were added concurrently for 72 h or when Vinblastine was added for 24 h followed by compound I for a further 48 h. The data obtained are summarised below in FIGS. 13 and 14 using the example of the $IC_{50}$ response curves to Vinblastine in the presence and absence of 0.3 µM Compound I when added concurrently.

Example 257

The effect of the compound 4-(2,6-dichloro-benzoylamino)-1H-pyrazole-3-carboxylic acid piperidin-4-ylamide ("Compound I") in combination with cisplatin was assessed using the following technique:

1. $IC_{50}$ Shift Assay

Human colon carcinoma cell line HT29 (ECACC No. 91072201) cells were seeded onto 96-well tissue culture plates at a concentration of 5×10³ cells/well. Cells were allowed to recover overnight prior to addition of compound(s) or vehicle control (0.2% DMSO) as follows;

|  |  | Compound I |  |  |  |  |  | Compound I |  |  |  |  |  |
|---|---|---|---|---|---|---|---|---|---|---|---|---|---|
|  | Conc | a | b | c | d | e | Control | a | b | c | d | e | Control |
| Cisplatin | a |  |  |  |  |  |  |  |  |  |  |  |  |
|  | b |  |  |  |  |  |  |  |  |  |  |  |  |
|  | c |  |  |  |  |  |  |  |  |  |  |  |  |
|  | d |  |  |  |  |  |  |  |  |  |  |  |  |
|  | e |  |  |  |  |  |  |  |  |  |  |  |  |
|  | f |  |  |  |  |  |  |  |  |  |  |  |  |
|  | g |  |  |  |  |  |  |  |  |  |  |  |  |
|  | Control |  |  |  |  |  |  |  |  |  |  |  |  |

Compounds were added according to one of the following schedules;
g) Concurrent for 72 hours.
h) Compound I for 24 hours followed by cisplatin for 48 hours.
i) Cisplatin for 24 hours followed by Compound I for 48 hours.

Following a total of 72 hours compound incubation, Alamar Blue™ was added to a final concentration of 10% (v/v) and incubated at 37° C. for 6 hours. Fluorescent product was quantified by reading at d535/25x (excitation) and d590/20m (emission) on a Fusion Reader (Perkin Elmer). The $IC_{50}$ for cisplatin in the presence of varying doses of Compound I was determined. Synergy was determined when the $IC_{50}$ shifted down in the presence of sub-effective doses of Compound I. Additivity was determined when the response to cisplatin and Compound I together resulted in an effect equivalent to the sum of the two compounds individually. Antagonistic effects were defined as those causing the $IC_{50}$ to shift upwards, i.e. those where the response to the two compounds was less than the sum of the effect of the two compounds individually.

Figure 15:
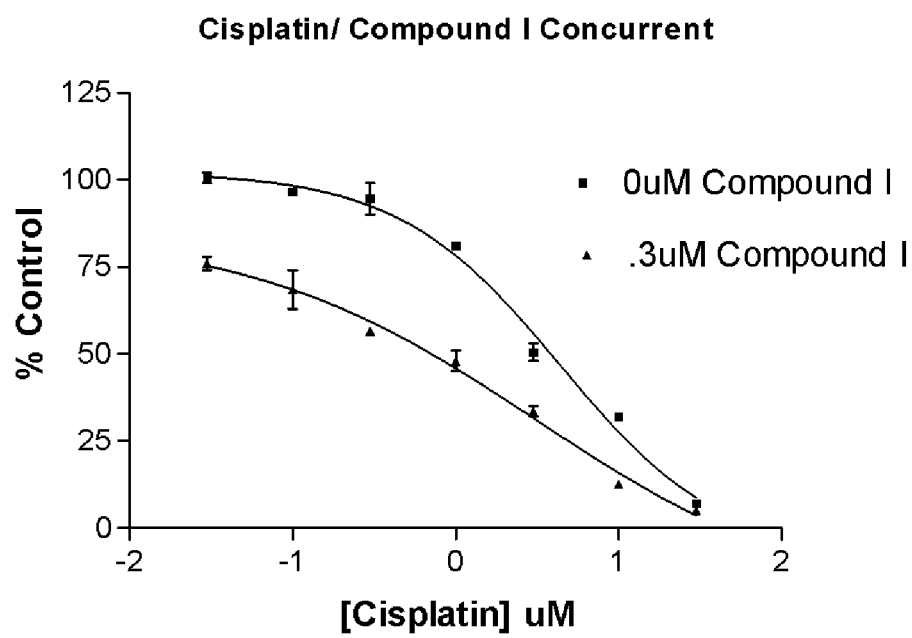
FIG. 15 depicts the percent control proliferation in A2780 cells for Cisplatin in the presence and absence of 0.3 μM Compound I added concurrently, using the example of the $IC_{50}$ response curves to Cisplatin.
Figure 16:
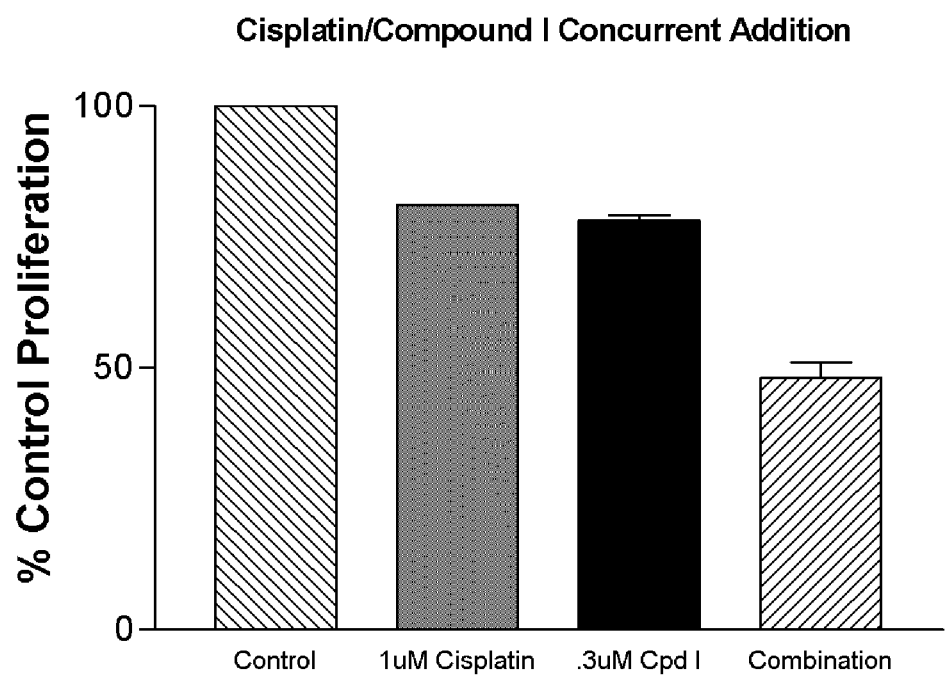
FIG. 16 depicts the percent control proliferation in A2780 cells for Cisplatin in the presence and absence of either 1 uM cisplatin, 0.3 uM Compound I or both added concurrently using the example of percentage control proliferation following each treatment regimen.

Combinations of compound I and Cisplatin were shown to be additive in the $IC_{50}$ shift assay performed in A2780 cells. This effect was observed when compounds were added concurrently for 72 h or when Cisplatin was added for 24 h followed by compound I for a further 48 h. The data obtained are summarised below in FIGS. 15 and 16 using the example of the $IC_{50}$ response curves to Cisplatin in the presence and absence of 0.3 µM compound I when added concurrently.

Example 258

The effect of the compound 4-(2,6-dichloro-benzoylamino)-1H-pyrazole-3-carboxylic acid piperidin-4-ylamide ("Compound I") in combination with etoposide was assessed using the following technique:

1. $IC_{50}$ Shift Assay

Human colon carcinoma cell line HT29 (ECACC No. 91072201) cells were seeded onto 96-well tissue culture plates at a concentration of 5×10³ cells/well. Cells were allowed to recover overnight prior to addition of compound(s) or vehicle control (0.2% DMSO) as follows;

|  |  | Compound I |  |  |  |  |  | Compound I |  |  |  |  |  |
|---|---|---|---|---|---|---|---|---|---|---|---|---|---|
|  | Conc | a | b | c | d | e | Control | a | b | c | d | e | Control |
| Etoposide | a |  |  |  |  |  |  |  |  |  |  |  |  |
|  | b |  |  |  |  |  |  |  |  |  |  |  |  |
|  | c |  |  |  |  |  |  |  |  |  |  |  |  |
|  | d |  |  |  |  |  |  |  |  |  |  |  |  |
|  | e |  |  |  |  |  |  |  |  |  |  |  |  |
|  | f |  |  |  |  |  |  |  |  |  |  |  |  |
|  | g |  |  |  |  |  |  |  |  |  |  |  |  |
|  | Control |  |  |  |  |  |  |  |  |  |  |  |  |

Compounds were added according to one of the following schedules;
j) Concurrent for 72 hours.
k) Compound I for 24 hours followed by etoposide for 48 hours.
l) Etoposide for 24 hours followed by Compound I for 48 hours.

Following a total of 72 hours compound incubation, Alamar Blue™ was added to a final concentration of 10% (v/v) and incubated at 37° C. for 6 hours. Fluorescent product was quantified by reading at d535/25x (excitation) and d590/20m (emission) on a Fusion Reader (Perkin Elmer). The $IC_{50}$ for etoposide in the presence of varying doses of Compound I was determined. Synergy was determined when the $IC_{50}$ shifted down in the presence of sub-effective doses of Compound I. Additivity was determined when the response to etoposide and Compound I together resulted in an effect equivalent to the sum of the two compounds individually. Antagonistic effects were defined as those causing the $IC_{50}$ to shift upwards, i.e. those where the response to the two compounds was less than the sum of the effect of the two compounds individually.

Figure 17:
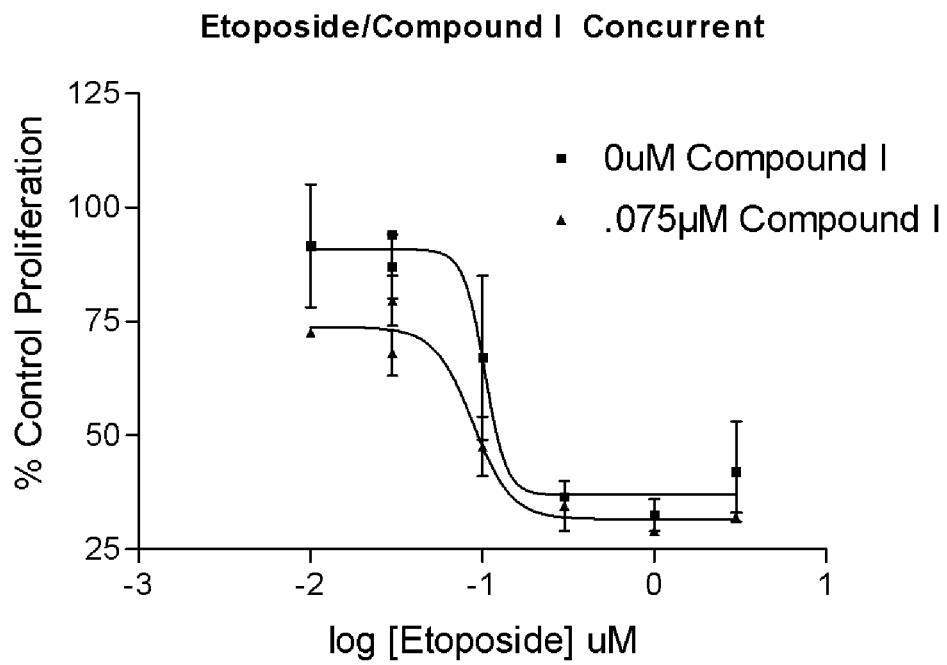
FIG. 17 depicts the percent control proliferation in A2780 cells for Etoposide in the presence and absence of 0.075 μM Compound I added concurrently, using the example of the $IC_{50}$ response curves to Etoposide.
Figure 18:
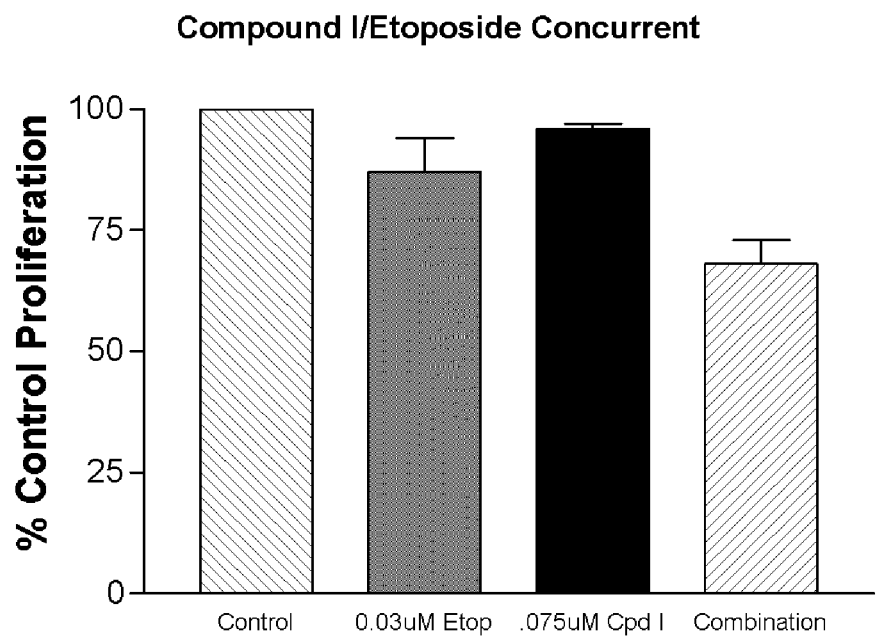
FIG. 18 depicts the percent control proliferation in A2780 cells for Etoposide in the presence and absence of either 0.03 uM Etoposide, 0.075 uM Compound I or both added concurrently using the example of percentage control proliferation following each treatment regimen.

Combinations of Compound I and Etoposide were shown to be additive in the $IC_{50}$ shift assay performed in A2780 cells. This effect was observed when compounds were added concurrently for 72 h or when Etoposide was added for 24 h followed by compound I for a further 48 h. The data obtained are summarised below in FIGS. 17 and 18 using the example of the $IC_{50}$ response curves to Etoposide in the presence and absence of 0.075 µM Compound I when added concurrently.

Pharmaceutical Formulations

Example 259 i) Lyophilised Formulation I

Aliquots of formulated compound of formula (0), (I°), (I), (Ia), (Ib), (II), (III), (IV), (IVa), (Va), (Vb), (VIa), (VIb), (VII) or (VIII) and sub-groups thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

ii) Injectable Formulation II

A formulation for i.v. delivery by injection or infusion can be prepared by dissolving the compound of formula (0), (I°), (I), (Ia), (Ib), (II), (III), (IV), (IVa), (Va), (Vb), (VIa), (VIb), (VII) or (VIII) and sub-groups thereof as defined herein (e.g. in a salt form) in water at 20 mg/ml. The vial is then sealed and sterilised by autoclaving.

iii) Injectable Formulation III

A formulation for i.v. delivery by injection or infusion can be prepared by dissolving the compound of formula (0), (I°), (I), (Ia), (Ib), (II), (III), (IV), (IVa), (Va), (Vb), (VIa), (VIb), (VII) or (VIII) and sub-groups thereof as defined herein (e.g. in a salt form) in water containing a buffer (e.g. 0.2 M acetate pH 4.6) at 20 mg/ml. The vial is then sealed and sterilised by autoclaving.

iv) Injectable Formulation IV

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

v) Injectable Formulation V

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

vi) Subcutaneous Injection Formulation VI

A composition for sub-cutaneous administration is prepared by mixing a compound of the formula (I) with pharmaceutical grade corn oil to give a concentration of 5 mg/ml. The composition is sterilised and filled into a suitable container.

vii) Tablet Formulation

A tablet composition containing a compound of the formulae (I°) or (I) or an acid addition salt thereof as defined herein is prepared by mixing 50 mg of the compound or its salt with 197 mg of lactose (BP) as diluent, and 3 mg magnesium stearate as a lubricant and compressing to form a tablet in known manner.

(viii) Capsule Formulation

A capsule formulation is prepared by mixing 100 mg of a compound of the formulae (I°) or (I) or an acid addition salt thereof as defined herein with 100 mg lactose and filling the resulting mixture into standard opaque hard gelatin capsules.

(ix) Lyophilised Formulation

Aliquots of formulated compound of formulae (I°) or (I) or an acid addition salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(x) Concentrate for Use in i.v. Administration

An aqueous buffered solution is prepared by dissolving 4-(2,6-dichlorobenzoylamino)-1H-pyrazole-3-carboxylic acid piperidin-4-ylamide methanesulphonate at a concentration of 20 mg/ml in a 0.2M sodium acetate/acetic acid buffer at a pH of 4.6.

The buffered solution is filled, with filtration to remove particulate matter, into a container (such as class 1 glass vials) which is then sealed (e.g. by means of a Florotec stopper) and secured (e.g. with an aluminium crimp). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. For intravenous administration, the solution can be dosed as is, or can be injected into an infusion bag (containing a pharmaceutically acceptable excipient, such as 0.9% saline or 5% dextrose), before administration.

(xi) Injectable Formulation of a Camptothecin Compound

A parenteral pharmaceutical formulation for administration by injection and containing a camptothecin compound can be prepared by dissolving 100 mg of a water soluble salt of the camptothecin compound (for example a compound as described in EP 0321122 and in particular the examples therein) in 10 ml of sterile 0.9% saline and then sterilising the solution and filling the solution into a suitable container Example 256

Determination of the crystal structure of 4-(2,6-dichlorobenzoylamino)-1H-pyrazole-3-carboxylic acid piperidin-4-ylamide methanesulphonate by X-ray diffraction The compound 4-(2,6-dichlorobenzoylamino)-1H-pyrazole-3-carboxylic acid piperidin-4-ylamide methanesulphonate was prepared as described in Example 1. The crystal used for the diffraction experiment was a colourless plate with dimensions 0.05×0.08×0.14 mm³ obtained by precipitation from a water solution by 2-propanol. Crystallographic data were collected at 93 K using CuKα radiation (λ=1.5418 Å) from a Rigaku rotating anode RU3HR, Osmic blue confocal optics and a Rigaku Jupiter CCD detector. Images were collected in two w scans at 2θ=15 and 90° with a detector to crystal distance of 67 mm. Data collection was controlled by CrystalClear software and images were processed and scaled by Dtrek. Due to a high absorption coefficient (µ=4.01 mm⁻¹) data had to be corrected using $4^{th}$ order Fourier absorption correction. It was found that the crystals belong to an orthorhombic space group Pbca (#61) with crystal lattice parameters at 93 K a=8.90(10), b=12.44(10), c=38.49(4) Å, α=β=γ=90°. The numbers in brackets represents the deviation (s.u., standard uncertainty).

The crystals described above and the crystal structure form a further aspect of the invention.

The crystal structure was solved using direct methods implemented in SHELXS-97. Intensity data for a total of 2710 unique reflections in a resolution range from 20-0.9 Å (2.3<θ<58.87) were used in the refinement of 271 crystallographic parameters by SHELXL-97. Final statistical parameters were: wR2=0.2115 (all data), R1=0.0869 (data with I>2σ(I)) and goodness of fit S=1.264.

Figure 19:
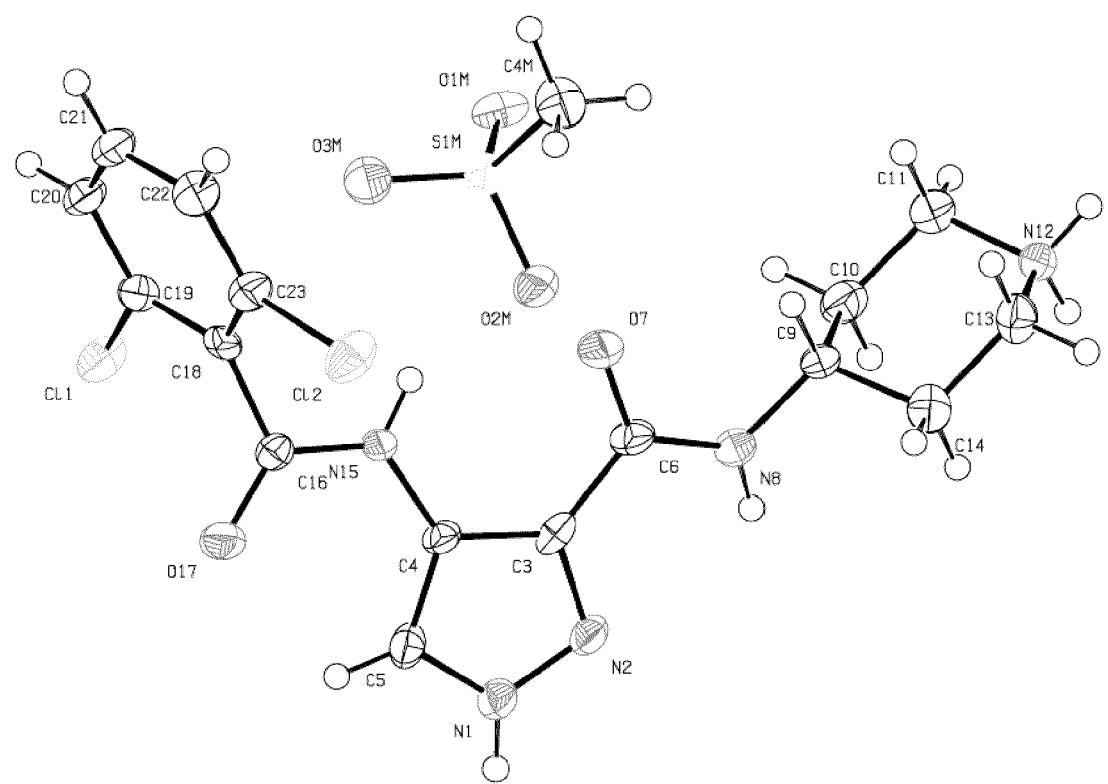
FIG. 19 depicts the crystal structure of 4-(2,6-dichlorobenzoylamino)-1H-pyrazole-3-carboxylic acid piperidin-4-ylamide methanesulphonate, which was solved as described below.

One molecule of protonated free base and one mesylate anion were found in the asymmetric unit. The elemental composition of the asymmetric unit was $C_{17}H_{21}Cl_2N_5O_5S$ and the calculated density of the crystals is 1.49 $Mg/m^3$. Hydrogen atoms were generated on geometrical grounds while the location of heteroatom bound hydrogen atoms was confirmed by inspection of Fo-Fc difference maps. The positional and thermal parameters of hydrogen atoms were constricted to ride on corresponding non-hydrogen atoms. The thermal motion of non-hydrogen atoms was modeled by anisotropical thermal factors (see FIG. 19).

The crystal structure contains one intramolecular (N15H . . . O7 2.690 Å) and five intermolecular hydrogen bonds (see packing figure FIG. 20). Three of them link the protonated piperidine nitrogen with two mesylate anions. The first mesylate anion is linked through a single H-bond N12H12A . . . O2M 2.771 Å, while the second is involved in a bifurcated H-bond with interactions N12H12B . . . O1M 2.864 Å and N12H12B . . . O2M 3.057 Å. The remaining mesylate oxygen O3M is involved in a hydrogen bond N8H8 . . . O3M 2.928 Å. Neighbouring protonated free base molecules are linked together by a H-bond N15H15 . . . O7 2.876 Å, as well as by relatively long contact N15H15 . . . N2 3.562 Å and stacking of phenyl and pyrazole rings. These interactions are propagated infinitely along the b axis. Crystal packing contains 2D layers (in the ab plane) of mesylate anions sandwiched by an extensive network of charged H-bonds with two layers of protonated free base cations. The compact 2D sandwich layers are joined together along the c axis by stacking of phenyl rings and involving chlorine . . . phenyl interaction with C12 . . . C18 3.341 Å.

Figure 20:
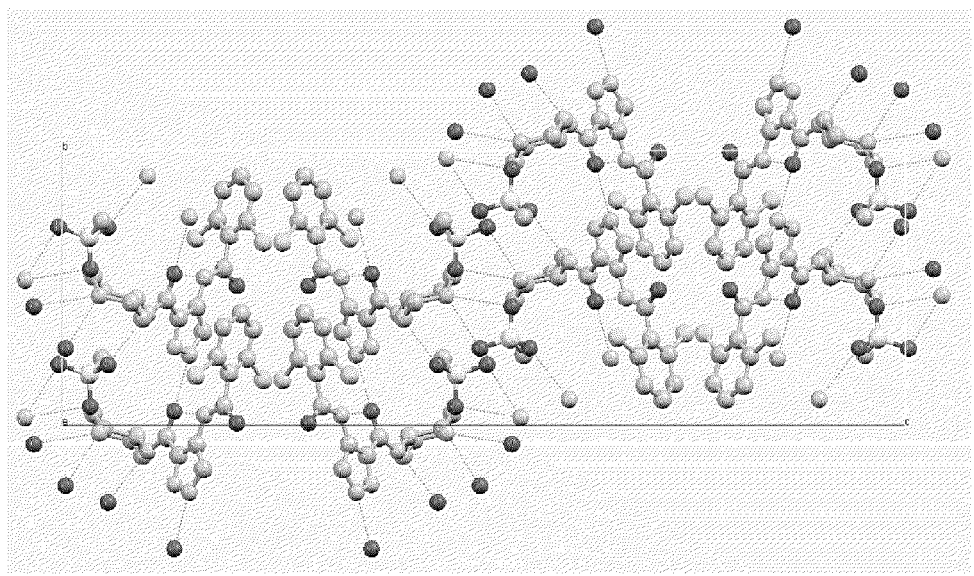
FIG. 20 depicts a graphical representation of the structure of 4-(2,6-dichlorobenzoylamino)-1H-pyrazole-3-carboxylic acid piperidin-4-ylamide methanesulphonate, generated by X-ray diffraction study.

A graphical representation of the structure generated by the X-ray diffraction study is provided in FIG. 20.

The coordinates for the atoms making up the structure of the 4-(2,6-dichlorobenzoylamino)-1H-pyrazole-3-carboxylic acid piperidin-4-ylamide methanesulphonate are as set out in Table 2.

TABLE 2 space group: Pbca
unit cell at 93K with a, b & c having 5% s.u.:
a = 8.9
b = 12.4
c = 38.5
alpha = beta = gamma = 90
Coordinates in cif format:
loop_
_atom_site_label
_atom_site_type_symbol
_atom_site_fract_x
_atom_site_fract_y
_atom_site_fract_z
_atom_site_U_iso_or_equiv
_atom_site_adp_type TABLE 2-continued _atom_site_occupancy
_atom_site_symmetry_multiplicity
_atom_site_calc_flag
_atom_site_refinement_flags
_atom_site_disorder_assembly
_atom_site_disorder_group
S1M S 0.13517(17) 0.18539(13) 0.03193(5) 0.0286(5) Uani 1 1 d . . .
O1M O 0.1193(5) 0.2208(3) −0.00409(14) 0.0326(13) Uani 1 1 d . . .
O2M O 0.1551(5) 0.0681(3) 0.03330(13) 0.0331(13) Uani 1 1 d . . .
O3M O 0.0151(5) 0.2217(4) 0.05453(14) 0.0368(13) Uani 1 1 d . . .
C4M C 0.3036(8) 0.2420(6) 0.0475(2) 0.0355(19) Uani 1 1 d . . .
H4M1 H 0.3855 0.2197 0.0329 0.053 Uiso 1 1 calc R . .
H4M2 H 0.3212 0.2181 0.0708 0.053 Uiso 1 1 calc R . .
H4M3 H 0.2959 0.3189 0.0471 0.053 Uiso 1 1 calc R . .
Cl1 Cl 0.26158(17) 0.18137(12) 0.34133(5) 0.0325(5) Uani 1 1 d . . .
Cl2 Cl 0.75698(19) 0.16766(13) 0.26161(5) 0.0366(6) Uani 1 1 d . . .
N1 N 0.6277(6) −0.2419(4) 0.34903(16) 0.0276(14) Uani 1 1 d . . .
H1 H 0.5932 −0.3064 0.3484 0.033 Uiso 1 1 calc R . .
N2 N 0.7505(5) −0.2150(4) 0.36663(16) 0.0286(15) Uani 1 1 d . . .
C3 C 0.7635(7) −0.1082(5) 0.36163(19) 0.0265(17) Uani 1 1 d . . .
C4 C 0.6453(7) −0.0708(5) 0.34039(18) 0.0211(16) Uani 1 1 d . . .
C5 C 0.5616(7) −0.1594(5) 0.3322(2) 0.0277(18) Uani 1 1 d . . .
H5 H 0.4770 −0.1623 0.3181 0.033 Uiso 1 1 calc R . .
C6 C 0.8878(7) −0.0454(5) 0.3760(2) 0.0269(17) Uani 1 1 d . . .
O7 O 0.9037(5) 0.0506(3) 0.36722(14) 0.0368(13) Uani 1 1 d . . .
N8 N 0.9821(6) −0.0939(4) 0.39821(15) 0.0267(14) Uani 1 1 d . . .
H8 H 0.9626 −0.1584 0.4048 0.032 Uiso 1 1 calc R . .
C9 C 1.1147(7) −0.0417(5) 0.41139(19) 0.0253(17) Uani 1 1 d . . .
H9 H 1.1272 0.0261 0.3987 0.030 Uiso 1 1 calc R . .
C10 C 1.1019(8) −0.0148(5) 0.4502(2) 0.0330(18) Uani 1 1 d . . .
H10A H 1.0156 0.0315 0.4540 0.040 Uiso 1 1 calc R . .
H10B H 1.0866 −0.0804 0.4633 0.040 Uiso 1 1 calc R . .
C11 C 1.2429(7) 0.0412(5) 0.4630(2) 0.0349(19) Uani 1 1 d . . .
H11A H 1.2533 0.1102 0.4515 0.042 Uiso 1 1 calc R . .
H11B H 1.2355 0.0538 0.4878 0.042 Uiso 1 1 calc R . .
N12 N 1.3784(6) −0.0279(4) 0.45532(16) 0.0258(14) Uani 1 1 d . . .
H12A H 1.4618 0.0069 0.4623 0.031 Uiso 1 1 calc R . .
H12B H 1.3716 −0.0892 0.4676 0.031 Uiso 1 1 calc R . .
C13 C 1.3929(7) −0.0546(6) 0.4181(2) 0.0314(18) Uani 1 1 d . . .
H13A H 1.4790 −0.1013 0.4147 0.038 Uiso 1 1 calc R . .
H13B H 1.4098 0.0107 0.4049 0.038 Uiso 1 1 calc R . .
C14 C 1.2538(7) −0.1097(6) 0.4049(2) 0.0356(19) Uani 1 1 d . . .
H14A H 1.2425 −0.1785 0.4165 0.043 Uiso 1 1 calc R . .
H14B H 1.2639 −0.1231 0.3802 0.043 Uiso 1 1 calc R . .
N15 N 0.6215(5) 0.0371(4) 0.33108(16) 0.0256(14) Uani 1 1 d . . .
H15 H 0.6768 0.0852 0.3408 0.031 Uiso 1 1 calc R . .
C16 C 0.5183(7) 0.0697(5) 0.30805(18) 0.0213(15) Uani 1 1 d . . .
O17 O 0.4336(5) 0.0082(3) 0.29260(13) 0.0309(12) Uani 1 1 d . . .
C18 C 0.5120(6) 0.1890(5) 0.30170(17) 0.0195(15) Uani 1 1 d . . .
C19 C 0.3923(7) 0.2486(5) 0.31620(19) 0.0252(16) Uani 1 1 d . . .
C20 C 0.3785(7) 0.3569(5) 0.30904(19) 0.0267(17) Uani 1 1 d . . .
H20 H 0.2991 0.3957 0.3185 0.032 Uiso 1 1 calc R . .
C21 C 0.4814(7) 0.4078(5) 0.28805(19) 0.0270(17) Uani 1 1 d . . .
H21 H 0.4708 0.4808 0.2834 0.032 Uiso 1 1 calc R . .
C22 C 0.6005(7) 0.3518(5) 0.27375(19) 0.0294(18) Uani 1 1 d . . .
H22 H 0.6702 0.3865 0.2597 0.035 Uiso 1 1 calc R . .
C23 C 0.6142(7) 0.2425(5) 0.2807(2) 0.0286(17) Uani 1 1 d . . .

Example 257

Preparation of 4-(2,6-dichloro-benzoylamino)-1H-pyrazole-3-carboxylic acid piperidin-4-ylamide acetic acid salt

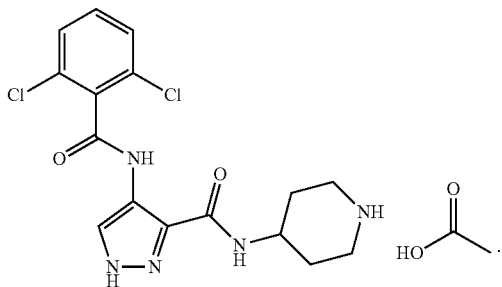

To a solution of 4-(2,6-dichloro-benzoylamino)-1H-pyrazole-3-carboxylic acid piperidin-4-ylamide hydrochloride salt (20.6 g, 50 mmol) in water (500 ml) stirring at ambient temperature was added sodium bicarbonate (4.5 g, 53.5 mmol). The mixture was stirred for 1 hour and the solid formed collected by filtration and dried in vacuo azeotroping with toluene (×3) to give the corresponding free base of 4-(2,6-dichloro-benzoylamino)-1H-pyrazole-3-carboxylic acid piperidin-4-ylamide.

$^1$H NMR (400 MHz, DMSO-d$_6$) δ 10.20 (s, 1H), 8.30 (s, 1H), 8.25 (d, 1H), 7.60-7.50 (m, 3H), 3.70 (m, 1H), 3.00 (d, 2H), 2.50 (m, 2H), 1.70 (d, 2H), 1.50 (m, 2H).

To a stirred suspension of 4-(2,6-dichloro-benzoylamino)-1H-pyrazole-3-carboxylic acid piperidin-4-ylamide (10.0 g, 26.2 mmol) in methanol (150 ml) was added glacial acetic acid (15 ml, 262 mmol) at ambient temperature. After 1 h, a clear solution was obtained which was reduced in vacuo azeotroping with toluene (×2). The residue was then triturated with acetonitrile (2×100 ml) and the solid dried in vacuo to give 4-(2,6-dichloro-benzoylamino)-1H-pyrazole-3-carboxylic acid piperidin-4-ylamide acetic acid salt (10.3 g) as a white solid.

$^1$H NMR (400 MHz, DMSO-d$_6$) δ 10.20 (s, 1H), 8.40 (d, 1H), 8.35 (s, 1H), 7.60-7.50 (m, 3H), 3.85 (m, 1H), 3.00 (d, 2H), 2.60 (t, 2H), 1.85 (s, 3H), 1.70 (d, 2H), 1.55 (m, 2H)

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

---

What is claimed is:

1. A combination comprising a proteasome inhibitor and a compound the formula (VIb):

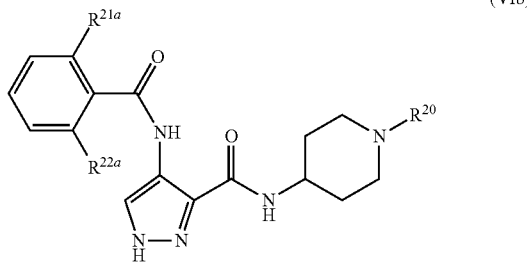

or salts or tautomers or N-oxides thereof;
wherein $R^{20}$ is selected from hydrogen and methyl;
$R^{21a}$ is selected from fluorine and chlorine; and
$R^{22a}$ is selected from fluorine, chlorine and methoxy.

2. A combination according to claim 1 wherein the compound of the formula (VIb) is 4-(2,6-dichloro-benzoylamino)-1H-pyrazole-3-carboxylic acid piperidin-4-ylamide or a salt thereof.

3. A combination according to claim 2 wherein the combination comprises a salt of 4-(2,6-dichloro-benzoylamino)-1H-pyrazole-3-carboxylic acid piperidin-4-ylamide formed with methanesulphonic acid.

4. A combination according to claim 1 wherein the proteasome inhibitor and compound of formula (VIb) are physically associated.

5. The combination of claim 1 wherein the proteasome inhibitor and compound of formula (VIb) are non-physically associated.

6. A method of inhibiting tumour growth in a mammal, which method comprises administering to the mammal an effective tumour growth-inhibiting amount of a combination according to claim 1.

7. A method for treating or managing cancer in a patient suffering from, or being at risk of suffering from a cancer, said method comprising administering to said patient a therapeutically effective amount of a combination according to claim 1.

8. A method of enhancing or potentiating the response rate in a patient suffering from a cancer where the patient is being treated with a cytotoxic compound or signalling inhibitor, or an ancillary agent, or two or more further anti-cancer agents, which method comprises administering to the patient, in combination with the cytotoxic compound or signalling inhibitor, or an ancillary agent, or two or more further anti-cancer agents, a combination as defined in claim 1.

9. A combination according to claim 1 wherein the proteasome inhibitor is bortezimib.

10. A combination according to claim 1 wherein the combination further includes an additional agent selected from erythropoietin (EPO), granulocyte macrophage-colony stimulating factor (GM-CSF), granulocyte-colony stimulating factor (G-CSF), zoledronate, pamidronate, ibandronate, dexamethazone, prednisone, prednisolone, leucovorin, folinic acid and megestrol acetate.

11. A combination according to claim 2 wherein the proteasome inhibitor and compound of formula (VIb) are physically associated.

12. The combination of claim 2 wherein the proteasome inhibitor and compound of formula (VIb) are non-physically associated.

13. A combination according to claim 3 wherein the proteasome inhibitor and the salt of 4-(2,6-dichloro-benzoylamino)-1H-pyrazole-3-carboxylic acid piperidin-4-ylamide are physically associated.

14. The combination of claim 3 wherein the proteasome inhibitor and the salt of 4-(2,6-dichloro-benzoylamino)-1H-pyrazole-3-carboxylic acid piperidin-4-ylamide are non-physically associated.

15. A combination according to claim 2 wherein the proteasome inhibitor is bortezimib.

16. A combination according to claim 3 wherein the proteasome inhibitor is bortezimib.

17. A combination according to claim 4 wherein the proteasome inhibitor is bortezimib.

18. A combination according to claim 5 wherein the proteasome inhibitor is bortezimib.

19. A method of inhibiting tumour growth in a mammal, which method comprises administering to the mammal an effective tumour growth-inhibiting amount of a combination according to claim 2.

20. A method of inhibiting tumour growth in a mammal, which method comprises administering to the mammal an effective tumour growth-inhibiting amount of a combination according to claim 3.

21. A method for treating or managing cancer in a patient suffering from, or being at risk of suffering from a cancer, said method comprising administering to said patient a therapeutically effective amount of a combination according to claim 2.

22. A method for treating or managing cancer in a patient suffering from, or being at risk of suffering from a cancer, said method comprising administering to said patient a therapeutically effective amount of a combination according to claim 3.

* * * * *

UNITED STATES PATENT AND TRADEMARK OFFICE
CERTIFICATE OF CORRECTION

| | | |
|---|---|---|
| PATENT NO. | : 8,404,718 B2 | Page 1 of 1 |
| APPLICATION NO. | : 12/752772 | |
| DATED | : March 26, 2013 | |
| INVENTOR(S) | : Curry et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 310 days.

Signed and Sealed this
Eighth Day of October, 2013

Teresa Stanek Rea
*Deputy Director of the United States Patent and Trademark Office*